US008409172B2

(12) United States Patent
Moll et al.

(10) Patent No.: US 8,409,172 B2
(45) Date of Patent: Apr. 2, 2013

(54) SYSTEMS AND METHODS FOR PERFORMING MINIMALLY INVASIVE PROCEDURES

(75) Inventors: Frederic H. Moll, Woodside, CA (US); Daniel T. Wallace, Burlingame, CA (US); Gregory J. Stahler, San Jose, CA (US); Christopher R. Carlson, Menlo Park, CA (US); Federico Barbagli, San Francisco, CA (US)

(73) Assignee: Hansen Medical, Inc., Mountain View, CA (US)

( * ) Notice: Subject to any disclaimer, the term of this patent is extended or adjusted under 35 U.S.C. 154(b) by 1083 days.

(21) Appl. No.: 11/833,969

(22) Filed: Aug. 3, 2007

(65) Prior Publication Data

US 2008/0058836 A1    Mar. 6, 2008

Related U.S. Application Data

(60) Provisional application No. 60/835,592, filed on Aug. 3, 2006, provisional application No. 60/838,075, filed on Aug. 15, 2006, provisional application No. 60/840,331, filed on Aug. 24, 2006.

(51) Int. Cl.
*A61B 17/00* (2006.01)

(52) U.S. Cl. .............................. 606/1; 606/130; 128/898

(58) Field of Classification Search ............... 606/1–2.5, 606/10, 13–16, 34, 130; 600/433–435, 466, 600/585, 101; 604/96.1, 523, 544; 607/1, 607/88–89; 969/1–2.5, 10, 13–16, 34, 130
See application file for complete search history.

(56) References Cited

U.S. PATENT DOCUMENTS

| 4,961,738 | A |   | 10/1990 | Mackin |  |
|---|---|---|---|---|---|
| 5,025,778 | A | * | 6/1991 | Silverstein et al. | 600/104 |
| 5,370,675 | A | * | 12/1994 | Edwards et al. | 607/101 |
| 5,458,612 | A |   | 10/1995 | Chin |  |
| 5,492,131 | A | * | 2/1996 | Galel | 600/585 |
| 6,106,521 | A | * | 8/2000 | Blewett et al. | 606/41 |
| 6,296,608 | B1 | * | 10/2001 | Daniels et al. | 600/104 |

(Continued)

FOREIGN PATENT DOCUMENTS

WO    2008014425    1/2008

OTHER PUBLICATIONS

PCT Invitation to pay additional fees and Partial International Search Report for PCT/US2007/075225, Applicant Hansen Medical Inc., Form PCT/ISA/206, dated Apr. 2, 2008 (10 pages).

(Continued)

*Primary Examiner* — Henry M Johnson, III
(74) *Attorney, Agent, or Firm* — Vista IP Law Group LLP

(57) ABSTRACT

A robotic surgical system includes an instrument driver and an instrument assembly operatively coupled to the instrument driver such that mechanisms of the instrument driver operate or control movement, operation, or both, of components of the instrument assembly. The instrument assembly components include an elongate flexible guide instrument, an optical light source, a camera and a working tool, wherein the light source, camera, and working tool are carried in one or more lumens of the guide instrument. An operator control station is operatively coupled to the instrument driver via a remote communication link. The instrument assembly further includes an inflatable visualization balloon carried on a distal end portion of the guide instrument, the light source and camera having distal ends located within an interior of the balloon, the balloon comprising a lumen extending from the guide instrument to a distal facing wall of the balloon, such that the working instrument may extend from a respective lumen of the guide instrument through the balloon lumen to contact body tissue when the distal end of the guide instrument is positioned in an interior body region.

14 Claims, 177 Drawing Sheets

U.S. PATENT DOCUMENTS

| | | | |
|---|---|---|---|
| 6,327,492 B1 * | 12/2001 | Lemelson | 600/434 |
| 6,400,980 B1 * | 6/2002 | Lemelson | 600/478 |
| 6,423,009 B1 * | 7/2002 | Downey et al. | 600/461 |
| 6,695,871 B1 * | 2/2004 | Maki et al. | 607/89 |
| 7,171,255 B2 * | 1/2007 | Holupka et al. | 600/427 |
| 2002/0087049 A1 * | 7/2002 | Brock et al. | 600/114 |
| 2002/0087151 A1 * | 7/2002 | Mody et al. | 606/15 |
| 2003/0040737 A1 | 2/2003 | Merril et al. | |
| 2004/0097788 A1 | 5/2004 | Mourlas et al. | |
| 2004/0243123 A1 | 12/2004 | Grasso, III et al. | |
| 2005/0085693 A1 * | 4/2005 | Belson et al. | 600/146 |
| 2005/0119668 A1 | 6/2005 | Teague et al. | |
| 2005/0197623 A1 | 9/2005 | Leeflang et al. | |
| 2005/0203382 A1 * | 9/2005 | Govari et al. | 600/424 |
| 2005/0222554 A1 | 10/2005 | Wallace et al. | |
| 2006/0057560 A1 | 3/2006 | Hlavka et al. | |
| 2006/0111692 A1 | 5/2006 | Hlavka et al. | |
| 2007/0043338 A1 | 2/2007 | Moll et al. | |
| 2007/0078327 A1 * | 4/2007 | Kindlein | 600/407 |
| 2007/0083193 A1 * | 4/2007 | Werneth et al. | 606/41 |
| 2007/0197896 A1 | 8/2007 | Moll et al. | |

OTHER PUBLICATIONS

PCT International Search Report for PCT/US2007/075225, Applicant Hansen Medical, Inc., Forms PCT/ISA/210 and 220, dated Jul. 30, 2008 (8 pages).

PCT Written Opinion of the International Search Authority for PCT/US2007/075225, Applicant Hansen Medical, Inc., Form PCT/ISA/237, dated Jul. 30, 2008 (11 pages).

* cited by examiner

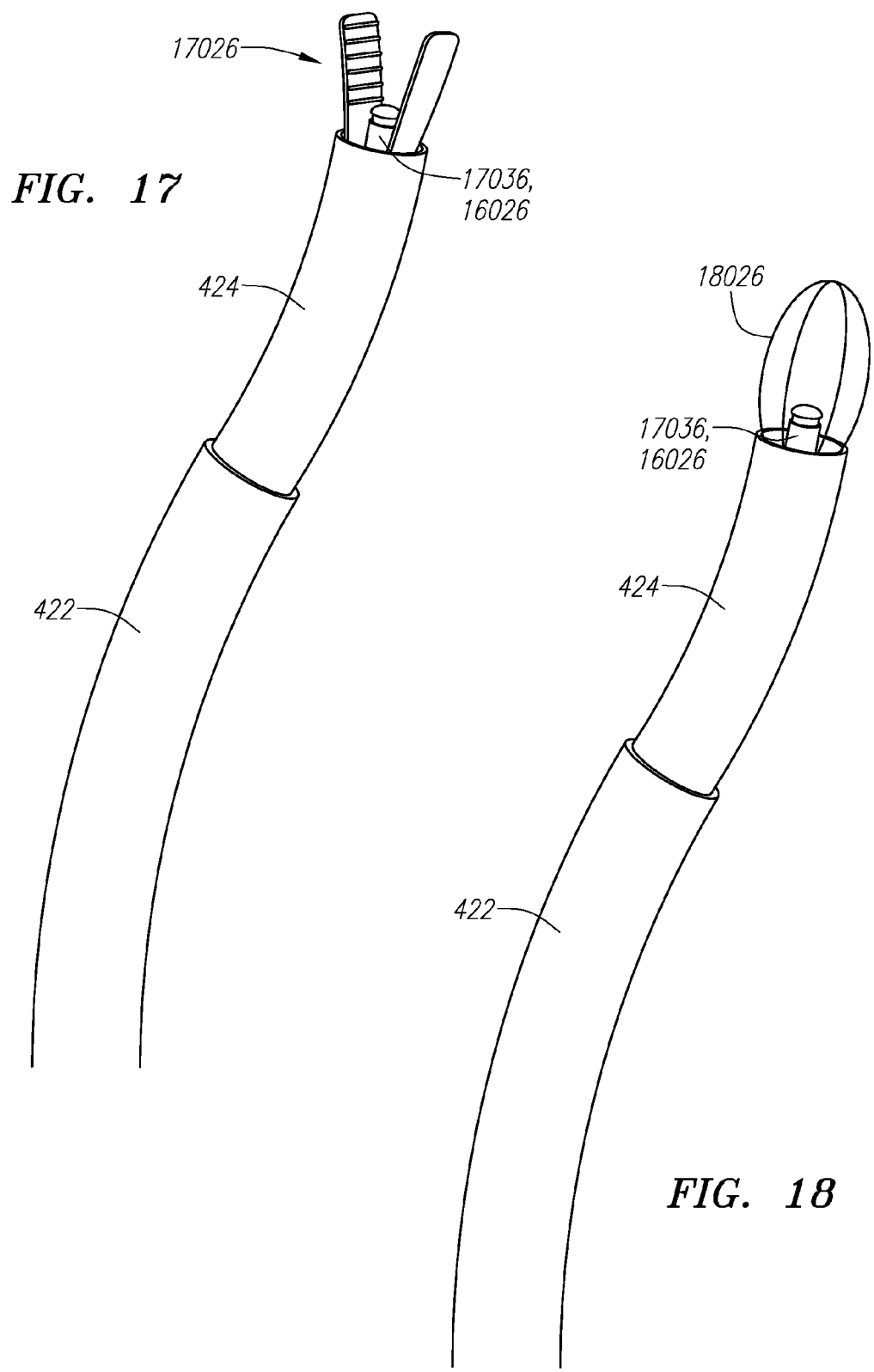

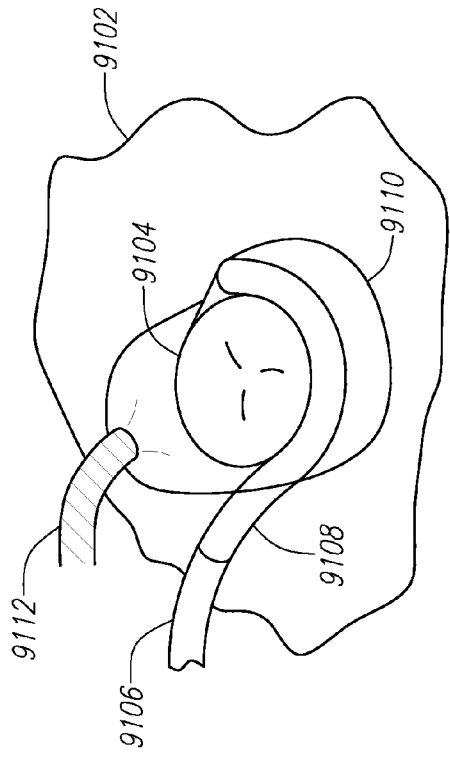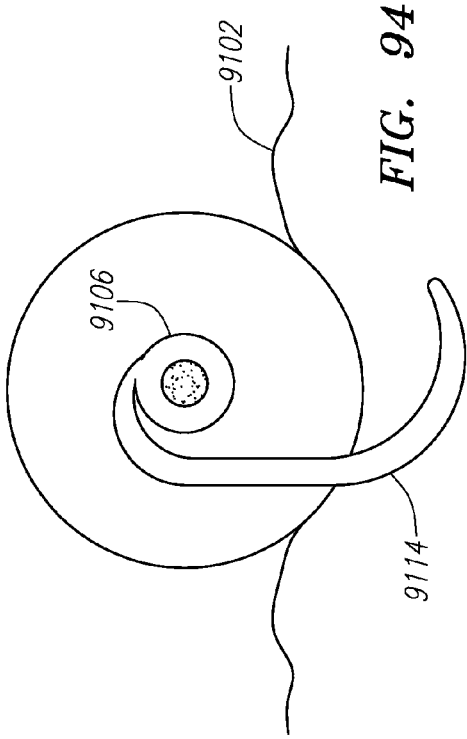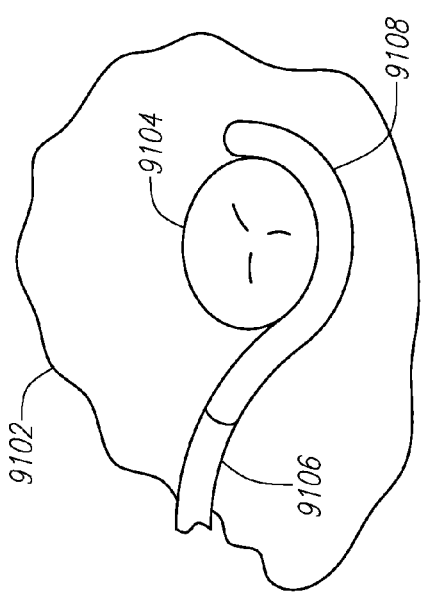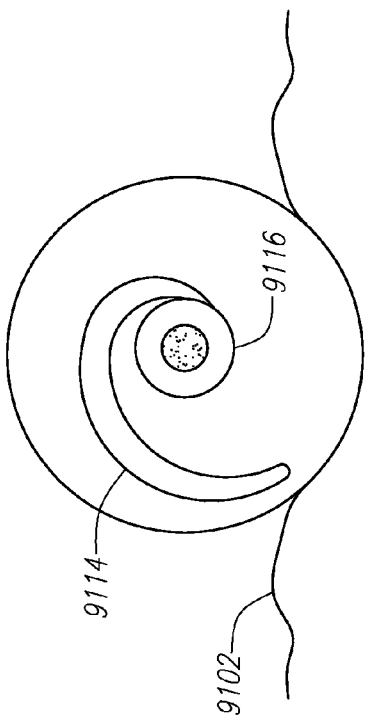
FIG. 91
FIG. 92
FIG. 93
FIG. 94

SYSTEMS AND METHODS FOR PERFORMING MINIMALLY INVASIVE PROCEDURES

RELATED APPLICATION DATA

The present application claims the benefit under 35 U.S.C. §119 to U.S. Provisional patent application Ser. Nos. 60/835,592, filed on Aug. 3, 2006; 60/838,075, filed on Aug. 15, 2006; and 60/840,331, filed on Aug. 24, 2006. The foregoing applications, along with U.S. patent application Ser. No. 11/829,076, filed Jul. 26, 2007, are all incorporated by reference into the present application in their entirety for all purposes.

FIELD OF INVENTION

The invention relates generally to robotically controlled systems, such as telerobotic surgical systems, and more particularly to robotic catheter systems for performing minimally invasive diagnostic and therapeutic procedures.

BACKGROUND

Robotic diagnostic and interventional systems and devices are well suited for use in performing minimally invasive medical procedures, as opposed to conventional techniques wherein a patient's body cavity is open to permit the surgeon's hands access to the internal organs. There is a need for highly controllable yet minimally sized systems to facilitate imaging, diagnosis, and treatment of tissues which may lie deeply and/or concealed within the body cavity of a patient, and which may be accessed through natural body orifices or percutaneous incisions and by way of naturally-occurring pathways such as blood vessels or other bodily lumens.

SUMMARY OF THE INVENTION

In accordance with one aspect of the disclosed inventions, a robotic surgical system includes an instrument driver, an instrument assembly operatively coupled to the instrument driver such that mechanisms of the instrument driver operate or control movement, operation, or both, of components of the instrument assembly, and an operator control station operatively coupled to the instrument driver via a remote communication link. The instrument assembly components include an elongate flexible guide instrument, an optical light source, a camera and a working tool, wherein the light source, camera, and working tool are carried in one or more lumens of the guide instrument. The instrument assembly further includes an inflatable visualization balloon carried on a distal end portion of the guide instrument, the light source and camera having distal ends located within an interior of the balloon, the balloon comprising a lumen extending from the guide instrument to a distal facing wall of the balloon, wherein the working instrument may extend from a respective lumen of the guide instrument through the balloon lumen to contact body tissue when the distal end of the guide instrument is positioned in an interior body region. In one embodiment, the working instrument is a laser fiber, e.g., a lithotripsy laser fiber such as a Holmium YAG laser, which may be movable relative to the guide instrument. In other embodiments, the working instrument may be a tissue grasper or manipulator, or a basket apparatus, which may be movable relative to the guide instrument. In some embodiments, the instrument assembly components further include a sheath instrument, wherein the guide instrument is carried in a lumen of, and is movable relative to, the sheath instrument.

In accordance with another aspect of the disclosed inventions, a robotic surgical system includes an instrument driver, an instrument assembly operatively coupled to the instrument driver such that mechanisms of the instrument driver operate or control movement, operation, or both, of components of the instrument assembly, and an operator control station operatively coupled to the instrument driver via a remote communication link. The instrument assembly components include an elongate guide instrument sized for being positioned in a urethra, an image capture device and a working tool, wherein the image capture device and working tool are carried in one or more lumens of the guide instrument, wherein movement, operation, or both, of components of the instrument assembly are at least partially automatically controlled based on images obtained by the image capture device. In one embodiment, the working instrument is a laser fiber, e.g., a lithotripsy laser fiber such as a Holmium YAG laser, which may be movable relative to the guide instrument. In some embodiments, the image capture device is an imaging fiber. In some embodiments, a flush port is provided in fluid communication with a fluid flush lumen extending through the guide instrument. By way of non-limiting example, the fluid flush lumen may be provided in a tubular body that extends out of a distal end of the guide instrument. In some such embodiments, the tubular body has a distal end section that bends or curves back in a proximal facing direction, such that fluid discharged out of the flush port is directed at the distal end of the guide instrument. In some embodiments, the imaging device is carried in the tubular body. In some embodiments, the instrument assembly components further include a sheath instrument, wherein the guide instrument is carried in a lumen of, and is movable relative to, the sheath instrument. In some embodiments, a second working instrument (e.g., a wire loop apparatus or tissue grasper) may be carried in a lumen of the guide instrument.

In accordance with yet another aspect of the disclosed inventions, a robotic surgical system includes an instrument driver, an instrument assembly operatively coupled to the instrument driver such that mechanisms of the instrument driver operate or control movement, operation, or both, of components of the instrument assembly. The instrument assembly components include an elongate sheath instrument sized for positioning in a urethra, an elongate guide instrument carried in a lumen of and movable relative to the sheath instrument, and a resectoscope carried in a lumen of the guide instrument.

Other aspects and advantages of the present invention will become apparent from the following description, taken in conjunction with the accompanying drawings, illustrating by way of examples the principles of the invention.

BRIEF DESCRIPTION OF THE DRAWINGS

The present invention will be readily understood by the following detailed description, taken in conjunction with accompanying drawings, illustrating by way of examples the principles of the invention. The drawings illustrate the design and utility of preferred embodiments of the present invention, in which like elements are referred to by like reference symbols or numerals. The objects and elements in the drawings are not necessarily drawn to scale, proportion, or precise positional relationships; instead emphasis is focused on illustrating the principles of the invention.

FIG. 17 illustrates an instrument assembly with a grasper including an energy source configured for performing lithotripsy procedures.

FIG. 18 illustrates an instrument assembly with a basket tool including an energy source configured for performing lithotripsy procedures.

FIG. 91 through FIG. 95 respectively illustrates one embodiment of a method for deploying an angioplasty ring with a balloon apparatus.

FIG. 120 illustrates one embodiment of a robotic catheter system that includes data gloves.

FIG. 121 illustrates the operator control station of FIG. 120.

FIG. 122 illustrates another embodiment of an operator control station including a pair of data gloves.

FIG. 123 illustrate the various input devices of a control station.

FIG. 124 illustrates one embodiment of a data glove.

FIG. 125 illustrates one embodiment of a wired data glove

FIG. 126 illustrates one embodiment of a wireless data glove system.

FIG. 127 illustrates a display screen showing sensor data signals received by the system from the data gloves in accordance to one embodiment.

FIG. 128 illustrates a block diagram of the controls system flow for one embodiment.

DETAILED DESCRIPTION OF THE ILLUSTRATED EMBODIMENTS

Figure 1:
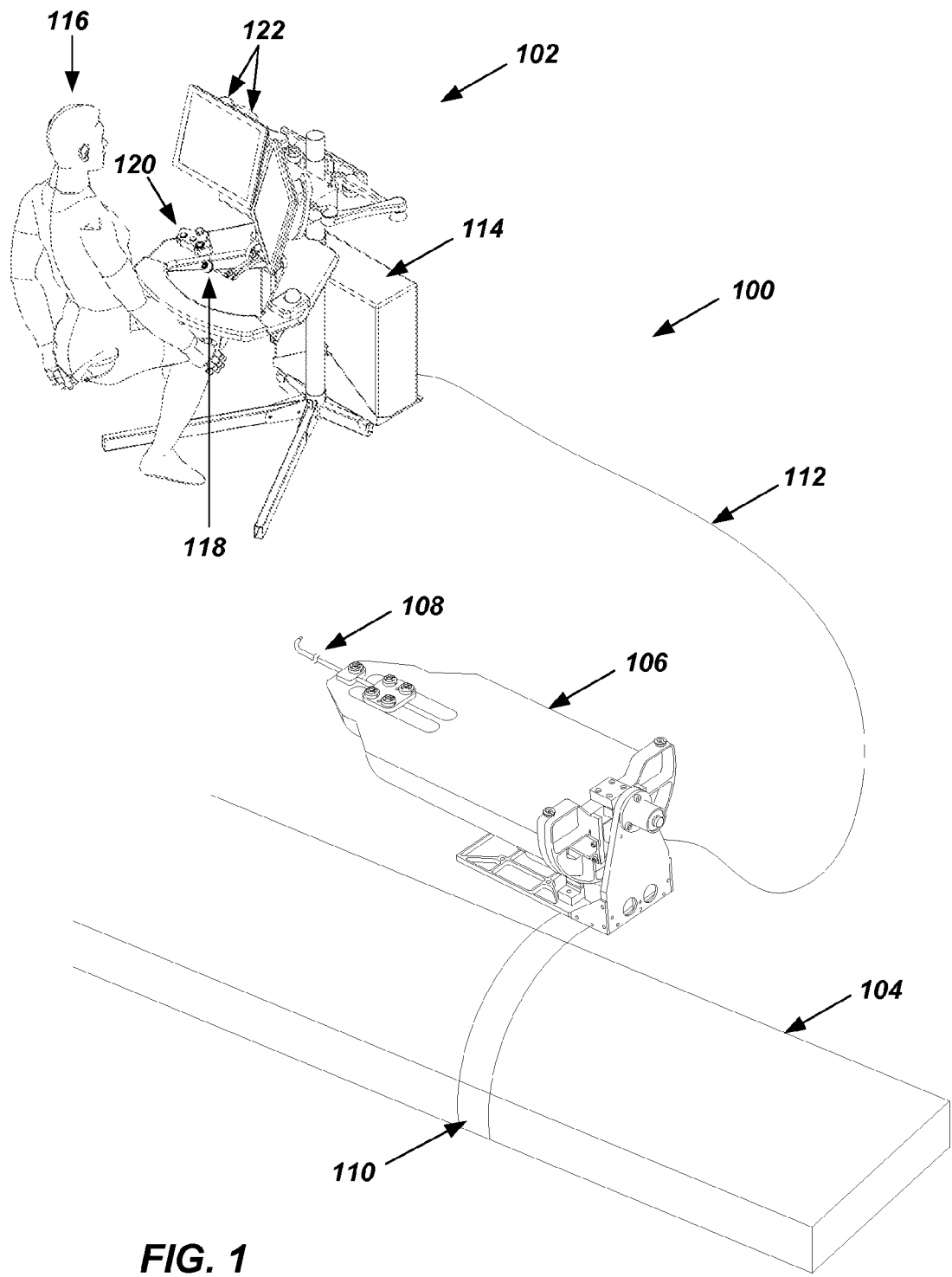
FIG. 1 illustrates one embodiment of a robotic surgical system.

Reference will now be made in detail to the preferred embodiments of the present invention, examples of which are illustrated in the accompanying drawings. While the invention will be described in conjunction with the preferred embodiments, it will be understood that they are not intended to limit the invention to these embodiments. On the contrary, the invention is intended to cover modifications, alternatives, and equivalents that may be included within the spirit and scope of the invention as defined by the appended claims. Furthermore, in the following detailed description of the embodiments, numerous specific details are set forth in order to provide a thorough understanding of the present invention. However, it will be readily apparent to one skilled in the art that the present invention may be practiced without these specific details. In other instances, well-known methods, procedures, and components have not been described in detail so as not to unnecessarily obscure aspects of the present invention.

Standard surgical procedures typically involve using a scalpel to create an opening of sufficient size to enable a surgical team to gain access to an area in the body of a patient for the surgical team to diagnose and treat one or more target sites. When possible, minimally invasive surgical procedures may be used instead of standard surgical procedures to minimize physical trauma to the patient and reduce recovery time for the patient to recuperate from the surgical procedures. Minimally invasive surgical procedures typically require using extension tools (e.g., catheters, etc.) to approach and address the target site through natural pathways (e.g., blood vessels, gastrointestinal tract, etc.) from a remote location either through a natural body orifice or a percutaneous incision. As can be appreciated, the surgeon may have limited information or feedback (e.g., visual, tactile, etc.) to accurately navigate the extension tools, such as one or more catheters, and place the working portions of the extension tools at precise locations to perform the necessary diagnostic and/or interventional procedures. Even with such potential limitations, minimally invasive surgical procedures may be more effective and beneficial for treating the patient, instead of standard open surgery.

Minimally invasive diagnostic and interventional operations may require the surgeon to remotely approach and address the operation or target site by using extension tools. The surgeon usually approaches the target site through either a natural body orifice or a small percutaneous incision in the body of the patient. In some situations, the surgeon may use multiple extension tools and approach the target site through one or more natural body orifices as well as small percutaneous incisions in the body of the patient. Typically, the natural body orifices or small incisions are located at some distance away from the target site. Extension tools (e.g., various types of catheters and surgical instruments) enter the body through one or more natural body orifices or small percutaneous incisions, and the extension tools are guided, navigated, manipulated, maneuvered, and advanced toward the target site typically by way of natural body pathways (e.g., blood vessels, esophagus, trachea, small intestine, large intestine, urethra, etc.). The extension tools might include one or more catheters as well as other surgical tools or instruments. The catheters may be manually controlled catheters or robotically operated catheters. In most situations, the surgeon has limited visual and tactile information to discern the location of the catheters and surgical instruments relative to the target site and/or other organs in the patient.

For example, in the treatment of cardiac arrhythmias such as atrial fibrillation (AF), cardiac ablation therapy is applied to the left atrium of the heart to restore normal heart function. For this operation, one or more catheters (e.g., sheath catheter, guide catheter, ablation catheter, endoscopic catheter, intracardiac echocardiography catheter, etc.) may be inserted through one or more natural orifices or one or more percutaneous incisions at the femoral vein near the thigh or pelvic region of the patient, which is located at some distance away from the operation or target site. In this example, the operation or target site for performing cardiac ablation is in the left atrium of the heart. Catheters may be guided (e.g., by a guide wire, a sheath, etc.), manipulated, maneuvered, and advanced toward the target site by way of the femoral vein to the inferior vena cava into the right atrium of the heart and through the interatrial septum to the left atrium of the heart. The catheters may be used separately or in combination of multiple catheters. Currently, the surgeon has limited visual and tactile information to assist him or her with maneuvering and controlling the catheters (separately or in combination). In particular, because of limited information and/or feedback, it is especially difficult for the surgeon to maneuver and control one or more distal portions of the catheters to perform cardiac ablation at precise locations or spots on the surface or wall of the left atrium of the heart. As will be explained below, embodiments of the present invention provide improved systems and methods that would facilitate imaging, diagnosis, address, and treatment of tissues which may lie deeply and/or concealed under other tissues or organs within the body cavity of a patient. With embodiments of the present invention, the surgeon may be able to position the catheter more precisely and accurately to address the operation or target sites. For example, with the improved imaging capability, the surgeon may be able to apply cardiac ablation at the desired locations or spots on the surface or wall of the left atrium of the heart in a more precise and accurate manner to address cardiac arrhythmias such as atrial fibrillation. In addition, U.S. patent application Ser. Nos. 11/185,432, filed on Jul. 19, 2005; 11/202,925, filed on Aug. 12, 2005; and 11/481,433, filed Jul. 3, 2006 are incorporated herein by reference in their entirety.

FIG. 1 illustrates one embodiment of a robotic surgical system (100), e.g., the Sensei™ Robotic Catheter System from Hansen Medical, Inc. in Mountain View, Calif., U.S.A., an operator control station (102) located remotely from an operating table (104) to which an instrument driver (106) and instrument assembly (108), e.g., the Artisan™ Control Catheter also from Hansen Medical, Inc. in Mountain View, Calif., U.S.A., are supported by an instrument driver mounting brace (110) that is mounted on the operating table (104). A wired connection (112) transfers signals between an electronics rack (114) at the operator control station (102) and instrument driver (106). The electronics rack (114) includes system hardware, software, firmware, and combinations thereof that substantially operate and perform the many functions of the robotic surgical system (100). The instrument driver mounting brace (110) is a substantially arcuate-shaped structural member configured to position the instrument driver (106) above a patient (not shown) who is lying on the operating table (104). The wired connection (112) may transmit manipulation and control commands from an operator or surgeon (116) who is working at the operator control station (102) to the instrument driver (106) to operate the instrument assembly (108) to perform minimally invasive operations on the patient who is lying on the operating table (104). The surgeon (116) may provide manipulation and control commands using a master input device (MID) (118). In addition, the surgeon may provide inputs, commands, etc. by using one or more keyboards (120), trackball, mouse, etc. The wired connection (112) may also transmit information (e.g., visual views, tactile or force information, position, orientation, shape, localization, electrocardiogram, map, model, etc.) from the instrument assembly (108), the patient, and monitors (not shown in this figure) to the electronics rack (114) for providing the necessary information or feedback to the operator or surgeon (116) to facilitate monitoring of the instrument assembly (108), the patient, and one or more target sites for performing precise manipulation and control of the instrument (108) during the minimally invasive surgical procedure. The wired connection (112) may be a hard wire connection, such as an electrical wire configured to transmit electrical signals (e.g., digital signals, analog signals, etc.), an optical fiber configured to transmit optical signals, a wireless link configured to transmit various types of signals (e.g., RF signals, microwave signals, etc.), or any combinations of electrical wire, optical fiber, wireless link, etc. The information or feedback may be displayed on one or more monitors (122) at the operator control station (102).

Figure 2:
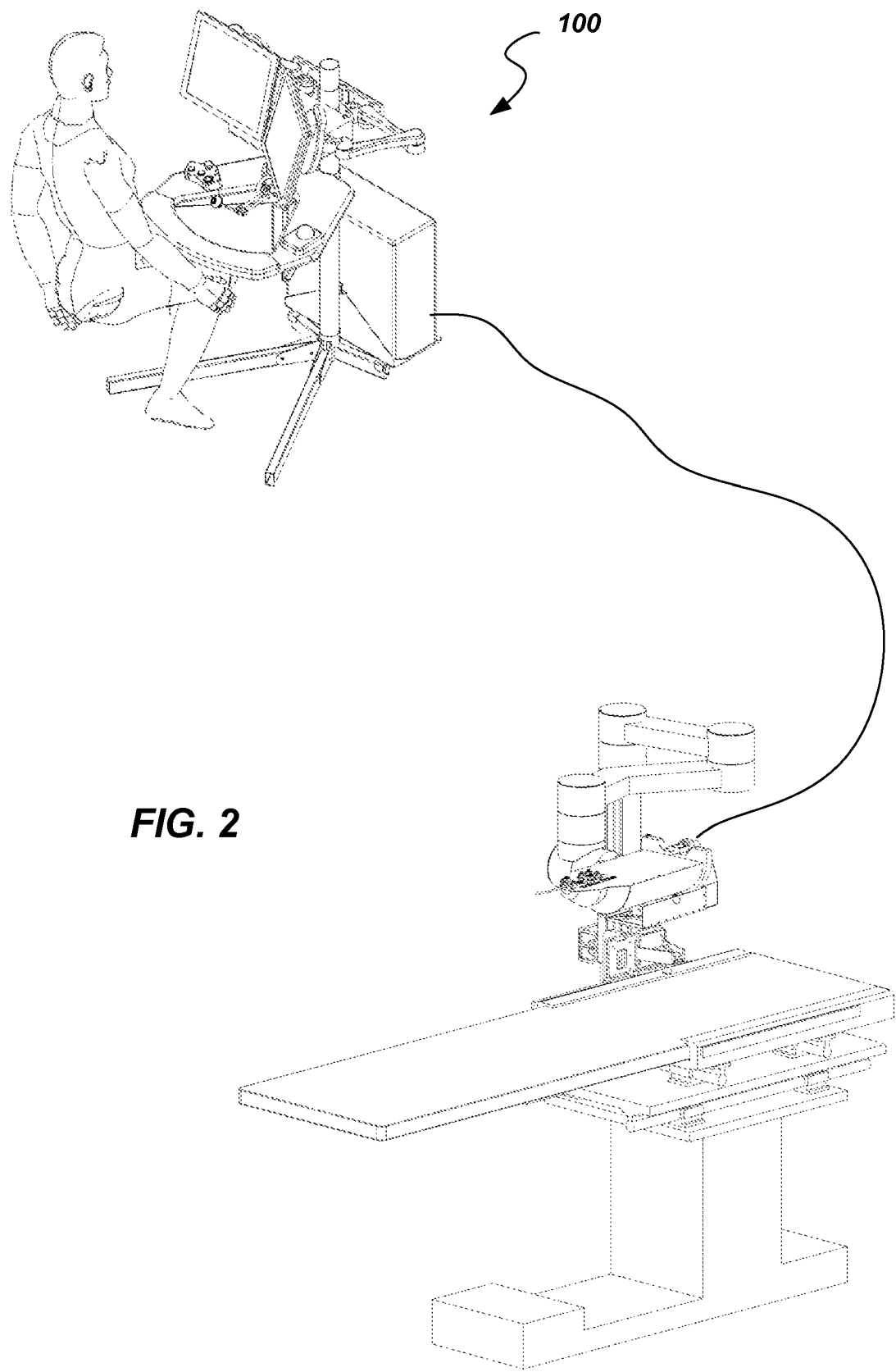
FIG. 2 illustrates another embodiment of a robotic surgical system.

FIG. 2 illustrates another embodiment of a robotic surgical system (100). For more detailed discussions of robotic surgical systems, please refer to U.S. Provisional Patent Application No. 60/644,505, filed on Jan. 13, 2005; U.S. Patent Application Publication No. 2007-0043338, filed on Jul. 3, 2006; and U.S. patent application Ser. No. 11/637,951, filed on Dec. 11, 2006; and they are incorporated herein by reference in their entirety.

Figure 3:
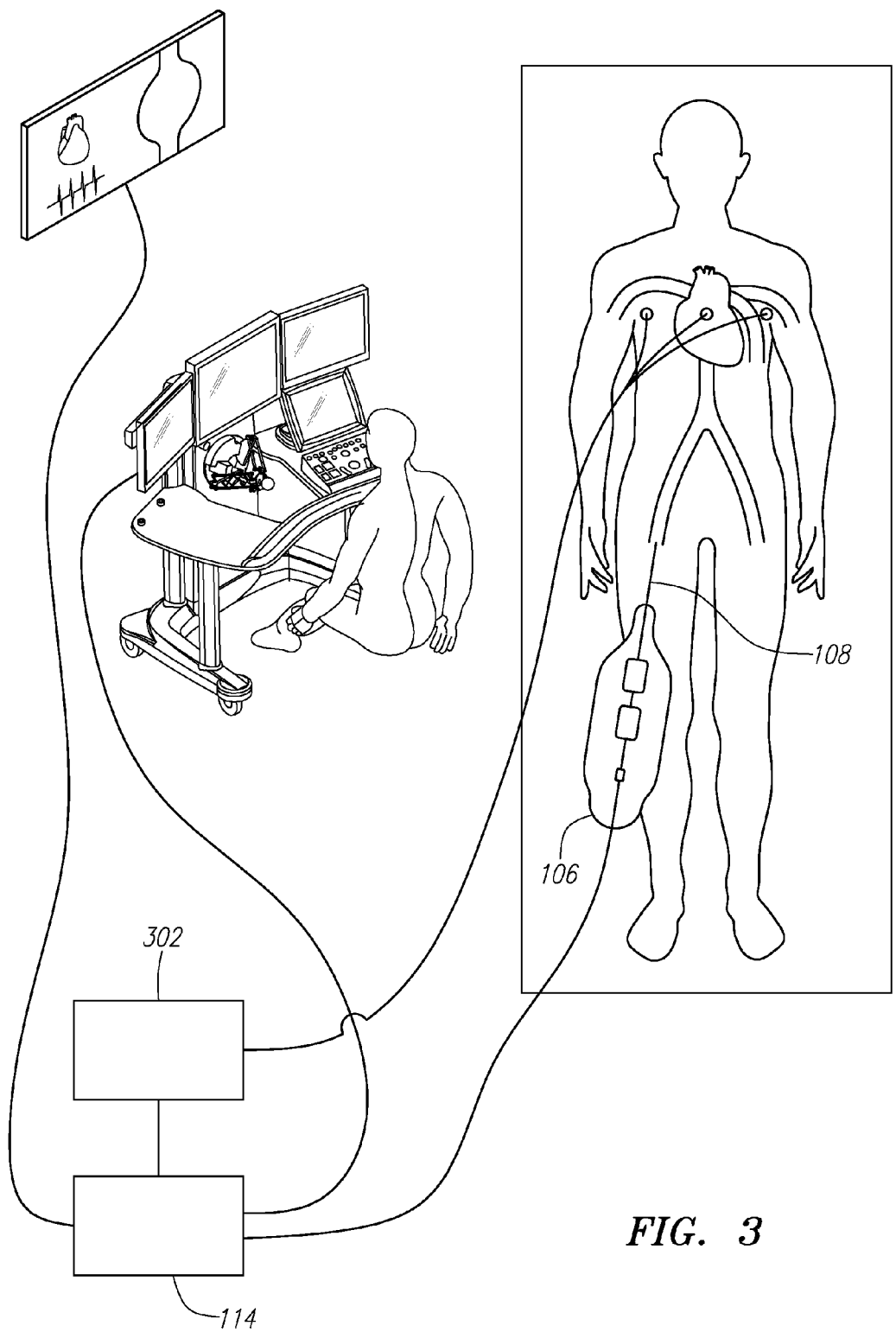
FIG. 3 illustrates one embodiment of a robotic surgical system being used to perform diagnostic and/or interventional operations on a patient.

FIG. 3 illustrates one embodiment of a robotic surgical system (100) configured to perform minimally invasive surgery using one or more instrument assemblies (108). For example, the instrument assembly (108) may include a sheath catheter, guide catheter, ablation catheter, endoscopic catheter, intracardiac echocardiography catheter, etc., or any combination thereof. In addition, surgical instruments or tools (e.g., lasers, optics, cutters, needles, graspers, scissors, baskets, balloons, etc.) may be attached or coupled to any one or combination of the catheters. In one embodiment, the instrument assembly (108) may be a catheter system that includes a sheath catheter, guide catheter, a surgical catheter, and/or surgical instrument, such as the Artisan™ Control Catheter available from Hansen Medical, Inc. at Mountain View, Calif., U.S.A. The instrument assembly (108) also includes all the control mechanisms to operate its various components, e.g., sheath catheter, guide catheter, a surgical catheter, and/or surgical instrument. The robotic surgical system (100) including the control station (102), instrument driver (106), instrument (108), and the wired connection (112) may be used to treat or perform cardiac related diseases, maladies, conditions, or procedures (e.g., atrial flutter, Wolf-Parkinson-White ("WPW"), atrioventricular nodal reentrant tachycardia ("AVNRT"), Ventricular tachycardia ("V-tach"), patent foramen ovale ("PFO"), left atrial appendage occlusion, pacing lead placement, chronic total occlusion ("CTO"), ventricular injection therapy, valve repair).

Figure 4A:
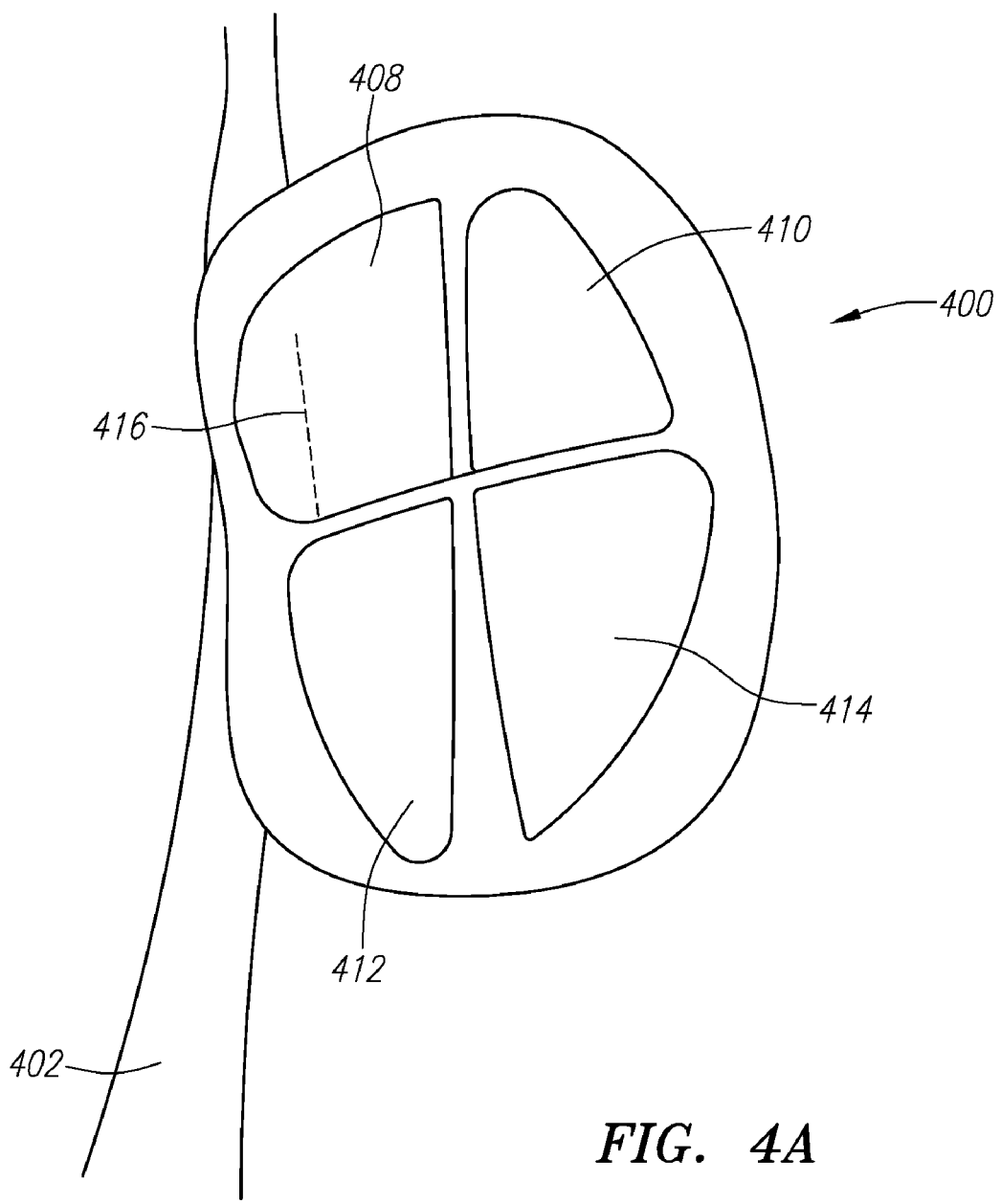
FIG. 4A illustrates a cross sectional view of a heart.
Figure 4B:
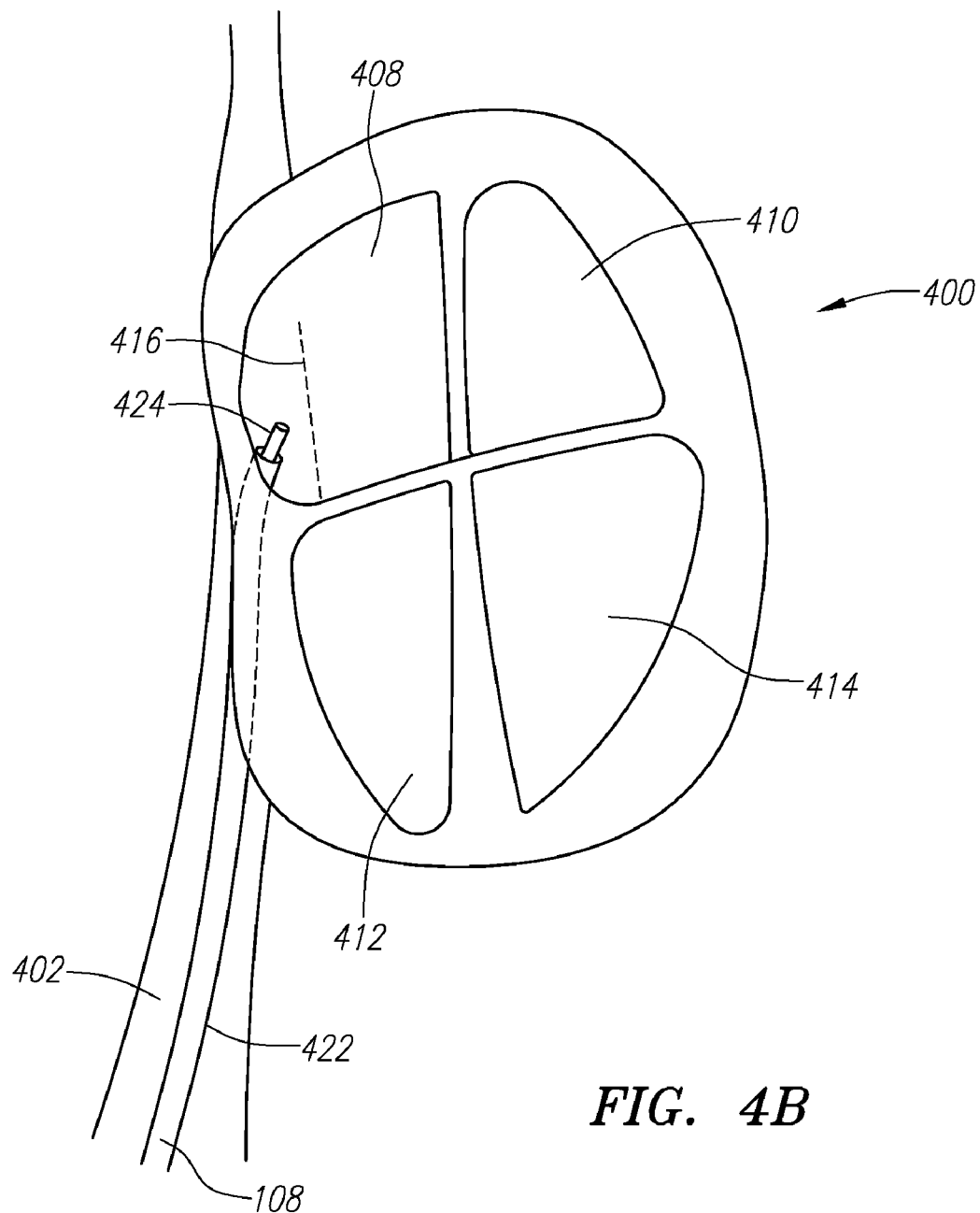
FIG. 4B illustrates an instrument assembly advanced into a chamber of the heart.
Figure 4C:
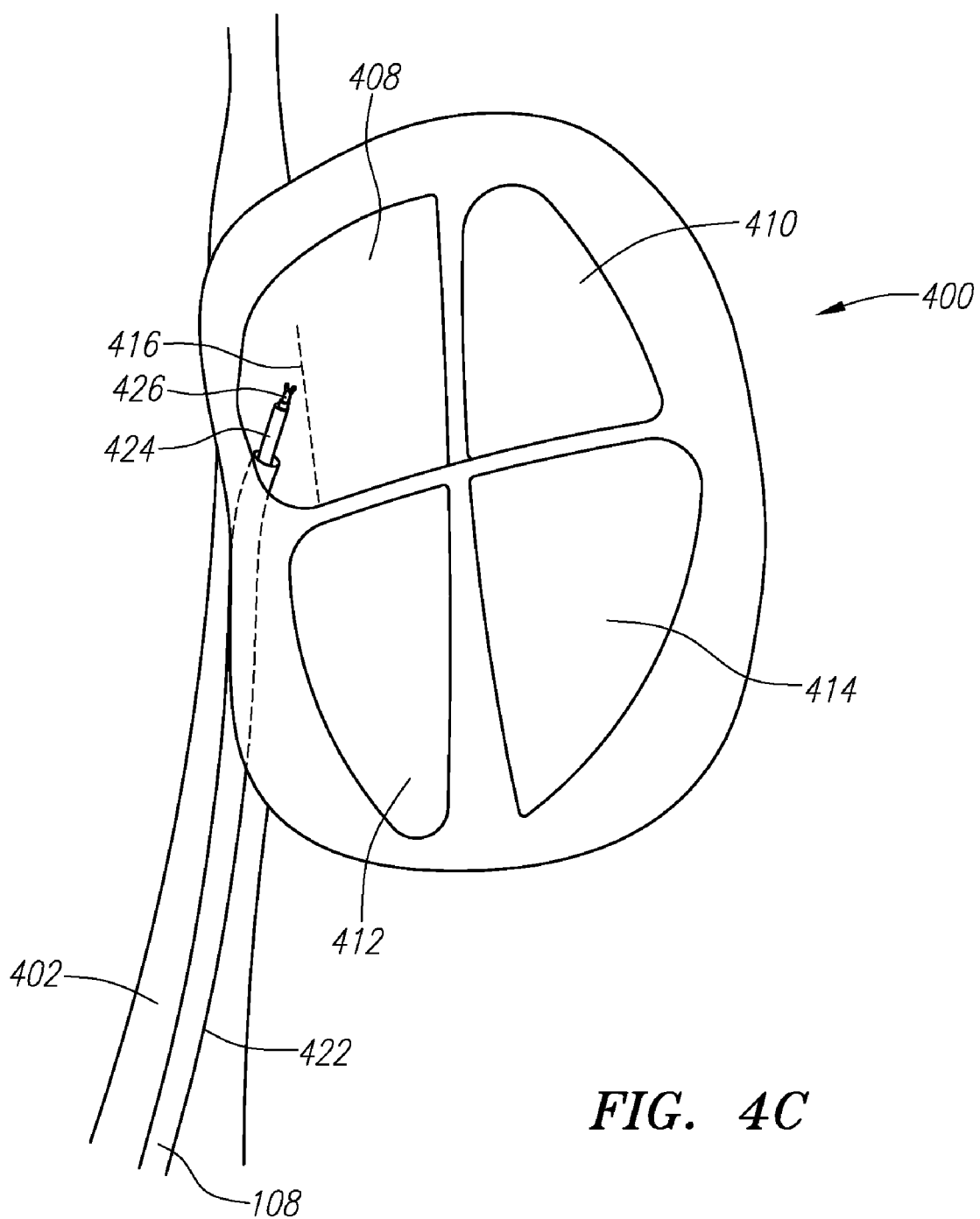
FIG. 4C illustrates an ablation tool advanced through the lumen of the instrument assembly into a chamber of the heart.

For example, atrial flutter is characterized by a rapid but organized and predictable pattern of beating of the atria. Similar to atrial fibrillation, the ventricles cannot respond to all of the atrial beats, which may cause blood to accumulate and collect or pool in the atria increasing the risk of stroke. FIG. 4A illustrates a cross sectional view of a heart (400). The cross sectional view illustrates the inferior vena cava (402), the right atrium (408), the left atrium (410), the right ventricle (412), and left ventricle (414). In addition, FIG. 4A illustrates a targeted location (416) (e.g., an area for linear lesion) for performing atrial flutter ablation lesion. FIG. 4B illustrates instrument (108) that may include a robotic sheath instrument or catheter (422) and a guide instrument or guide catheter (424) that have been navigated and positioned through the inferior vena cava (402) into the right atrium (408). Referring to FIG. 4C, an ablation tool (426) is depicted as having been navigated and placed through the working lumen of the guide instrument or guide catheter (424) and the ablation tool (426) is depicted as protruding slightly from the distal end of the guide instrument (424) to enable the guide instrument (424) to navigate the ablation tool (426) or the tip of the ablation tool (426) into position against portions of right atrium (408) to create the desired lesion (e.g., linear lesion), and preferably substantially treat or eliminate atrial flutter.

Figure 5A:
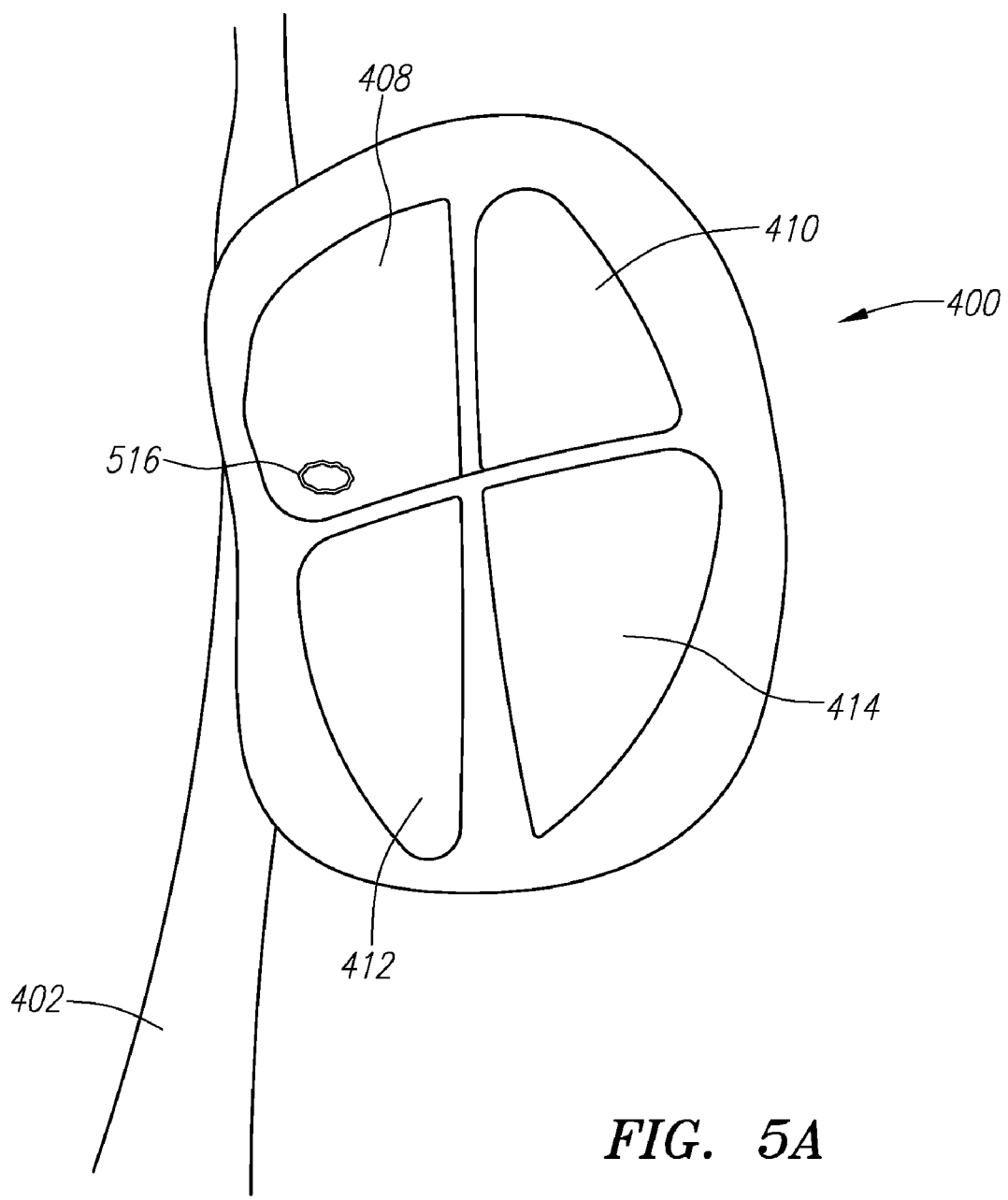
FIG. 5A illustrates a target of an operation site in a chamber of the heart.
Figure 5B:
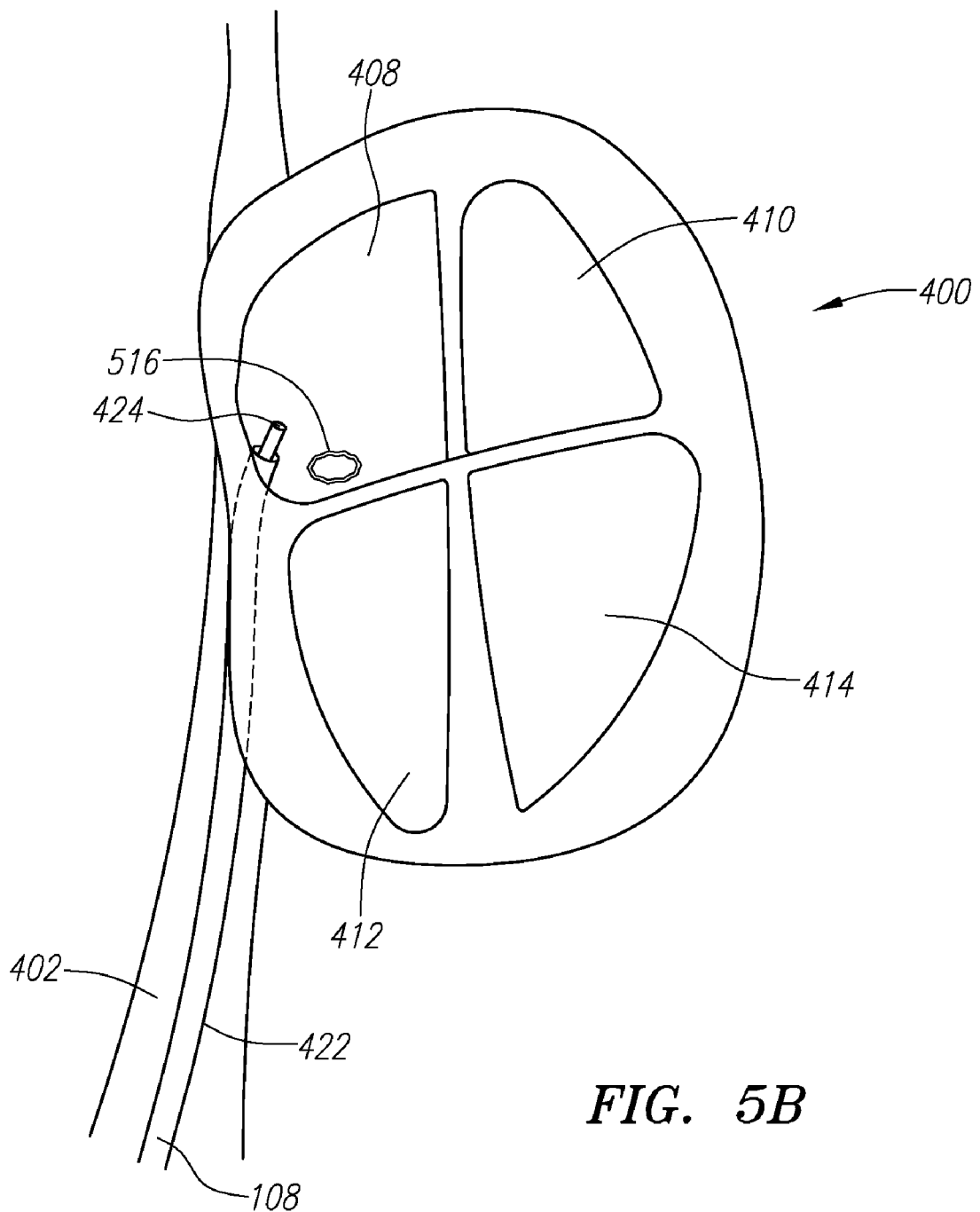
FIG. 5B illustrates an instrument assembly advanced toward a target site in a chamber of the heart.
Figure 5C:
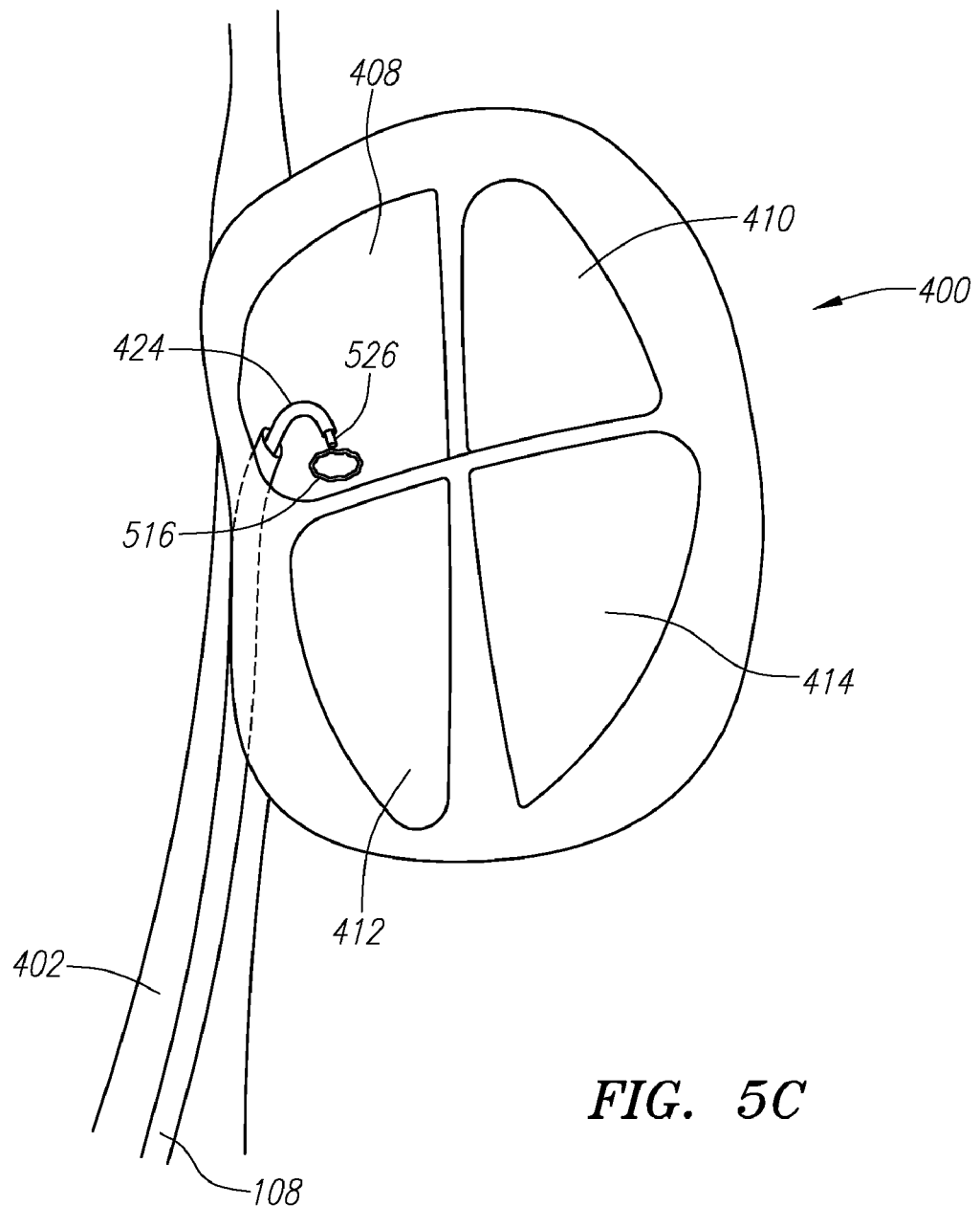
FIG. 5C illustrates an ablation tool advanced through a lumen of an instrument assembly toward a target site in a chamber of the heart.

Wolf-Parkinson-White ("WPW") is another type of arrhythmia that may be caused by an abnormal bridge of tissue, such as the eustachian ridge, which connects the atria and ventricles of the heart. This accessory pathway allows electrical signals to go back and forth between the atria and the ventricles without going through the heart's natural pacemaker, or atrioventricular node or AV node. If the signal ricochets back and forth, very fast heart rates and life-threatening arrhythmias can develop. Referring to FIG. 5A, an example of a targeted location (516) for an ablation lesion near or around the eustachian ridge is depicted. Referring to FIG. 5B, an instrument assembly (108) including a sheath instrument or sheath catheter (422) and a guide instrument or guide catheter (424) is depicted with the distal portions of the instruments (422 and 424) positioned in the right atrium (408). Referring to FIG. 5C, an ablation tool (526) is advanced through the working lumen or inner channel of the guide instrument (424) to a position wherein it may be utilized to contact and ablate desired portions of the targeted tissue.

Figure 6A:
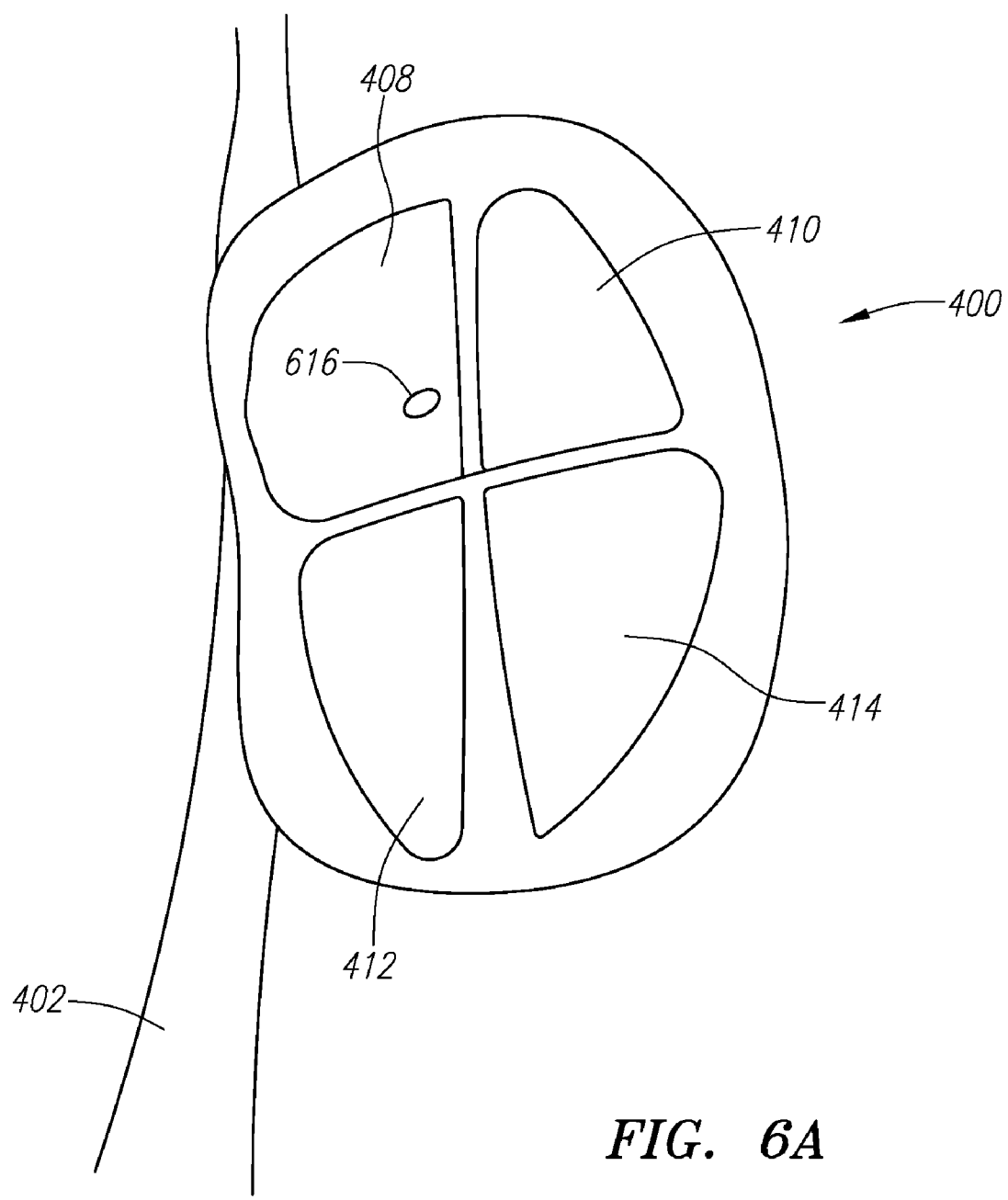
FIG. 6A through 6C respectively illustrate an instrument assembly and an ablation tool being used to address a target site related to atrioventricular nodal reentrant tachycardia.
Figure 6B:
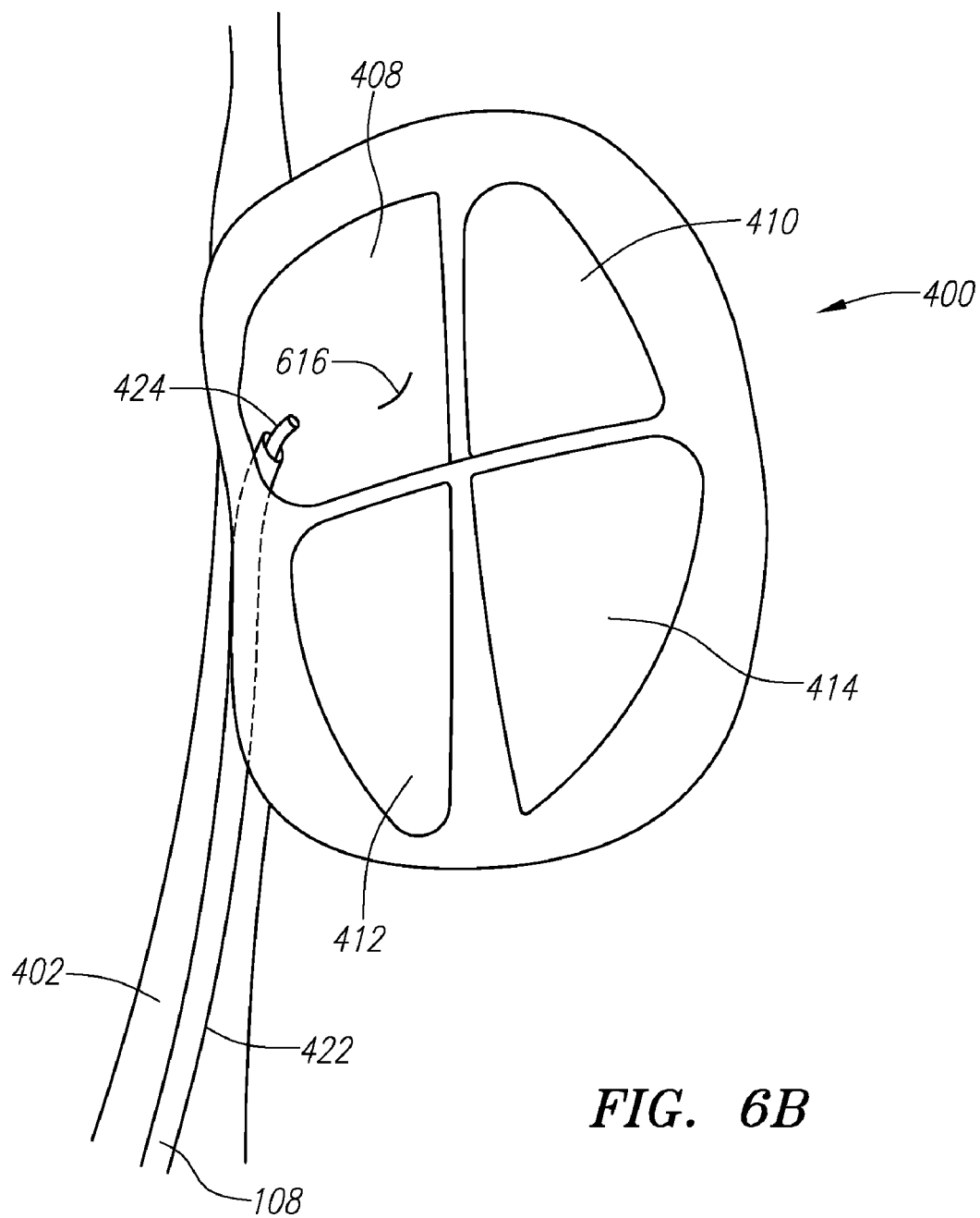
Figure 6C:
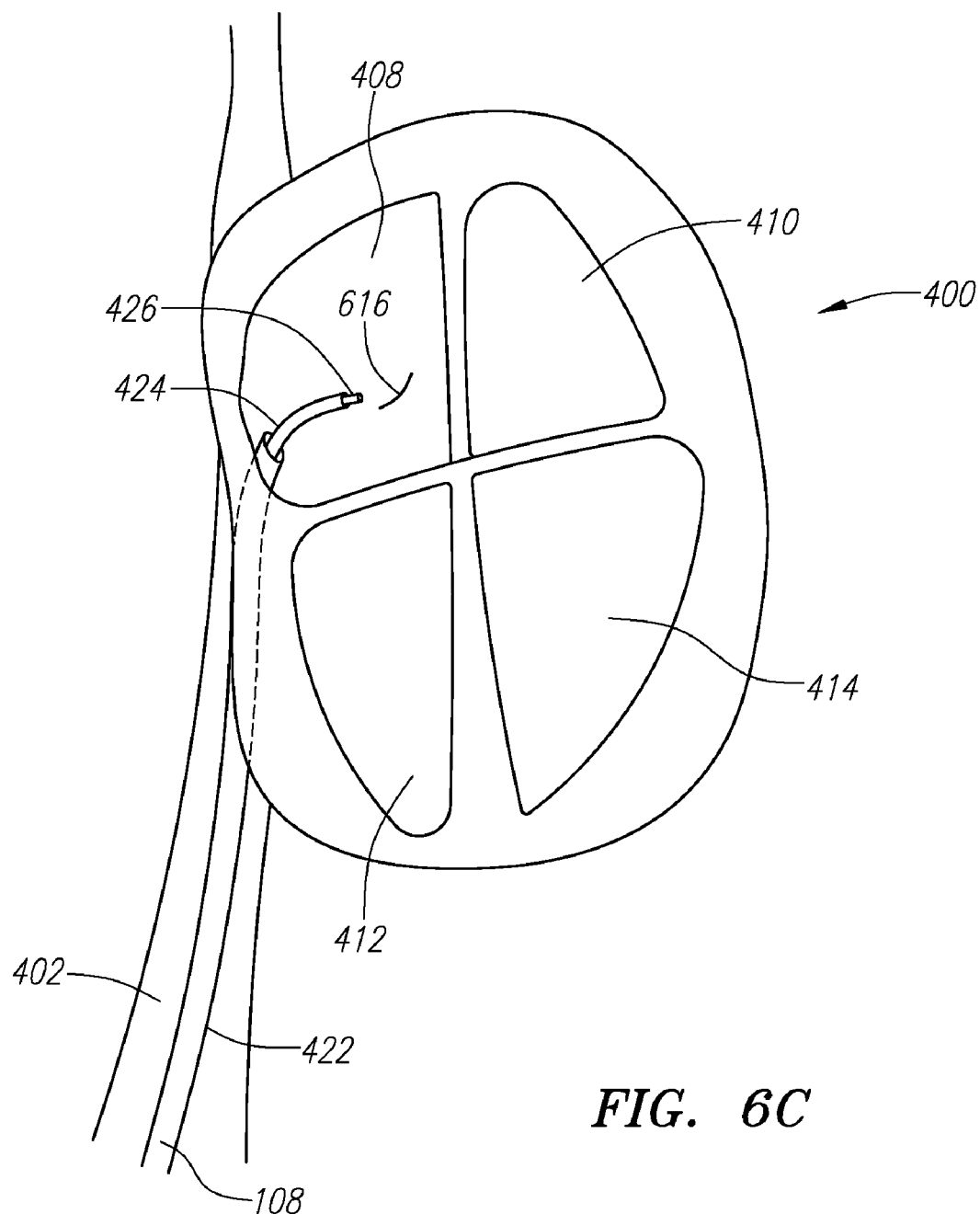

Atrioventricular Nodal Reentrant Tachycardia ("AVNRT") is a common form of arrhythmia that arises from the atria. There are two distinct pathways between the atria and ventricle, one fast and one slow. In AVNRT, the abnormal signal begins in the atria and transfers to the AV node. Instead of conducting down to the ventricle, the signal is returned to the atria. Referring to FIGS. 6A-6C, a sheath (422) and guide (424) instrument assembly (108) may be utilized, along with an ablation catheter (626) or ablation electrode (626), to create an ablation lesion (616) in the right atrium (408) to address aberrant conduction pathways causing AVNRT.

Figure 7A:
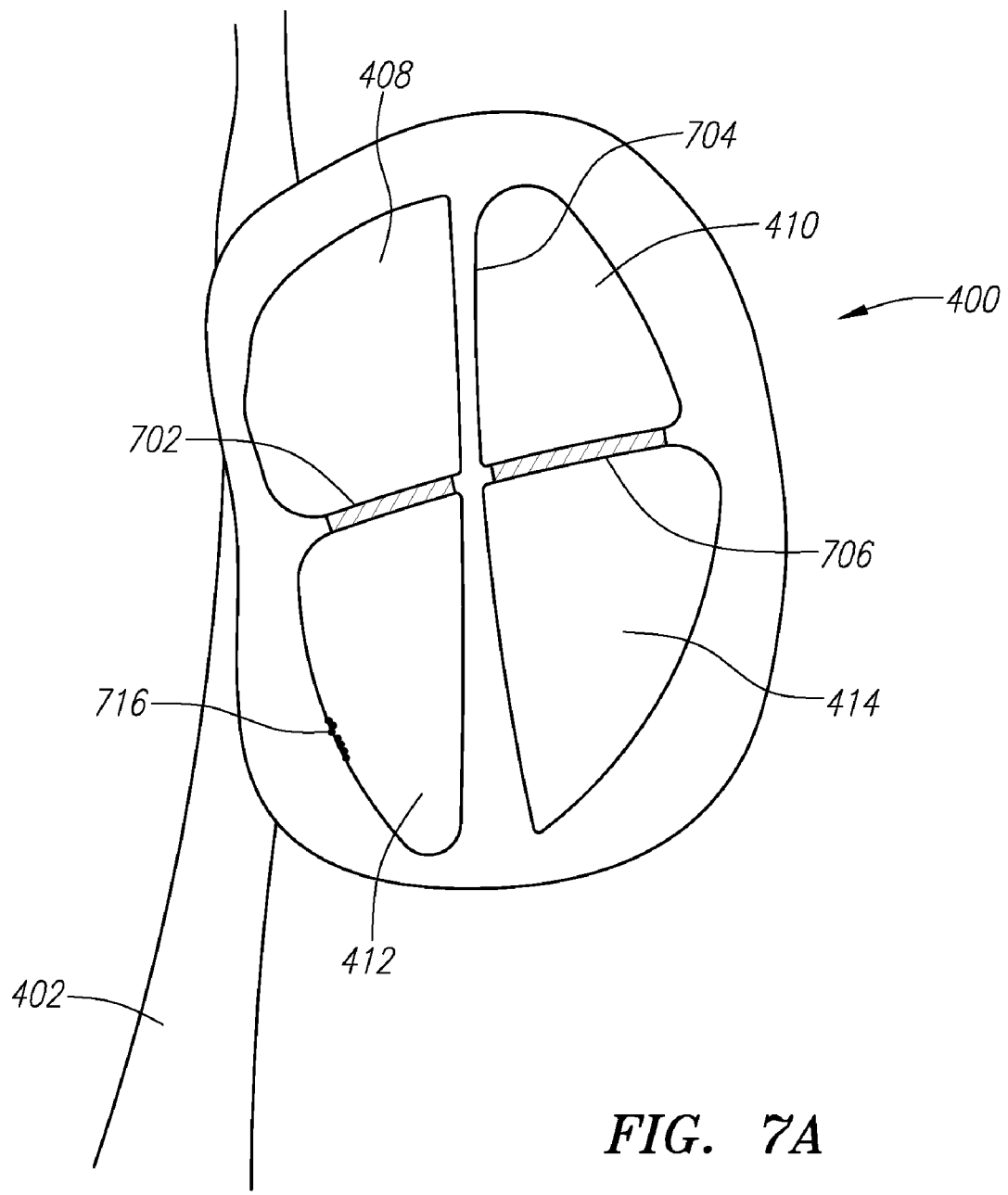
FIG. 7A through FIG. 7C respectively illustrates an instrument assembly and an ablation tool being used to address a target site related to ventricular tachycardia.
Figure 7B:
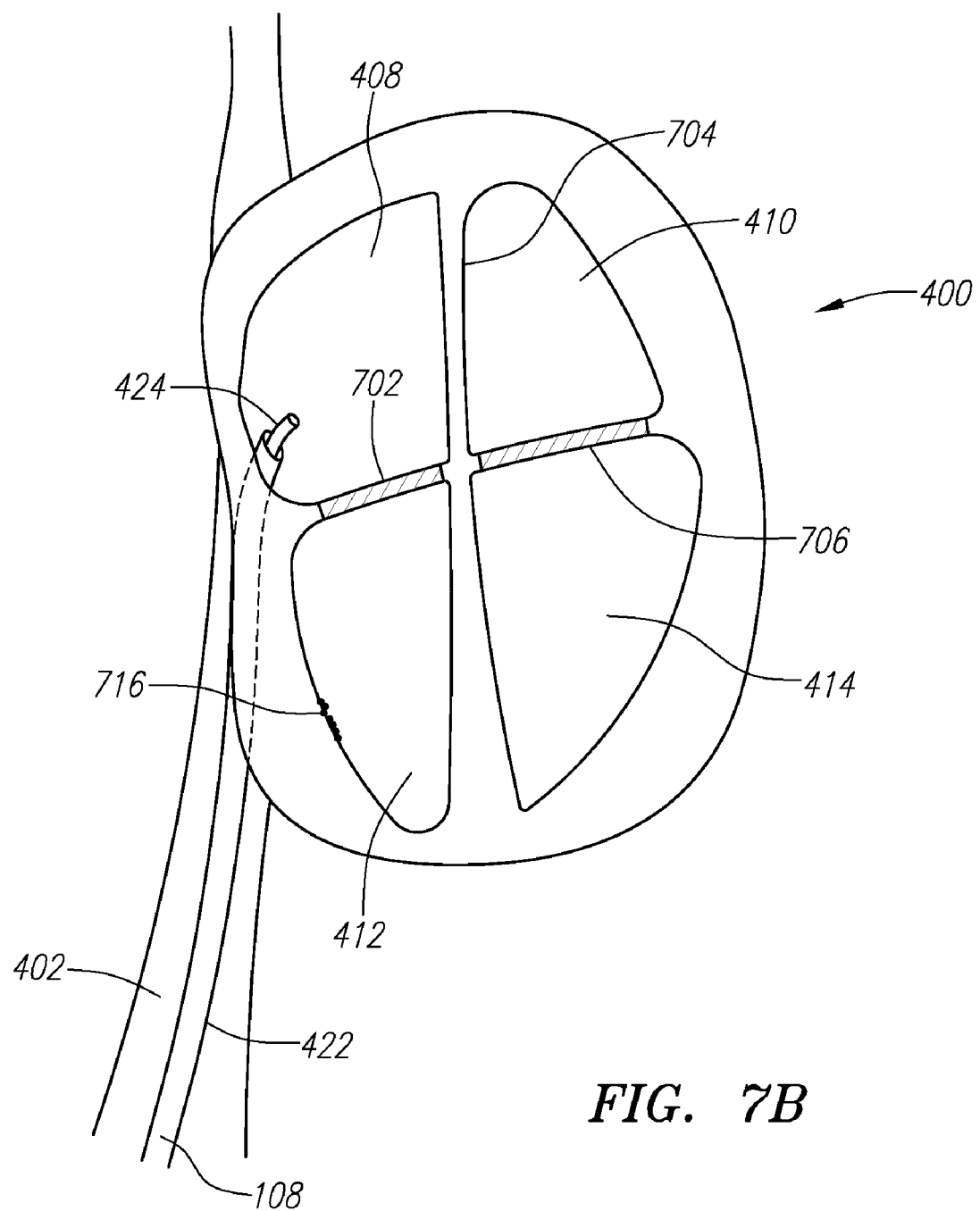
Figure 7C:
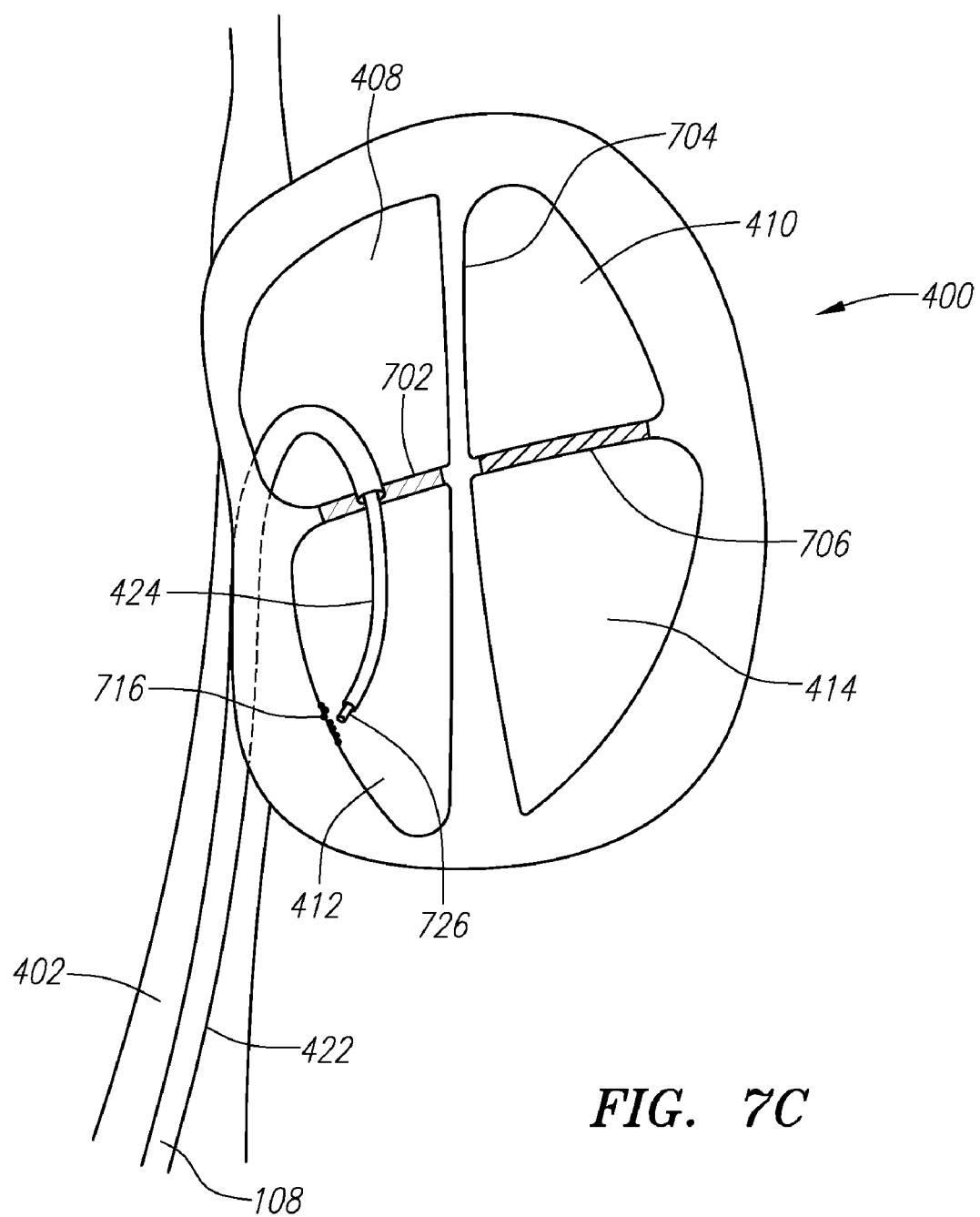
Figure 7D:
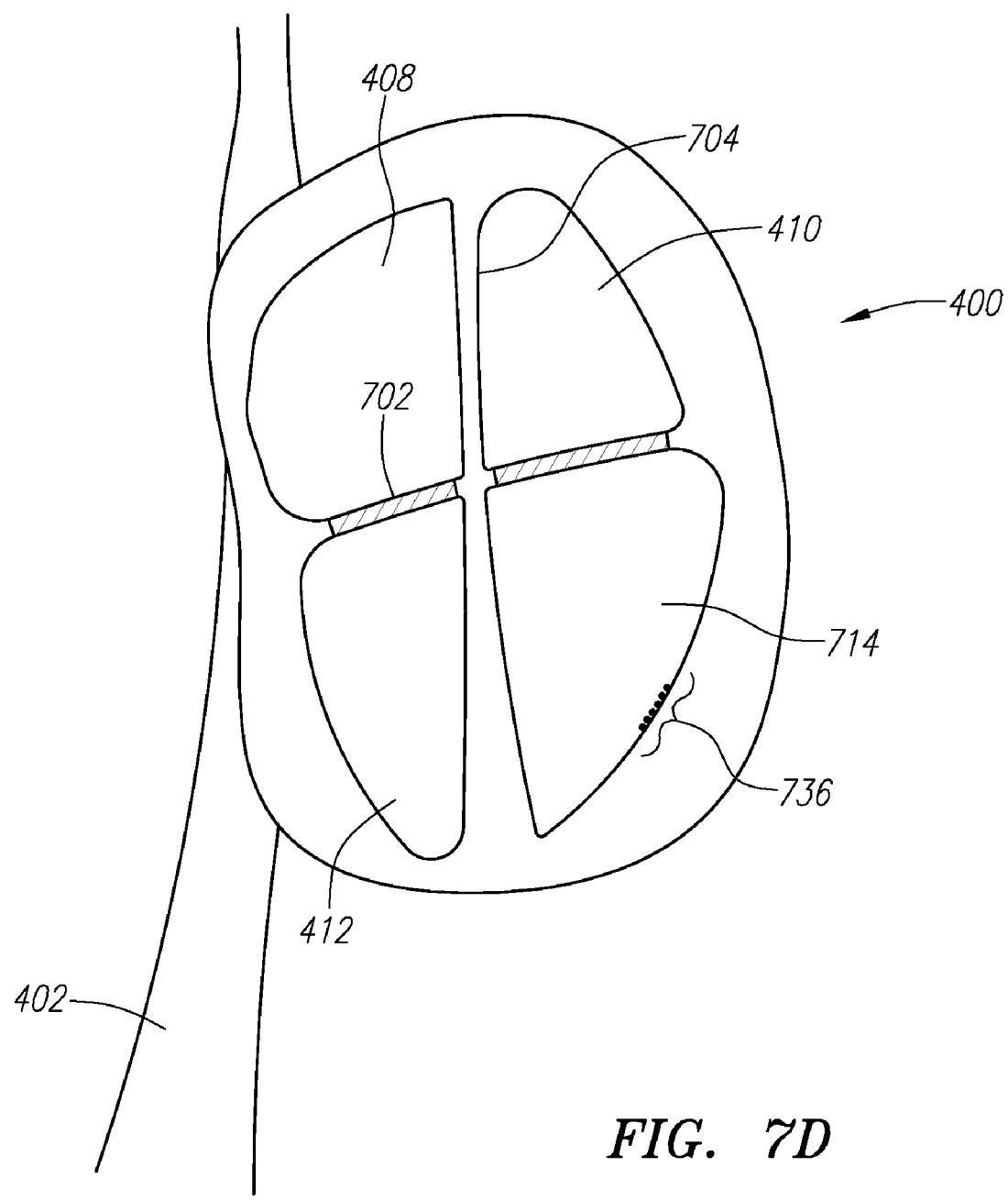
FIG. 7D through FIG. 7F respectively illustrates an instrument assembly being used to address a target site related to a left-sided ventricular tachycardia.
Figure 7E:
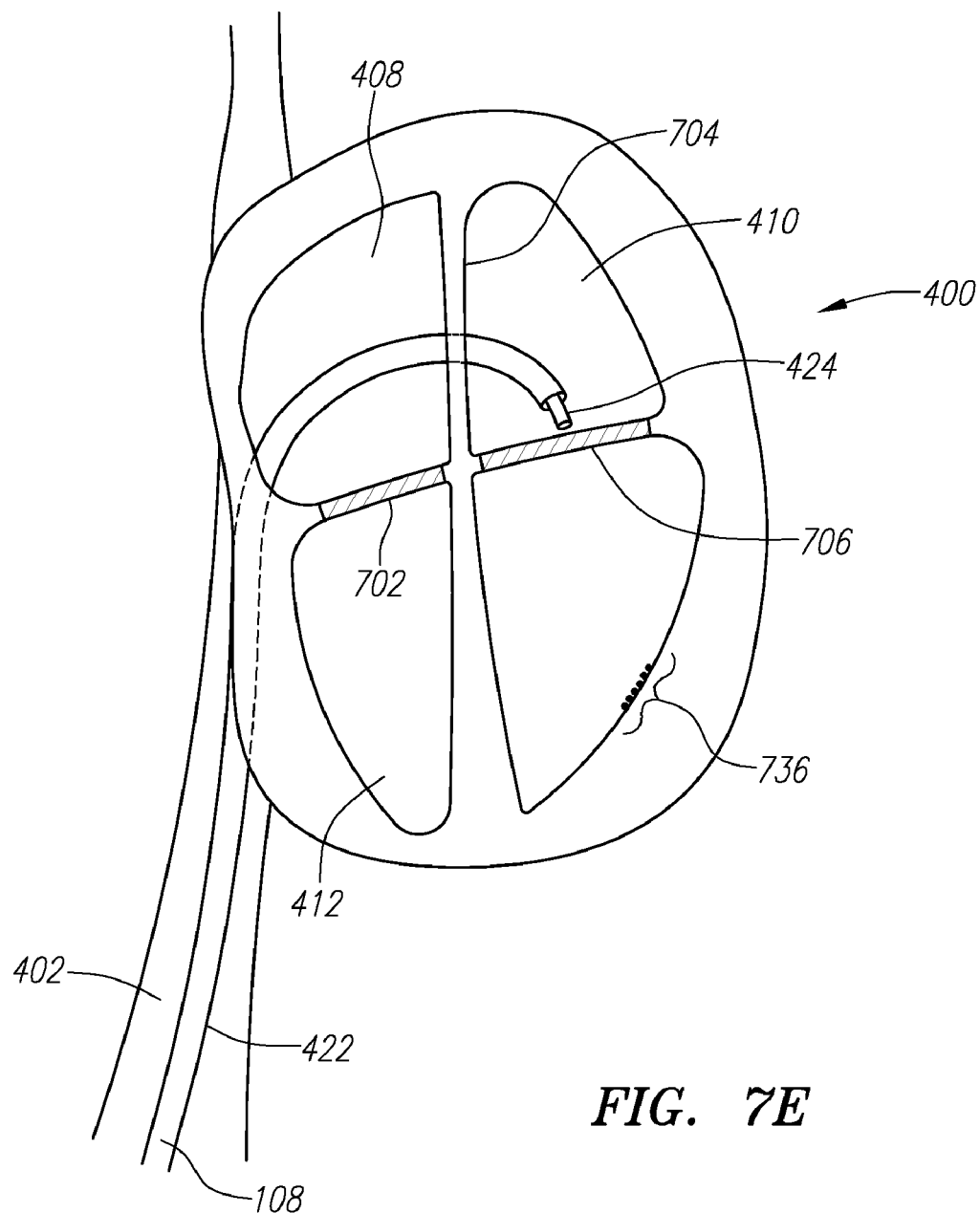
Figure 7F:
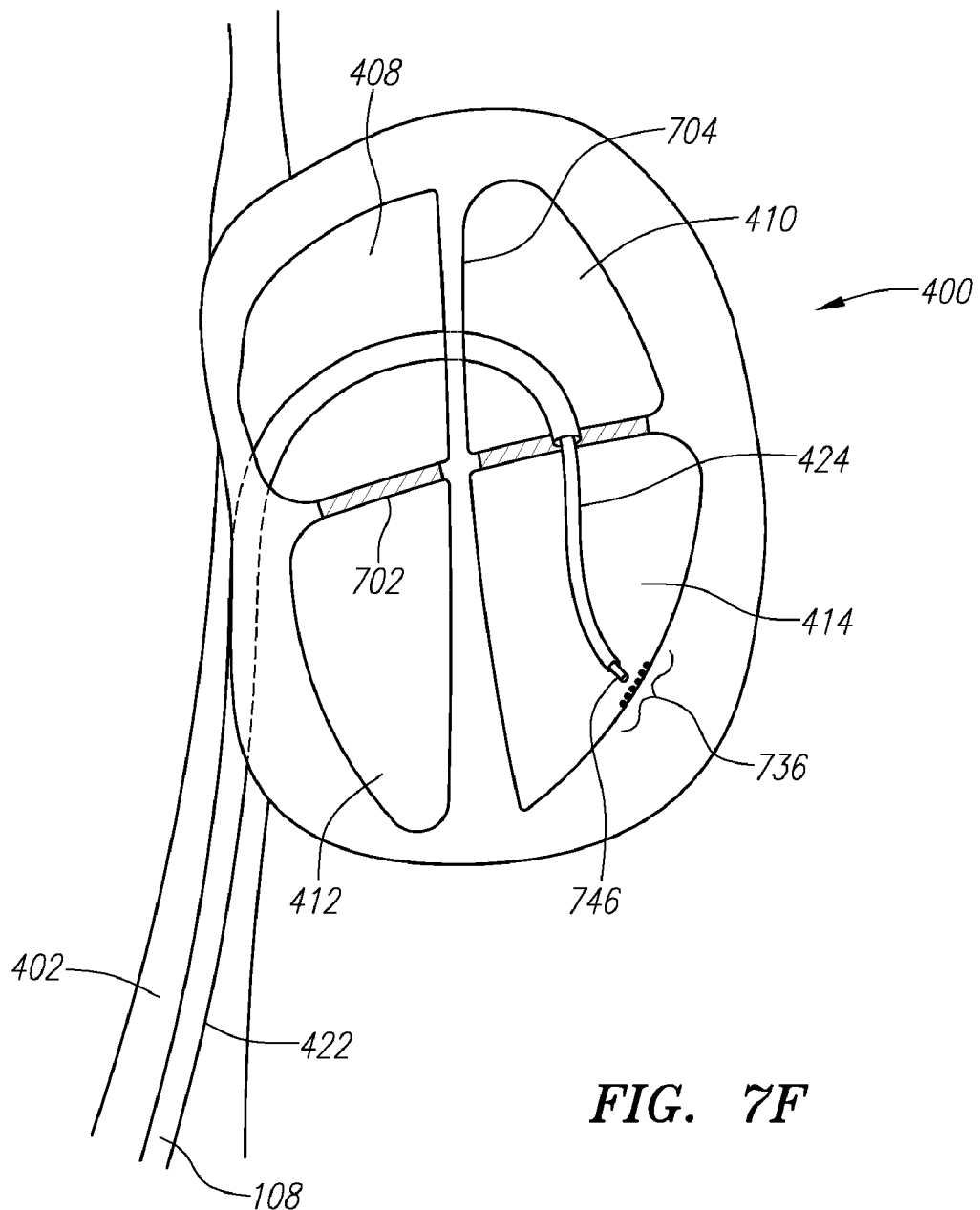
Figure 7G:
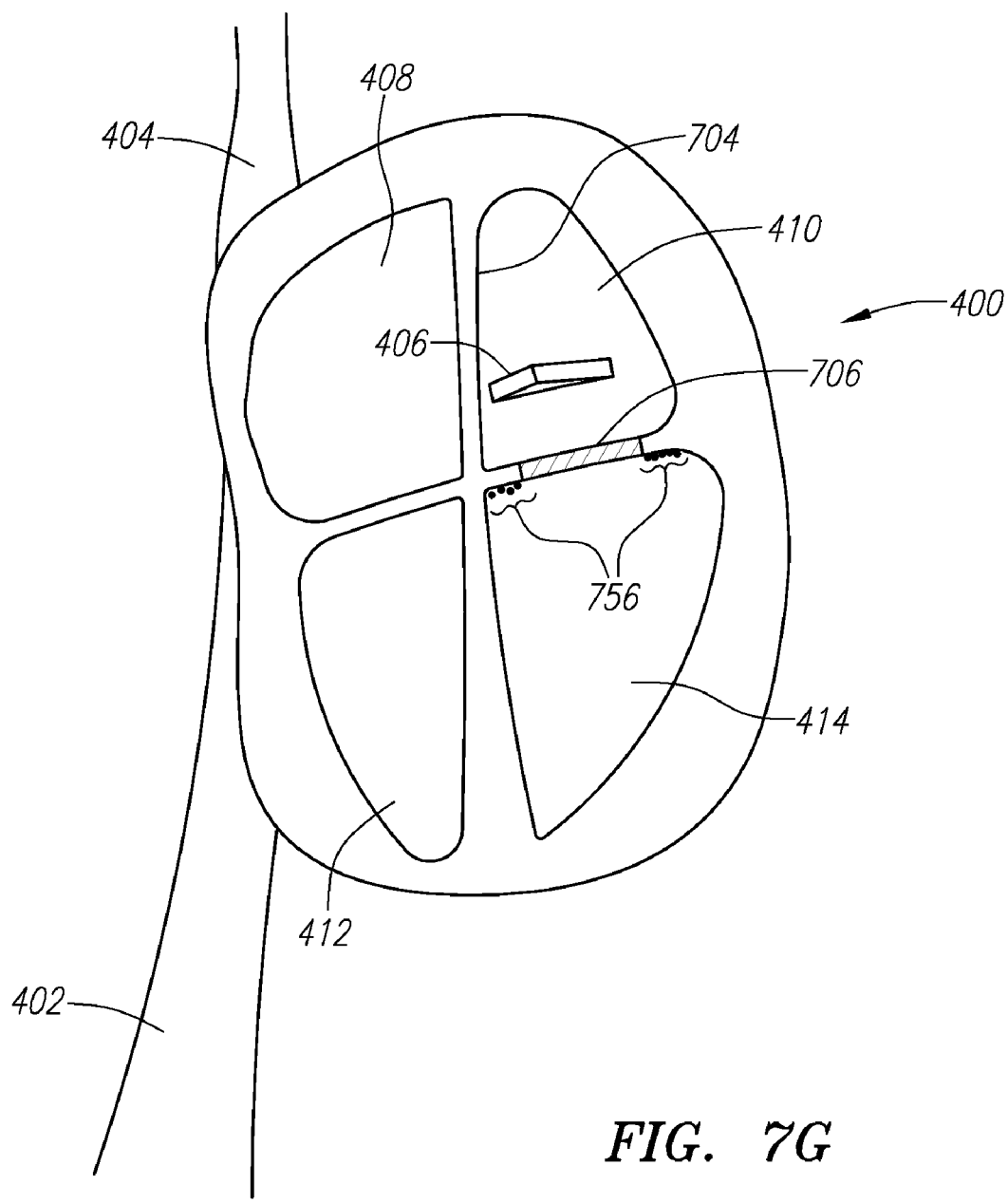
FIG. 7G through FIG. 7I respectively illustrates a retrograde approach to address a ventricular tachycardia condition.
Figure 7H:
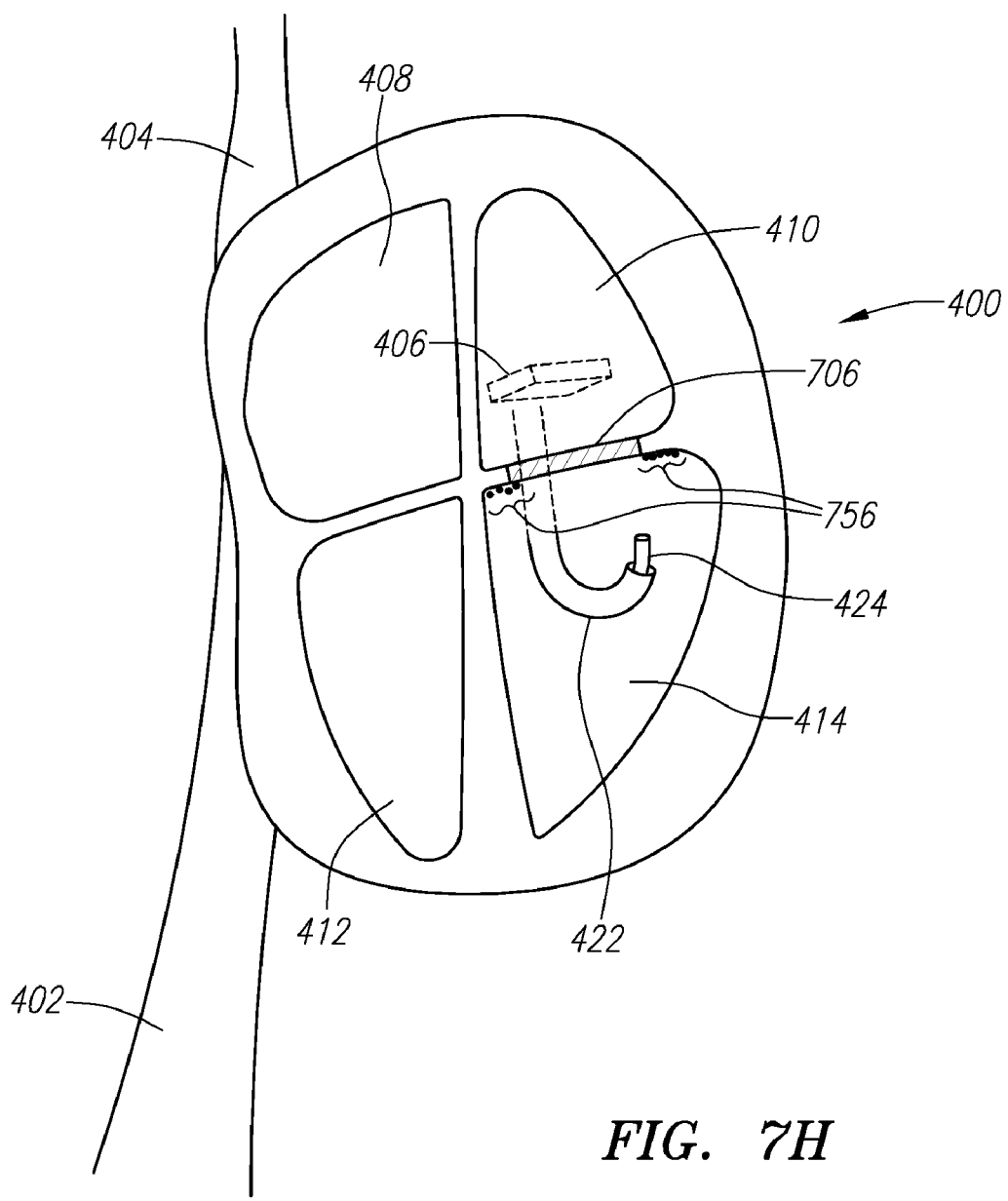
Figure 7I:
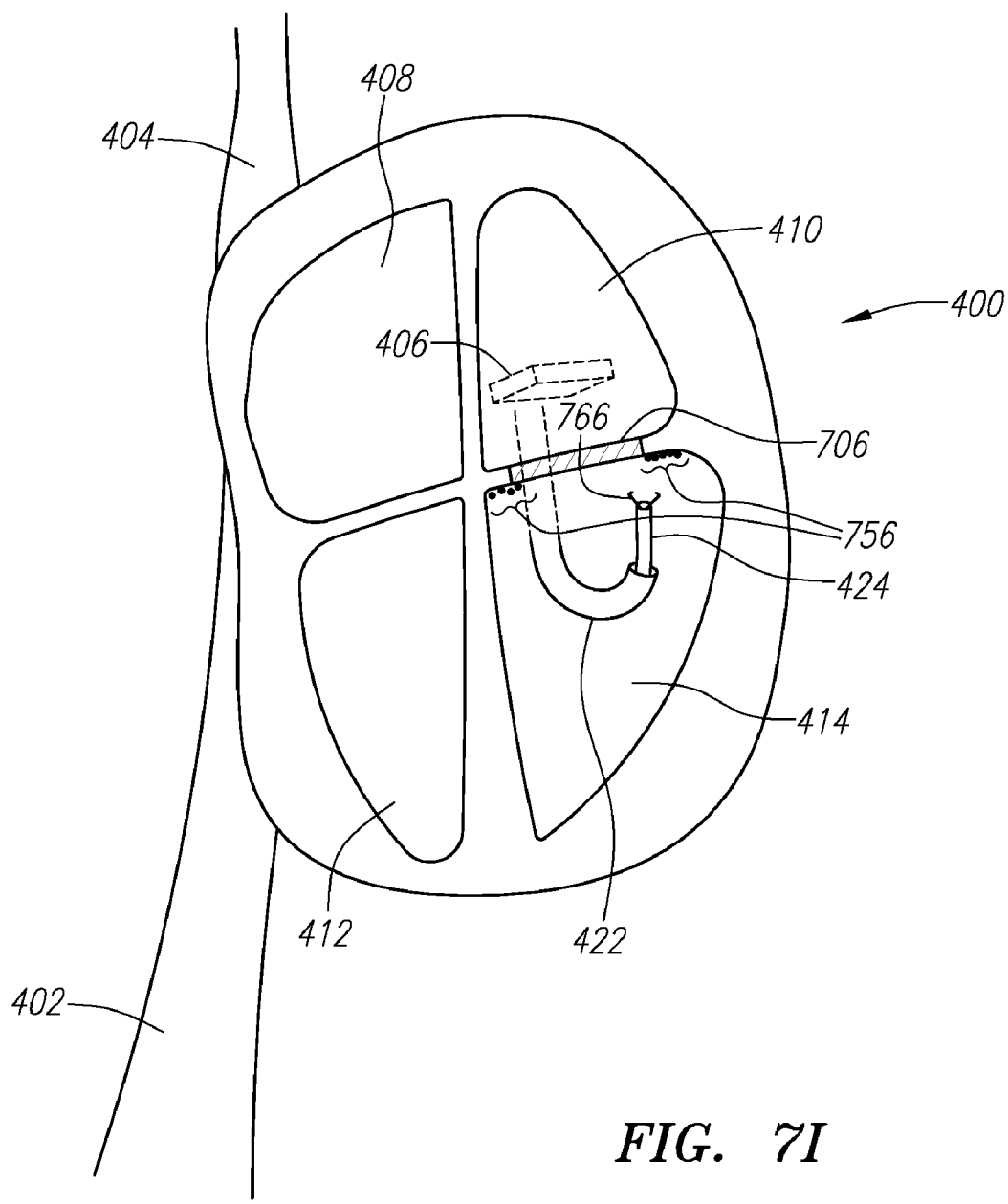

Ventricular tachycardia ("V-tach") is a condition arises from the lower chambers of the heart as the name implies. It is characterized by heart rates over 100 beats per minute, but heart rates often approach 200 beats per minute. At this rate, very little blood is actually pumped out of the heart to the brain and other organs. As such, extremely fast V-tach can be fatal. Referring to FIGS. 7A-7C, a sheath (422) and guide (424) instrument assembly (108) may be utilized, along with an ablation catheter (726) or ablation electrode (726), to create an ablation lesion (716) in, for example, the right ventricle (412), to address aberrant conduction pathways causing right-sided V-tach. To reach the targeted lesion location, the sheath (422) may be positioned adjacent the tricuspid valve (702), and the guide (424) may be navigated across the tricuspid valve (702) to deliver the ablation electrode (726) against the targeted tissue, as depicted in FIG. 7C. FIGS. 7D-7F depict a similar instrument configuration (108) is utilized to address a left-sided V-tach scenario by navigating across the septum (704), by way of a transseptal puncture, into the left atrium (410), and down through the mitral valve (706) into the left ventricle (414) and to the targeted left ventricular tissue lesion (736) where an ablation lesion may be created to prevent aberrant conduction related to V-tach. FIGS. 7G-7I depict a retrograde approach, through the aorta (404), across the aortic valve (406), and into the left ventricle (414), subsequent to which the sheath instrument (422) may be utilized to direct the guide instrument (424) and ablation tool (766) up toward the inferior mitral annulus region (756) where ablation lesions may be created to address a V-tach scenario.

A patent foramen ovale ("PFO") is an abnormal opening in the arterial septum which results in shunting of blood between the atrial chambers. PFOs are believed to be present in as many as 20% of the adult population and there is strong evidence that PFOs are responsible for the occurrence of a type of stroke, known as cryptogenic stroke, which occurs as a result of a blood clot in an otherwise healthy individual. Additionally, there is increasing evidence that the presence of a PFO is in some way related to the occurrence of migraine headache with aura in certain patients. Historically, PFOs have been treated with surgery, where the defect is sewn shut with direct suturing. Although this works well to close the defect, it requires open heart surgery and is very traumatic, which requires significant post-operative recovery. More recently, PFOs have been closed successfully with prosthetic patches that are delivered via a catheter based procedure. These procedures offer a minimally invasive approach, but require that the clinician leave prosthesis inside the heart to cover and occlude the PFO defect. The presence of foreign material inside the heart can lead to significant complications including infection, thrombus formation leading to stroke, development of cardiac arrhythmias, and dislodgment or migration of prosthesis that might necessitate surgical removal of the devices.

Figure 8A:
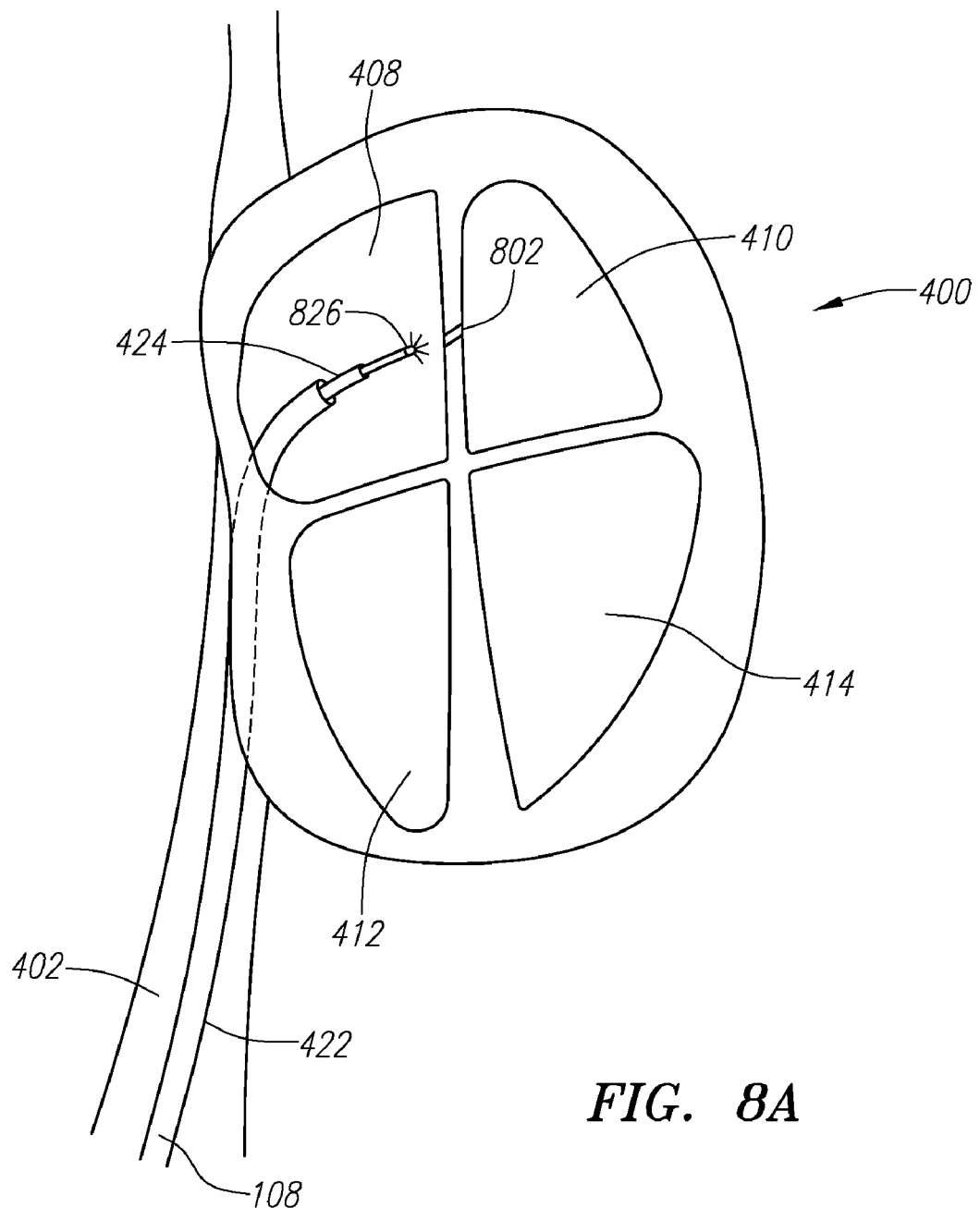
FIG. 8A illustrates an instrument assembly being used to treat a patent foramen ovale condition.
Figure 8B:
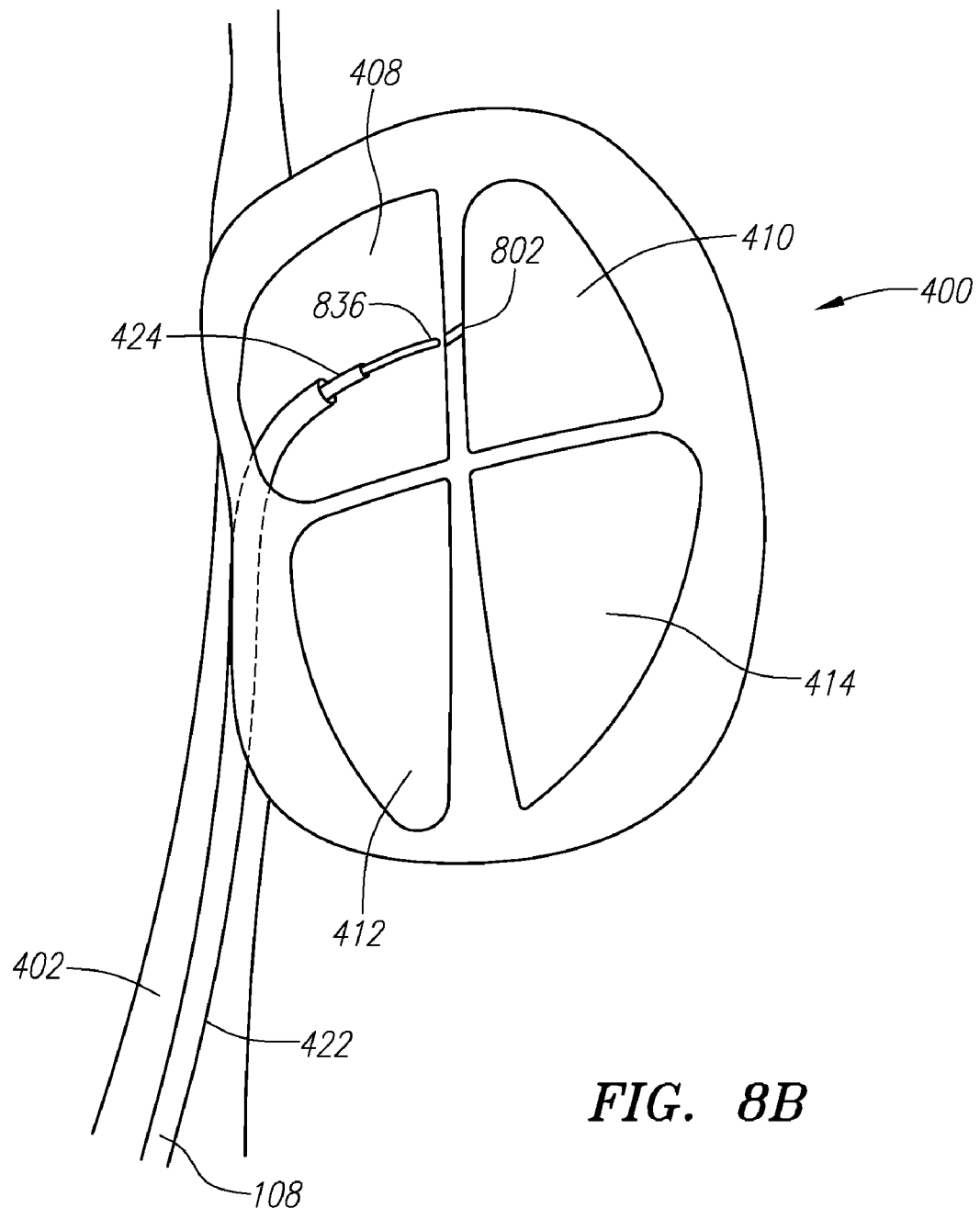
FIG. 8B illustrates an instrument assembly with an ablation tool being used to treat a patent foramen ovale condition.
Figure 8C:
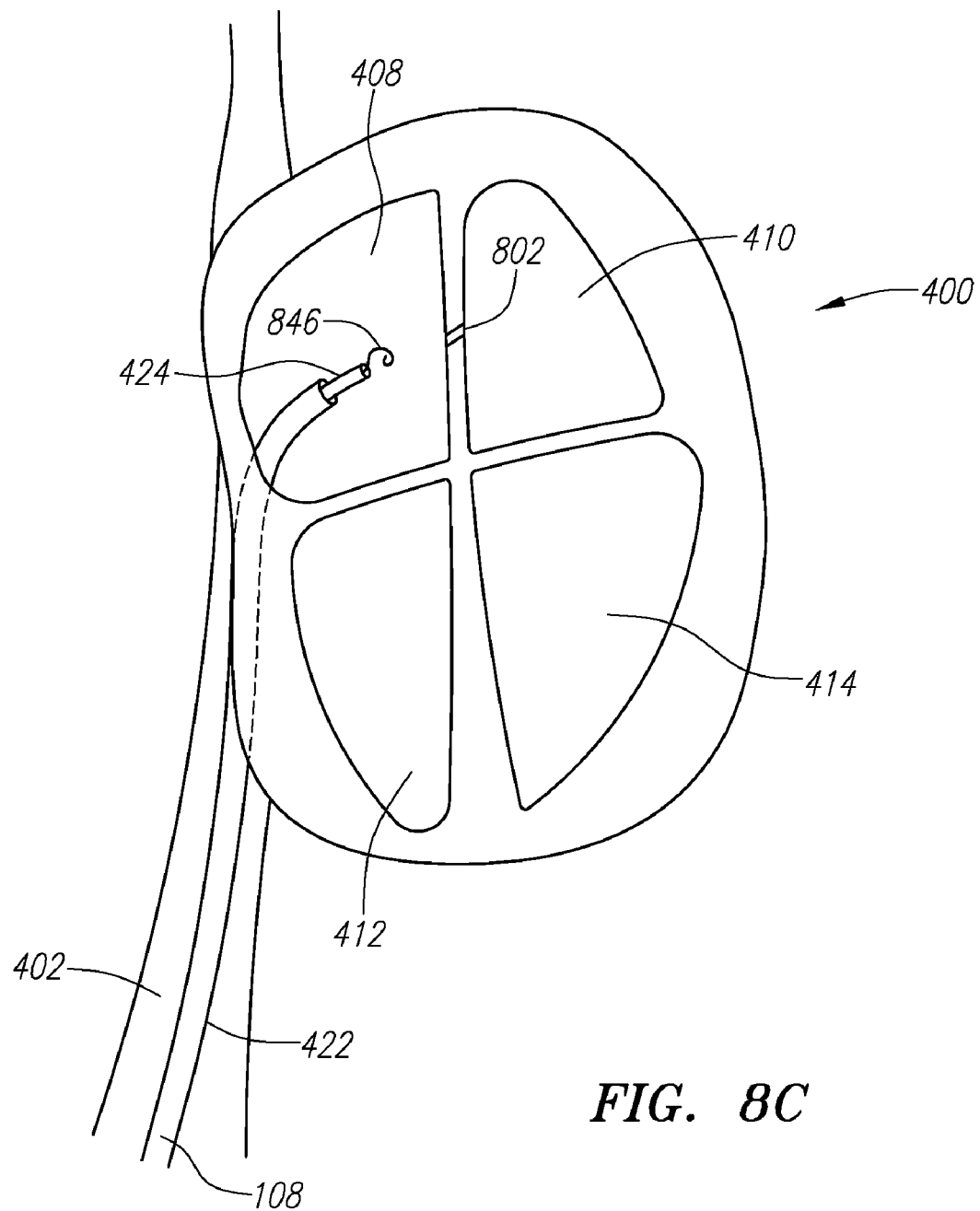
FIG. 8C and FIG. 8D respectively illustrates an instrument assembly with a suturing tool being used to treat a patent foramen ovale condition.
Figure 8D:
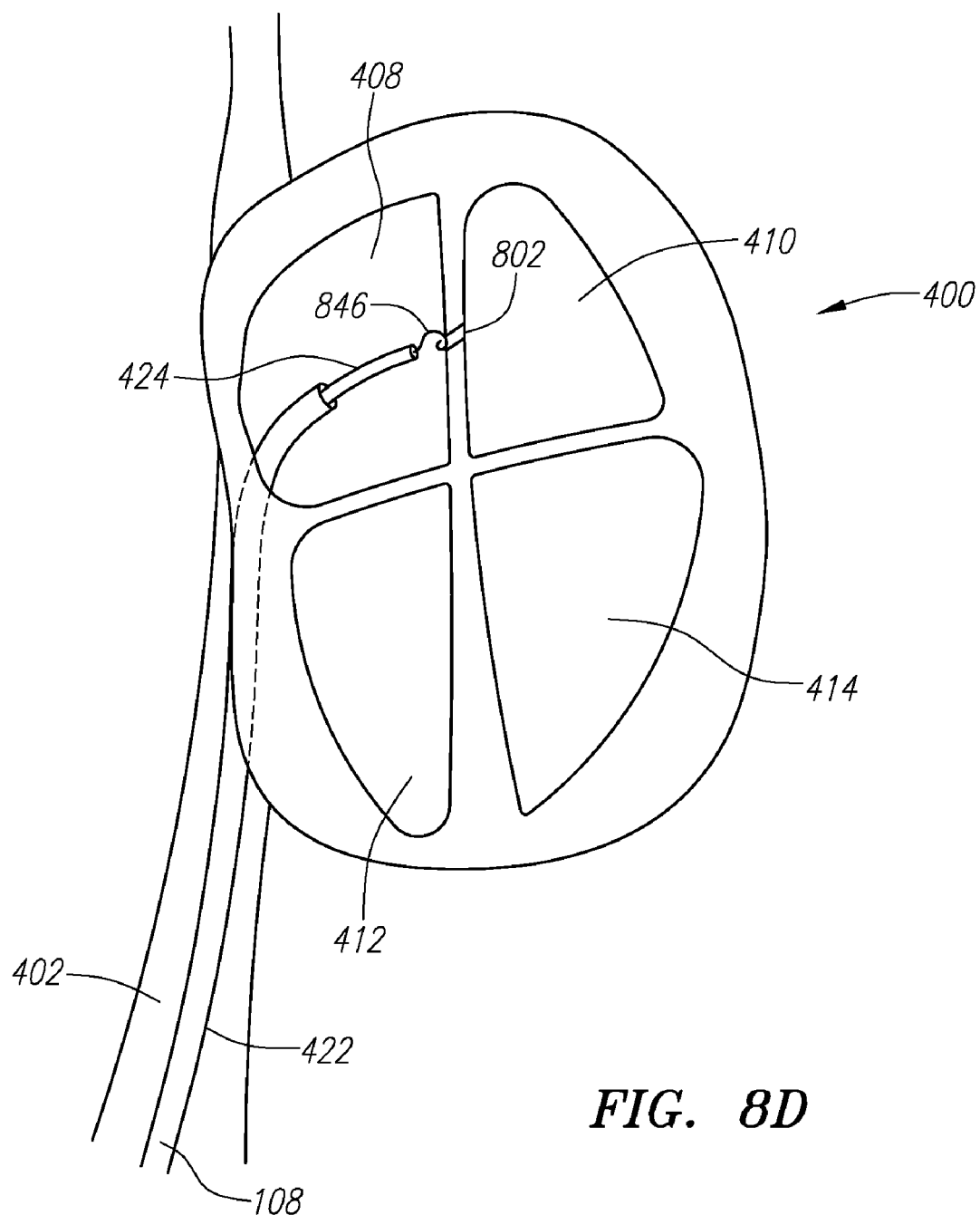
Figure 8E:
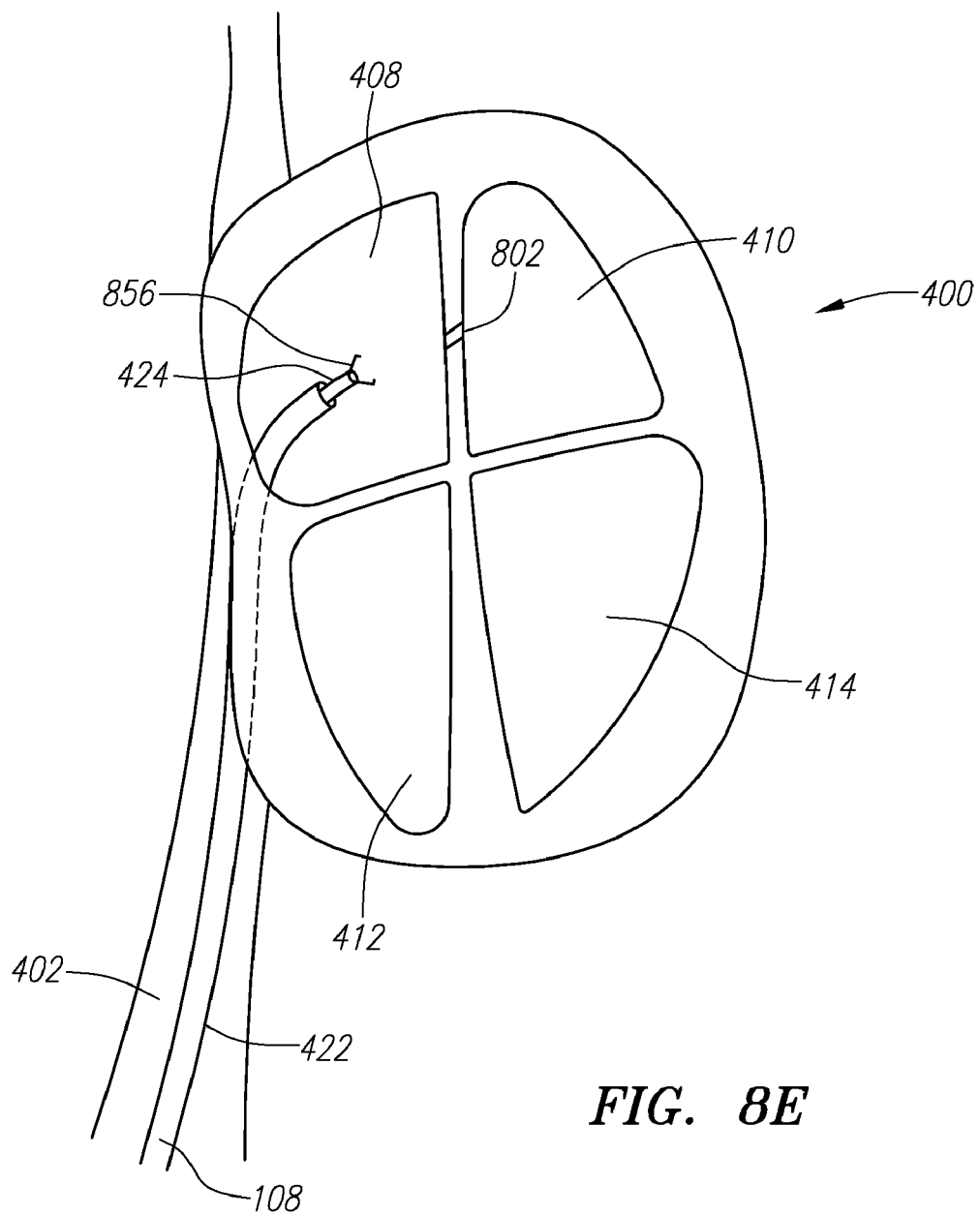
FIG. 8E and FIG. 8F respectively illustrates an instrument assembly with a clip application tool being used to treat a patent foramen ovale condition.
Figure 8F:
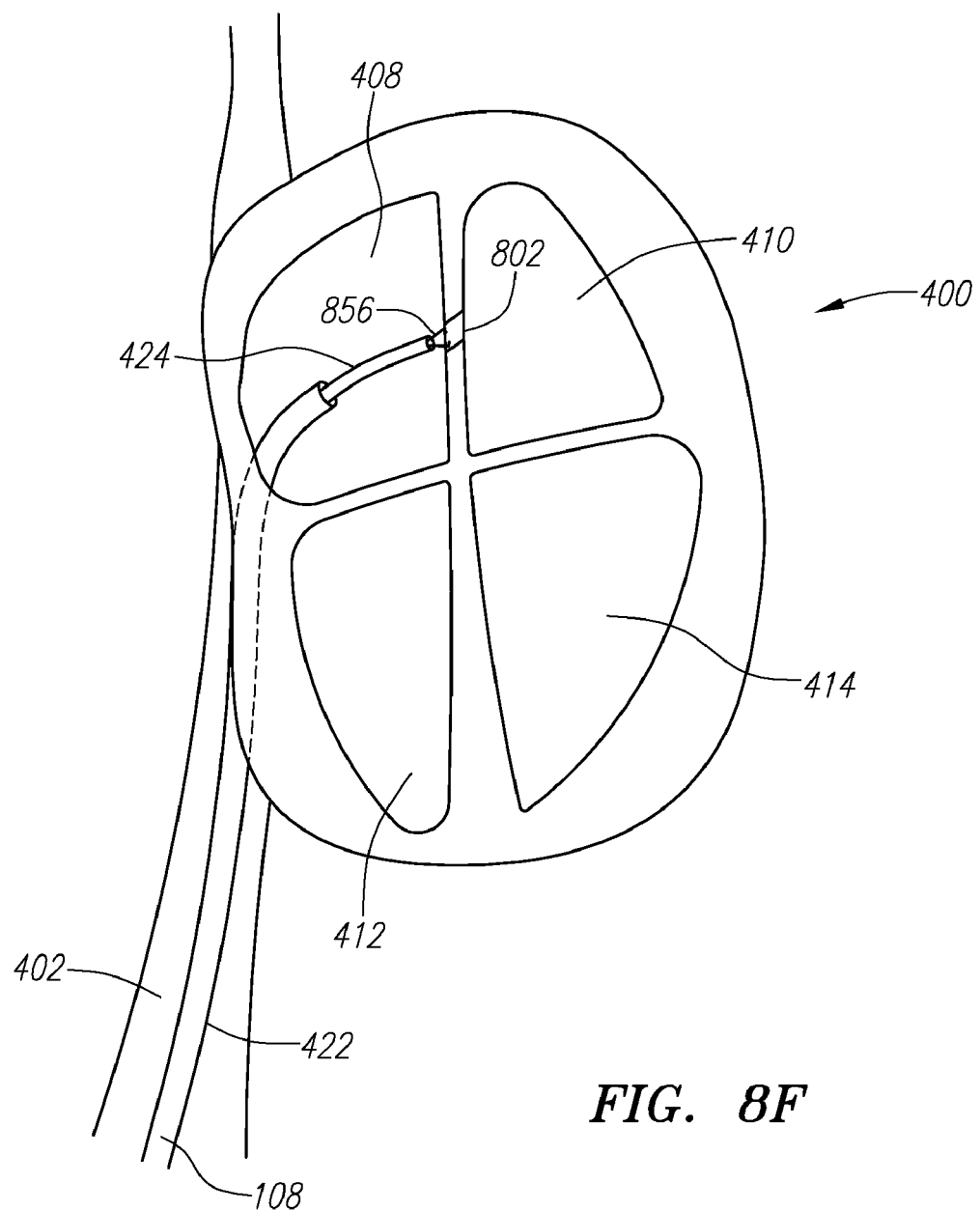
Figure 8G:
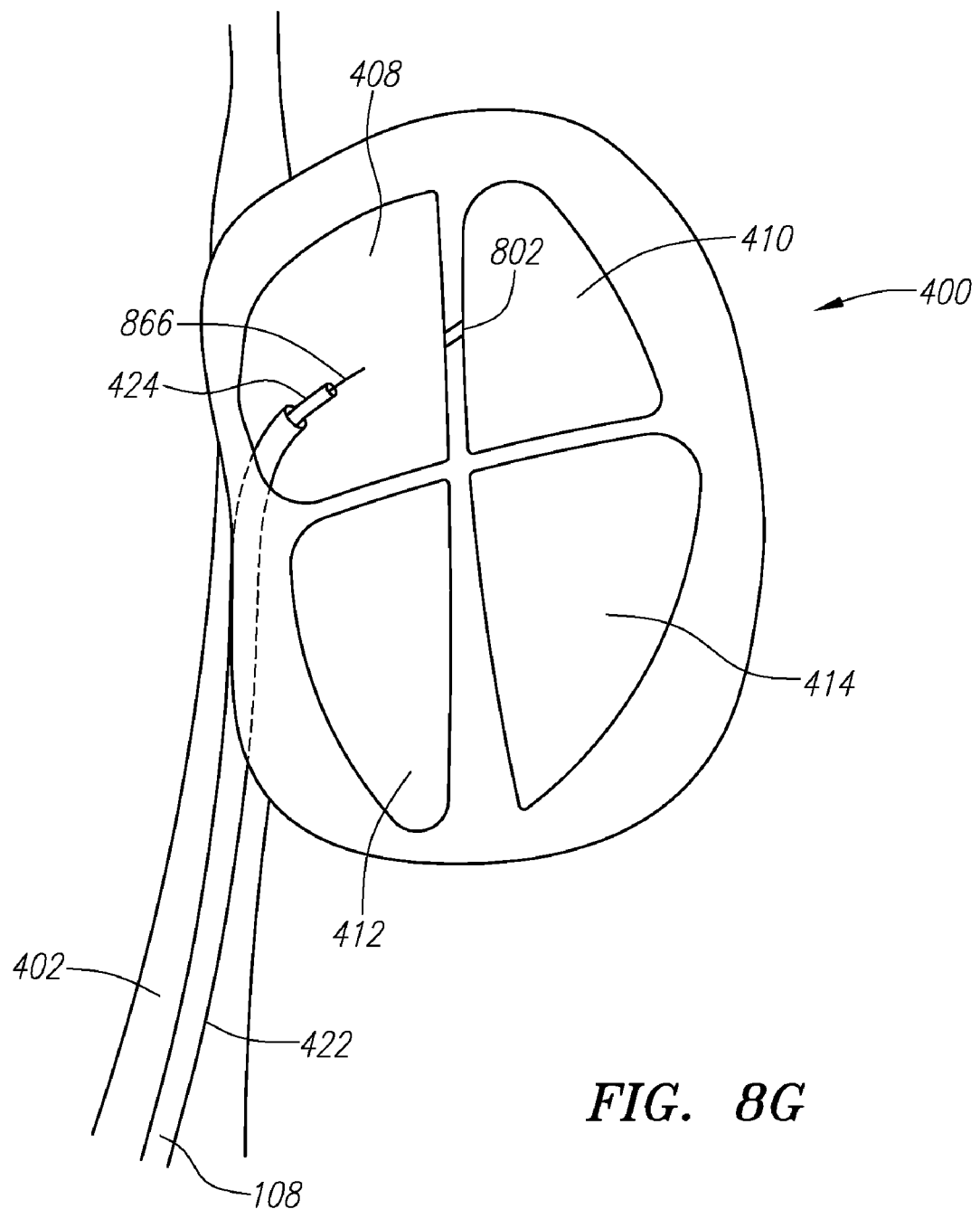
FIG. 8G and FIG. 8H respectively illustrates an instrument assembly with a needle instrument being used to treat a patent foramen ovale condition.
Figure 8H:
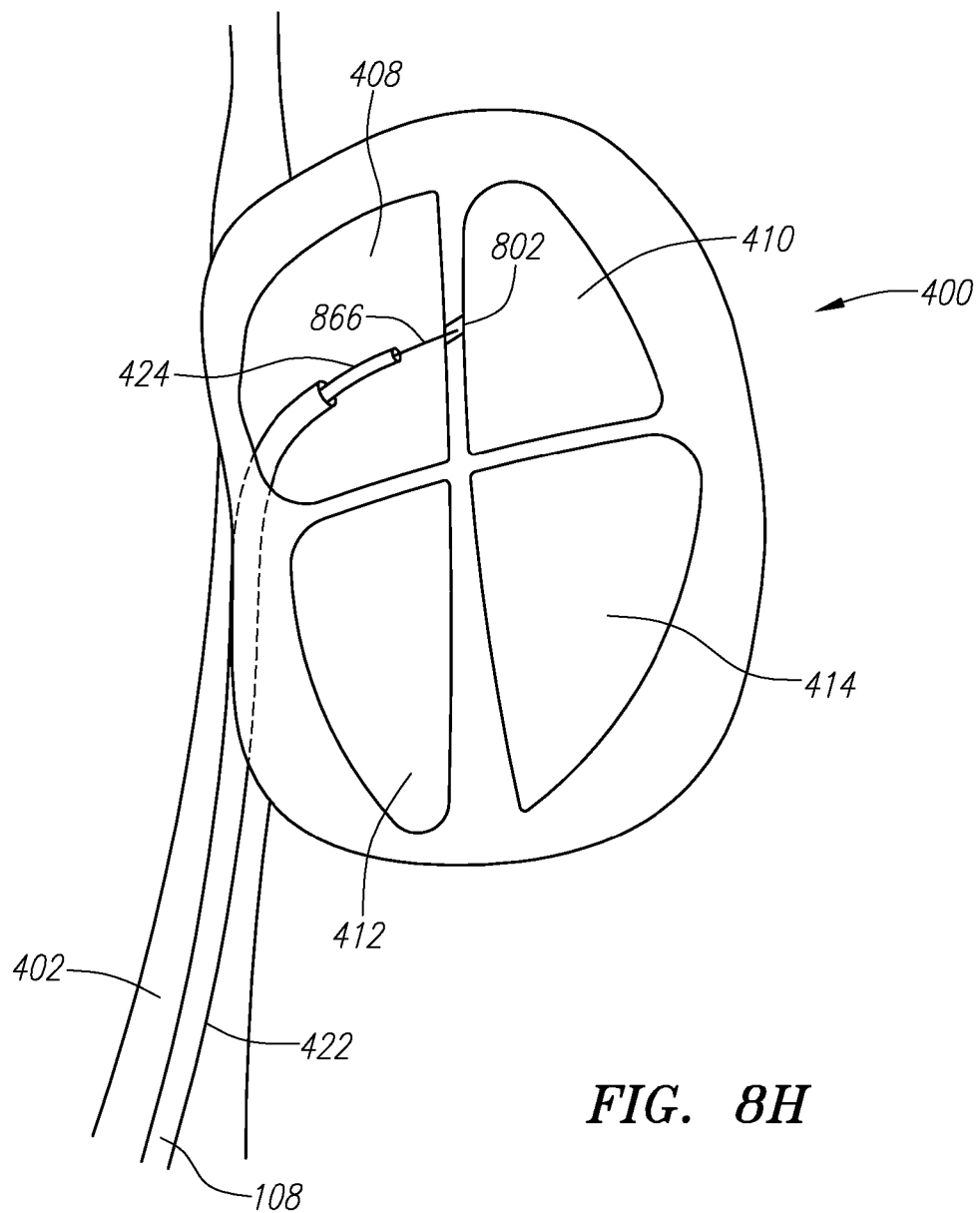
Figure 8I:
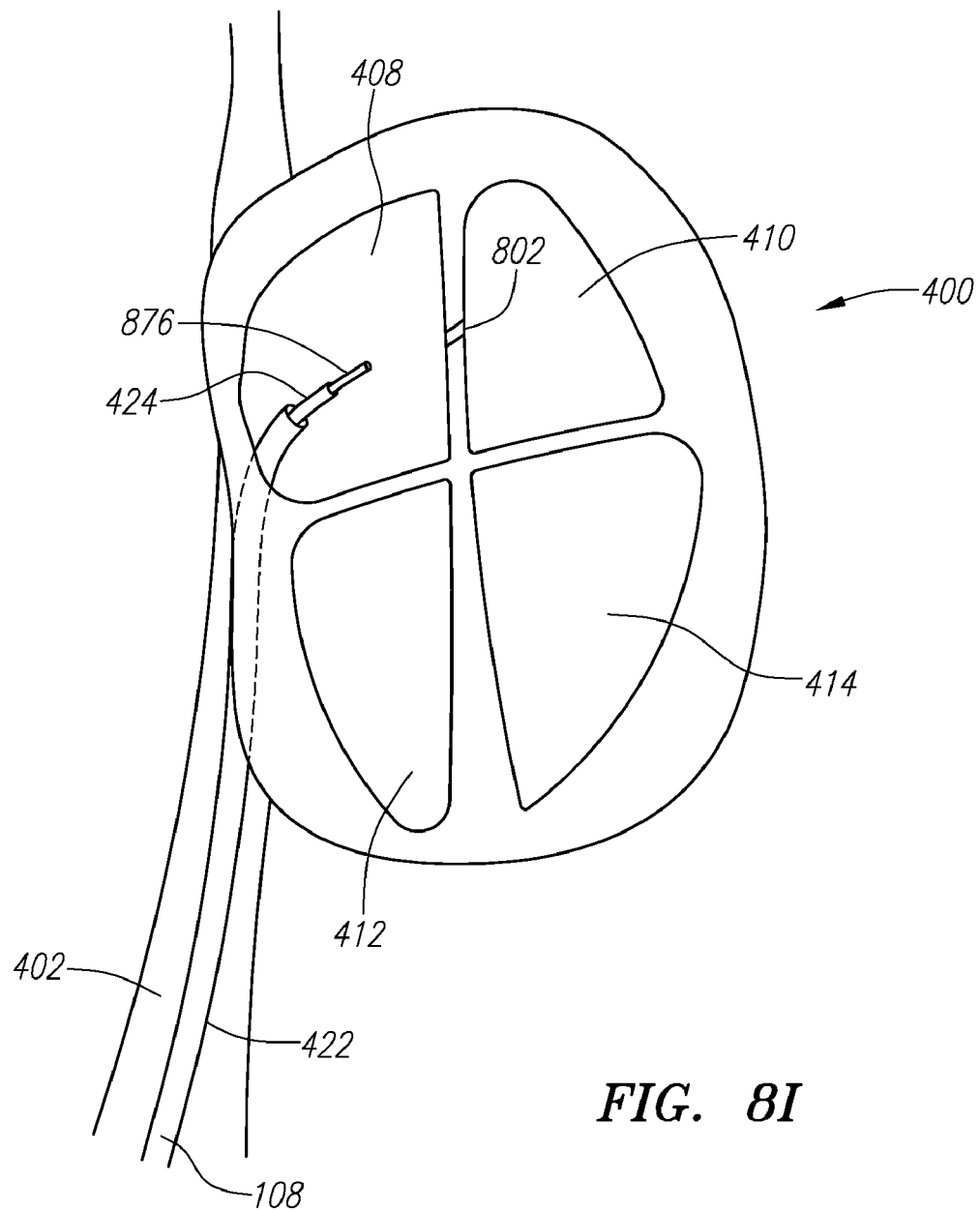
FIG. 8I and FIG. 8J respectively illustrates an instrument assembly with an irritation tool being used to treat a patent foramen ovale condition.
Figure 8J:
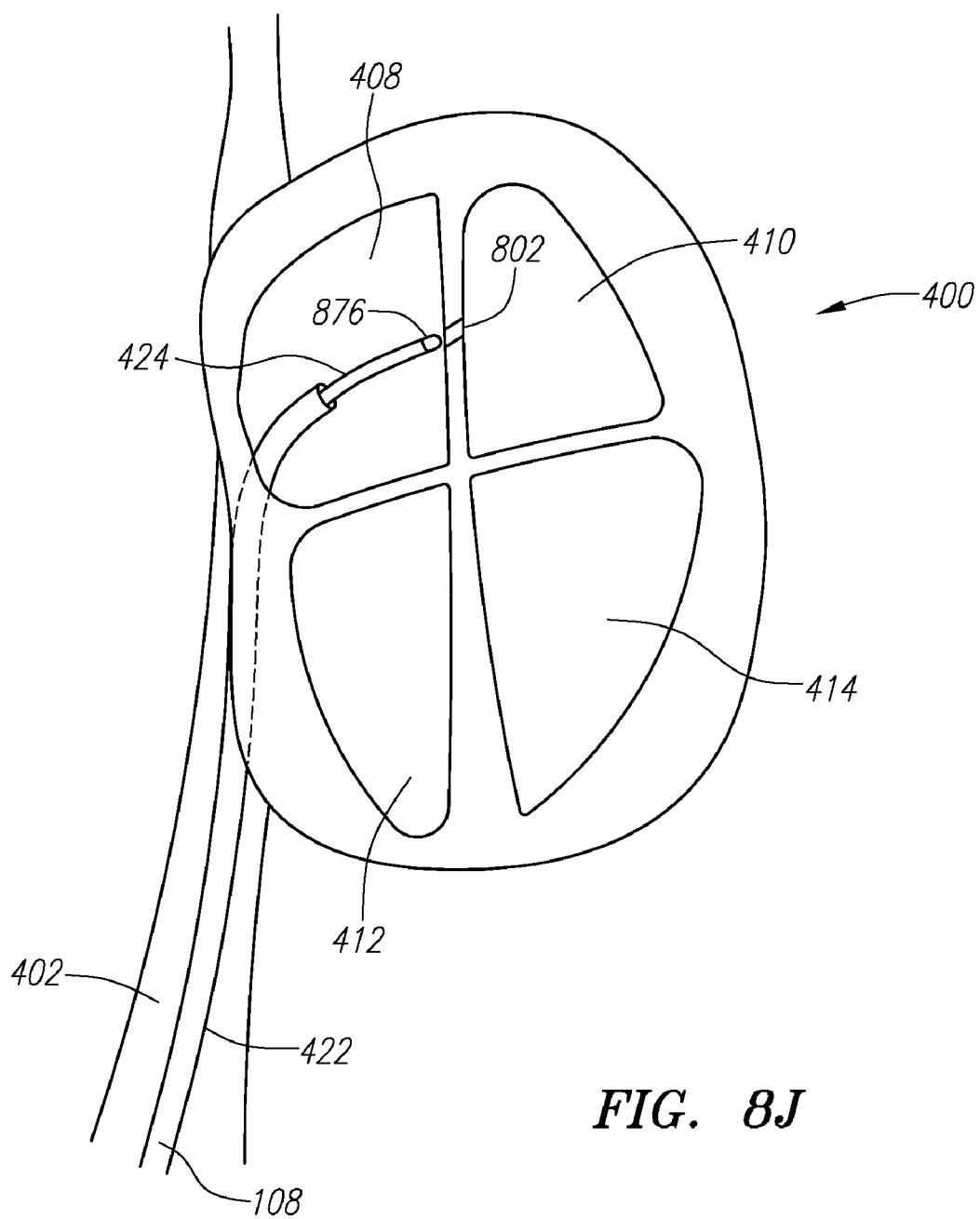

Referring to FIG. 8A, a sheath (422) and guide (424) instrument assembly (108) may be utilized to direct a laser fiber (826) to the location of a PFO (802) and use laser energy to ablate or "weld" the PFO (802) shut with a concomitant inflammation reaction. Referring to FIG. 8B, an ablation tool (836) is threaded through the working lumen of an instrument assembly (422, 424, 108) may be similarly used to tack a PFO (802) shut and induce a localized healing response. Referring to FIGS. 8C and 8D, a suturing tool (846) may be utilized to suture a PFO (802) shut. Referring to FIGS. 8E and 8F, a clip applying tool (856) may be utilized to clip a PFO (802) into a shut position. Referring to FIGS. 8G and 8H, a needle tool (866) advanced through the working lumen of a sheath (422) and guide (424) which are subsystems of the instrument assembly (108) may be utilized to irritate the tissue surrounding and/or forming the PFO (802), via full or partial thickness insertions of the needle (866) into the subject tissue, to induce a healing response sufficient to "scar" the PFO (802) shut. Referring to FIGS. 8I and 8J, an irritation tool (876) may be utilized to contact-irritate the subject tissue and induce a subsequent scarring shut of the PFO (802).

Figure 9A:
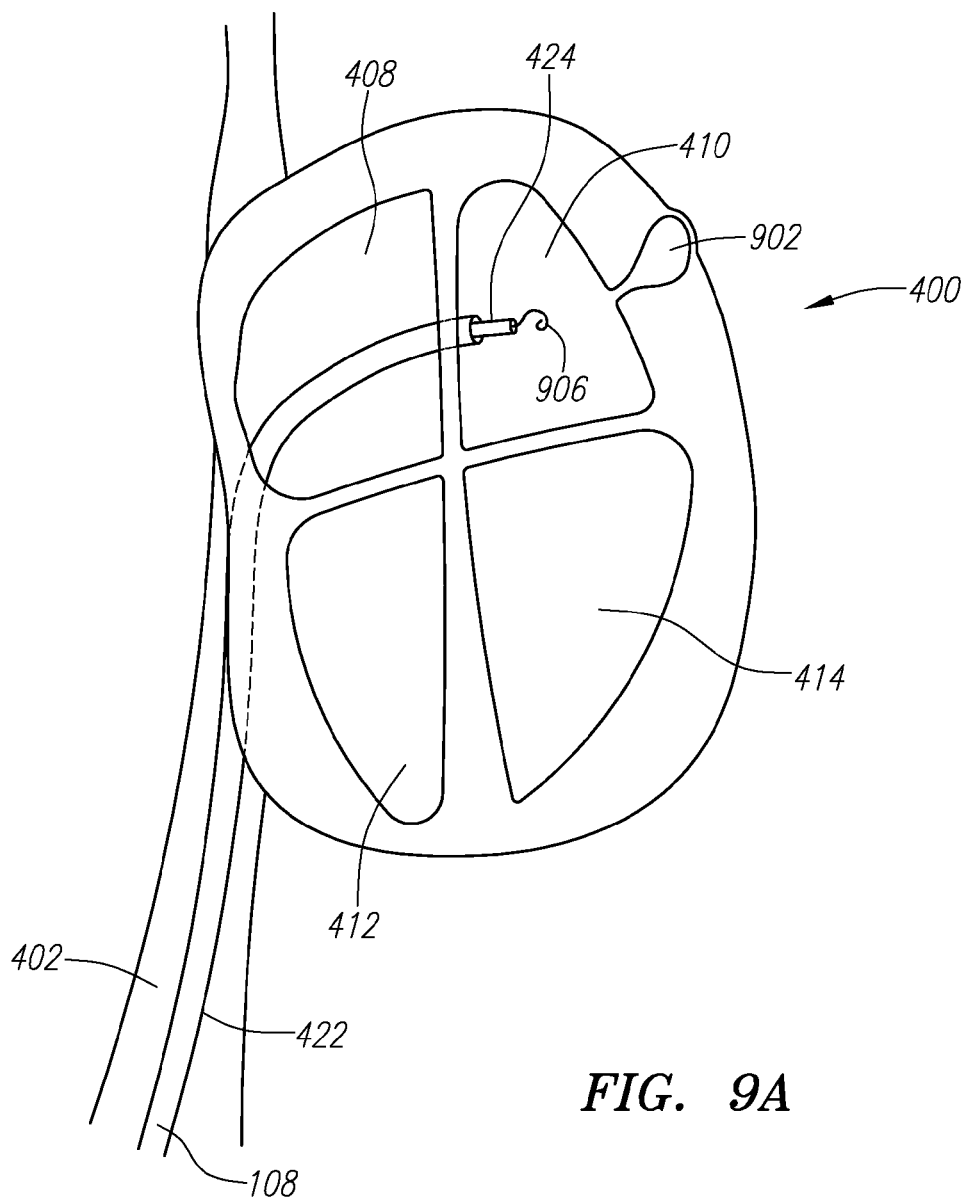
FIG. 9A and FIG. 9B respectively illustrates an instrument assembly with a suturing tool being used to treat a left atrial appendage occlusion condition.
Figure 9B:
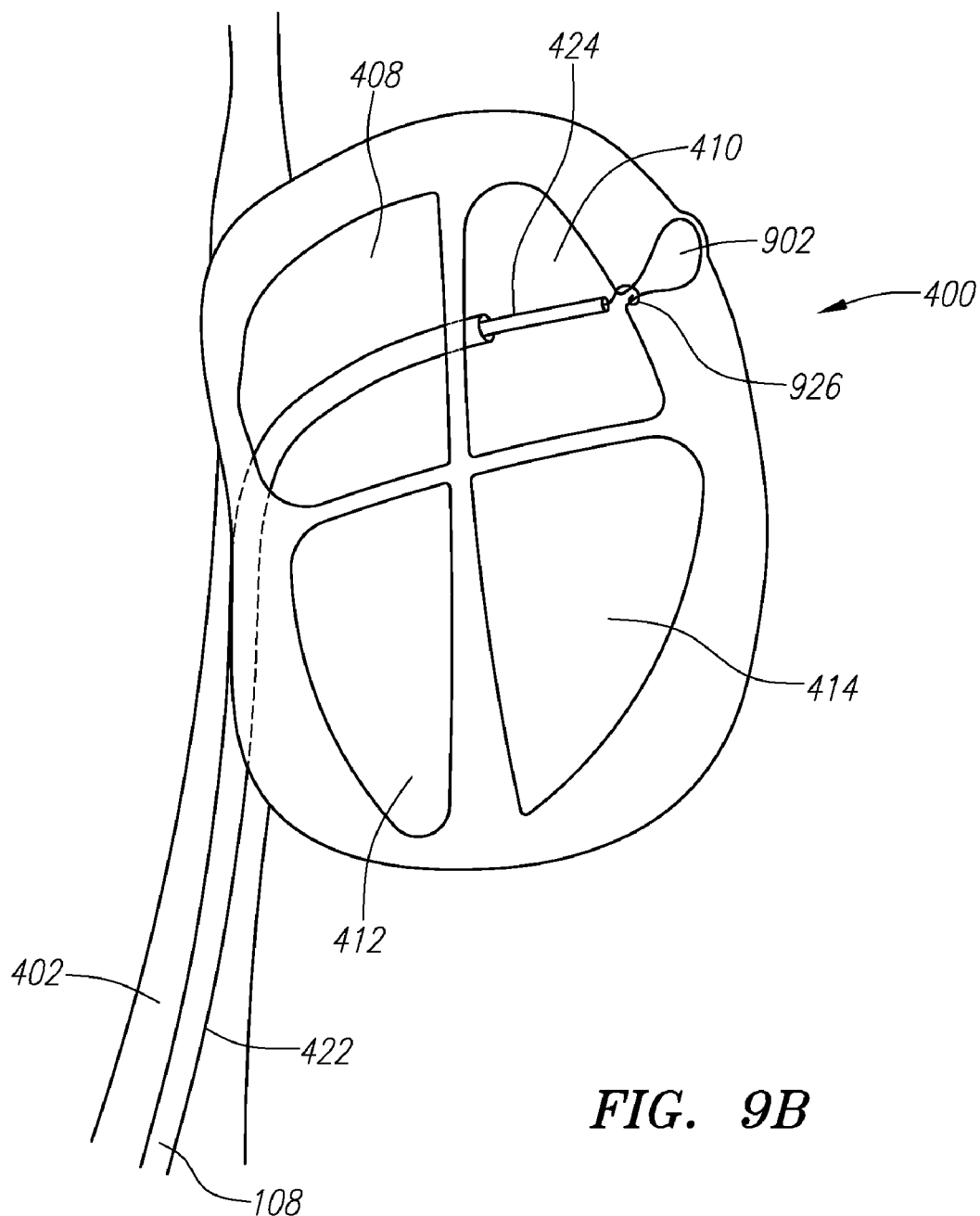
Figure 9C:
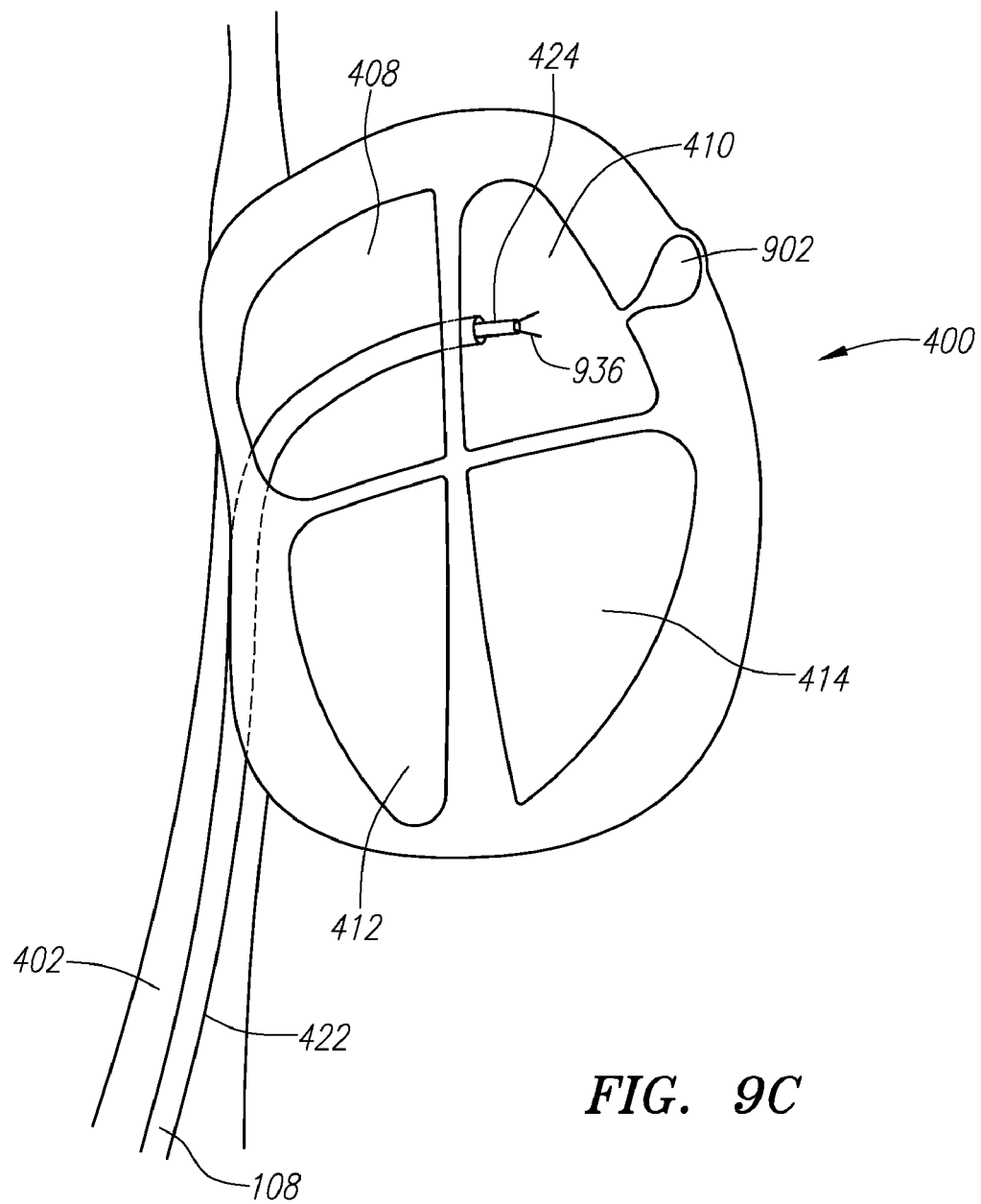
FIG. 9C through FIG. 9H respectively illustrates an instrument assembly coupled with various tools being used to treat a left atrial appendage occlusion condition.
Figure 9D:
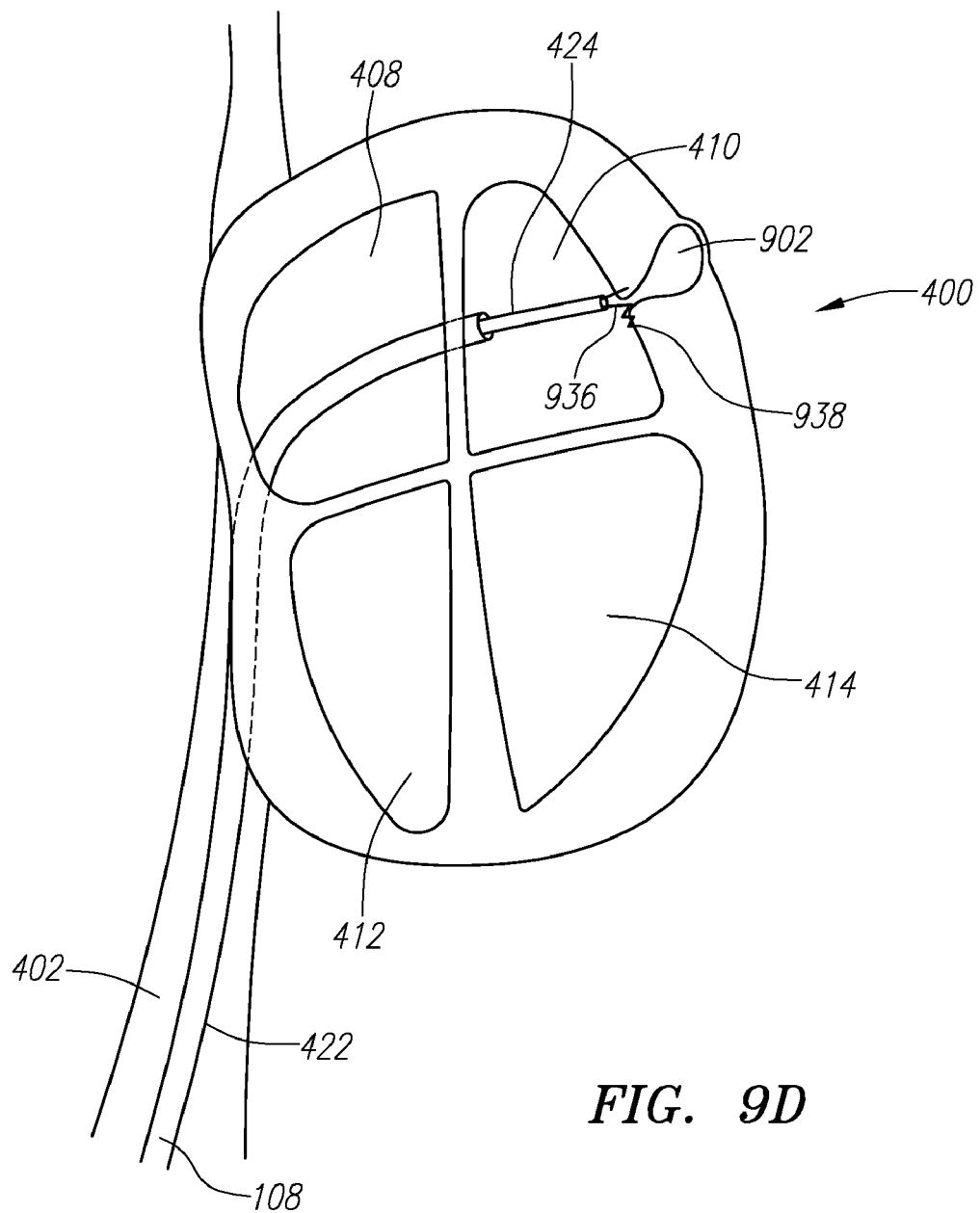
Figure 9E:
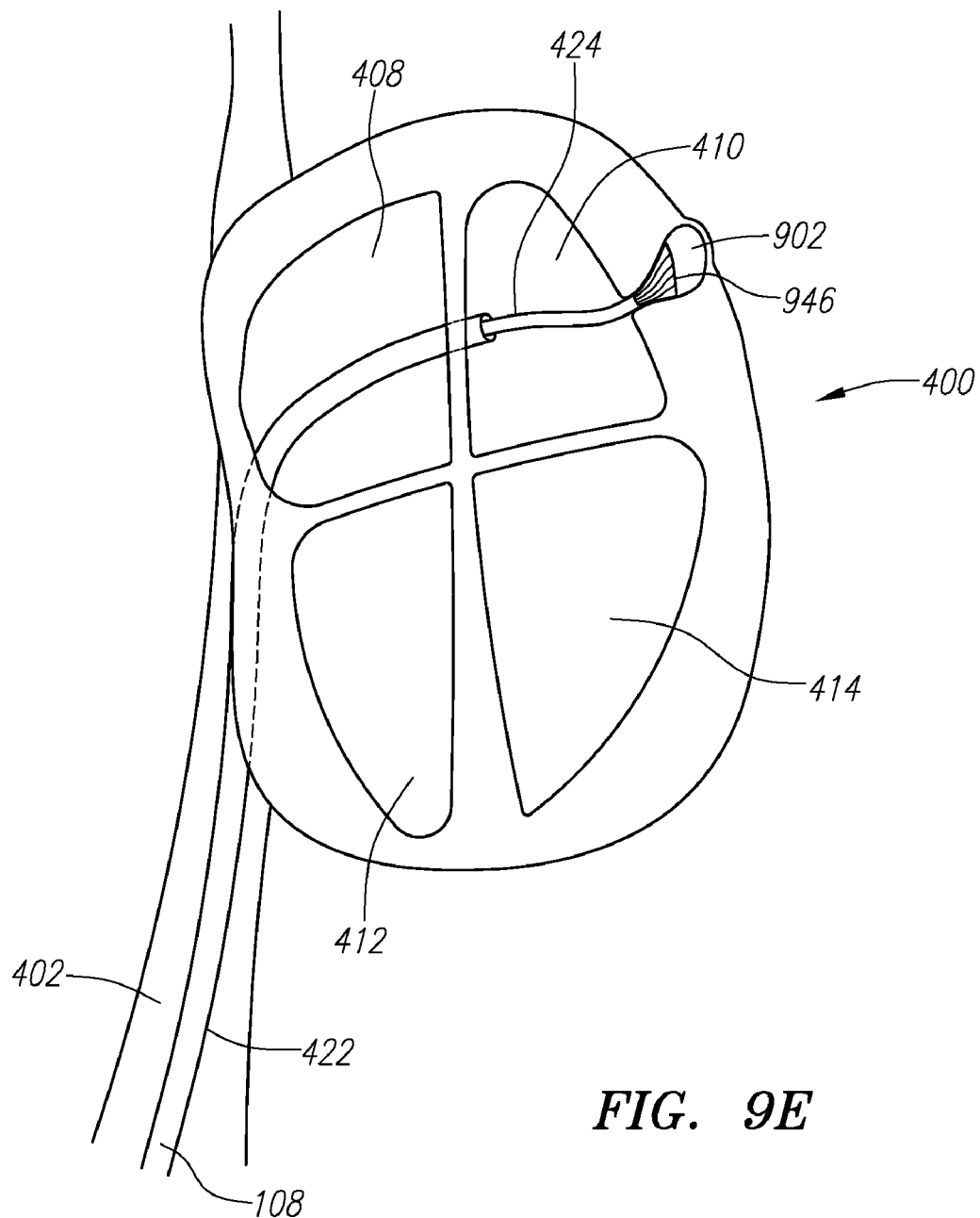
Figure 9F:
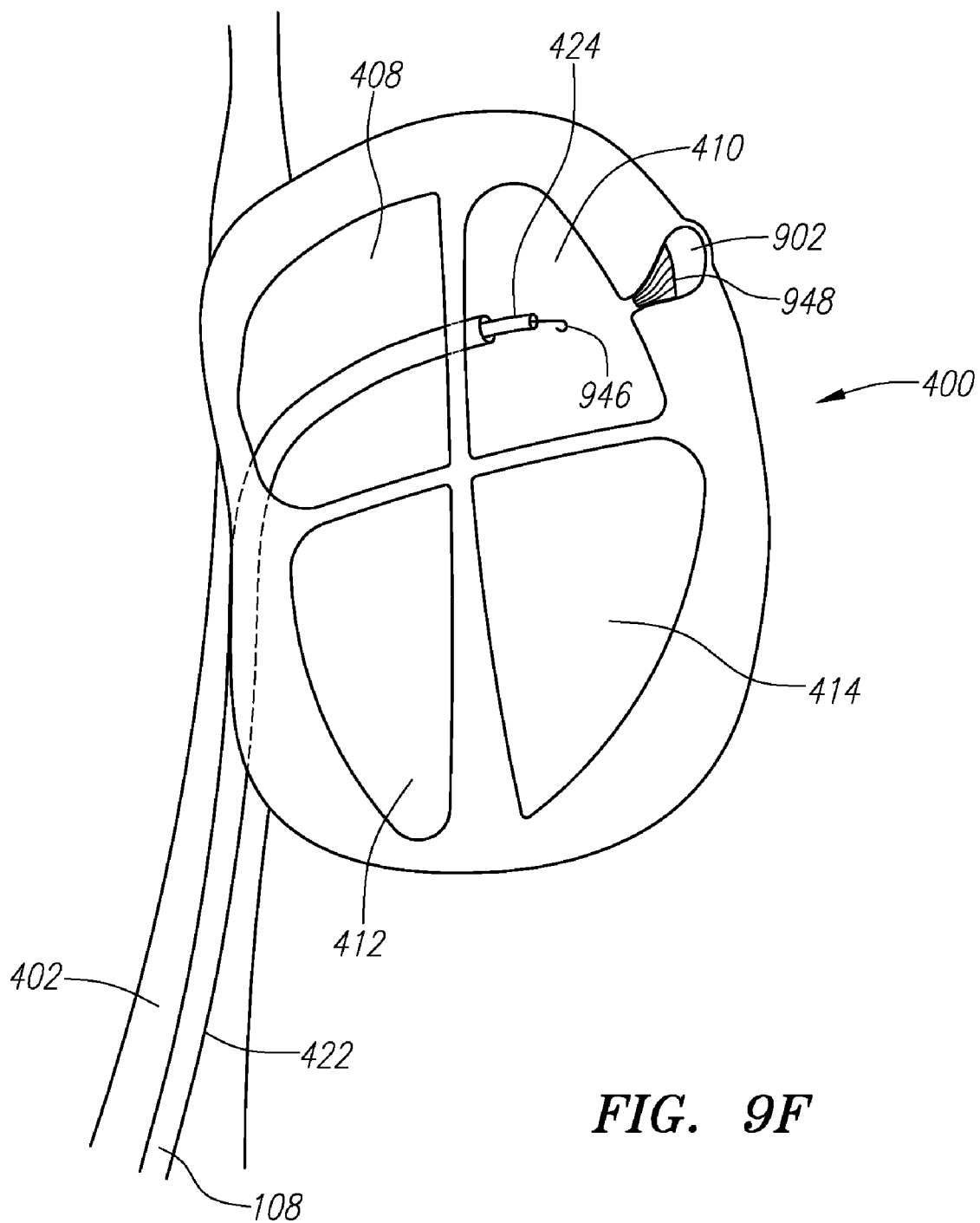
Figure 9G:
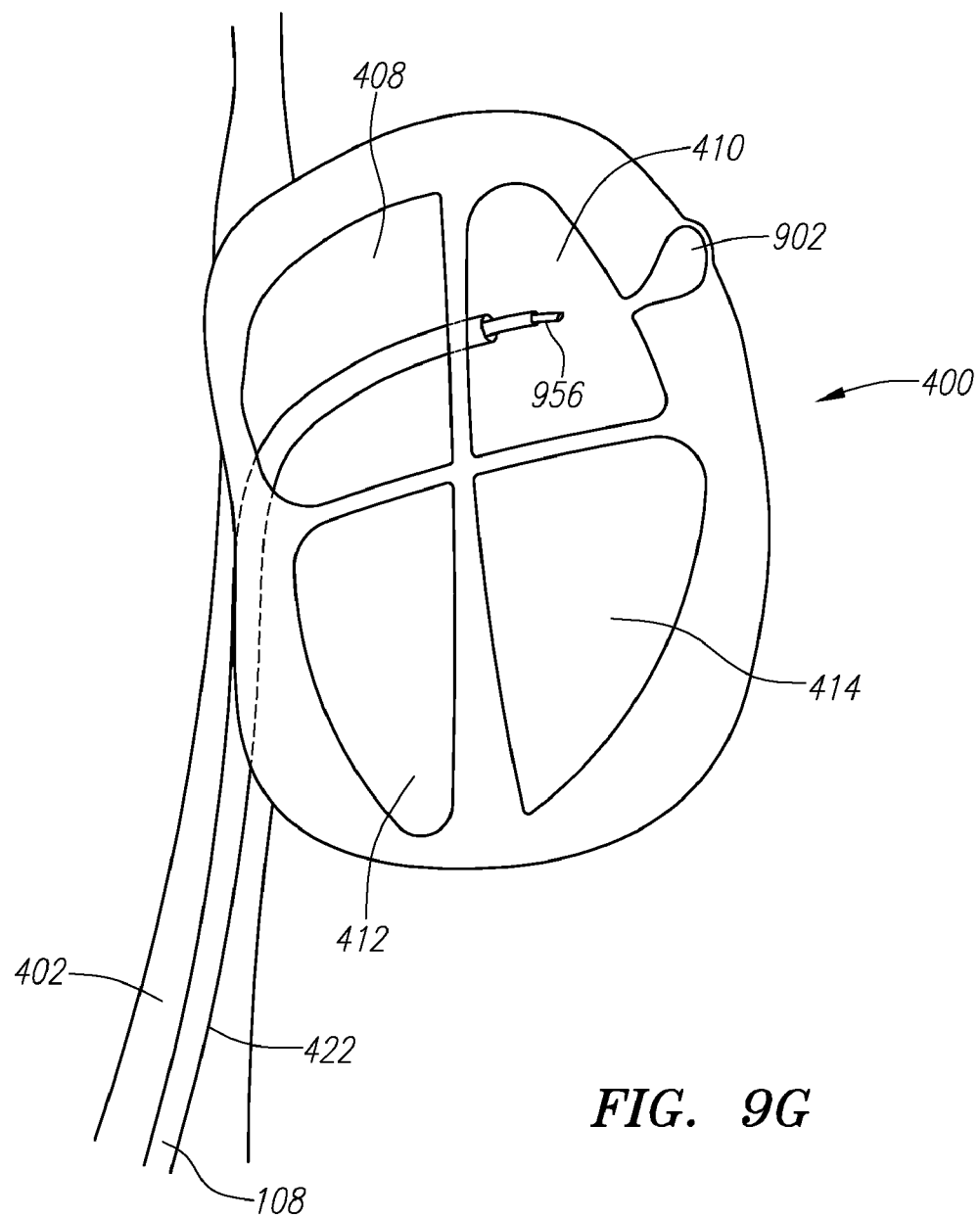
Figure 9H:
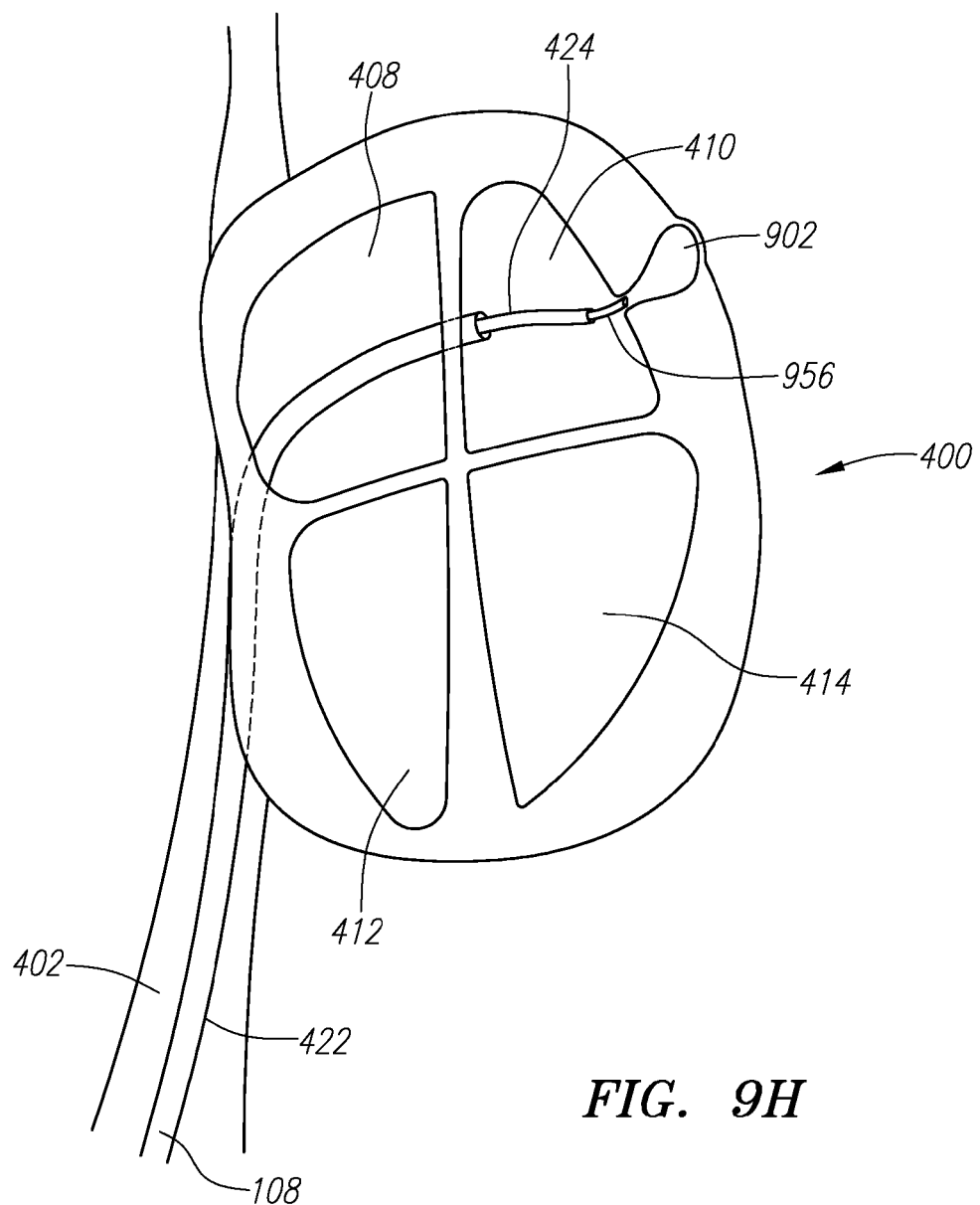

Left atrial appendage occlusion is anther cardiac abnormality. One of the significant clinical risks associated with atrial rhythm abnormalities is the development of blood clots in the atrial chamber which can result in stroke. An anatomic portion of the left atrium, referred to as the left atrial appendage ("LAA") is particularly susceptible to clot formation. One approach to eliminate the risk of clot formation in the LAA is the use of catheter-based devices that are capable of blocking blood flow and pooling of blood in the LAA, thereby reducing the risk of forming blood clots in the atrium. These devices may work well if they could be properly positioned and oriented at the opening of the LAA. Such precise placement can be exceedingly challenging with conventional catheter techniques. Embodiments of the present invention facilitate the process of performing the aforementioned procedure and accurately navigating the devices necessary to address the LAA. Referring to FIGS. 9A and 9B, a suturing tool (926) may be utilized to close the entrance of an LAA, as facilitated by a robotic instrument assembly such as that depicted (108, 422, 424). Similarly, a clip application tool (936) applying a clip (938), expandable prosthetic tool (946) applying expandable prosthetic (948) (such as that available from Atri-Tech corporation under the trade name "Watchman", and ablation tool (956) (i.e., to induce tissue welding to shut the entrance of the LAA) may be utilized to address the dangers of an open LAA, as depicted in FIGS. 9C-9H.

Pacing Lead Placement is another procedure performed to address cardiac abnormalities. Pacemakers have been used in cardiology for many years to treat rhythm abnormalities and improve cardiac function. More recently, many physicians have concluded that synchronistical pacing both ventricles of the heart is, in many patients, more effective than provide pacing at one ventricular location of the heart. This technique requires that one of the pacing leads be positioned at an optimal location in the wall of the left ventricle. In order to deliver the left ventricular lead, cardiologists often use a catheter based approach that delivers the pacing lead by introducing a cannula or tube into the coronary sinus. The coronary sinus is a vein that runs along the outside surface of the heart. Navigating this coronary sinus vein requires significant catheter manipulation and control. In addition, it also requires stability of the catheter tip when the proper anatomic location has been reached. Embodiments of the present invention facilitate placement of biventricular leads to their optimal locations to achieve the desired results.

Figure 10A:
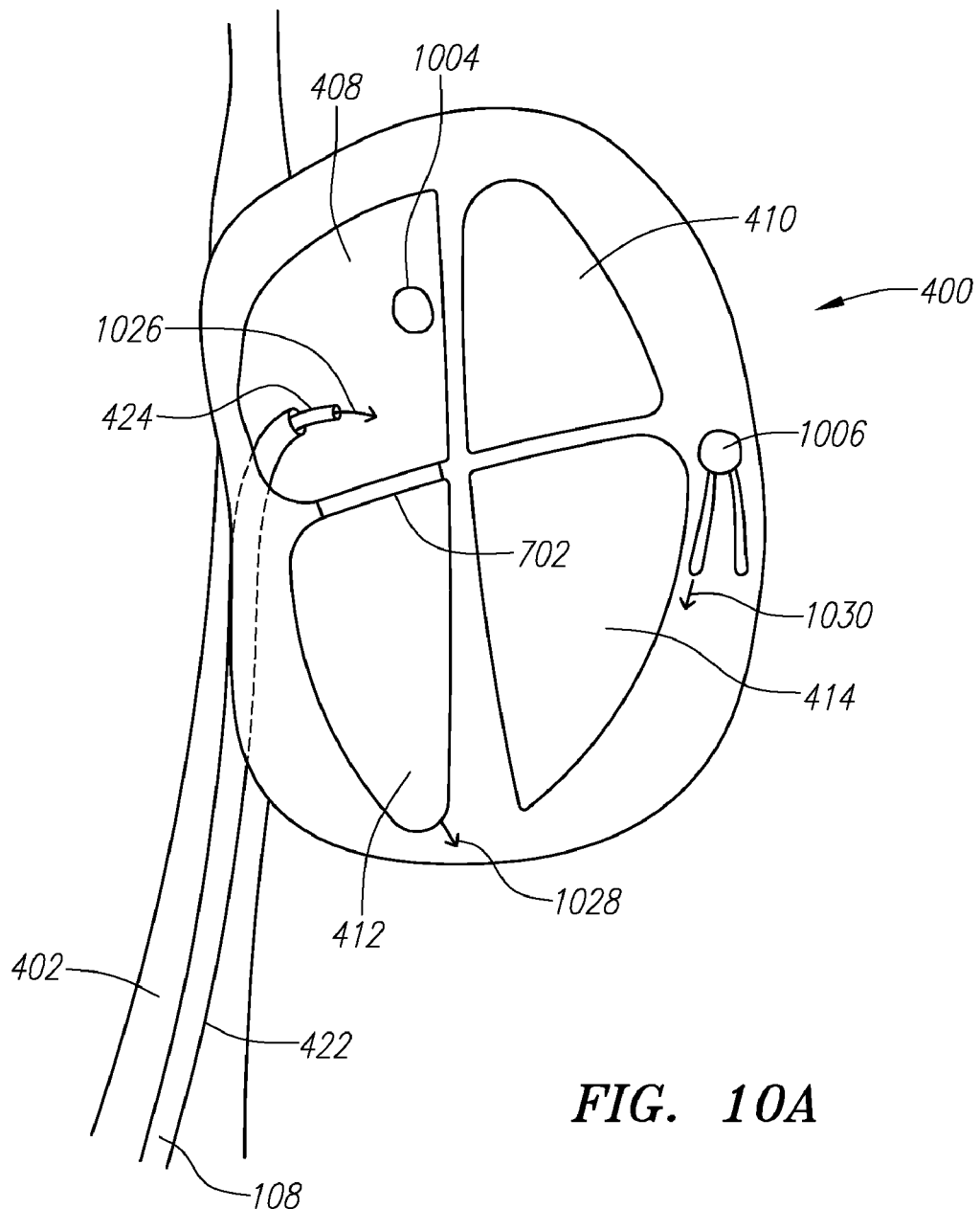
FIG. 10A and FIG. 10B respectively illustrates an instrument assembly with lead deploying tool.
Figure 10B:
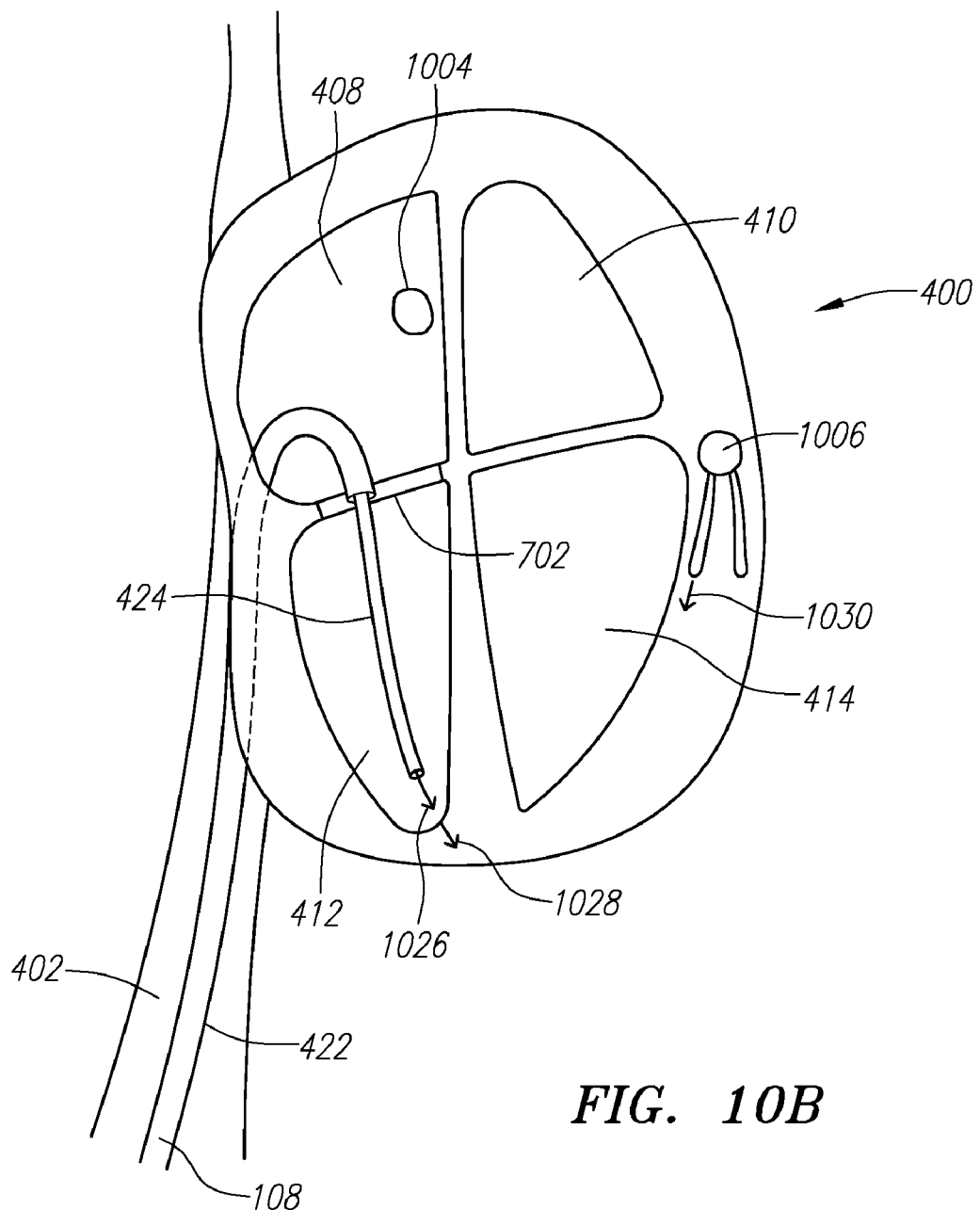
Figure 10C:
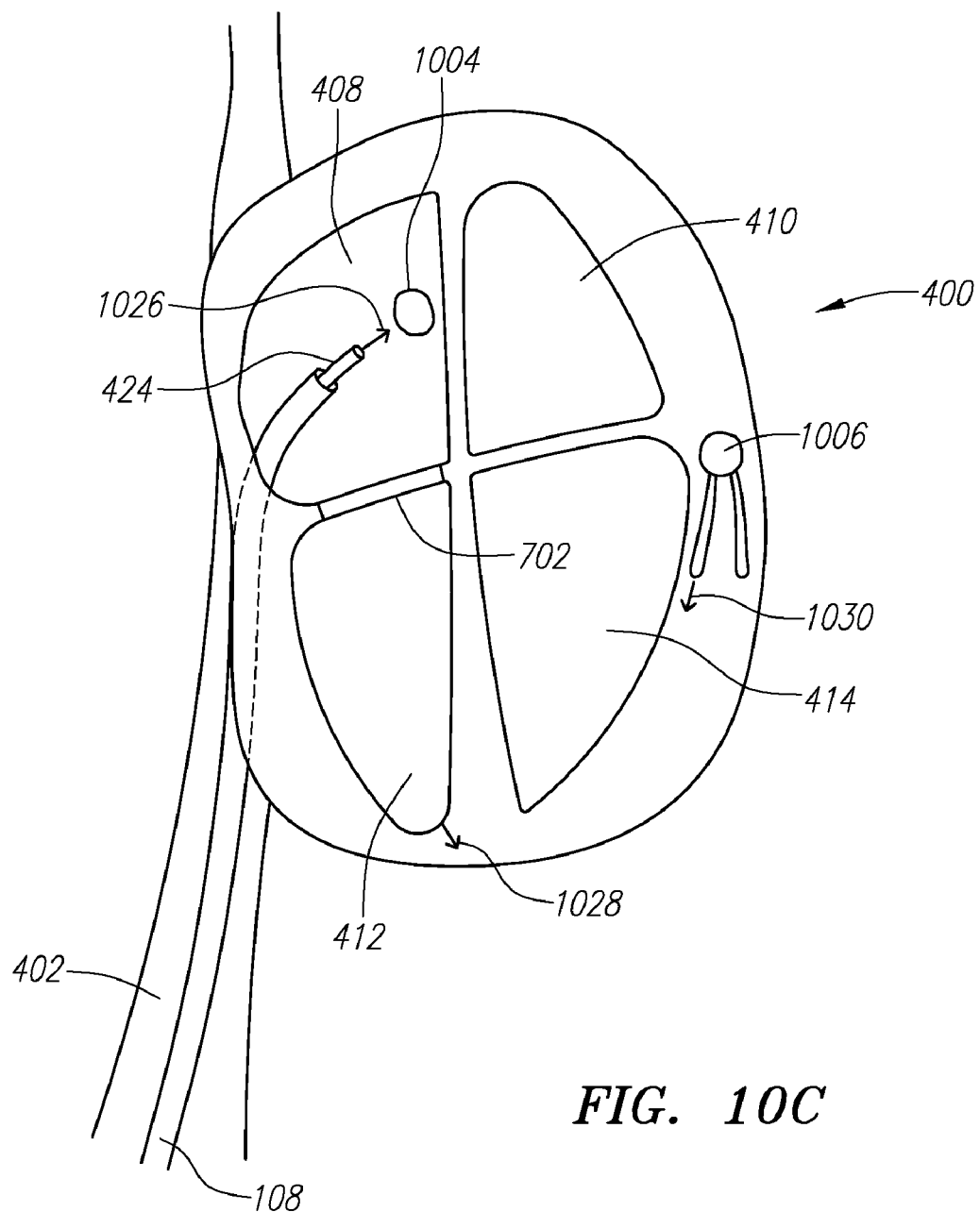
FIG. 10C and FIG. 10D respectively illustrates an instrument assembly deploying leads in the right and left atrium of the heart.
Figure 10D:
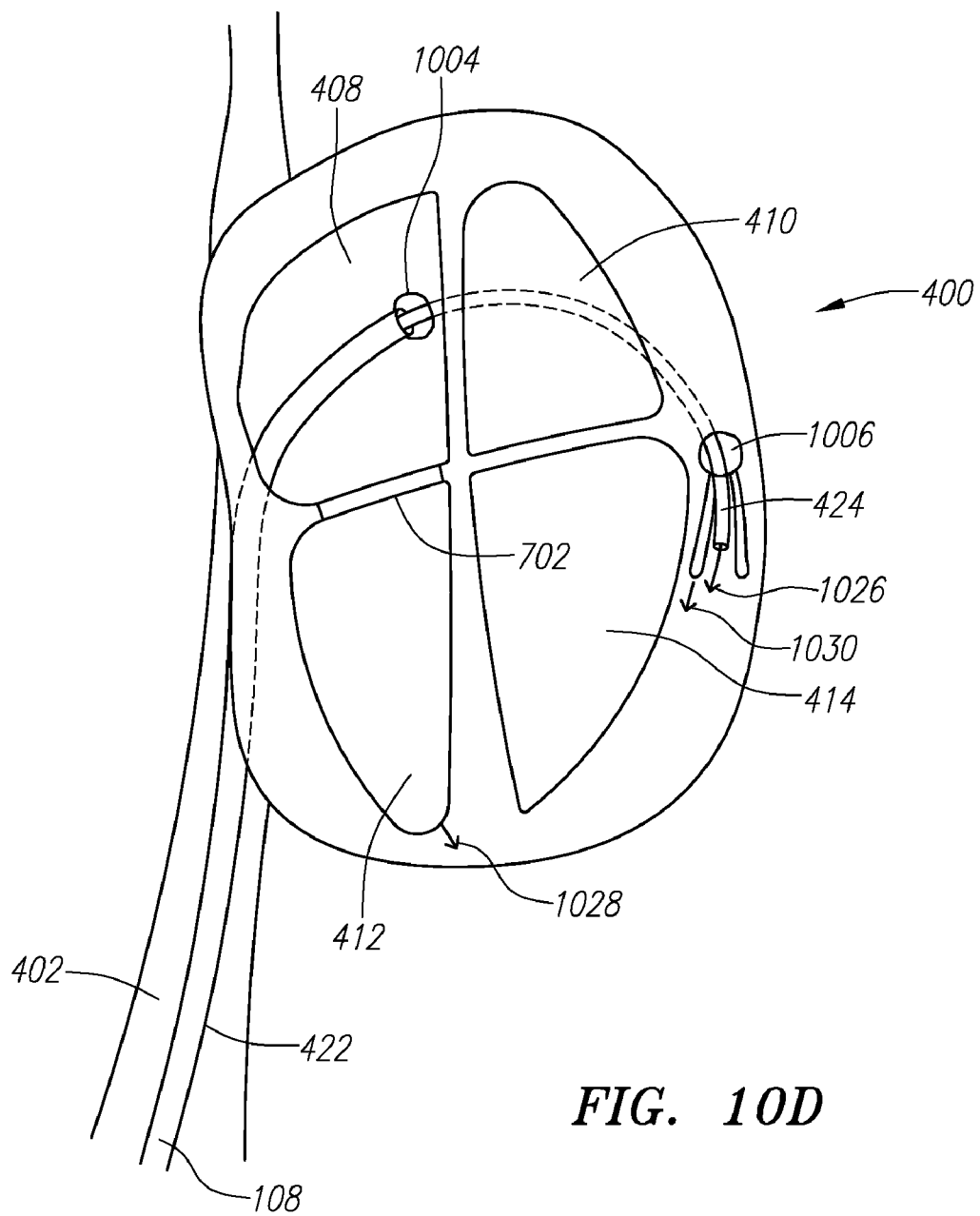

Referring to FIGS. 10A-10B, a sheath (422) and guide (424) instrument assembly (108) carrying a lead deploying tool (1026) may be advanced across the tricuspid valve (702) to press a lead (1028) into place at a targeted location (1002), such as a location adjacent the right ventricular apex. Referring to FIGS. 10C-10D, another pacing lead (1030) may be deployed at another targeted position by advancing a guide instrument (424) with a lead deploying tool (1026) through the coronary sinus (1004) to a desired location, such as a location adjacent or within one of the branches off of the coronary sinus in the left ventricular myocardium.

Figure 11A:
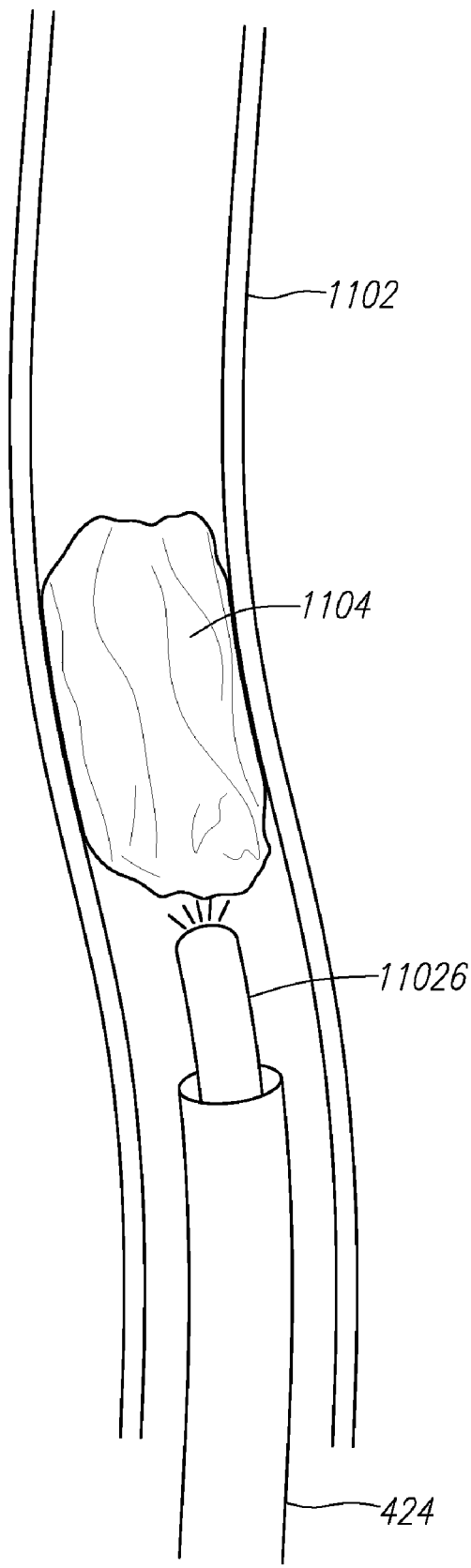
FIG. 11A through FIG. 11F respectively illustrates an instrument assembly with various tools being used to treat a chronic total occlusion condition.
Figure 11B:
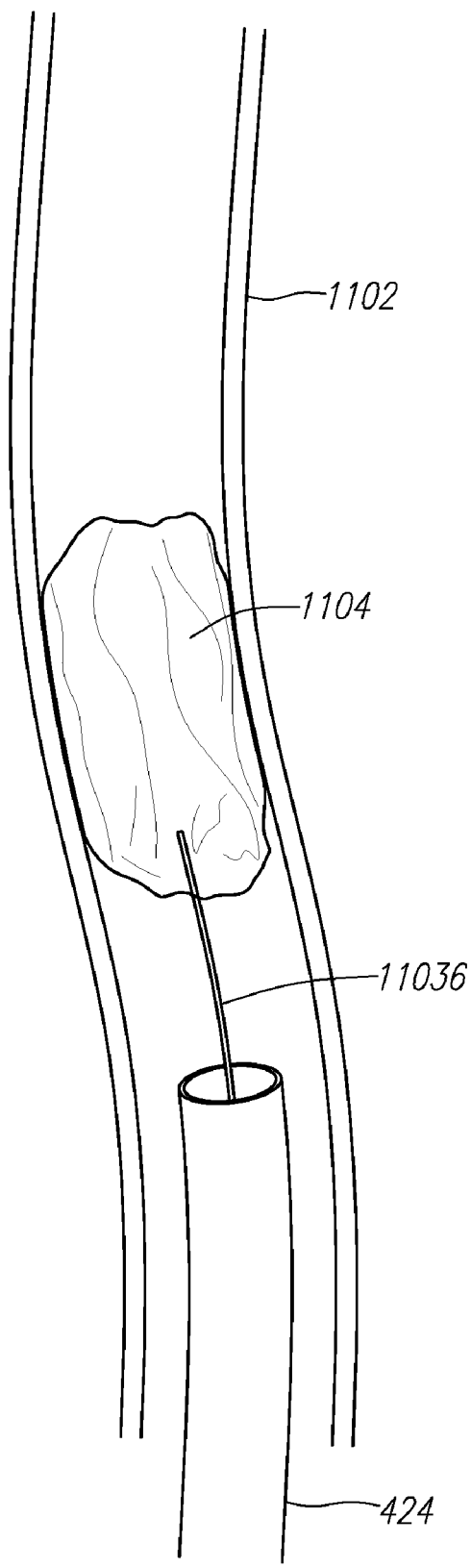
Figure 11C:
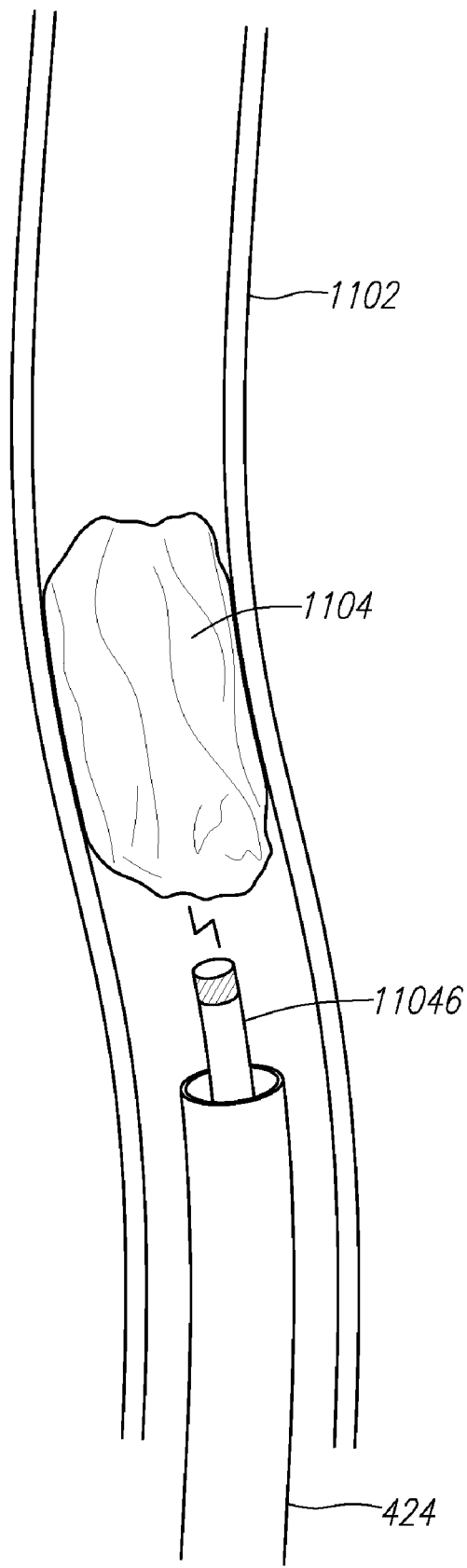
Figure 11D:
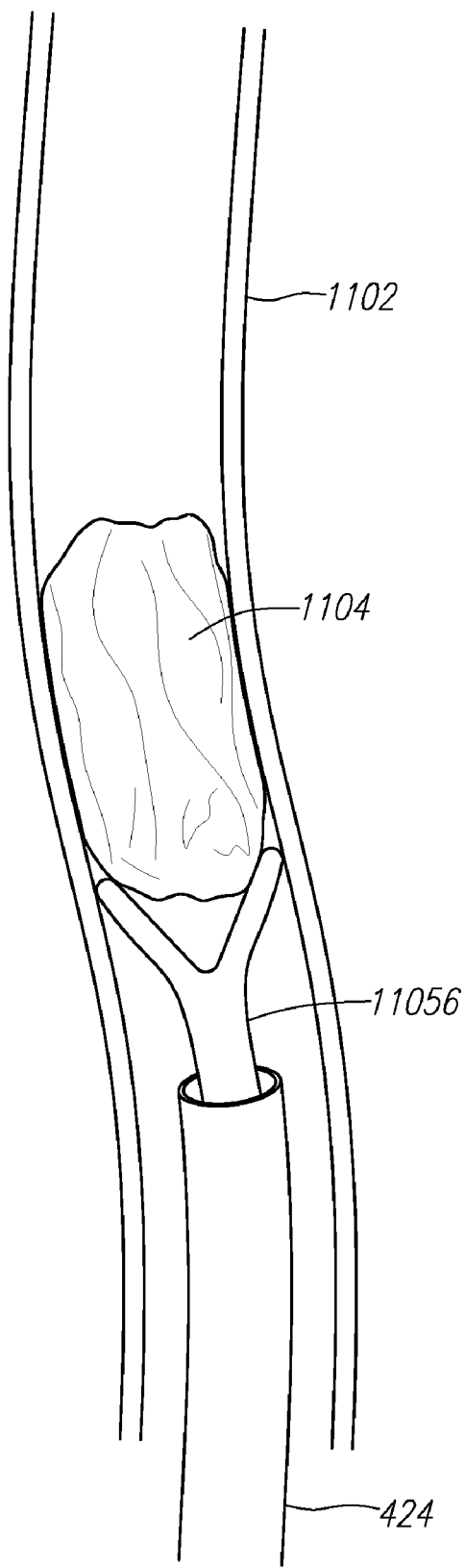
Figure 11E:
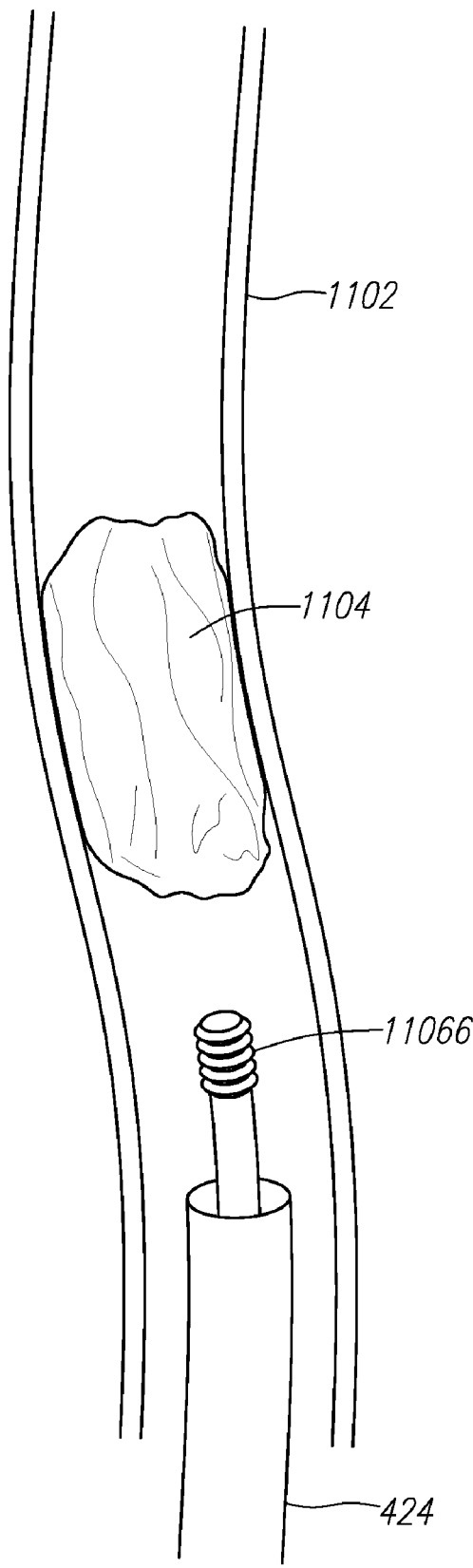
Figure 11F:
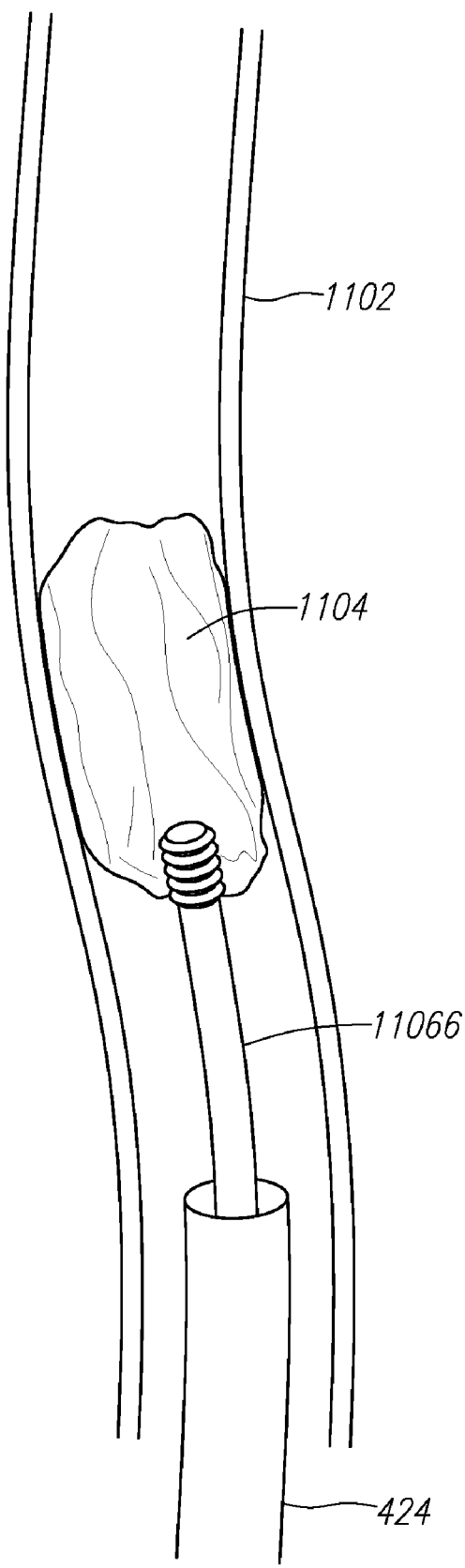

Chronic Total Occlusion ("CTO") is another cardiac malady or condition that may be addressed by using the robotic surgical system (100). Chronic total occlusions generally are blockages of the coronary vasculature system which prevent blood from passing. These occlusions create inadequate blood flow to the region of the heart that derives its blood from the occluded artery, and forces the affected region to survive based on collateral circulation from other vessels. Unlike partial occlusions, CTOs are difficult to pass a catheter or guide wire through because of the lack of any central lumen in the artery. As a result, conventional therapy of balloon dilation and stent placement is often impossible to perform, and the atrial lesion may be left untreated. Many specialized devices have been developed to try to pass through the center of a CTO lesion. However, procedures using these devices are often lengthy and are associated with significant complications and unsuccessful outcomes due to calcification of the lesion or inability to navigate the catheter tip through the center of the artery. The subject robotic catheter system (100), because of its ability to precisely control and stabilize the tip of the catheter as it is advanced, facilitates the crossing and removal of CTOs. For example, referring to FIG. 11A, a sheath (422) and guide (424) instrument assembly (108) may be utilized to advance an RF ablation tool (11026) into position where a CTO (1104) may be ablated with precision and destroyed and/or removed in a coronary artery (1102). FIG. 11B depicts another embodiment wherein an RF guidewire (11036) is advanced to destroy and/or remove a CTO (1104) in a coronary artery (1102). FIG. 11C depicts another embodiment wherein a laser fiber (11046) is utilized to destroy and/or remove a CTO (1104). FIG. 11D depicts another embodiment wherein a very small grasping tool (11056) is utilized to destroy and/or remove a CTO (1104). FIGS. 11E-11F depict another embodiment wherein a cutting/removing tool (11066), such as those available from Fox Hollow Corporation is utilized to destroy and/or remove a CTO (1104)

Figure 12A:
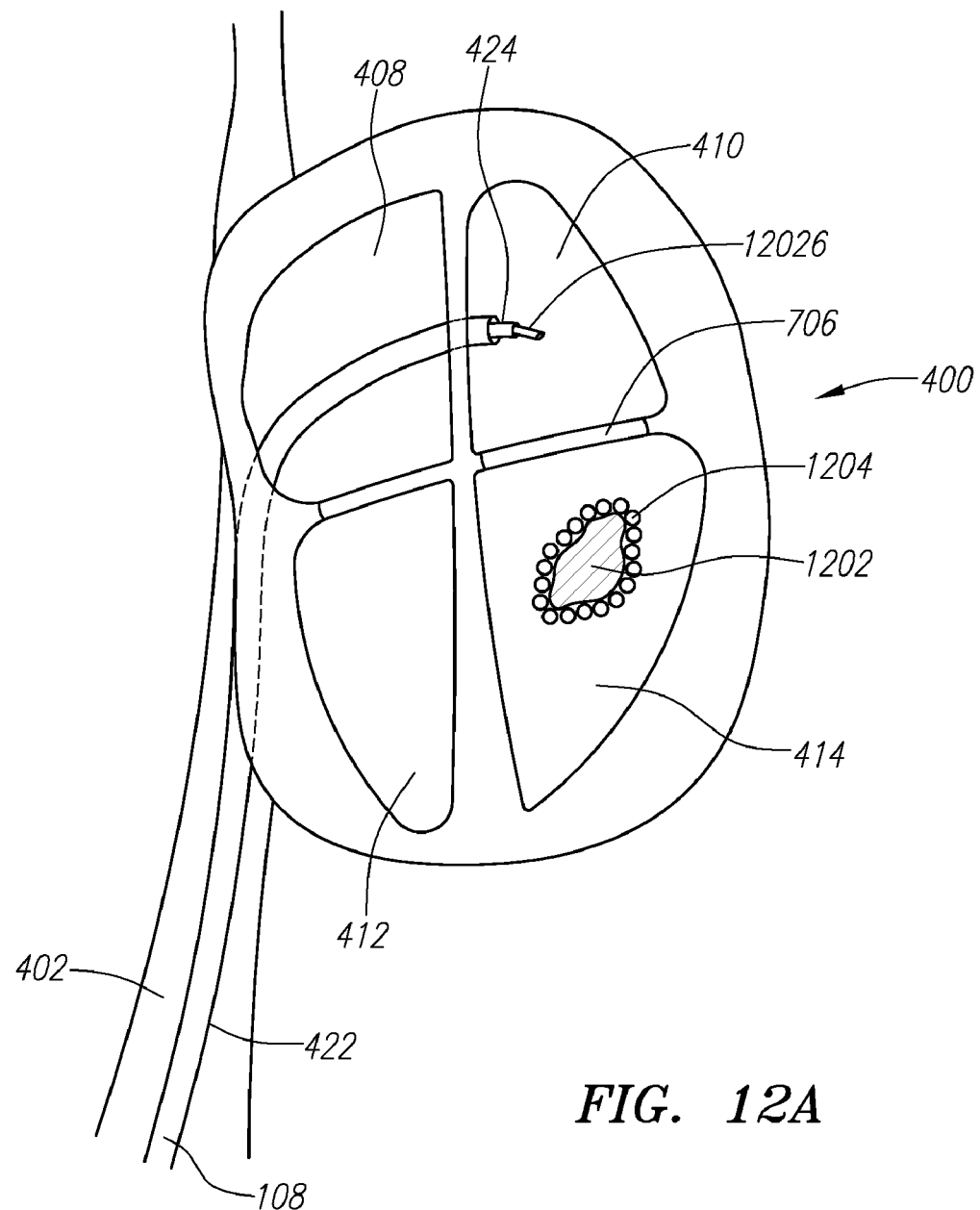
FIG. 12A and FIG. 12B respectively illustrates an instrument assembly with an injection tool being used to treat congestive heart failure condition.
Figure 12B:
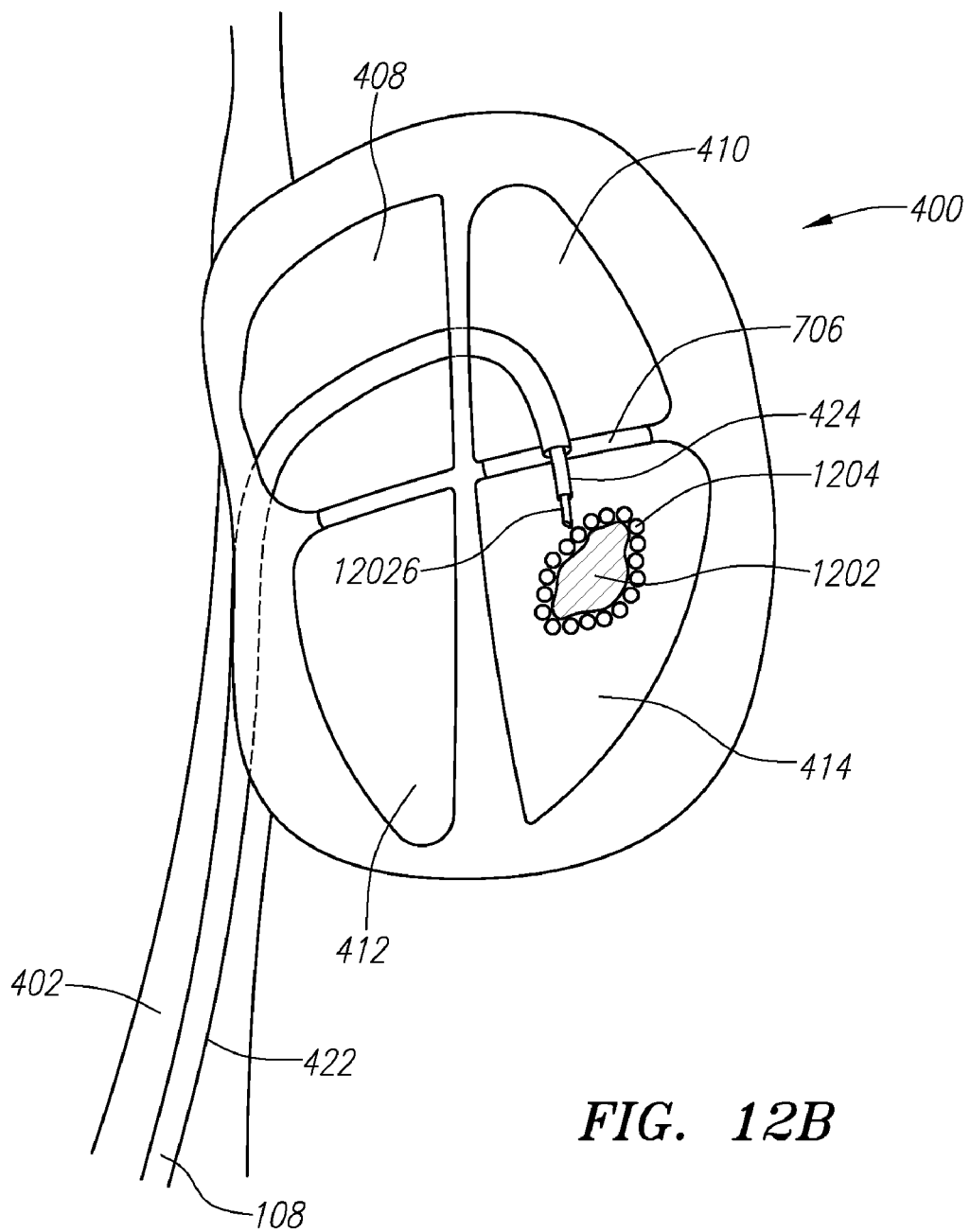
Figure 12C:
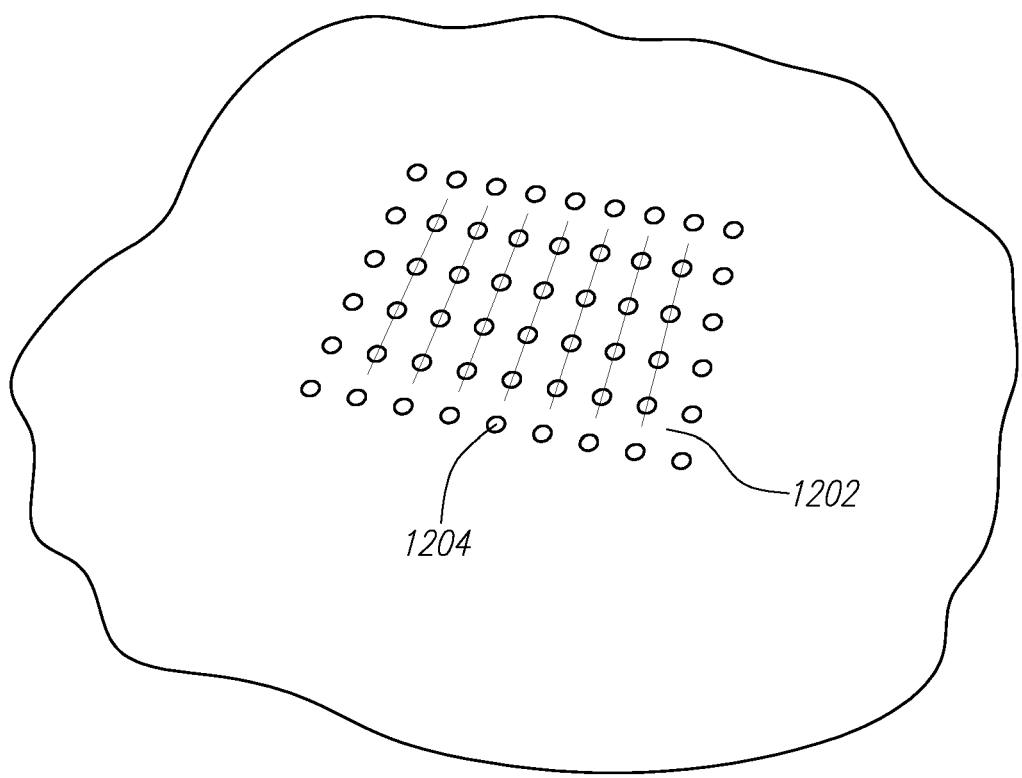
FIG. 12C illustrates one embodiment of an injection pattern for treating infracted tissue.

Robotic surgical system (100) may also be used to perform ventricular injection therapy. Many chronic heart maladies cause progressive deterioration of heart functions that often resulting in debilitating and fatal conditions commonly referred as congestive heart failure ("CHF"). In CHF, the heart muscle becomes less efficient, the chambers of the heart begin to dilate and cardiac function tends to deteriorate. As the heart muscle becomes weaker, the heart has to work harder to pump adequate amount of blood through the circulatory system. The harder the heart has to work, the more damage may be done to its structure and function. Typically, clinicians treat CHF with a variety of drugs that substantially decrease blood volume and increase contractility of the heart muscle. Recently, there have been investigations of techniques that could repair damaged muscle cells by directly injecting growth factors or healthy cells into injured or damaged muscles. These techniques have shown some promising results of healing the damaged muscle; however, these techniques require the drugs to be applied directly to the damaged muscle. Accordingly, the needle injector for delivering the drug to the damaged muscle in the heart must be precisely and accurate controlled in order to ensure direct delivery of the drugs to the damaged muscle. The subject robotic surgical system (100) is an effective means for delivering ventricular injections at the precise locations where clinicians desire to deliver drugs and cell therapies. Referring to FIGS. 12A-912B, an injection tool (12026) may be operatively coupled to the sheath (422) and guide (424) instrument assembly (108). The assembly (108, 422, 424, and 12026) is advanced transseptally into the left atrium, across the mitral valve, and into the left ventricle (414), as illustrated in the figures. With the guide instrument (424) advanced into the left ventricle (414) along with the injection tool (12026), a precision pattern (1204) of injections may be made, for example, around an infarcted tissue portion (1202), to start revascularization and/or rebuilding of such portion. In one embodiment, the pattern (1204) may be in a pattern of a matrix as illustrated in FIG. 12C. Several subsequent treatments may be applied to increase the rebuilding of such portion of tissue.

The robotic surgical system (100) may be used to perform a valve repair procedure. Heart valve disease is a common disorder which affects millions of patients and is characterized by a progressive deterioration of one or more of the heart's valvular mechanisms. Repair of heart valves has historically been accomplished by open heart surgery. Although such open heart surgery is often successful in improving valve function, however, there is also a high risk of death associated with open heart or heart valve surgeries. Even if such surgery is successful, there is a long period of post-operative recovery associated with open heart surgery. As a result, cardiologists tend to wait as long as possible before resorting to surgery in patients with deteriorating valve function.

Figure 13A:
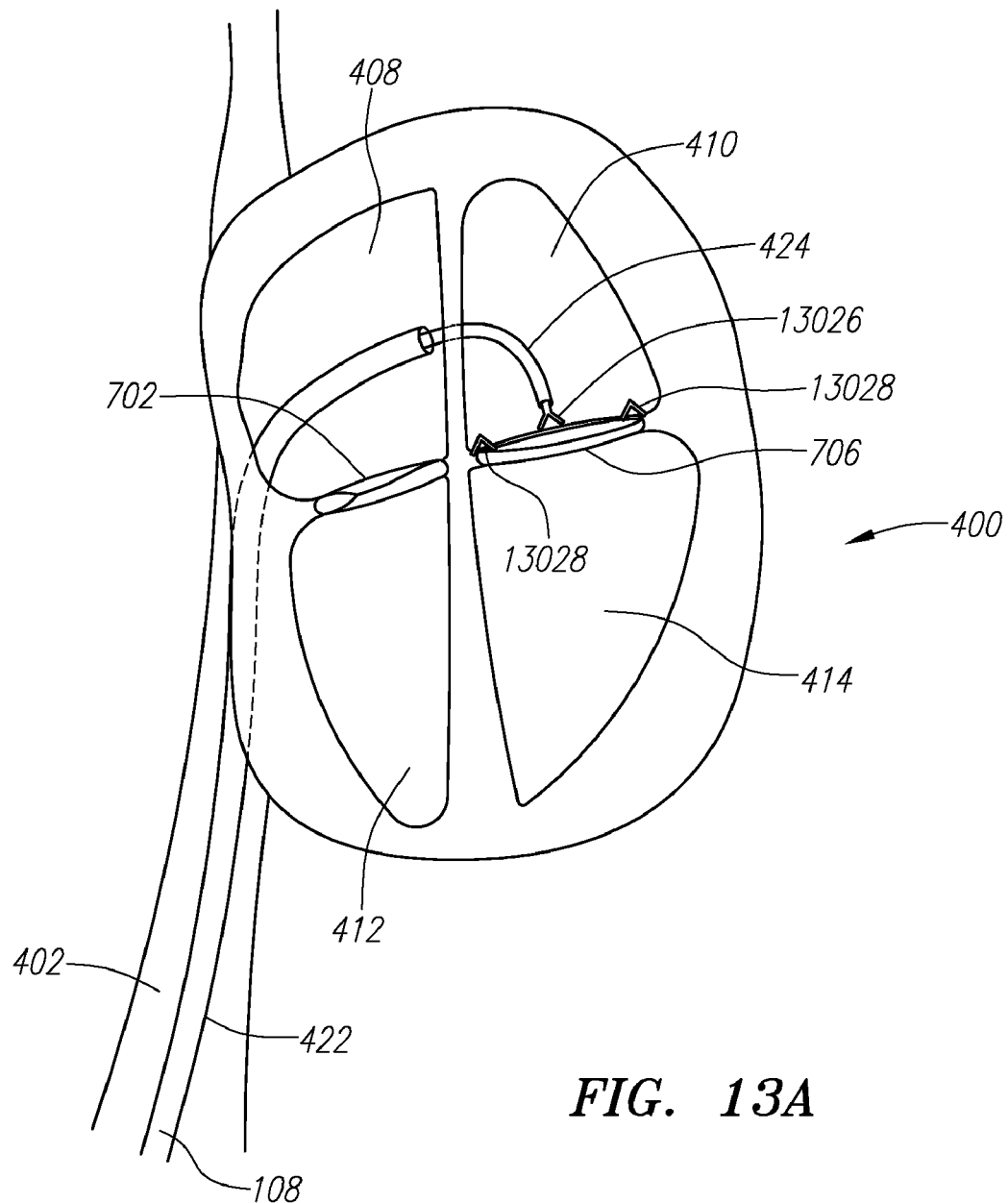
FIG. 13A through FIG. 13G respectively illustrates an instrument assembly with various tools being used to perform valve repair procedures.
Figure 13B:
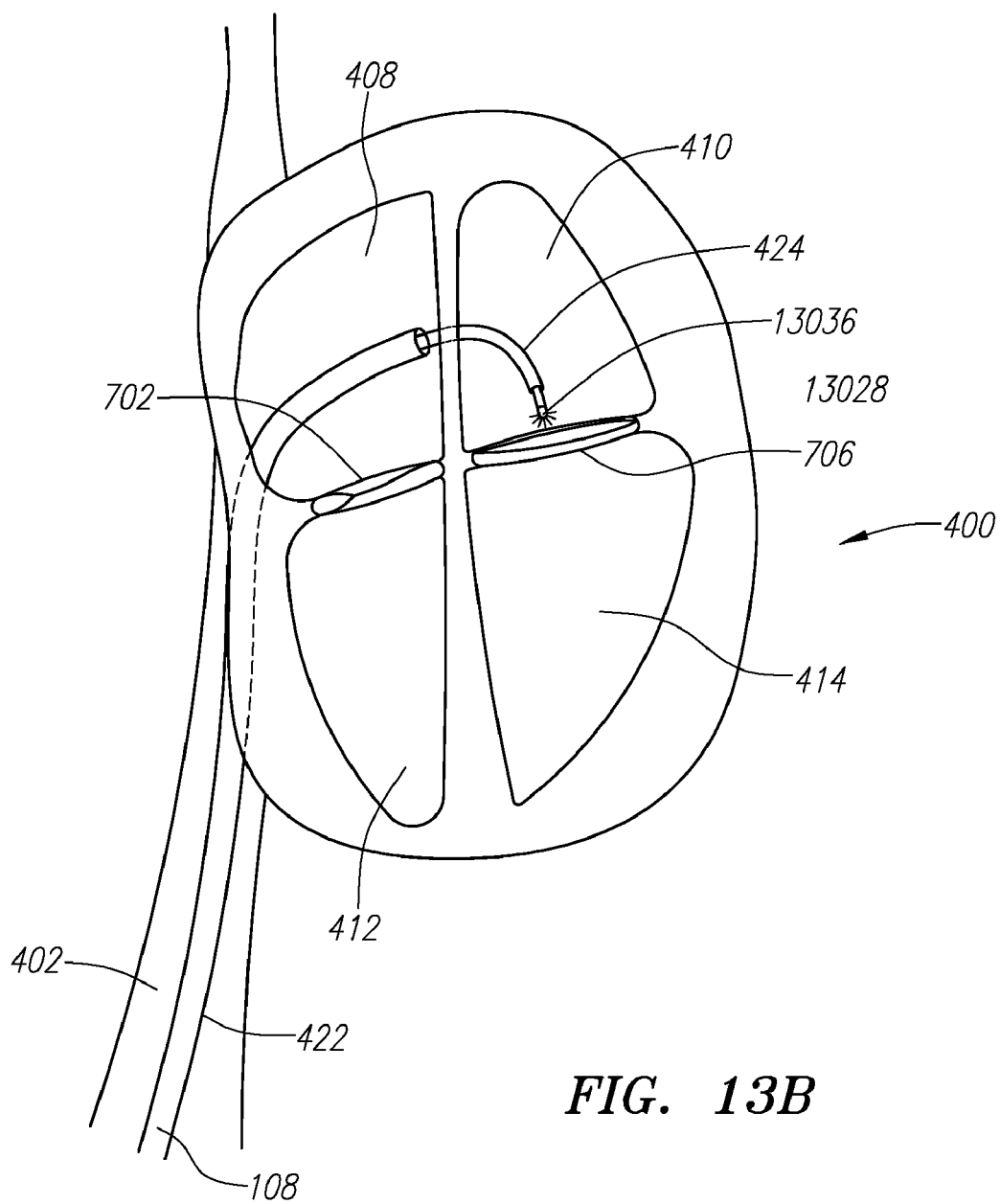
Figure 13C:
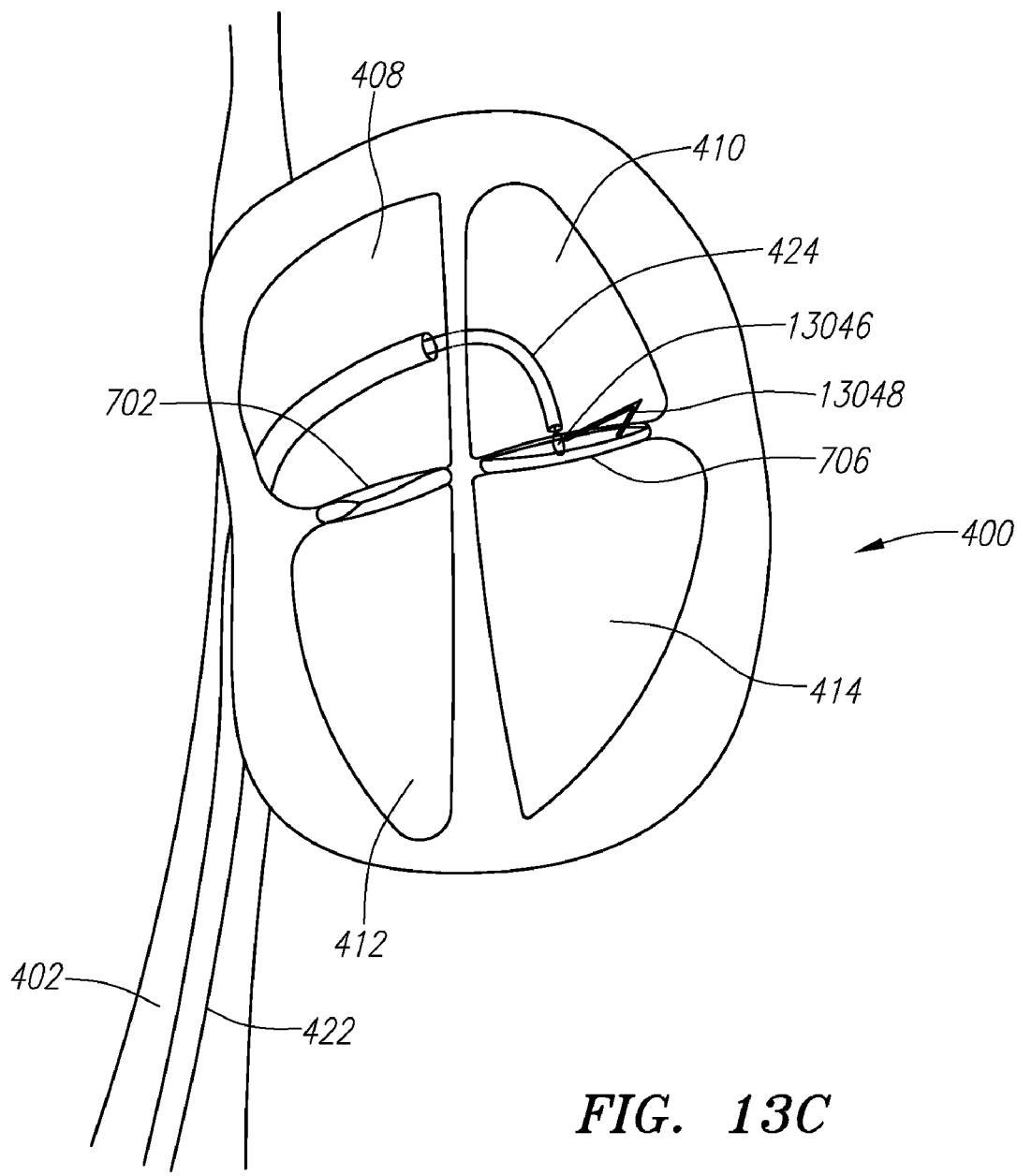
Figure 13D:
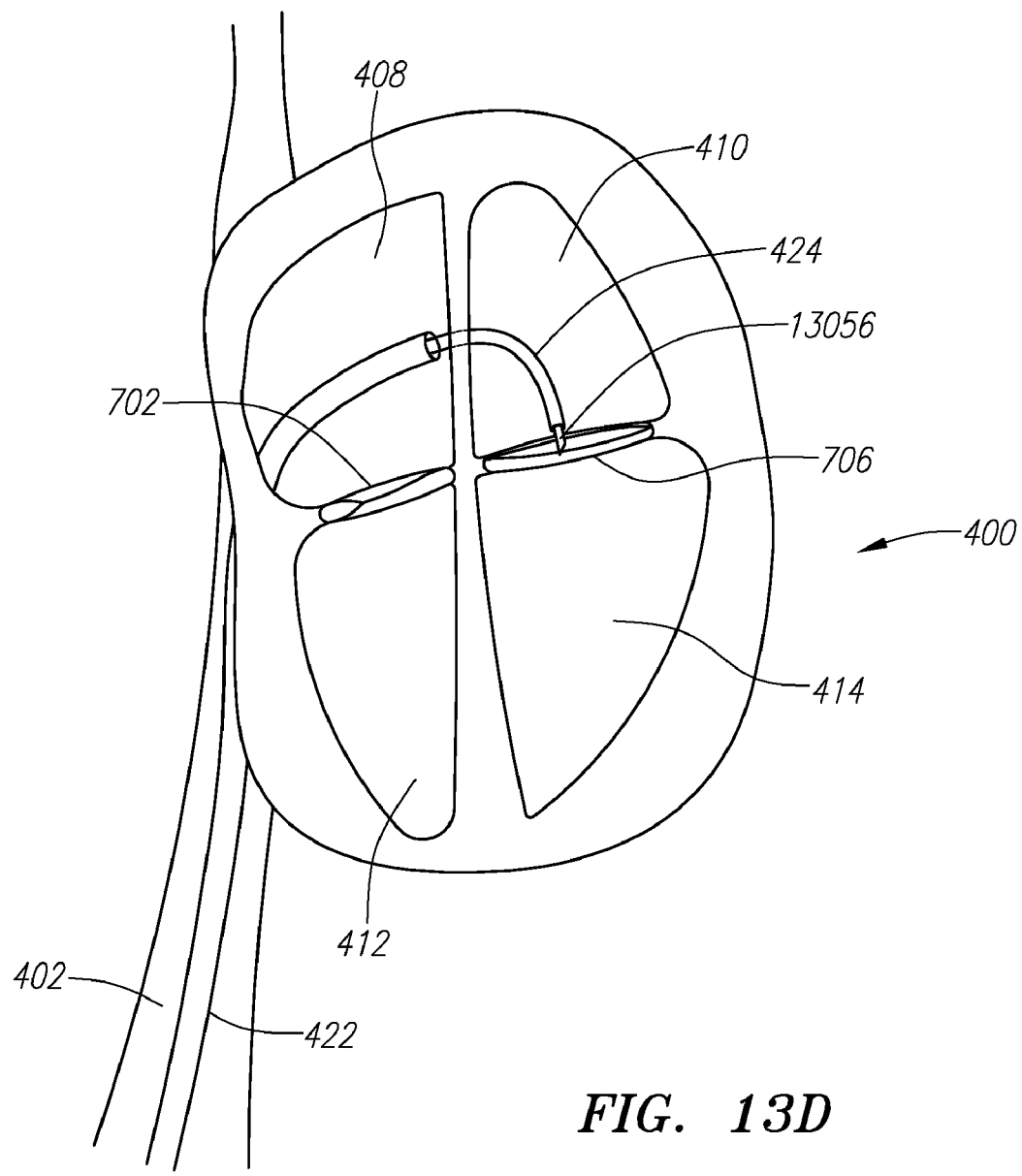
Figure 13E:
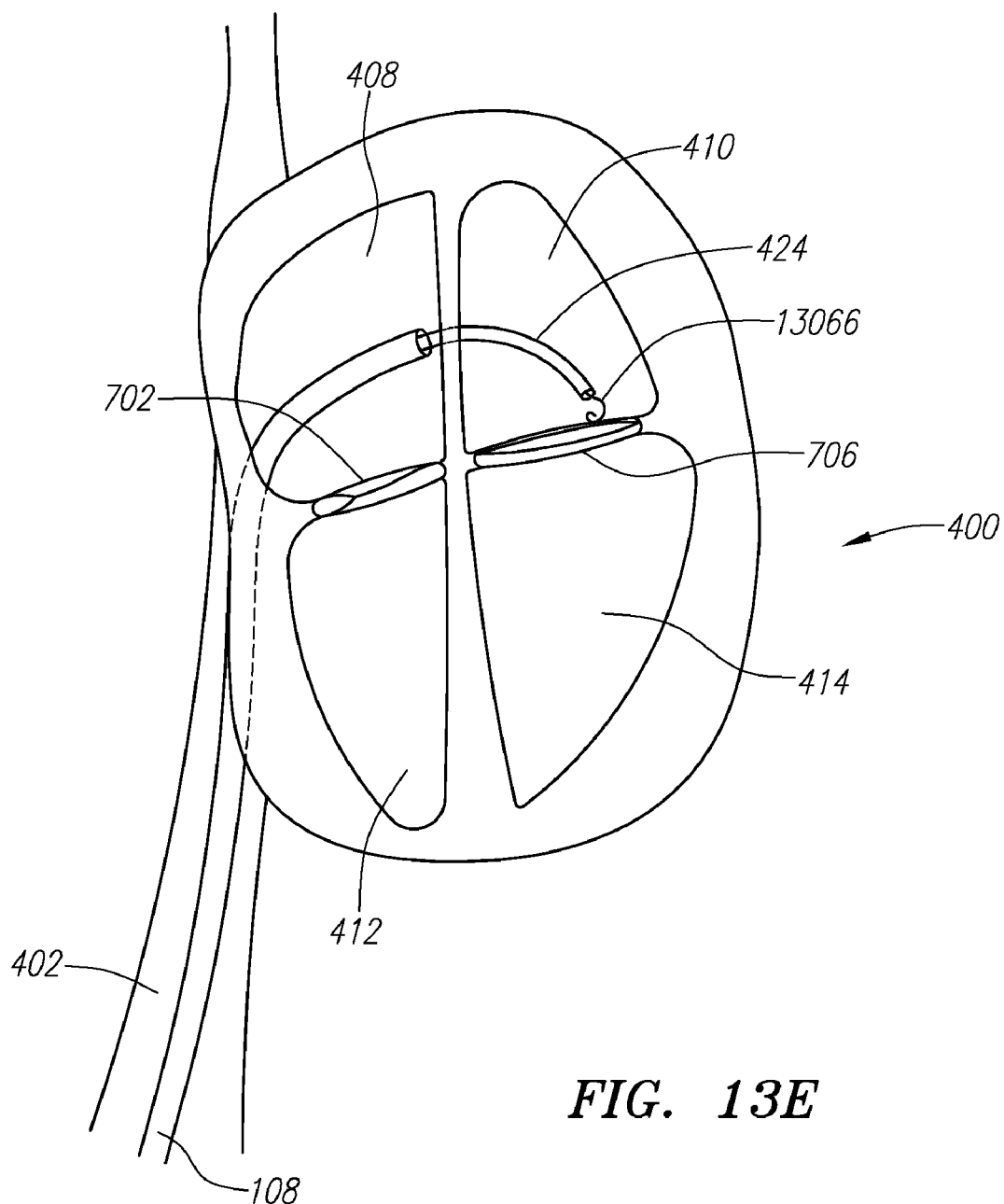
Figure 13F:
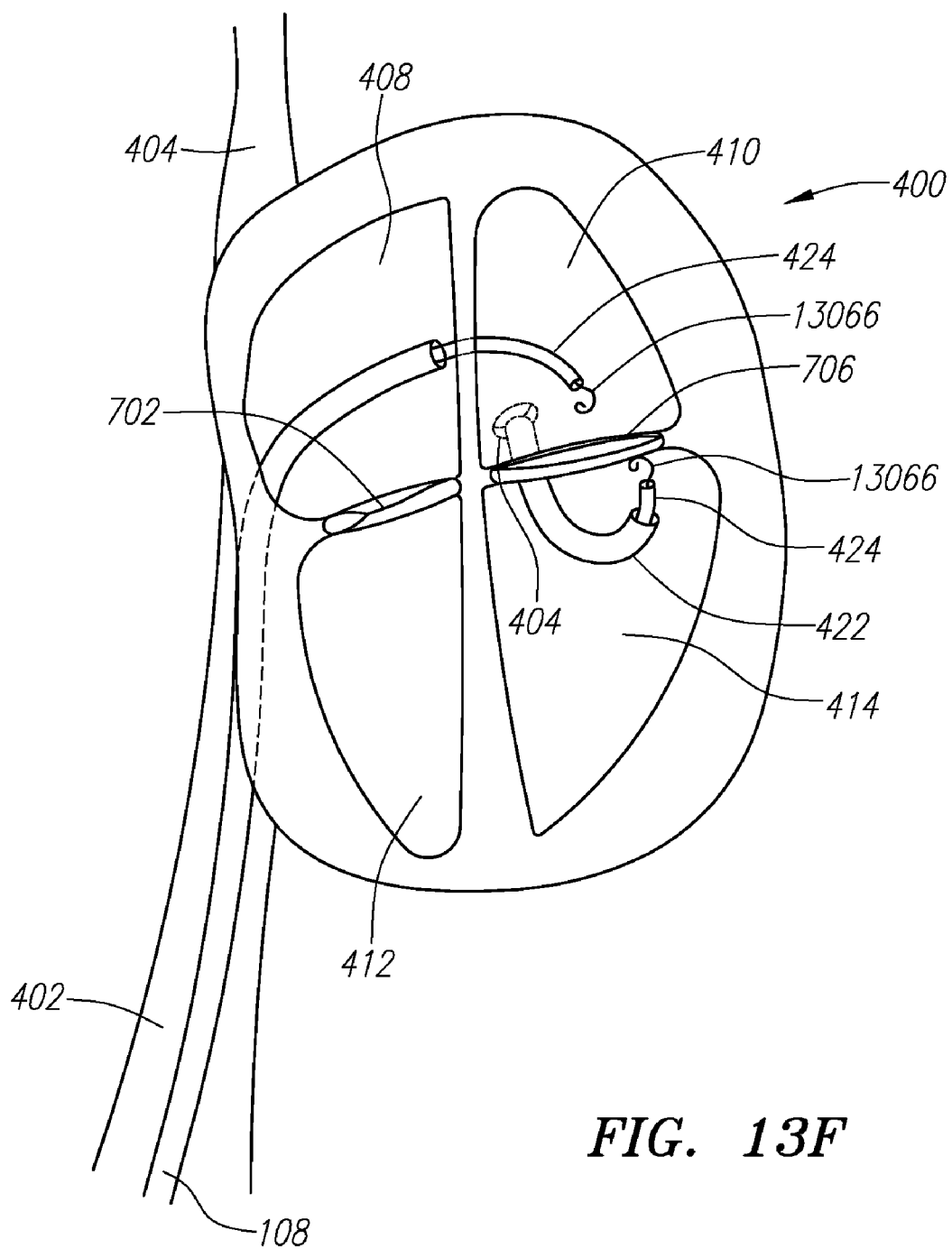
Figure 13G:
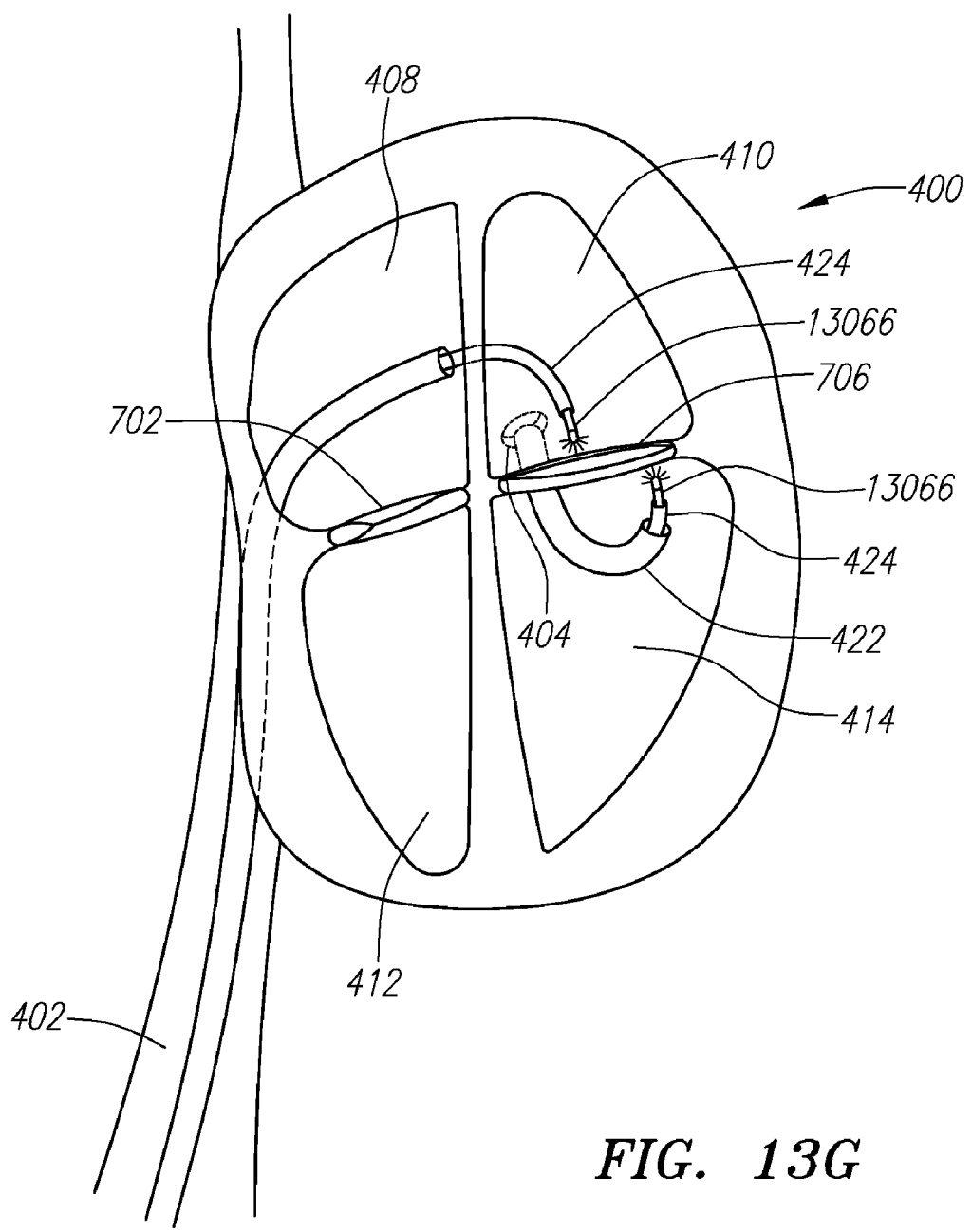
Figure 13H:
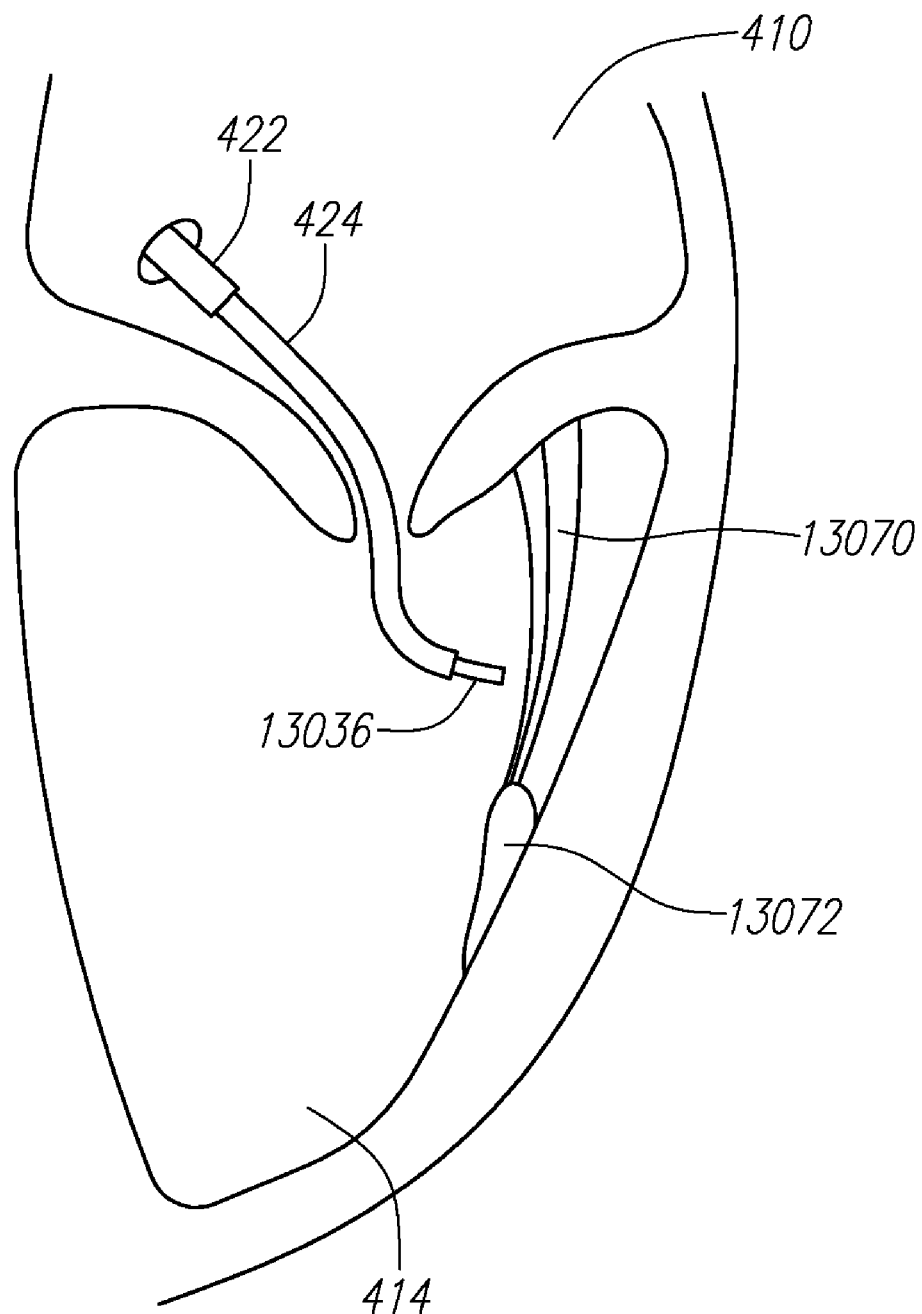
FIG. 13H and FIG. 13I illustrate the chords, chordae tendineae, or papillary muscle of the mitral valve leaflet being adjusted.
Figure 13I:
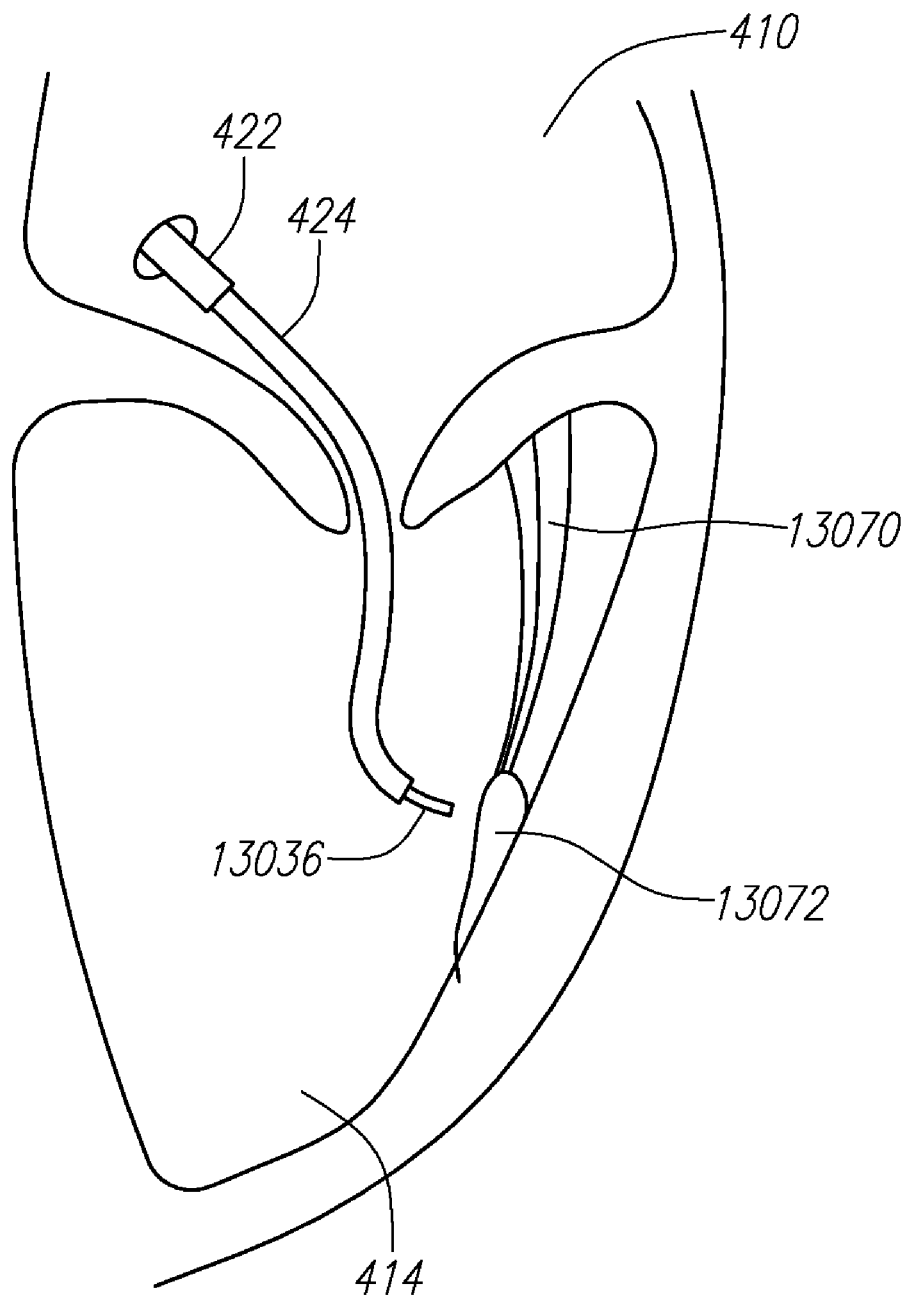

There is increasing interest in treating valve disease with less invasive procedures in order to encourage treatment in the earlier stages of the disease and potentially slow or stop the progression of heart failure. In recent years, catheter-based procedures have been developed for repairing valves in a surgical manner. As these procedures develop, physicians require a new generation of catheters that can be used like surgical tools and which can be precisely controlled, as may be provide by the subject robotic catheter system (100). Referring to FIG. 13A, a clip deployer (13026) may be utilized to deploy clips (13028) around the mitral annulus and adjust the geometry of the annulus. FIG. 13B depicts an ablation tool (13036) utilized to induce localized ablations to adjust or shrink the geometry of the mitral annulus. Similarly, an ablation tool (13036) may be used to adjust or shrink the geometry of the mitral valve leaflets. FIG. 13C depicts a clip or suture deploying tool (13046), such as those available from E-Valve Corporation, to position a clip or suture (13048) across the mitral leaflets in an Alfieri technique procedure, utilizing the precision and stability of the sheath (422) and guide (424) of the instrument assembly (108). FIG. 13D depicts a sheath (422) and guide (424) of instrument assembly (108) delivering a resecting tool (13056) which may be utilized to resect the mitral leaflets and improve coaptation. FIG. 13E depicts an antegrade approach using a suture tool (13066) to deploy sutures into the mitral annulus to modify the geometry of the mitral valve. FIG. 13F depicts both antegrade and retrograde instrument assemblies (e.g., 13066, etc.) to deploy sutures into the mitral annulus. FIG. 13G depicts both antegrade and retrograde ablation of the mitral annulus, for example by a bipolar electrode configuration formed by the electrodes carried by the opposing instrument assemblies (e.g., 13066). FIGS. 13H and 13I illustrate the positions of the mitral valve leaflets may be adjusted by adjusting (e.g., shortening, etc.) the length of the leaflet chords (13070), chordae tendineae (13070), or papillary muscle (13072) to ensure proper closure and/or alignment of the leaflets to prevent leakage by using a clip tool (13026) to deploy a clip (13028), an ablation tool (13036), a suturing tool (13046), etc.

Figure 14:
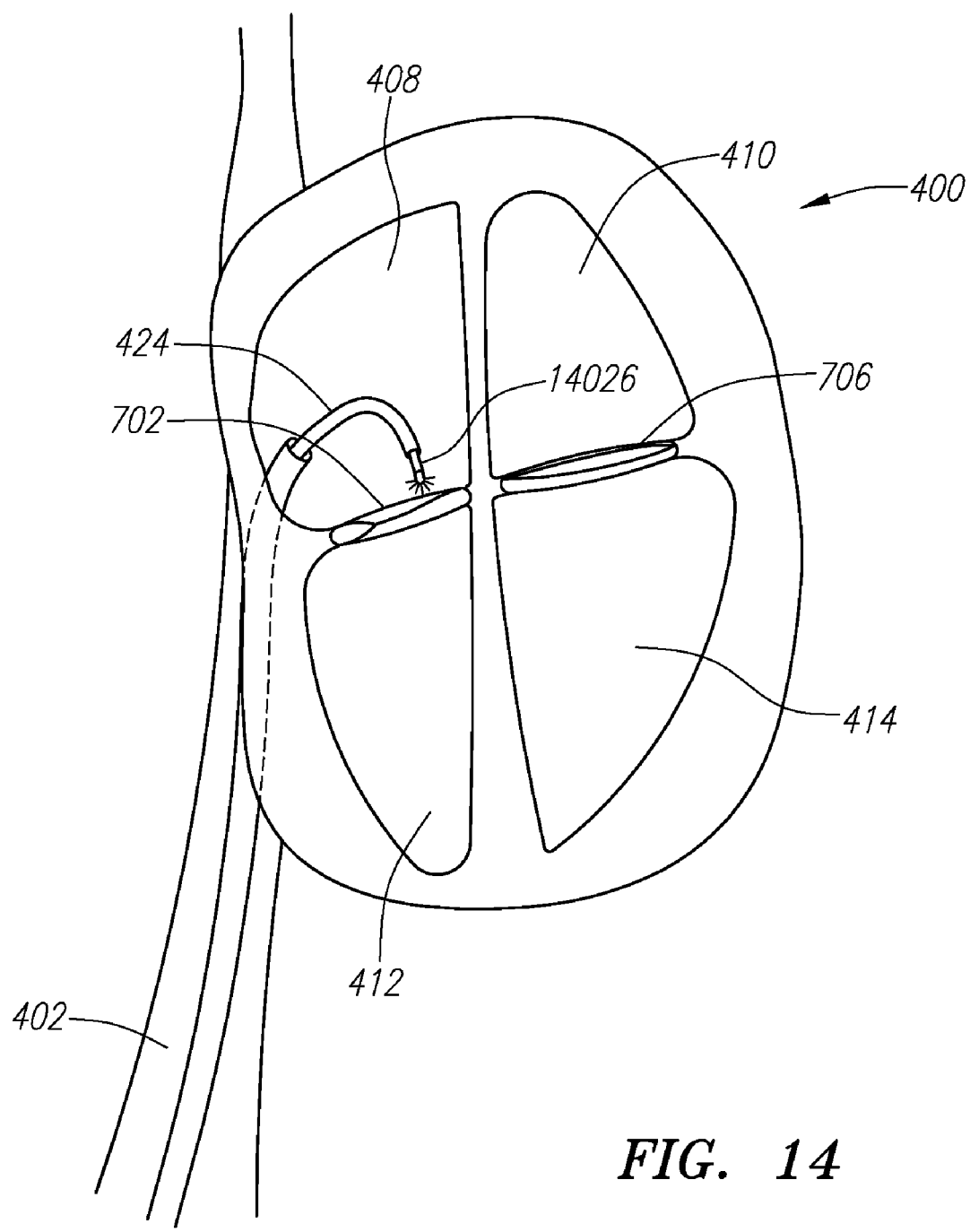
FIG. 14 illustrates an instrument assembly with an ablation tool being used to perform valve repair.

FIG. 14 depicts an ablation tool (14026), similar to the description and procedure as described above, modifying the geometry of the tricuspid valve (702). The configurations of tools similar to those as illustrated in FIGS. 13A-13G may be utilized on the tricuspid valve (702).

Figure 15A:
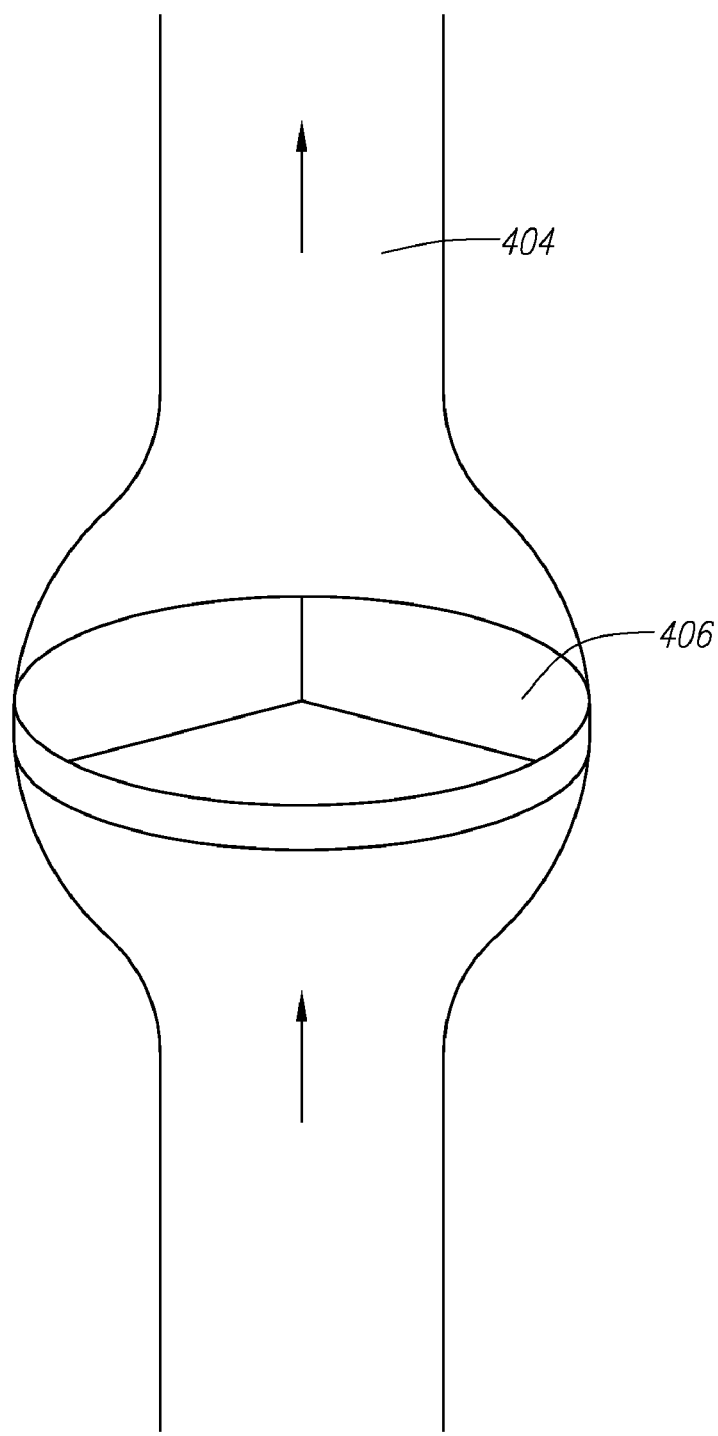
FIG. 15A through FIG. 15D illustrate a retrograde method to deploy an expandable aortic valve prosthetic to repair an aortic valve.
Figure 15B:
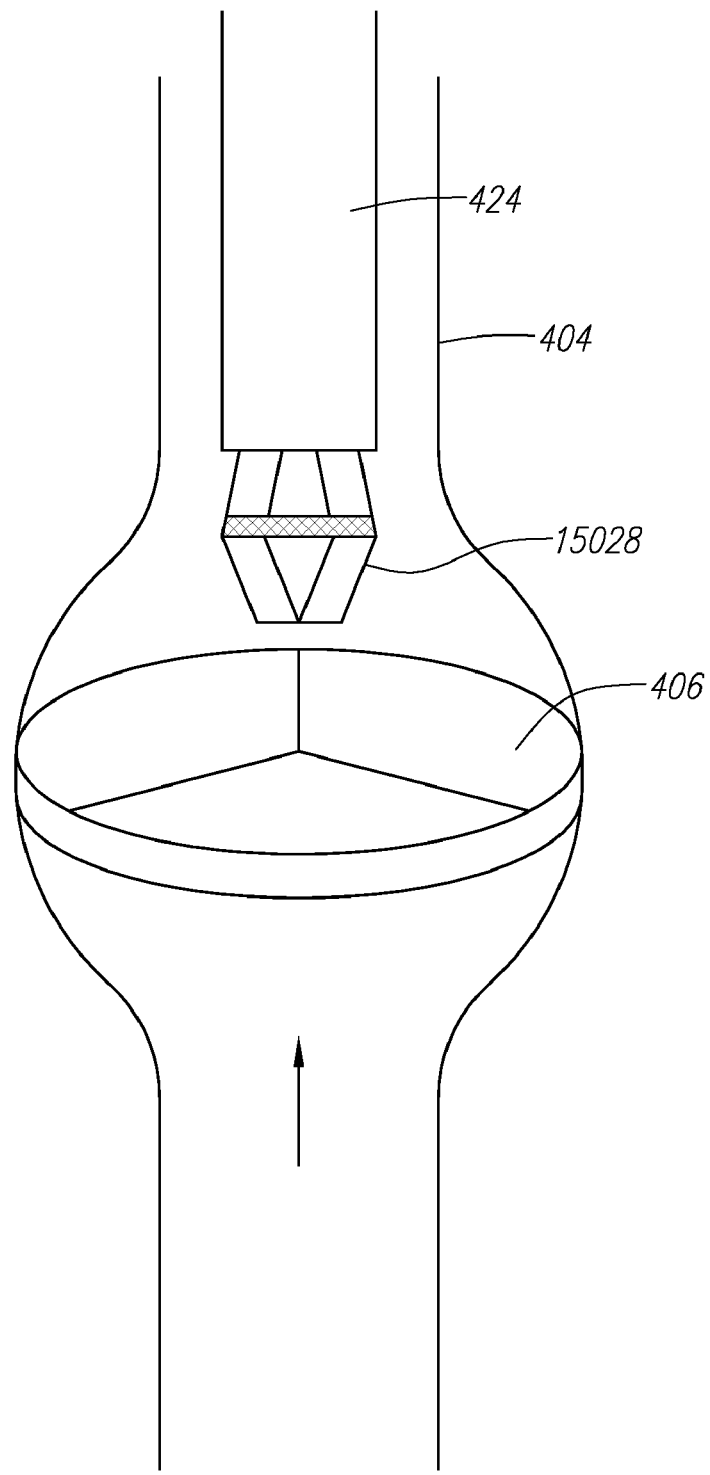
Figure 15C:
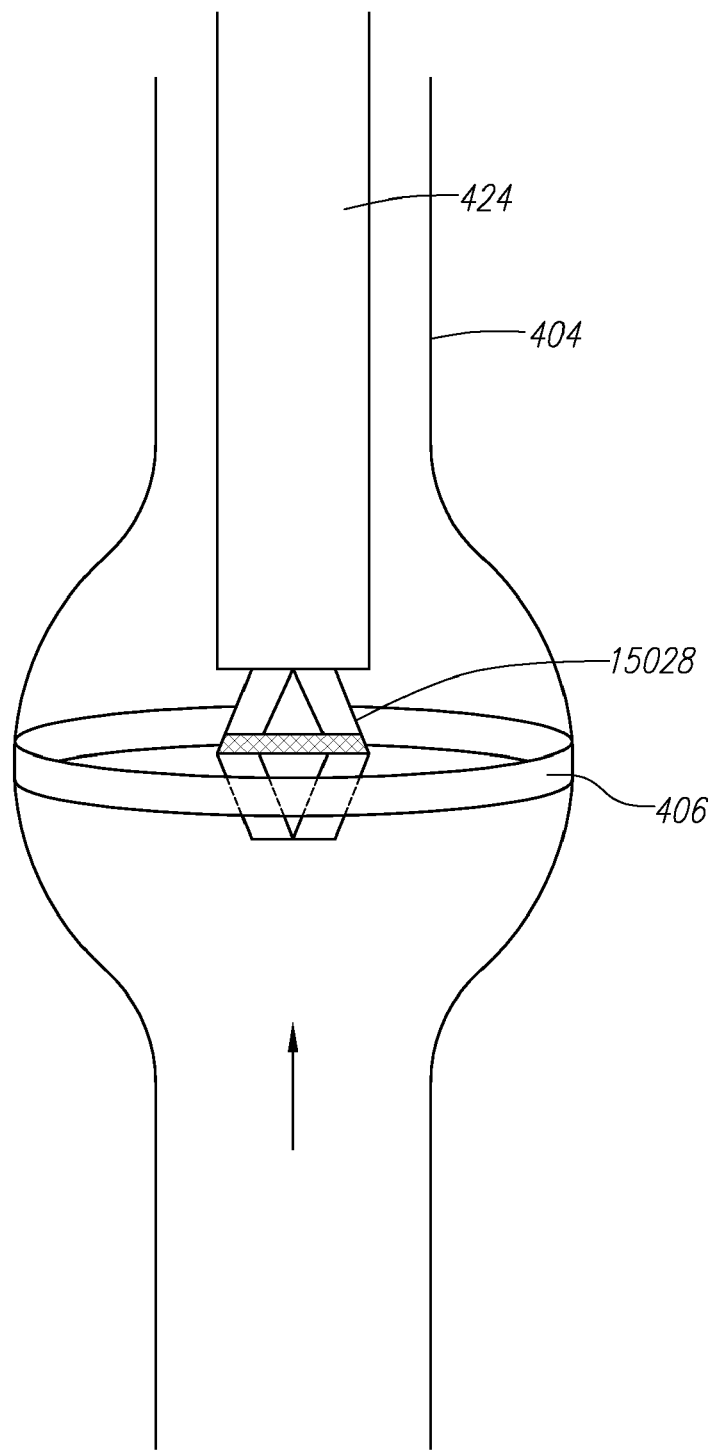
Figure 15D:
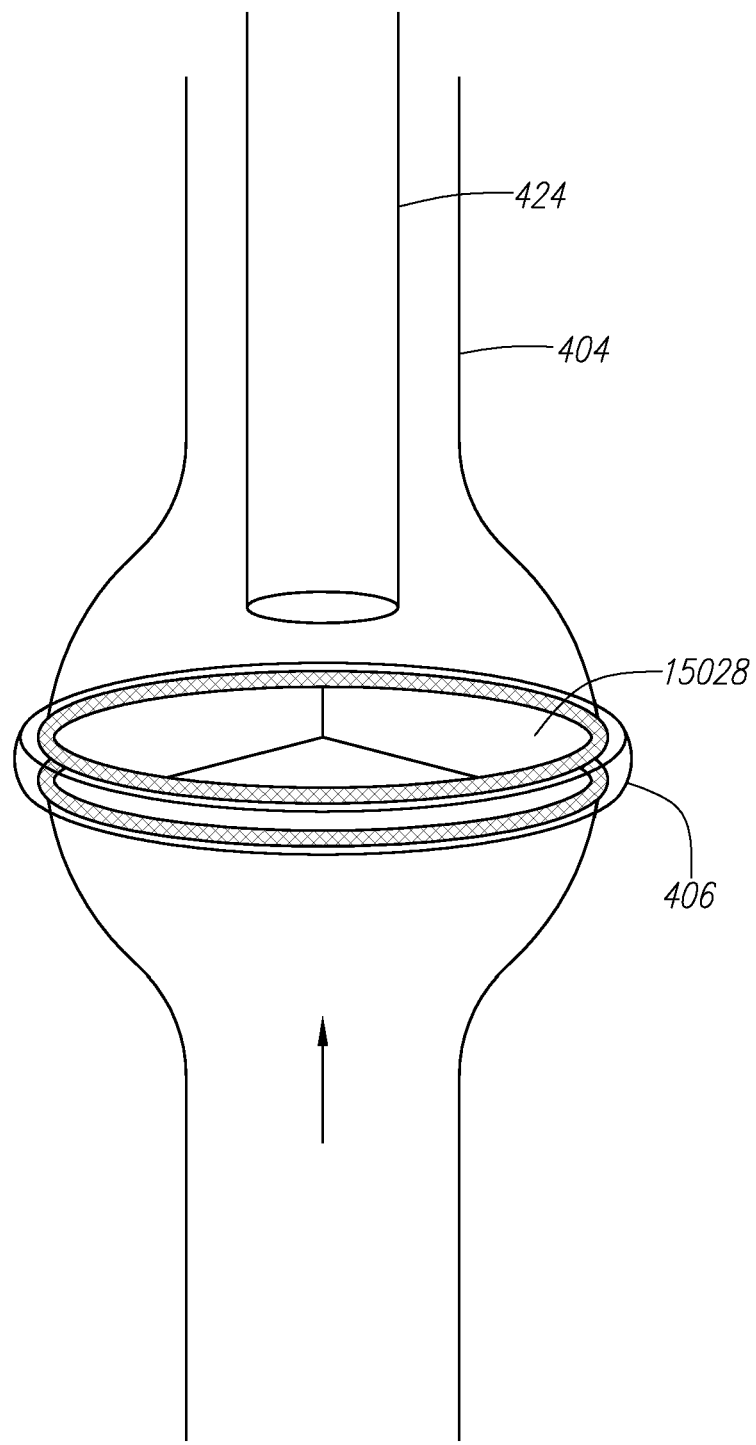
Figure 15E:
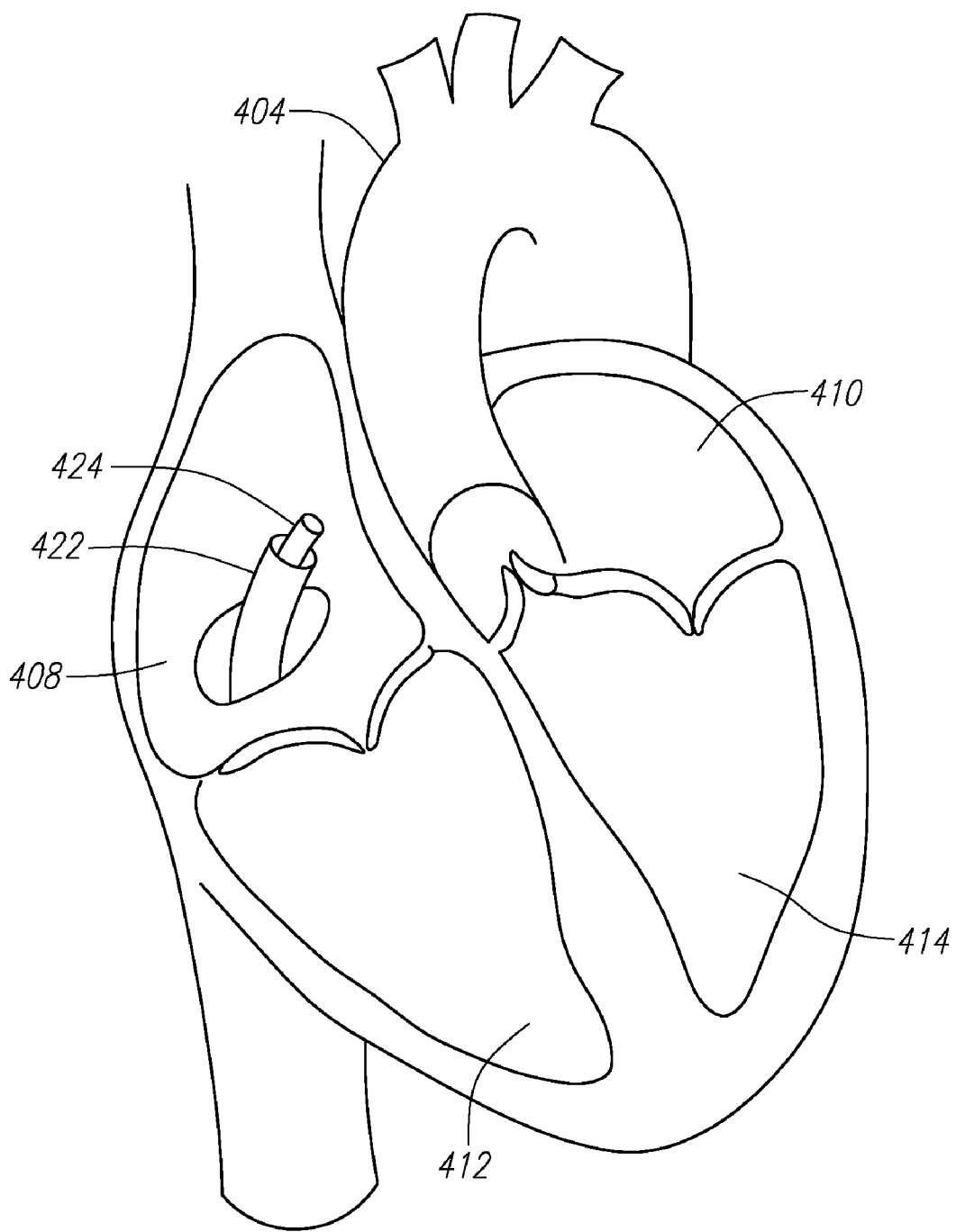
FIG. 15E through FIG. 15J illustrate a method of deploying an expandable valve prosthetic by way of the inferior vena cava through the septum and the mitral valve to the aortic valve.
Figure 15F:
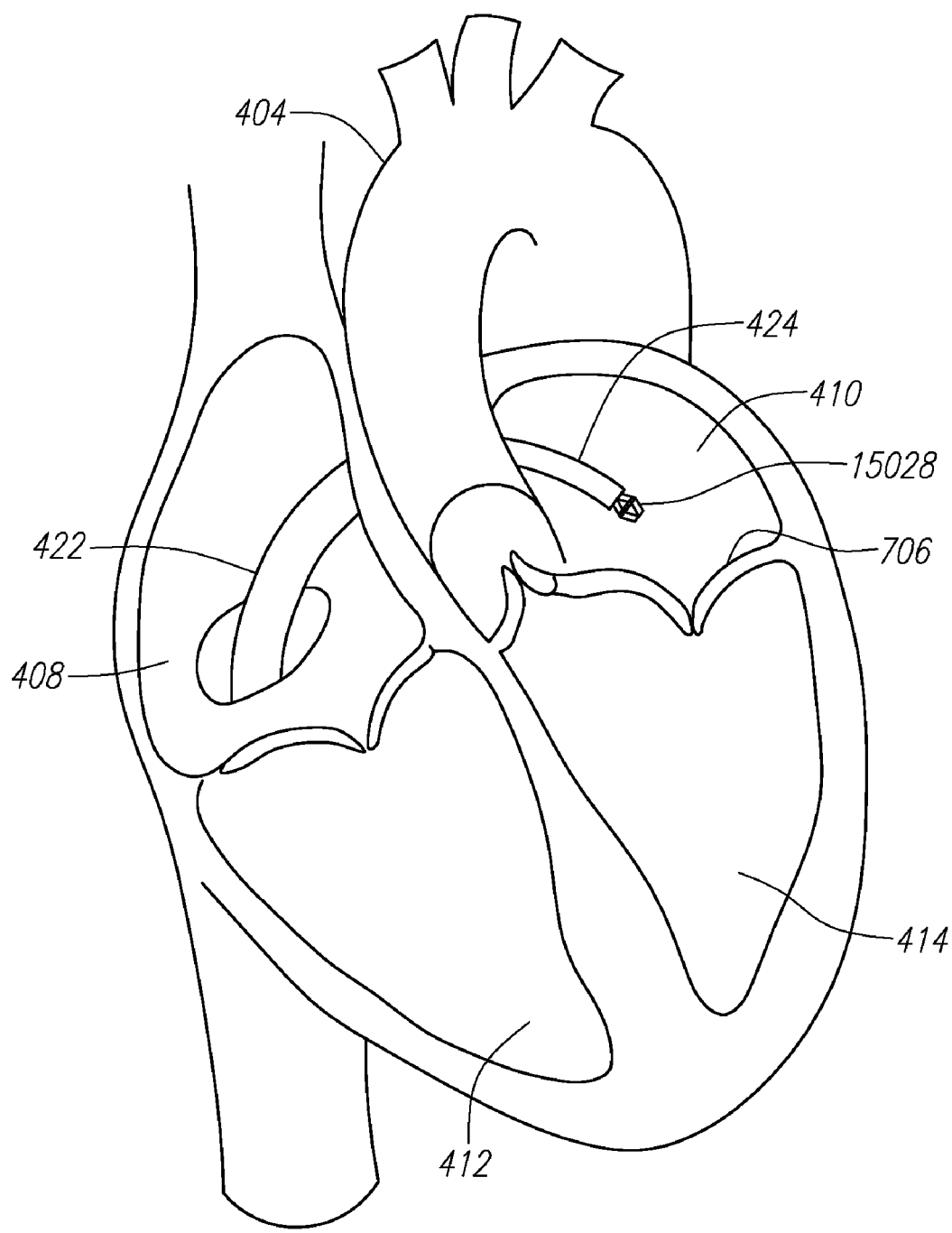
Figure 15G:
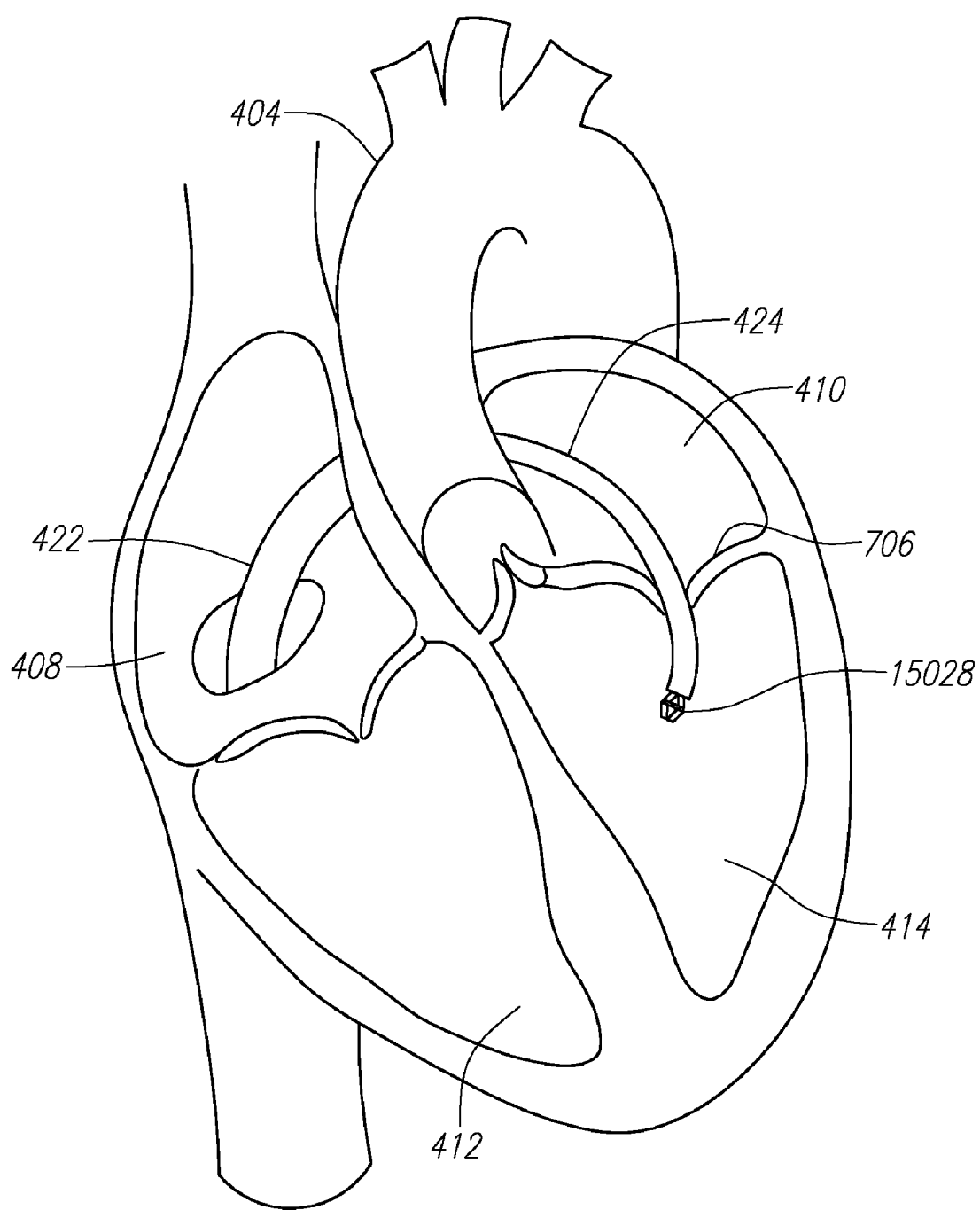
Figure 15H:
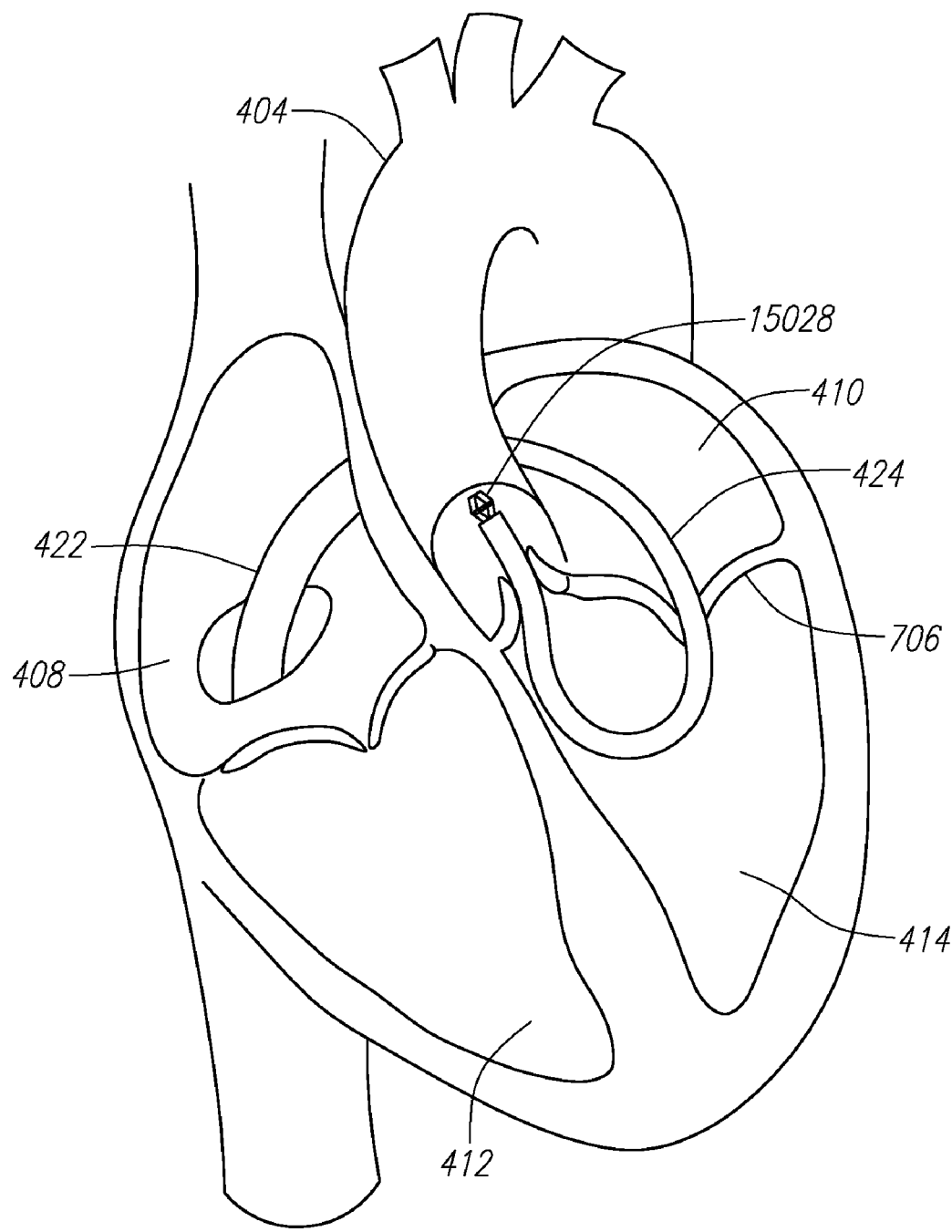
Figure 15I:
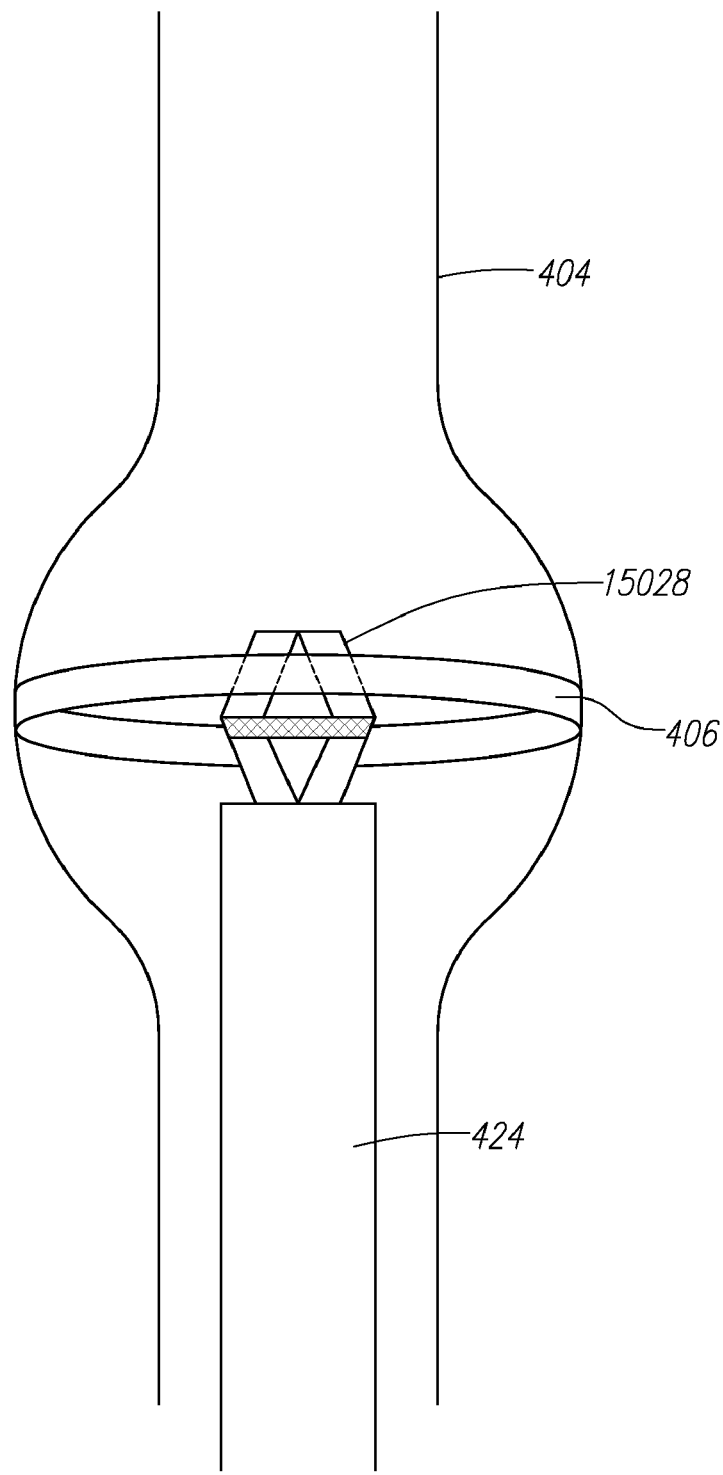
Figure 15J:
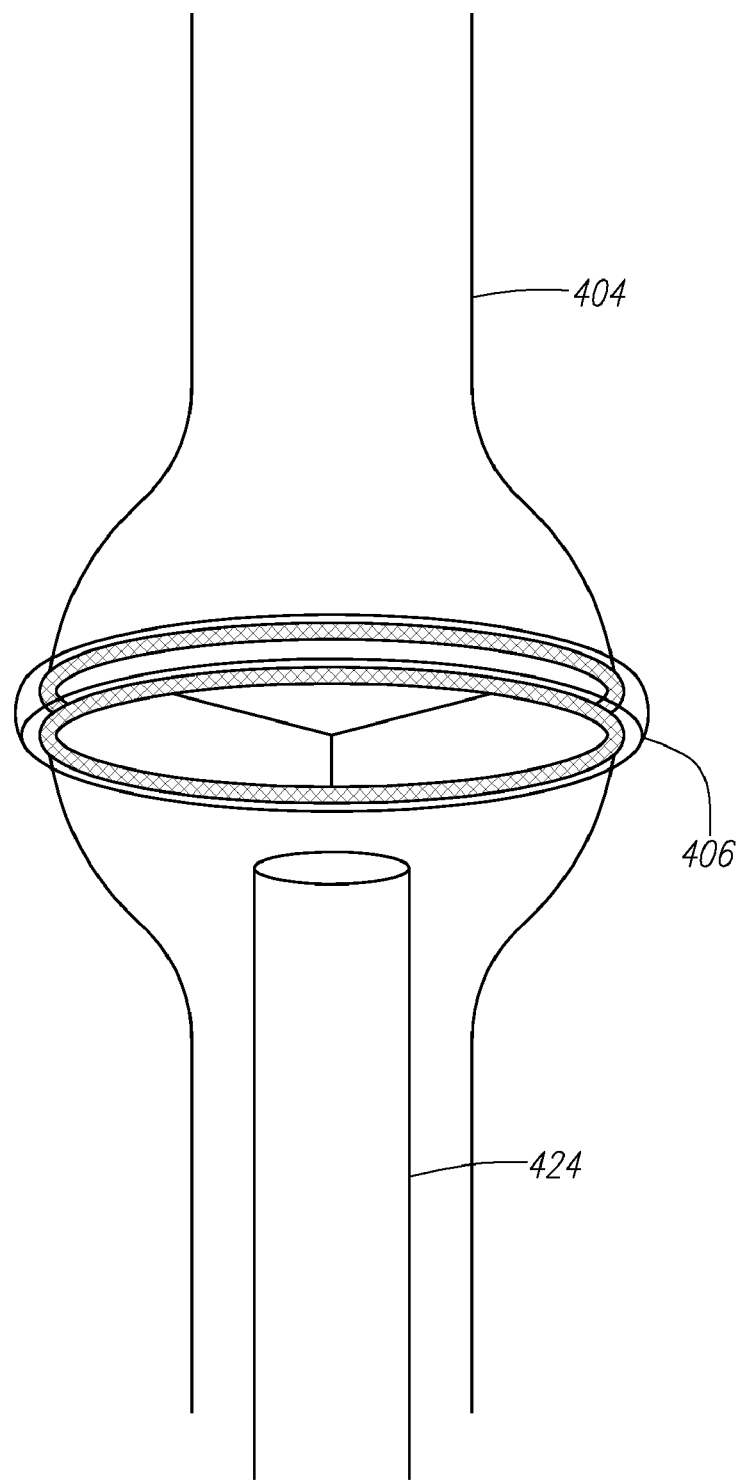
Figure 15K:
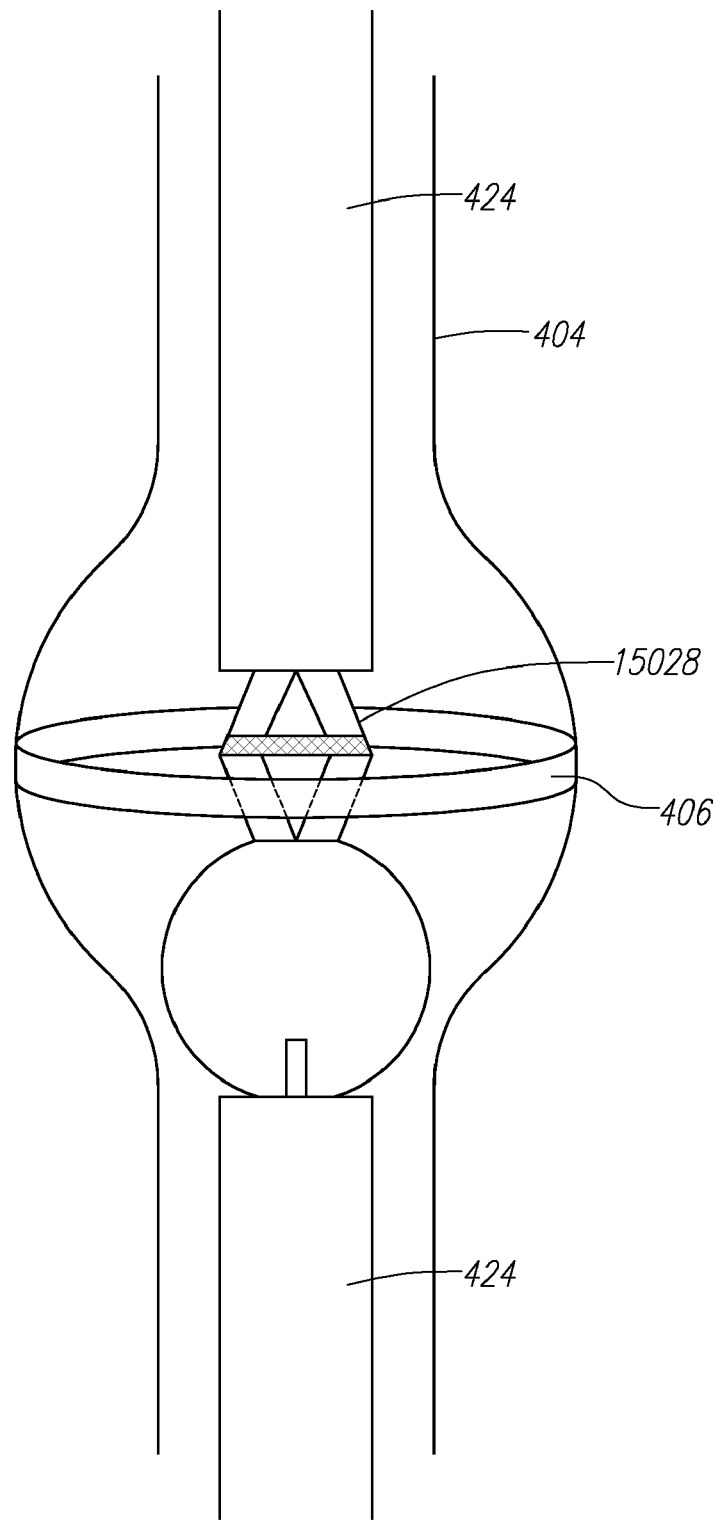
FIG. 15K illustrates a two-handed approach to deploy an expandable valve prosthetic.

FIG. 15A through FIG. 5D depict a robotic instrument assembly (108) using a retrograde approach to deploy an expandable aortic valve prosthetic (15028). Alternatively, FIG. 15E through FIG. 15J illustrate a robotic instrument assembly (108) being used by way of the inferior vena cava through the septum and the mitral valve, and then going up the aorta to deploy an expandable aortic valve prosthetic (15028) in the aorta. The methods as described may be referred a "single-handed" approach. That is, the expandable aortic valve prosthetic (15028) may be deployed by the method as illustrated in FIGS. 15A through 15D or the method as illustrated in FIG. 15E through FIG. 15J using one instrument assembly (108). Alternatively, the expandable aortic valve prosthetic (15028) may be deployed using a "two-handed" approach. That is, the expandable aortic valve prosthetic may be deployed using two robotic instrument assemblies (108). For example, a first instrument assembly (108) may be used to position or adjust the placement of the aortic valve prosthetic (15028) while a second instrument assembly (108) may be used to place the aortic valve prosthetic. FIG. 15K, illustrates one embodiment of a two-handed approach. As illustrated in FIG. 15K, an expandable valve prosthetic (15028) is being deployed by a first instrument assembly (108-422, 424) using a retrograde approach as illustrated in FIG. 15A through FIG. 15D. At the same time, a second instrument assembly (108-422, 424) with a positioning apparatus (e.g., a balloon with a scope, etc.) approaches the aortic valve (406) from different direction of deployment for the valve prosthetic (15028), such that the positioning apparatus assists with the placement or positioning of the prosthetic (15028) as it is being deployed.

Figure 16:
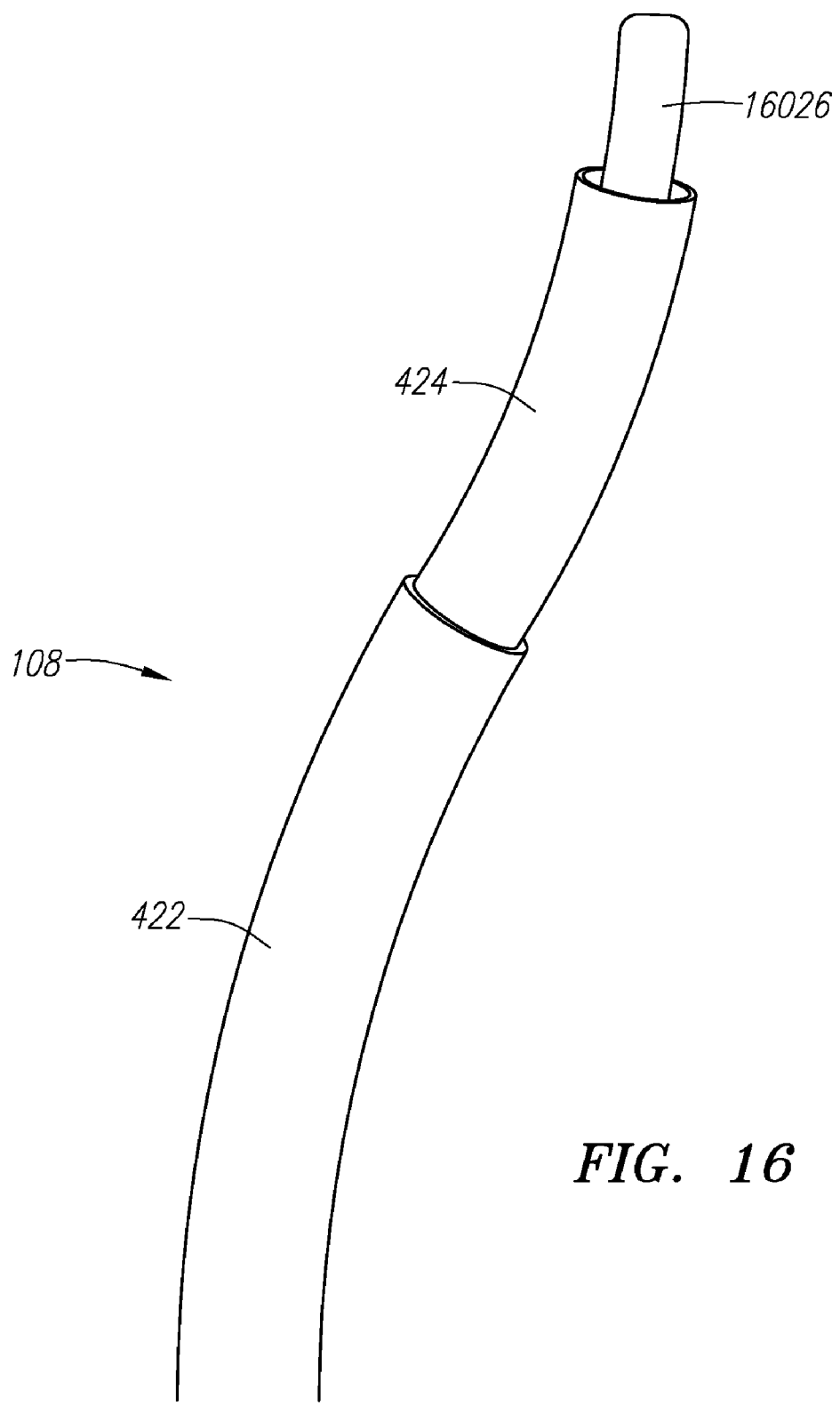
FIG. 16 illustrates an instrument assembly with a lithotripsy laser fiber for performing lithotripsy procedures.

In addition, the robotic surgical system (100) including the control station (102), instrument driver (106), instrument (108), and the wired connection (112) may be used to treat other diseases, maladies, or conditions in the tissues or organs of the digestive system, colon, urinary system, reproductive system, etc. For example, the robotic surgical system (100) may be used to perform Extracorporeal Shock Wave Lithotripsy (ESWL). FIG. 16 illustrates one embodiment of instrument (108) configured to perform ESWL. As illustrated in FIG. 16, instrument (108) may include a sheath catheter (422), a guide catheter (424), and a lithotripsy laser fiber (16026). Analogous to the discussion above, components or subsystems of the instrument (108) may be guided, manipulated, or navigated to the kidney to perform various operations. For example, subsystems of the instrument (108) may be guided, manipulated, or navigated to the kidney to remove kidney stones as oppose to similar components or subsystems of embodiments of the instrument (108), e.g., an ablation catheter, being guided, manipulated, or navigated to the left atrium of the heart to performing cardiac ablation to address cardiac arrhythmias. The lithotripsy laser fiber (16026) may include a quartz fiber coupled, connected to, or associated with a laser, such as a Holmium YAG laser, to apply energy to objects such as kidney stones, etc. In one configuration, the laser source may be positioned and interfaced with the fiber (16026) proximally, as in a typical lithotripsy configuration, with the exception that in the subject embodiment, the fiber (1602) is positioned down the working lumen of one or more robotic catheters (e.g., sheath catheter (422) and guide catheter (424)). All the necessary power source and control mechanisms including hardware and software to operate the laser may be located in the electronics rack (114) near the operator control station (102) of the robotic surgical system (100)

Since the distal tip of the lithotripsy fiber (16026) is configured to deliver energy to a target object, such as a kidney stone, the distal tip may be more generically described as an energy source. Indeed, in other embodiments, other energy sources, besides a laser, may be used to affect tissue. For example, in other embodiments, the energy source may be comprised of an RF electrode, an ultrasonic transducer, such as a high-frequency ultrasonic transducer, or other radiative, conductive, ablative, or convective energy source.

As may appreciated, the components or subsystems of instrument (108) may be configured with numerous different instruments or tool for performing various minimally invasive operations. For example, FIG. 17 depicts a guide instrument (424) operatively coupled to a grasper (17026) fitted with an energy source (17036), such as a lithotripsy laser fiber (16026) in a configuration wherein an object, such as a kidney stone, grasped within the clutches of the grasper (17026), may also be ablated, destroyed, fragmented, etc, by applied energy from the source (17036), which is positioned to terminate approximately at the apex of the grasper (17026) which it is likely to be adjacent to captured objects.

FIG. 18 depicts a similar configuration as the instrument assembly (108) including the sheath (422) and guide (424) that is illustrated in FIG. 17. FIG. 18 illustrates a basket tool (18026) and energy source (17036), such as a lithotripsy fiber (16026), positioned through the working lumen of the guide instrument (424). In each of the configurations depicted in FIG. 17 and FIG. 18, the energy source (17036) may be coupled to the pertinent capture device, or may be independently positioned through the working lumen of the guide instrument (424) to the desired location adjacent the capture device (17026, 18026). Each of the tools described herein, such as graspers, baskets, and energy sources, may be controlled proximally as they exit the proximal end of the working lumen defined by the guide instrument (424), or they may be actuated manually, automatically or electromechanically, for example through the use of electric motors and/or mechanical advantage devices. For example, in one embodiment, a configuration such as that depicted in FIG. 18, the sheath (422) and guide (424) instruments are preferably electromechanically operated utilizing an instrument driver (106) (not shown in these two figures) such as that described in the U.S. patent application Ser. No. 11/481,433, which is incorporated herein by reference in their entirety. The grasping mechanisms (17026, 18026) may be manually actuated, for example utilizing a positioning rod and tension wire, or electromechanically operated using a servomechanism or other proximal actuation devices. The energy source (17036) may be operated proximally utilizing a switch, such as a foot pedal or console switch, which is associated with the proximal energy control device (not shown in FIGS. 17 and 18).

Figure 19:
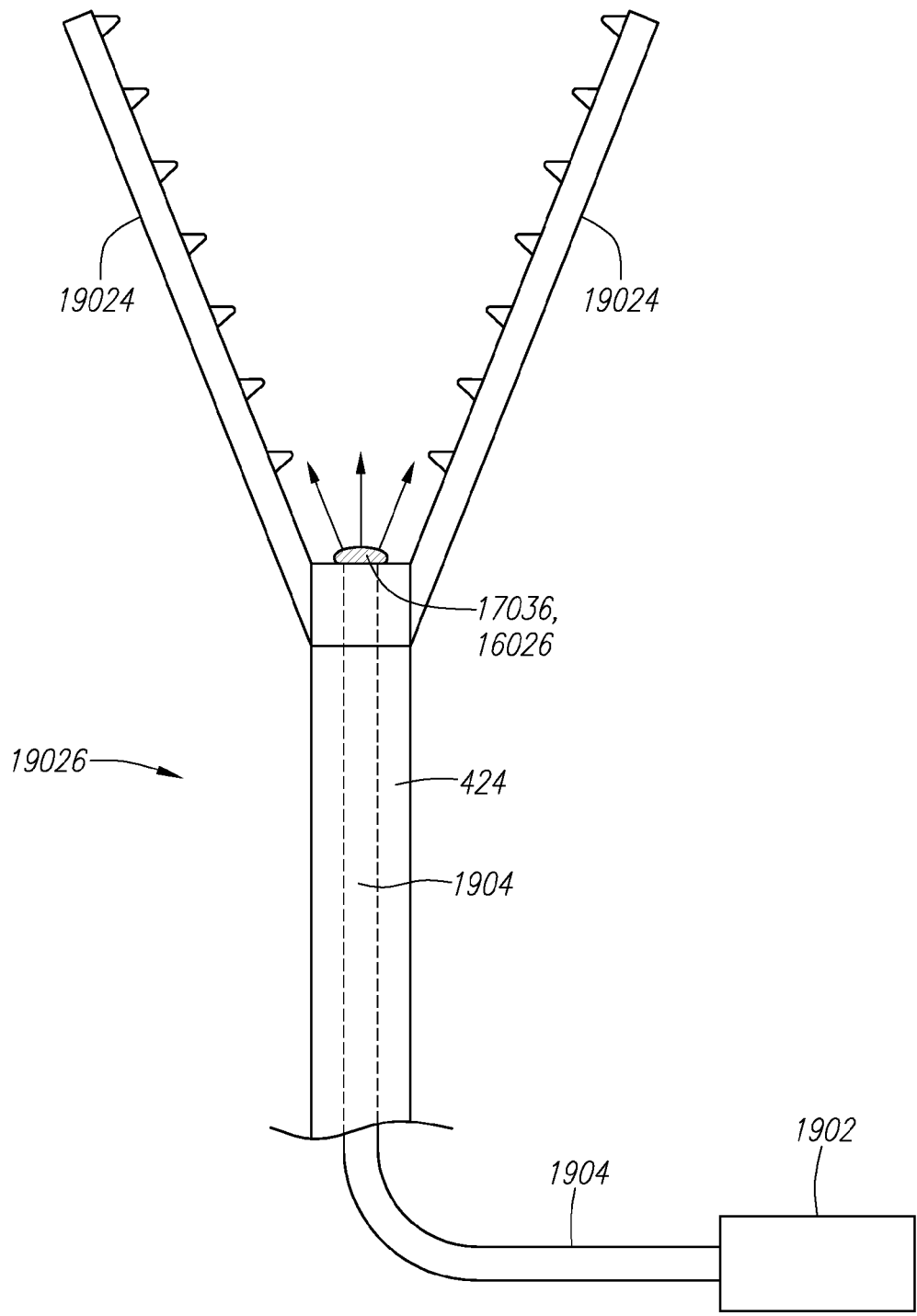
FIG. 19 illustrates an expandable grasping tool assembly including an energy source.

FIG. 19 depicts an expandable grasping tool assembly (19026) with an energy source (17036, 16026) mounted at the apex of the grasper mechanism. The energy source (17036, 16026) is proximally associated, by one or more transmission leads (1904), such as a fiber or wire, with a device (1902) such as an RF generator or laser energy source. The opposing jaws (19024) of the depicted grasping tool assembly (19026) are biased to spring outward, thus opening the grasper when unbiased. When pulled proximally into a confining structure, such as a lumen of a guide instrument (424), the hoop stress applied by the confining structure urges the jaws (19024) together, creating a powerful grasping action.

Figure 20:
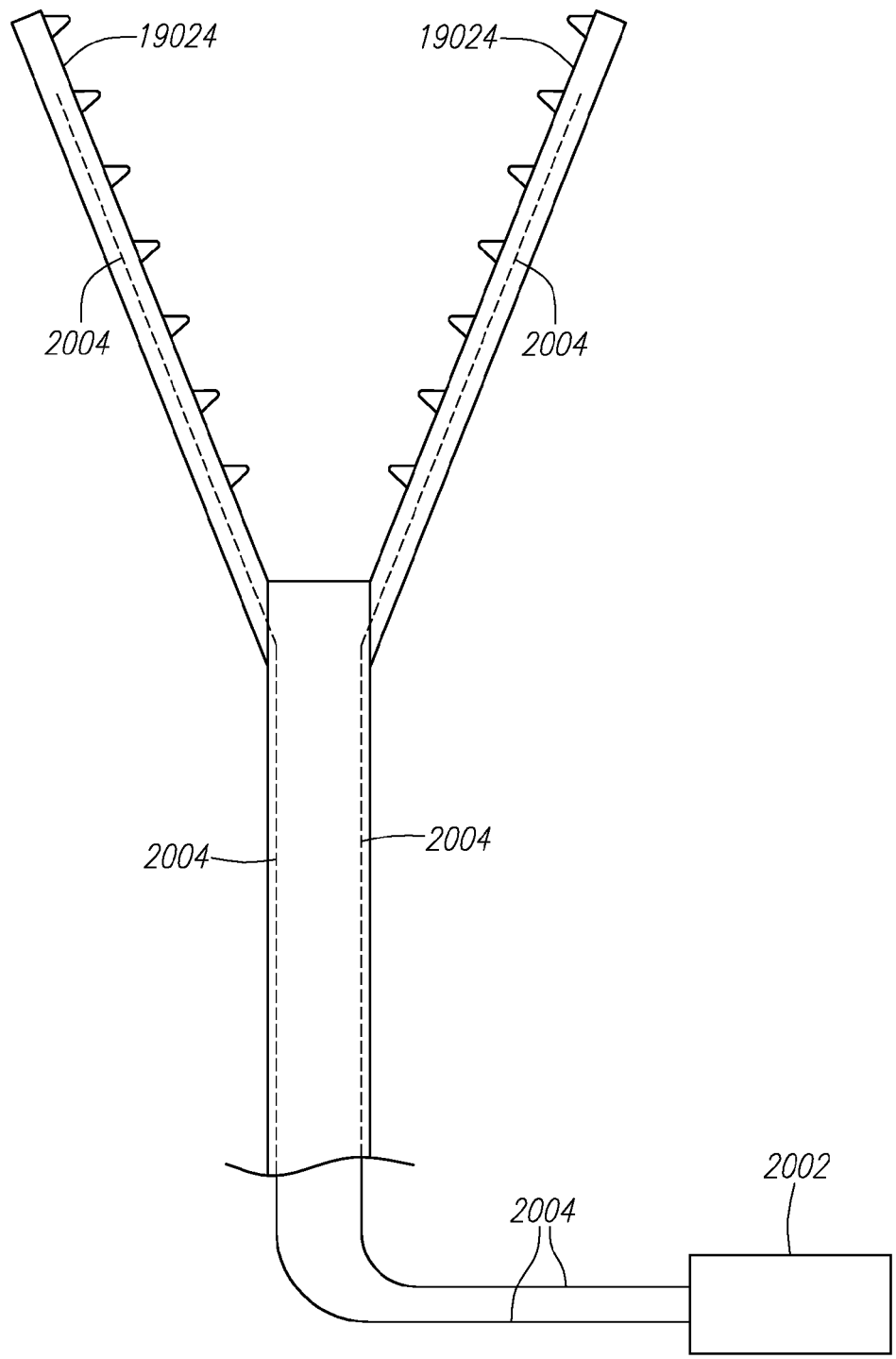
FIG. 20 illustrates a bipolar electrode grasper assembly.
Figure 21:
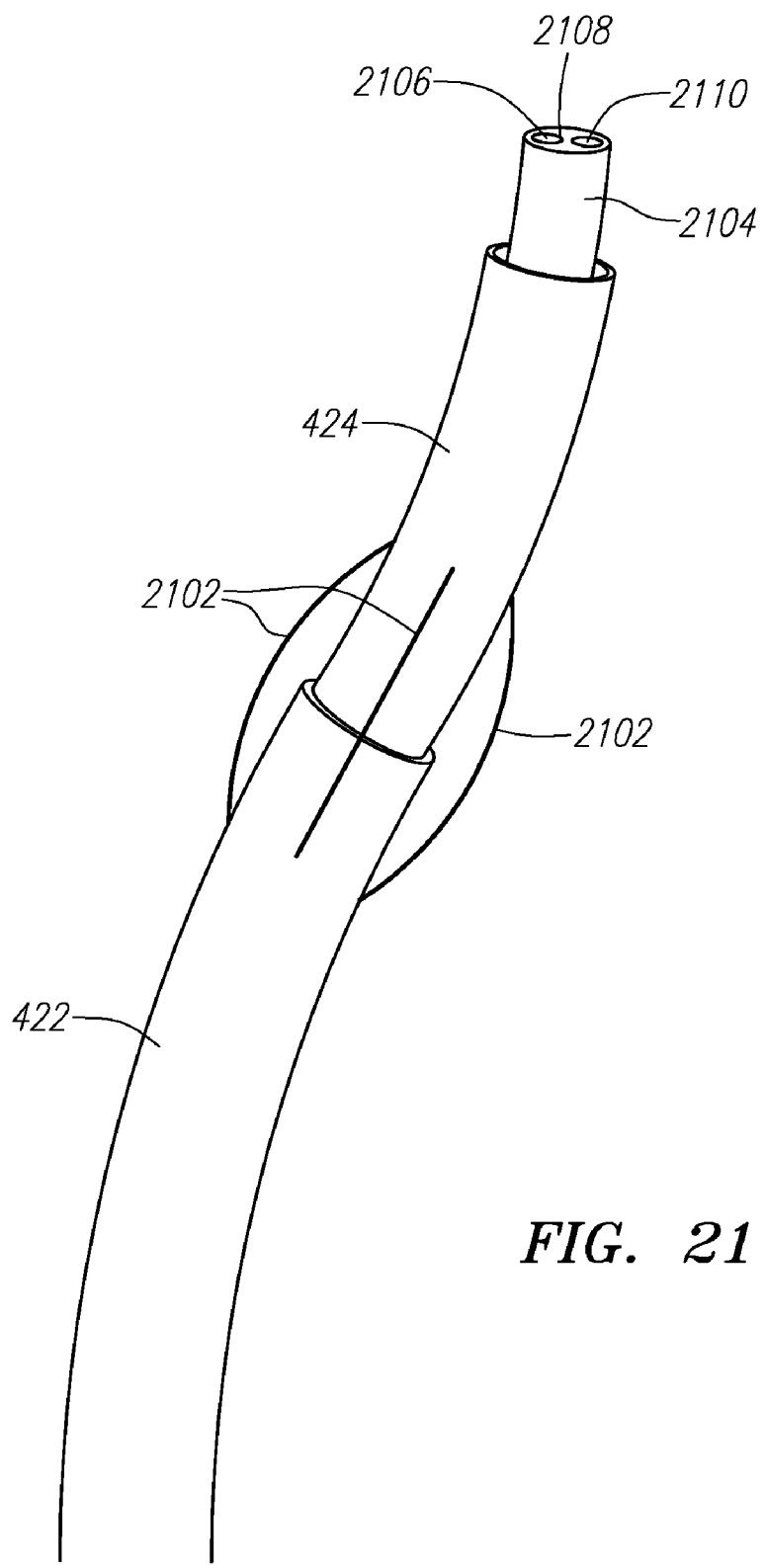
FIG. 21 illustrates an instrument assembly configured with basket arms.

FIG. 20 depicts a bipolar electrode grasper with a proximally associated RF generator or other energy source (2002). In this embodiment, each of the jaws (19024) is biased to swing outward, as in the embodiment depicted in FIG. 19, and each of the jaws (19024) also serves as an electrode for the bipolar pairing, to be able to apply energy to items or objects which may be grasped. Leads (2004) are depicted to couple the jaws (19024) with a proximally positioned energy source (2002), such as an RF generator FIG. 21 depicts a sheath instrument (422) coupled to a group of basket arms (2102) that are biased to bend inward (i.e., toward the longitudinal axis of the sheath/guide as depicted), and configured to grasp a stone or other object as the guide instrument (424) is withdrawn proximally into the sheath instrument (422). The depicted embodiment features an image capture device (2104) which may or may not have a lens (2106), illumination fibers (2108) to radiate light, infrared radiation, or other radiation, and a working lumen (2110) for positioning tools distally. The image capture device (2104), which may comprise a fiberscope, CCD chip, infrared imaging device, such as those available from CardioOptics Incorporated, ultrasound device, or other image capture device, may be used, for example, to search for objects such as stones, and when located, the guide instrument (424) may be withdrawn into the sheath instrument (422) to capture the object, which the entire assembly is gently advanced to ensure that the object remains close to the distal tip of the assembly for easy capture by the basket device (2102)

Figure 22:
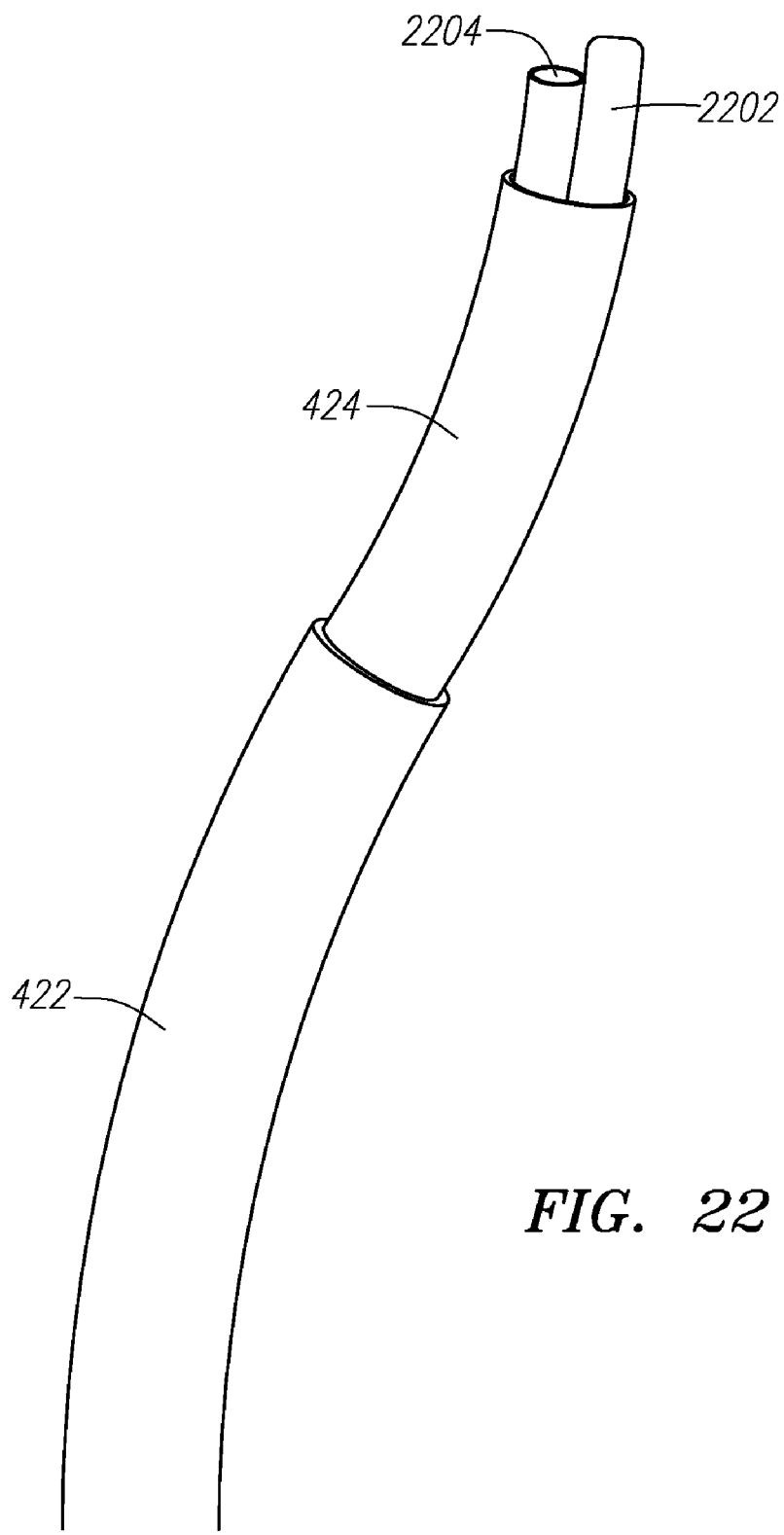
FIG. 22 illustrates an instrument assembly including a lithotripsy fiber and image capture device.

FIG. 22 depicts an assembly comprising a lithotripsy fiber (2202) and image capture device (2204) configured to enable the operator to see and direct the laser fiber (2202) to targeted structures, utilizing, for example, the high-precision navigability of the subject sheath (422) and guide (424) instrument assembly (108), and apply energy such as laser energy to destroy or break up such structures. Preferably the image capture device (2204) is positioned to include the position at which the energy source (such as a lithotripsy fiber 2202) as part of the field of view of the image capture device (2204)—i.e., to ensure that the operator can utilized the field of view to attempt to bring the energy source into contact with the desired structures.

Figure 23:
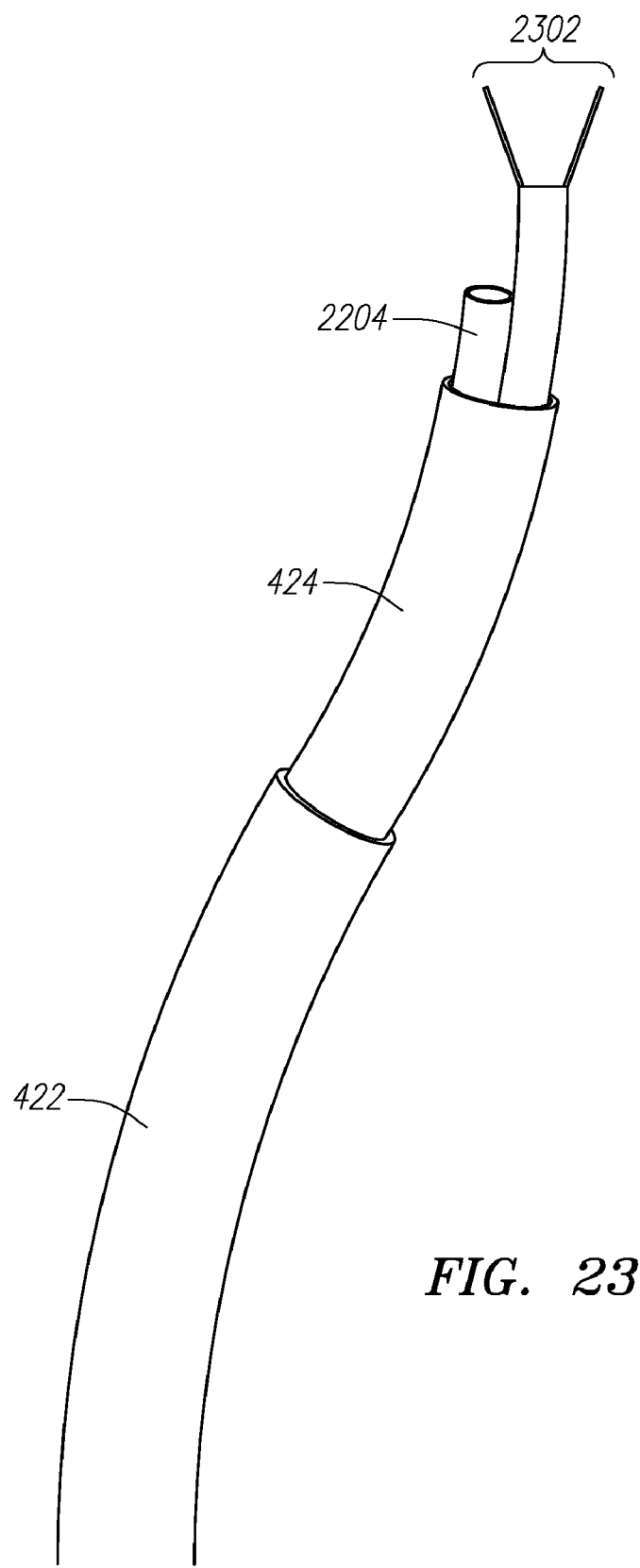
FIG. 23 illustrates an instrument assembly including a grasping tool.

FIG. 23 depicts a similar embodiment as the one shown in FIG. 22, which includes a grasping tool (2302) to grasp a stone or other object and bring it proximally toward the image capture device (2204), such that it may be examined, removed proximally through the working lumen of the guide instrument (424), etc.

Figure 24:
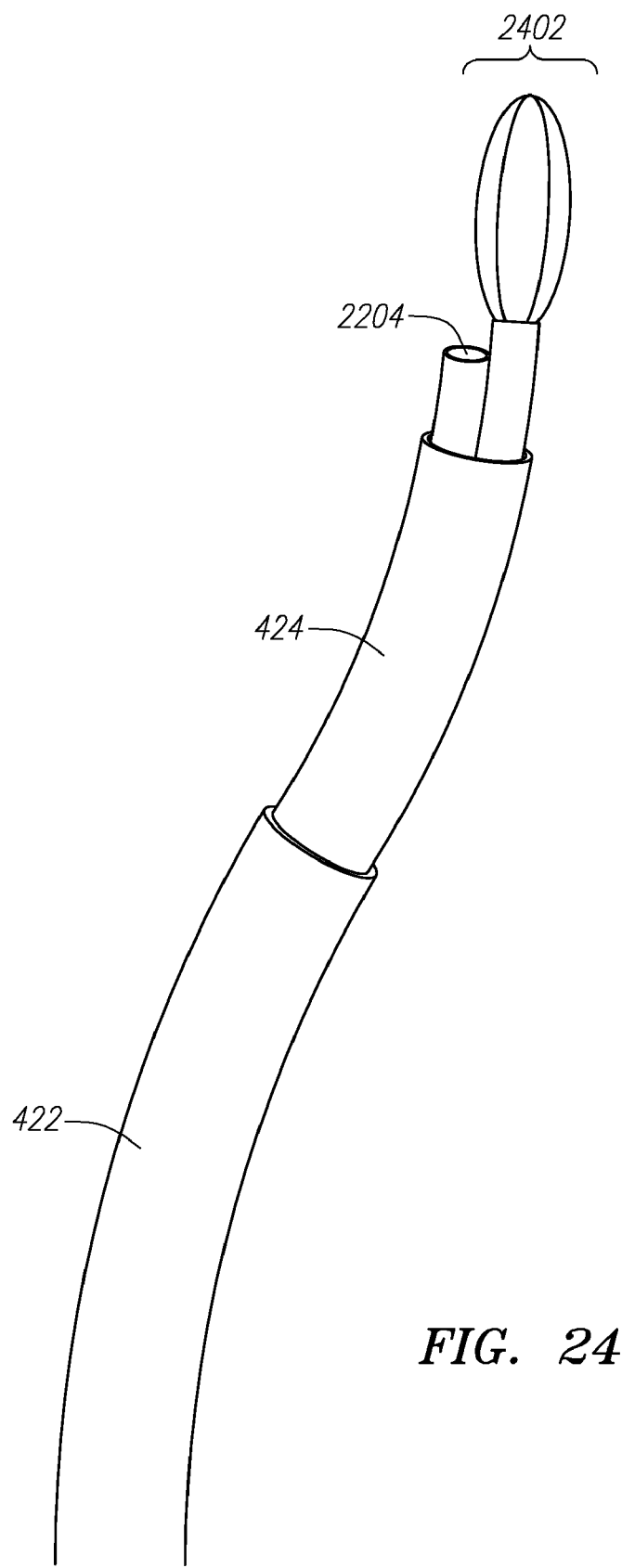
FIG. 24 illustrates an instrument assembly including a basket tool apparatus.
Figure 25:
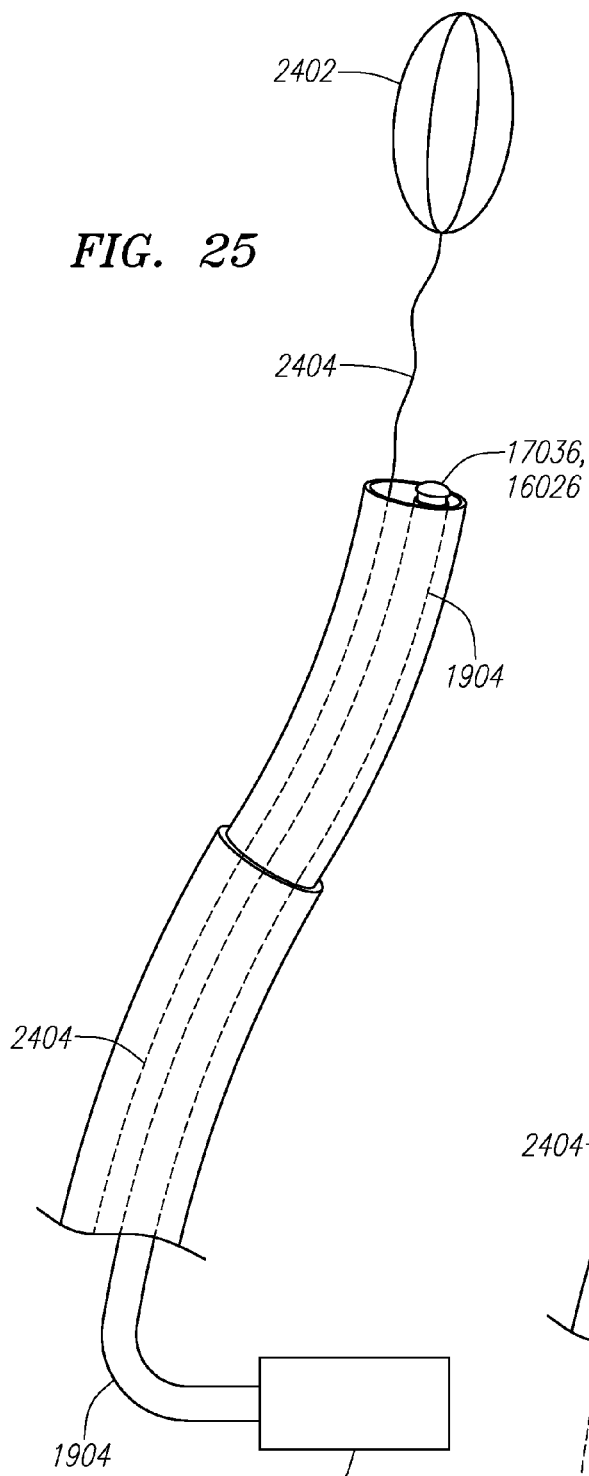
FIG. 25 and FIG. 26 respectively illustrates an operation of an instrument assembly with a basket tool apparatus.
Figure 26:
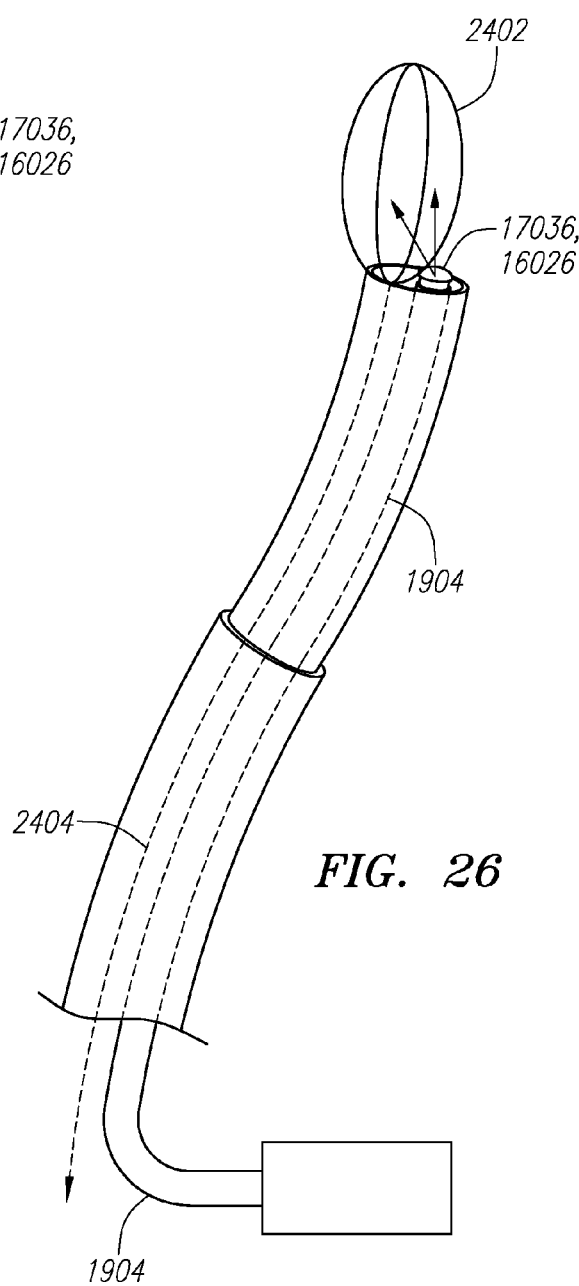

FIG. 24 illustrates another similar embodiment, which includes a basket tool (2402). FIG. 25 and FIG. 26, illustrate how an embodiment such as one depicted in FIG. 24 may be used to grasp and retrieve stones or other objects toward the distal portion of the guide (424). As the retrieved object approaches the guide (424), energy source (17036, 16026) breaks up the object in the basket tool (2402); this operation is similar to the operation in the embodiment illustrated in FIG. 18.

Figure 27:
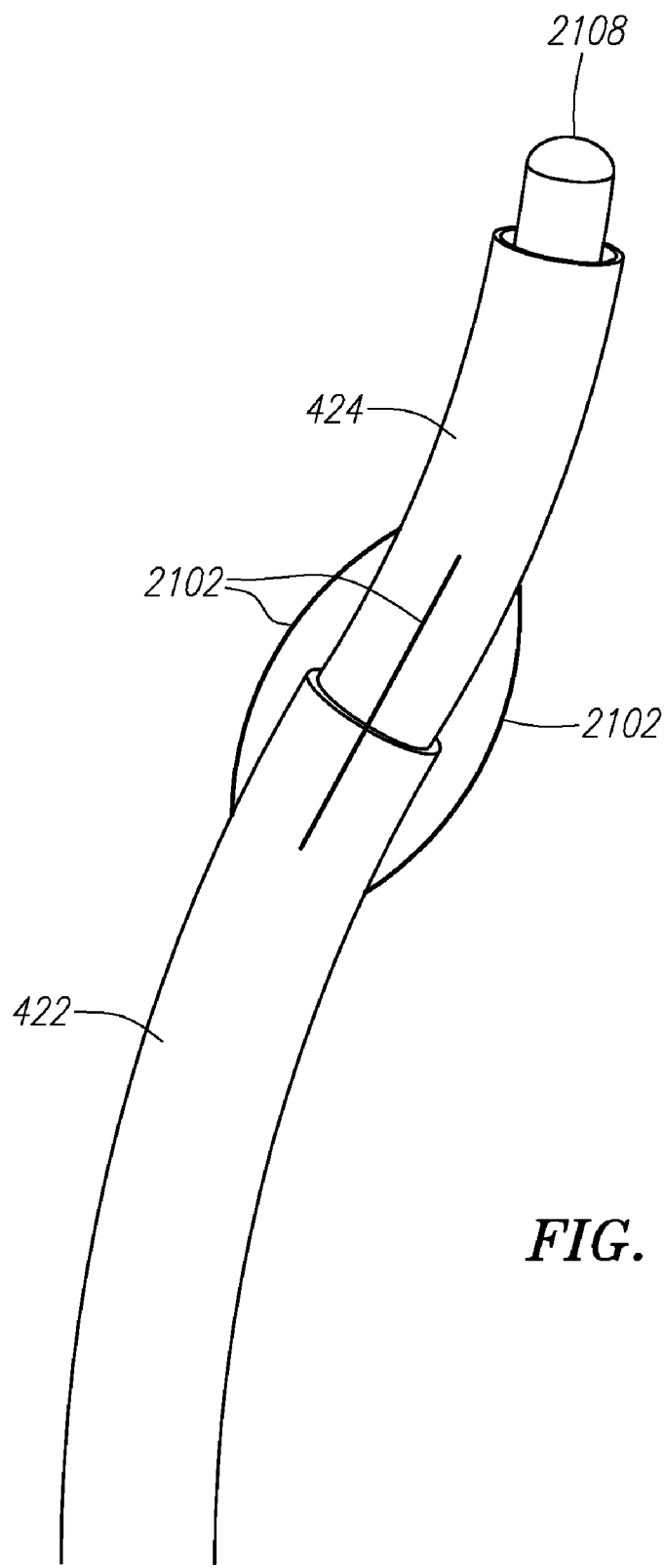
FIG. 27 illustrates an instrument assembly including a basket arm capture device and image capture device.

FIG. 27 depicts an embodiment with a proximal basket arm capture (2102) and an image capture device (2108). As described above in the portion of the description describing FIG. 21, when an object is observed with the image capture device (2108), the entire assembly may be advanced while the guide instrument (424) is withdrawn proximally into the sheath instrument (422) until the depicted basket capture arms (2102) are able to rotate toward the central axis of the guide instrument (424) working lumen and capture objects positioned adjacent the distal tip of the guide instrument (424)

Figure 28:
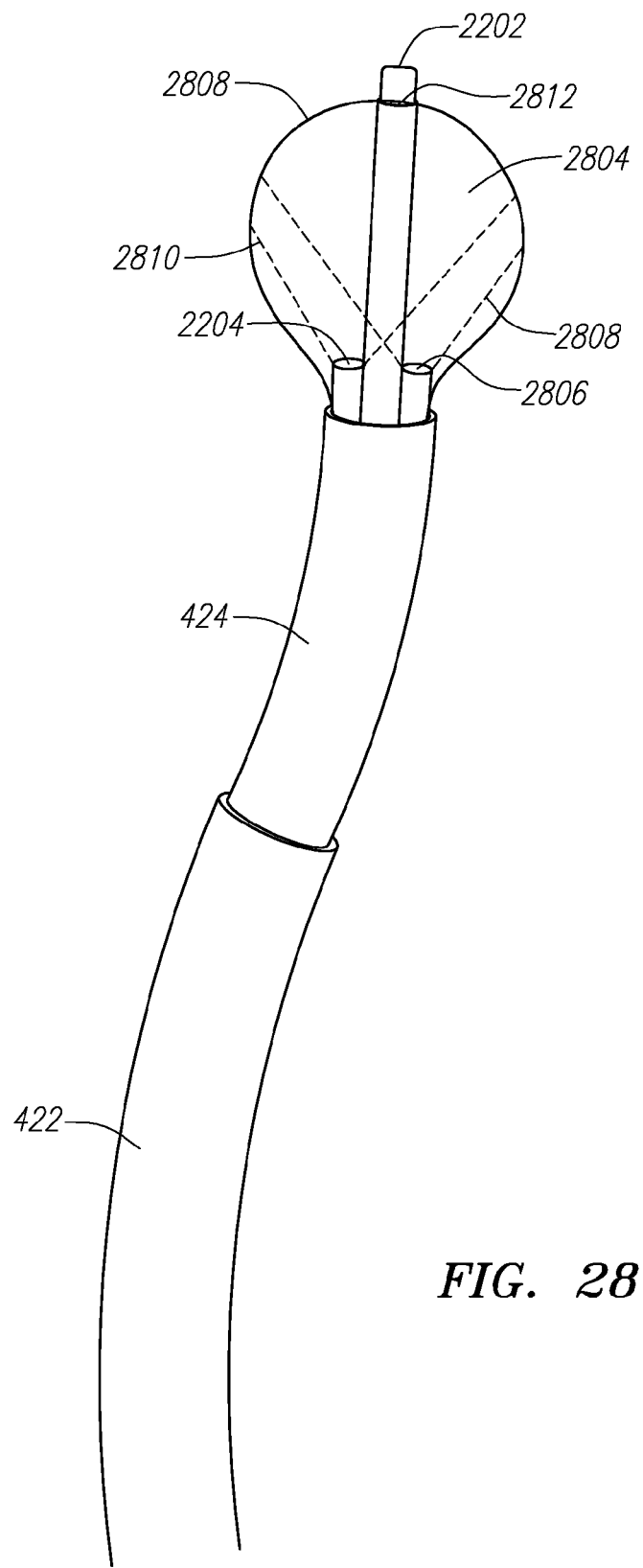
FIG. 28 illustrates an instrument assembly including a balloon apparatus.
Figure 29:
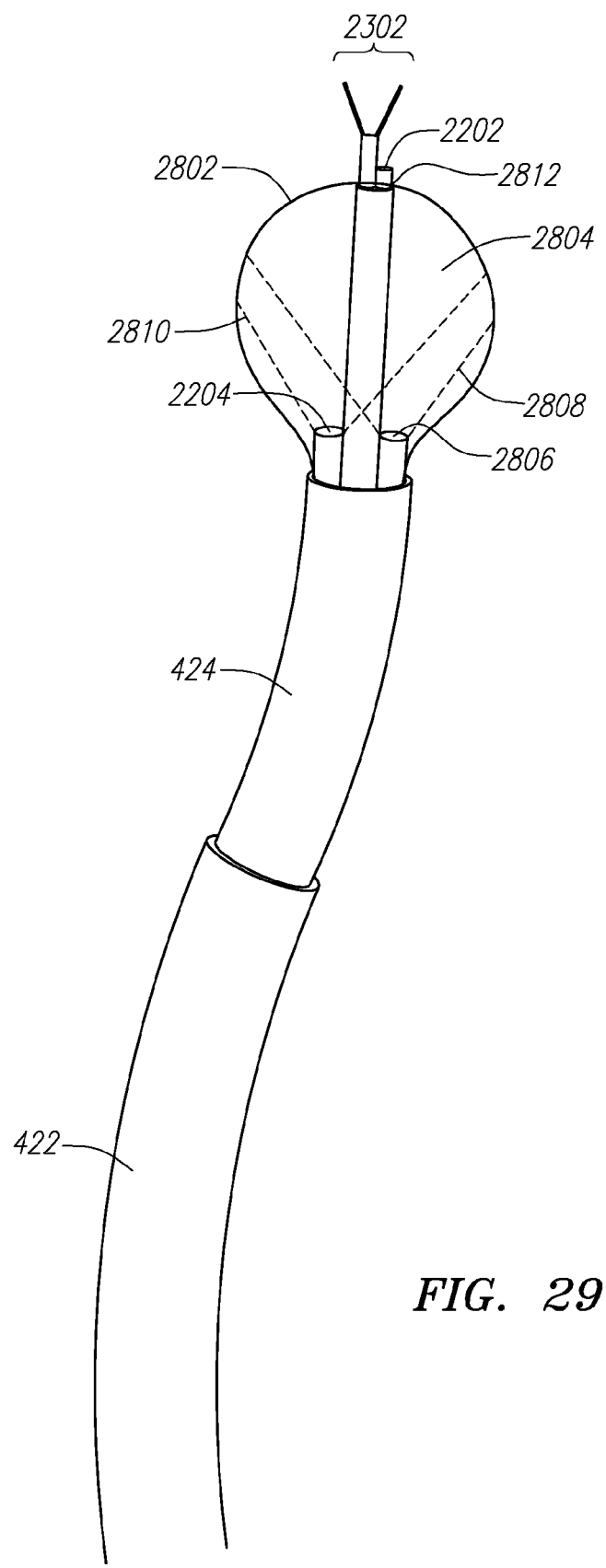
FIG. 29 illustrates an instrument assembly including another balloon apparatus.
Figure 30:
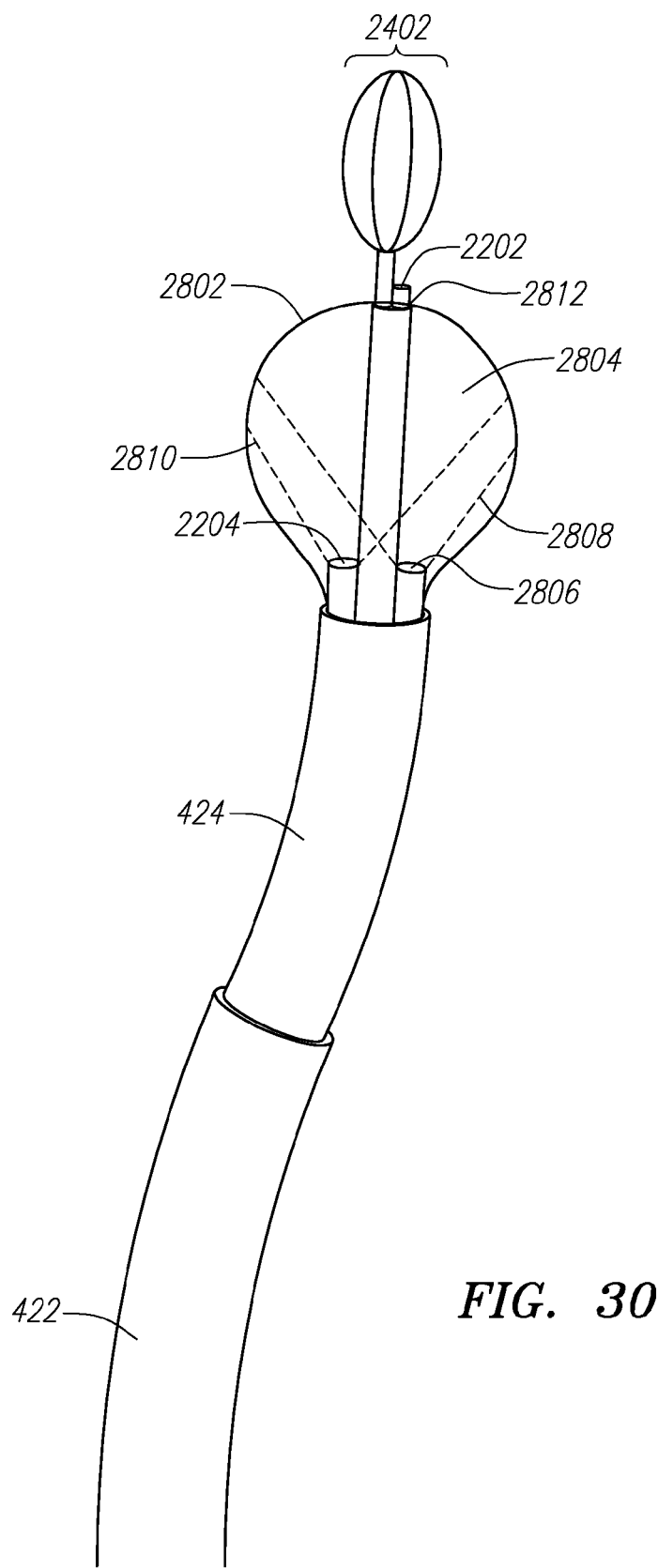
FIG. 30 illustrates an instrument assembly including yet another balloon apparatus.

FIG. 28 depicts a configuration with an inflatable balloon (2802) configured to be controllably filled with or evacuated of saline (2804), through which an image capture device (2204) and illumination source (2806) may be utilized to observe objects forward of the balloon that preferably fall within the field of broadcast (2808) of the illumination source (2806) and field of view (2810) of the image capture device (2204). The balloon (2802) also defines a working lumen (2812) through which various tools may be passed—such as a laser fiber (2202), as depicted. FIG. 29 depicts a similar embodiment also comprising a grasping tool (2302). FIG. 30 depicts a similar embodiment with a basket tool (2402).

Figure 31:
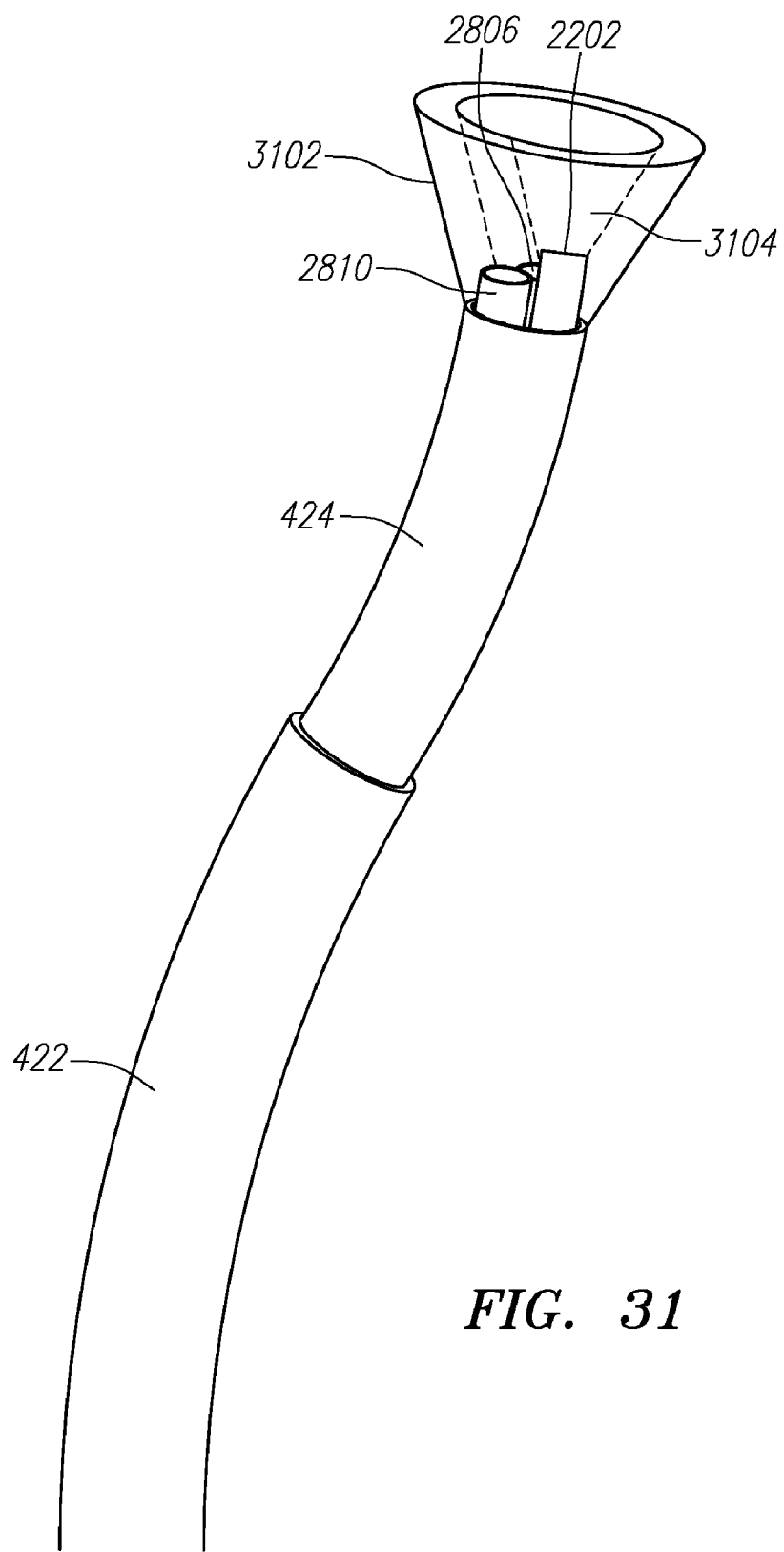
FIG. 31 through FIG. 33 respectively illustrates an instrument assembly including an inflatable balloon cuff apparatus.
Figure 32:
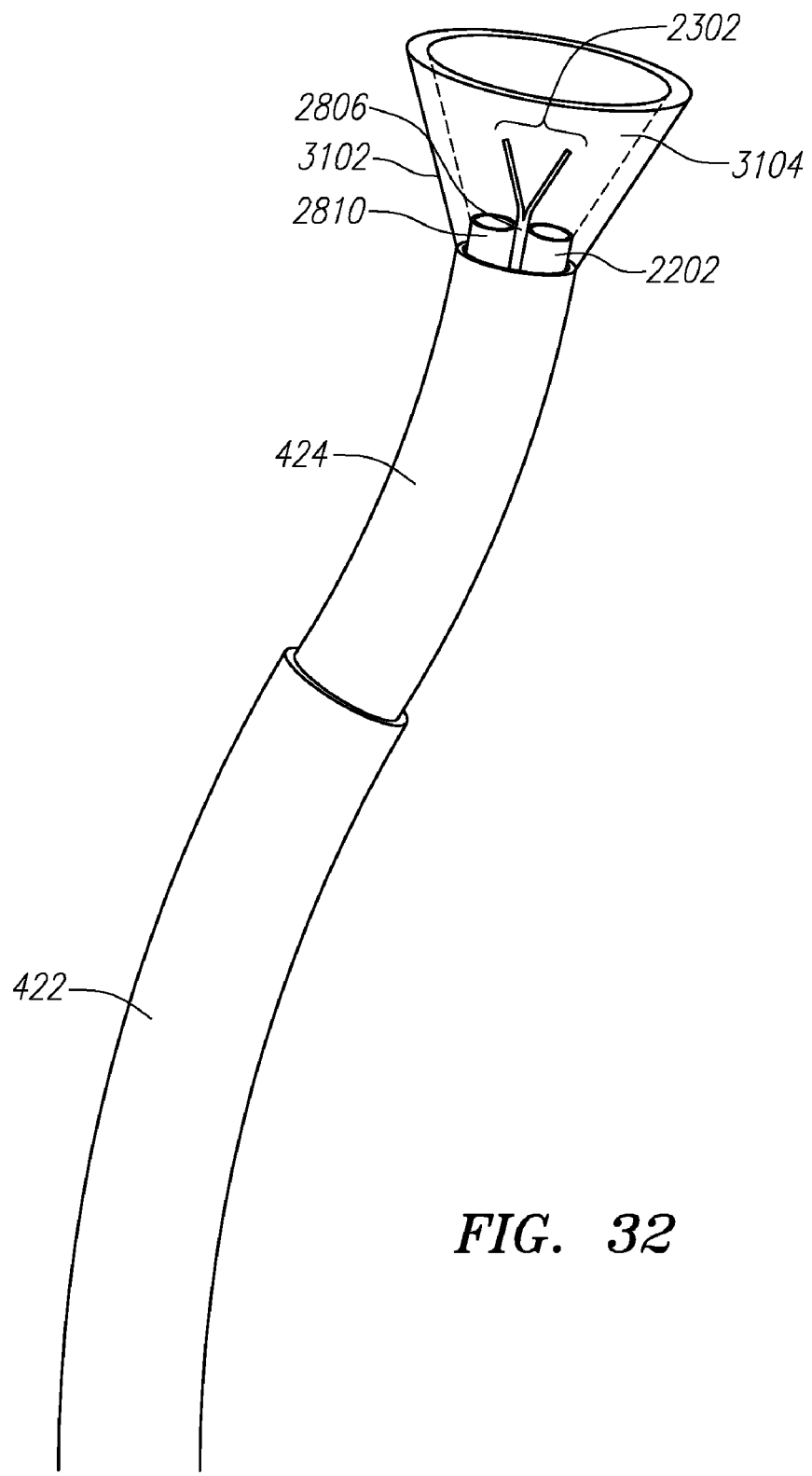
Figure 33:
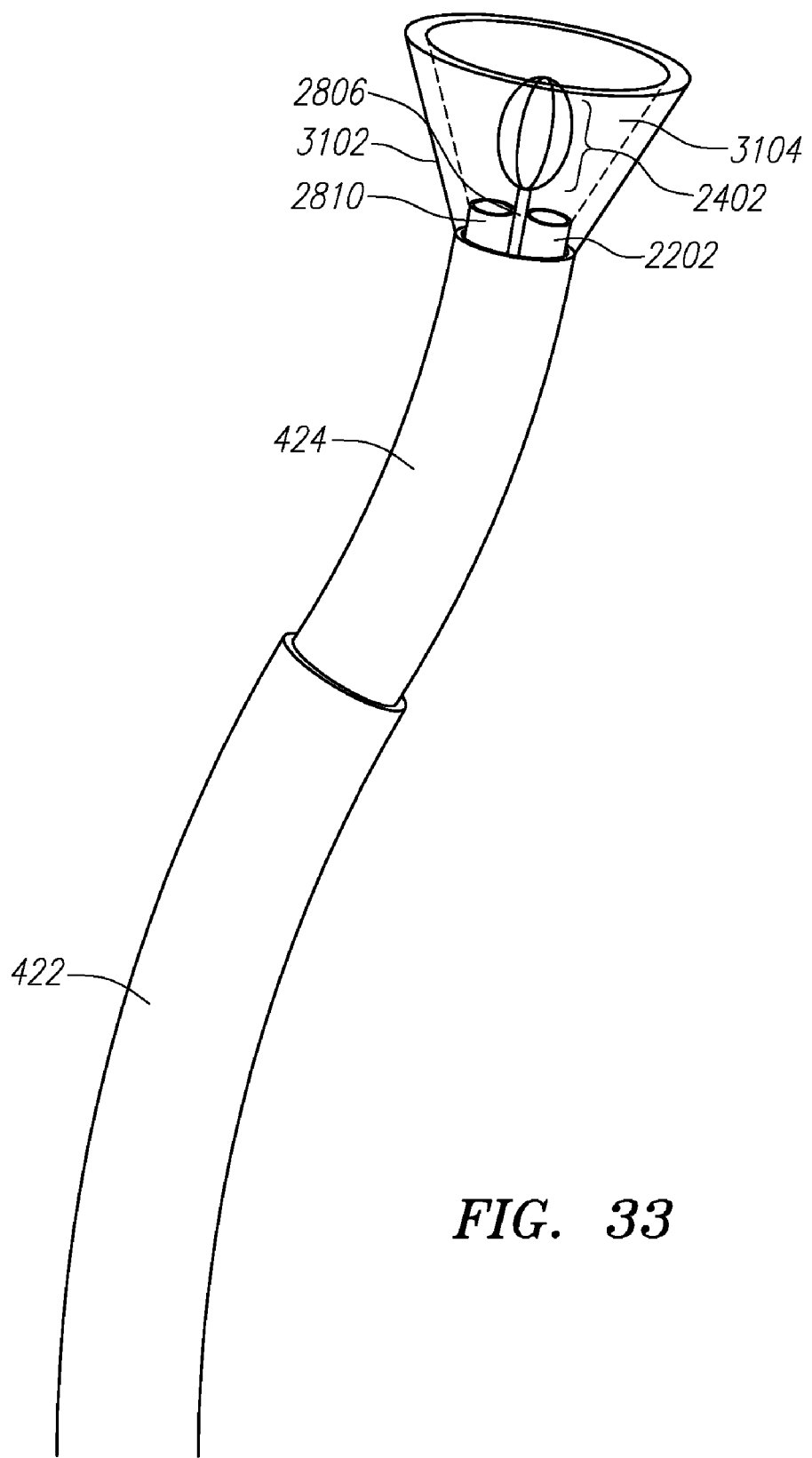

FIG. 31 through FIG. 33 depict similar embodiments which comprise an inflatable balloon cuff (3102) configured to provide a distal working volume (3104) which may be flushed with a saline flush port (2806). The inflatable balloon cuff (3102) preferably works not only as an atraumatic tip, but also as a means for keeping the image capture device (2810) positioned slightly proximally of structures that the inflatable balloon cuff (3102) may find itself against—thus providing a small amount of volume to image such structures without being immediately adjacent to them. With an optical fiberscope as an image capture device (2810), it may be highly valuable to maintain a translucent saline-flushed working volume (3104) through which the image capture device (2810) may be utilized to image the activity of objects, such as tissues and/or kidney stones, as well as the relative positioning of tools, such as fibers, graspers, baskets, etc., from proximal positions into the working volume (3104)—which may be used, for example, to grasp and/or modify or destroy stones or other structures. The inflatable balloon cuff (3102) may be advanced to the desired operational theater, such as the calices of a kidney, in an uninflated configuration, and then inflated in situ to provide the above functionality. Alternatively, the cuff (3102) may be inflated before completing the navigation to the operational theater, to provide atraumatic tip functionality as well as image capture guidance and deflection from adjacent objects, during navigation to the desired operational theater.

Figure 34:
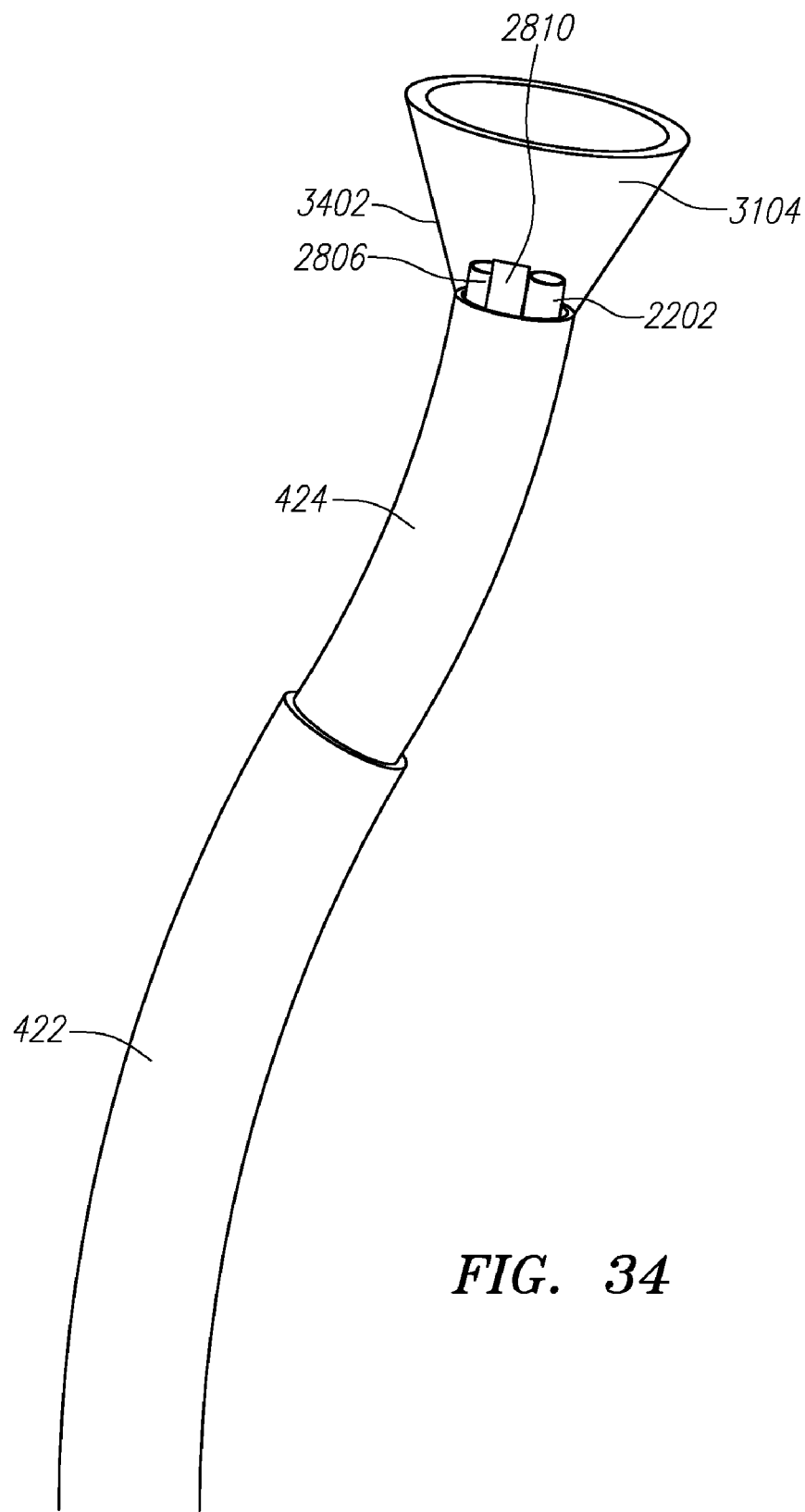
FIG. 34 through FIG. 36 respectively illustrate an instrument assembly including a flexible balloon cuff apparatus.
Figure 35:
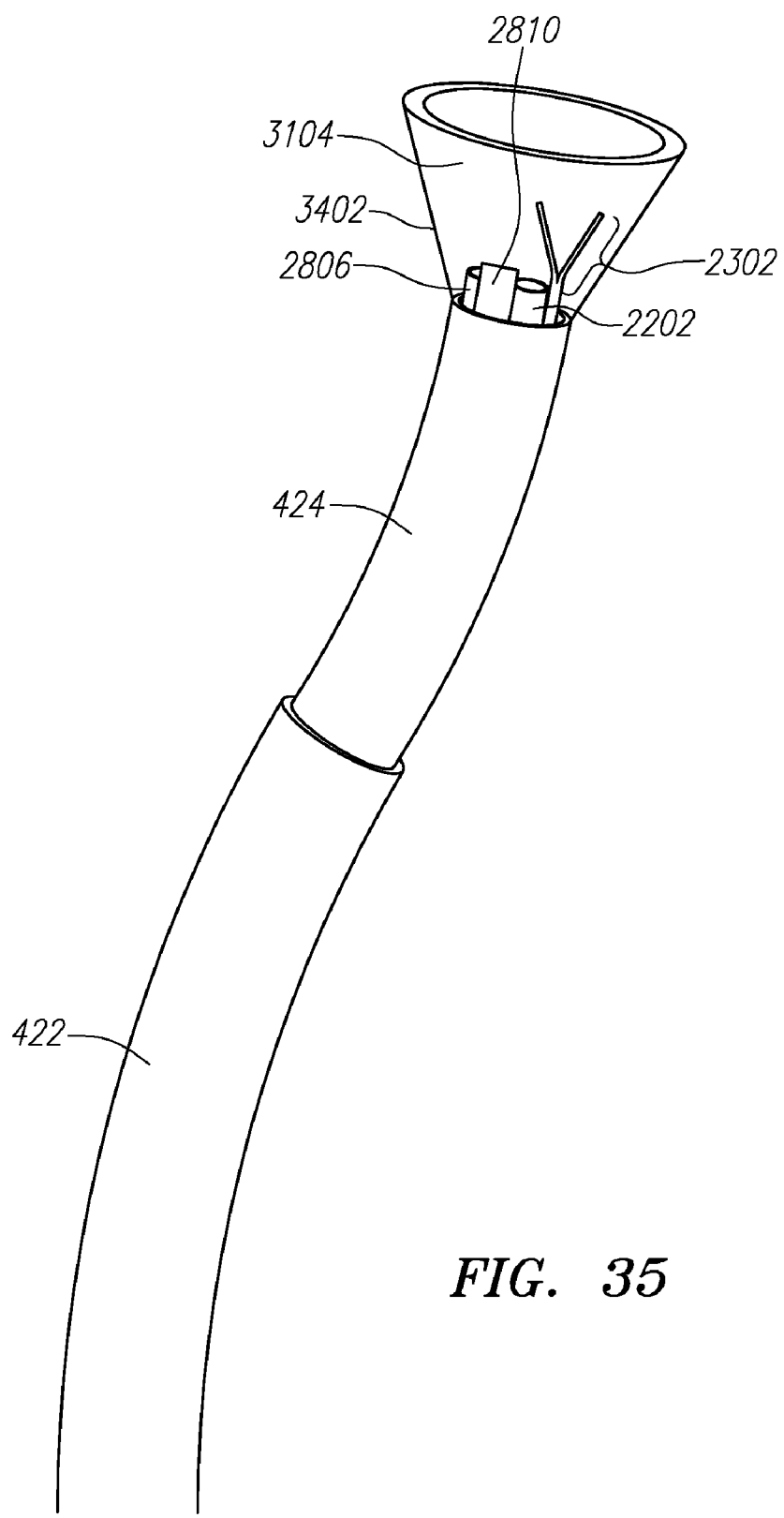
Figure 36:
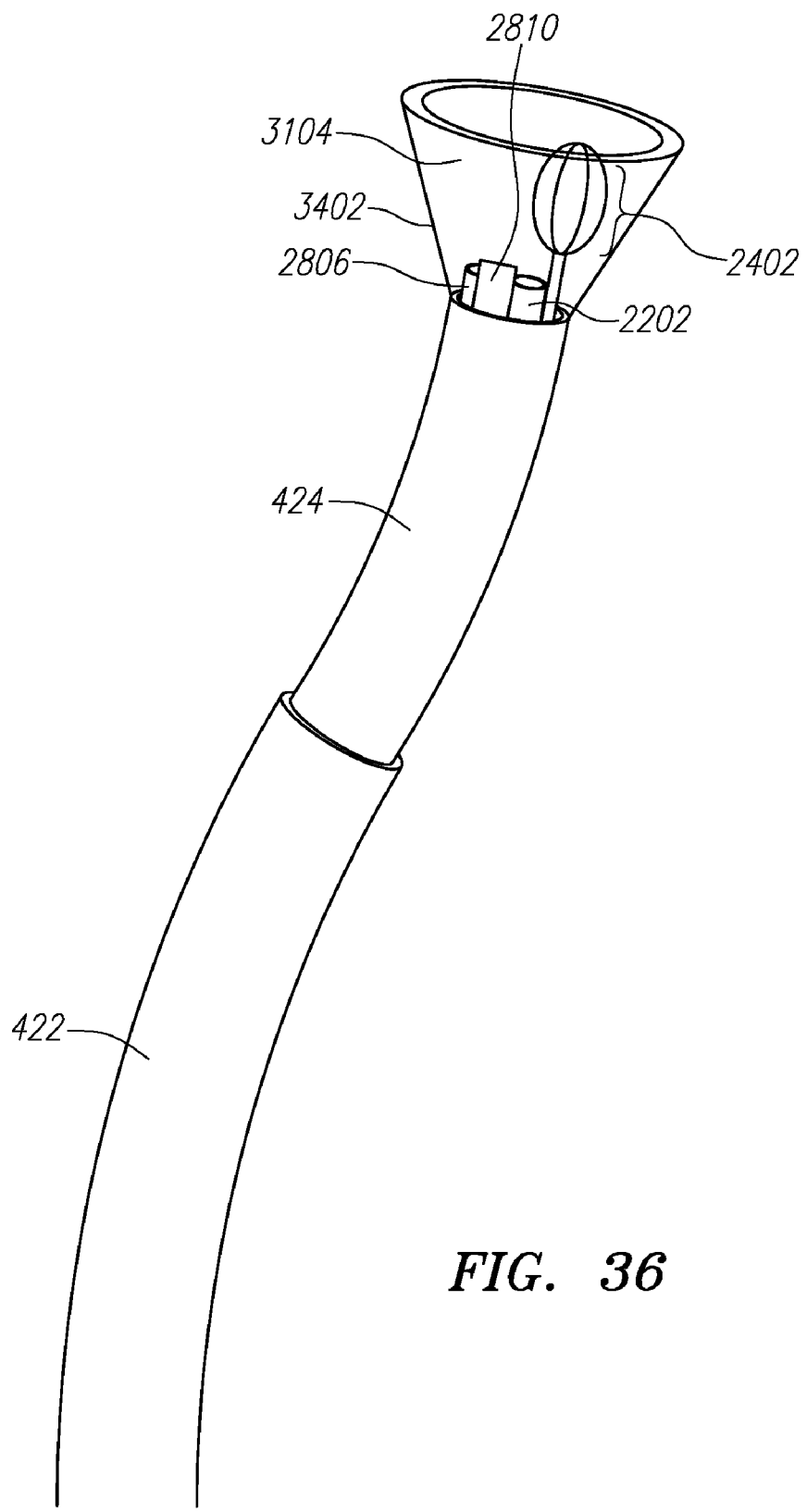
Figure 37:
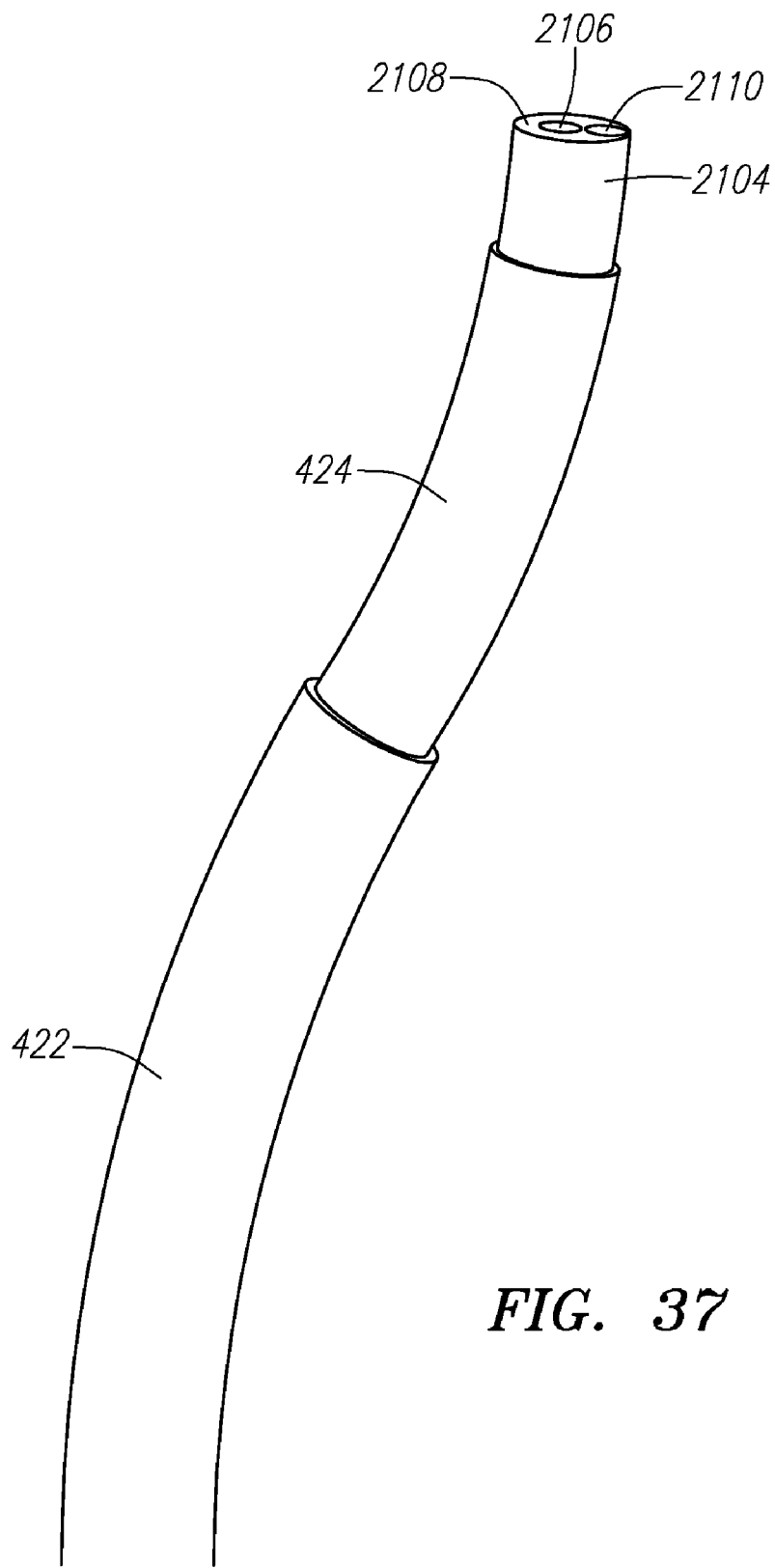
FIG. 37 and FIG. 38 respectively illustrates an instrument assembly including image capture apparatuses.

FIG. 34 through FIG. 36 depict similar embodiments, but with a flexible cuff (3402), preferably comprising a soft polymer material, rather than an inflatable cuff (3102) as in the previous set of figures. The flexible cuff (3402) is configured to have similar functionalities as those described in reference to the inflatable cuff (3102) above.

Figures 38, 39, 40:
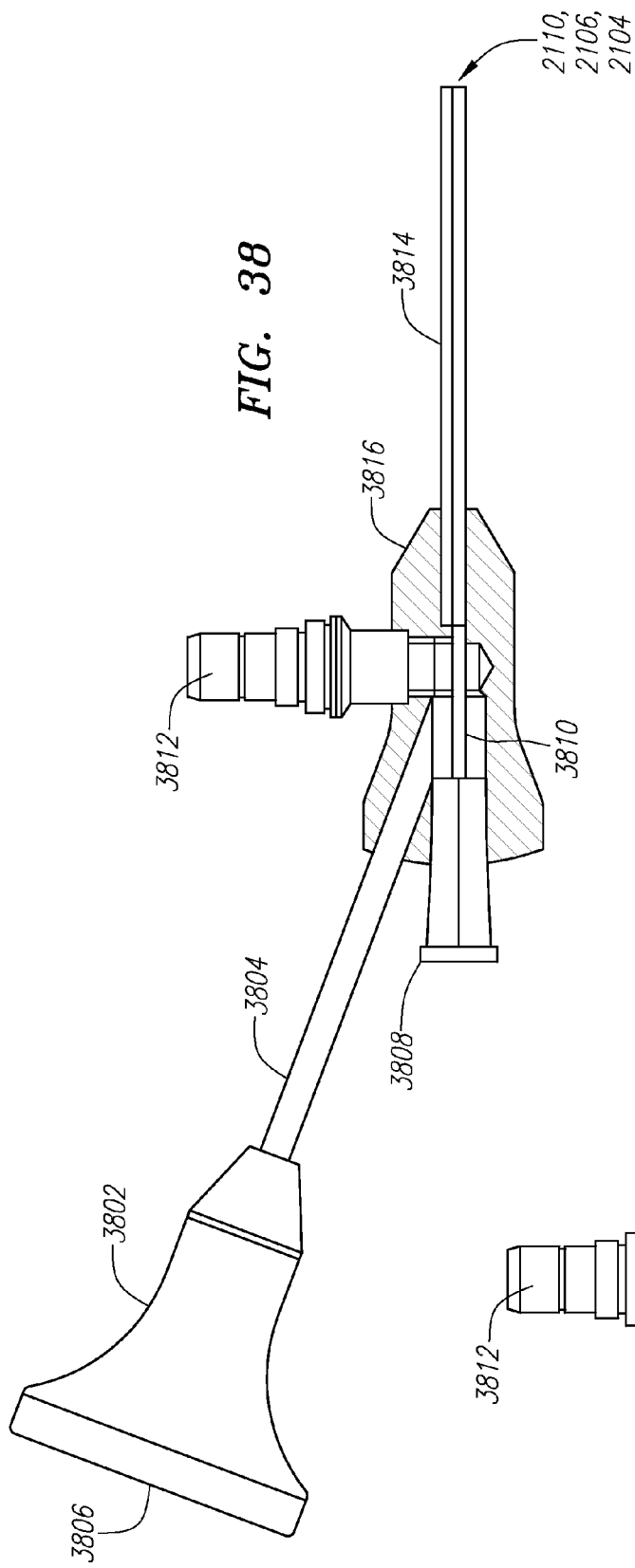
FIG. 39 through FIG. 40 respectively illustrates detailed views of the image capture assembly.
Figure 41:
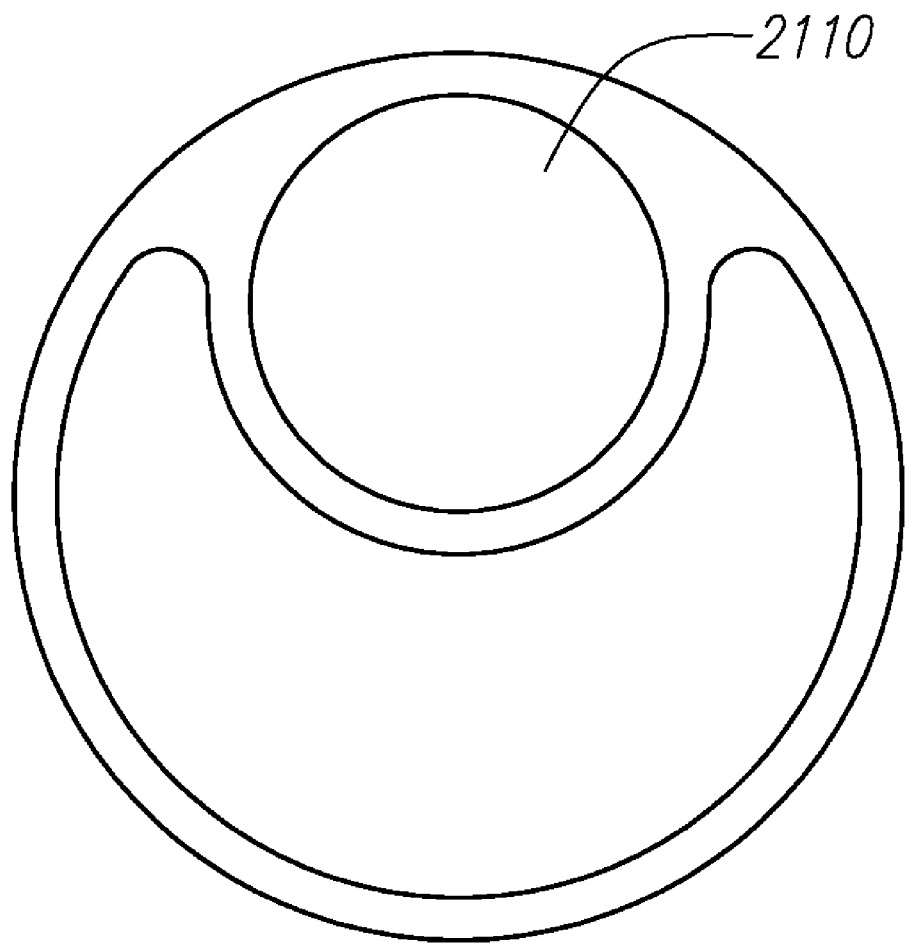
FIG. 41 illustrates a cross sectional view of a tubular structure for housing the image capture device assembly.
Figure 42:
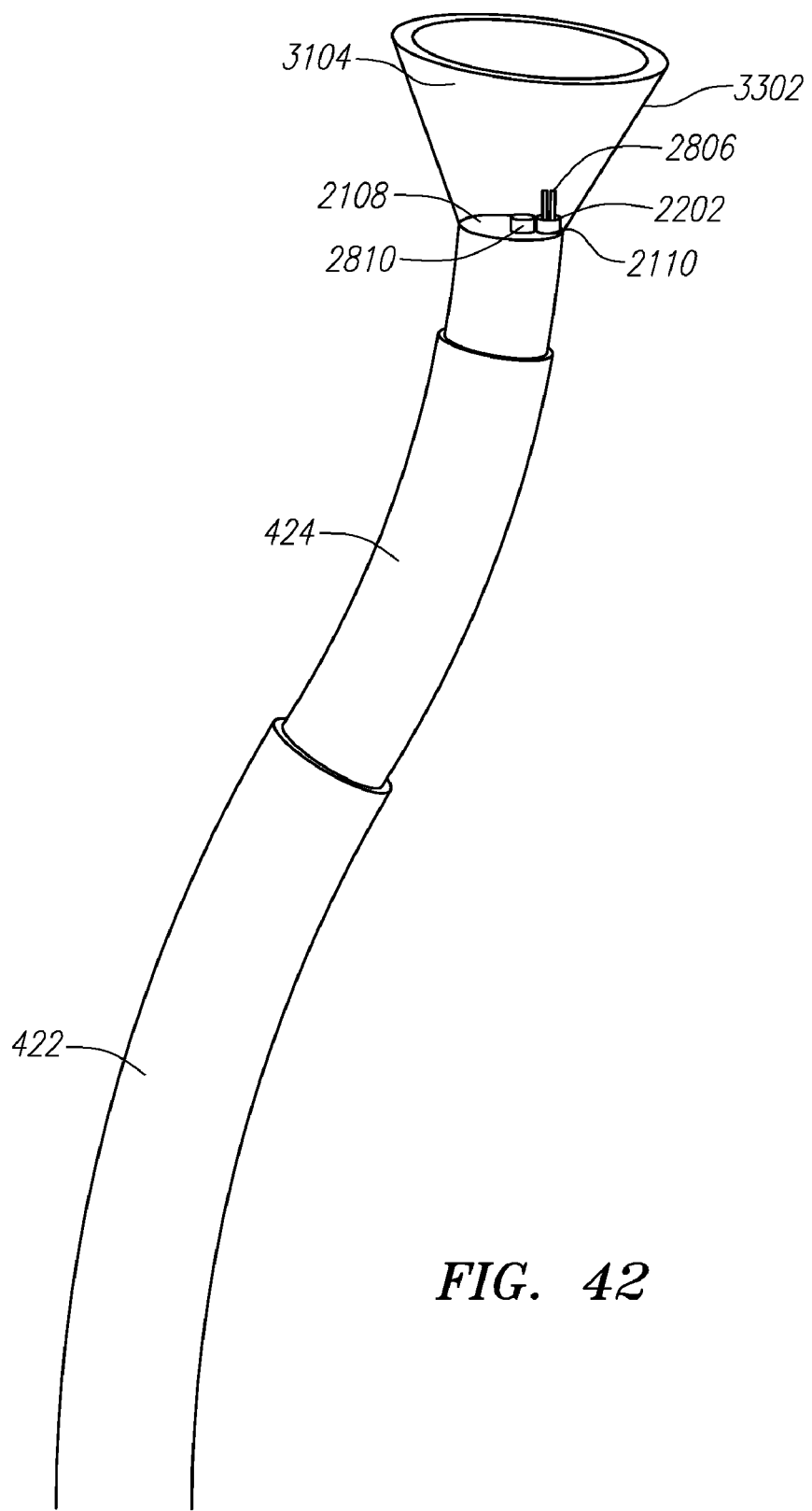
FIG. 42 through FIG. 45 respectively illustrates variations of embodiments of image capture assembly.
Figure 43:
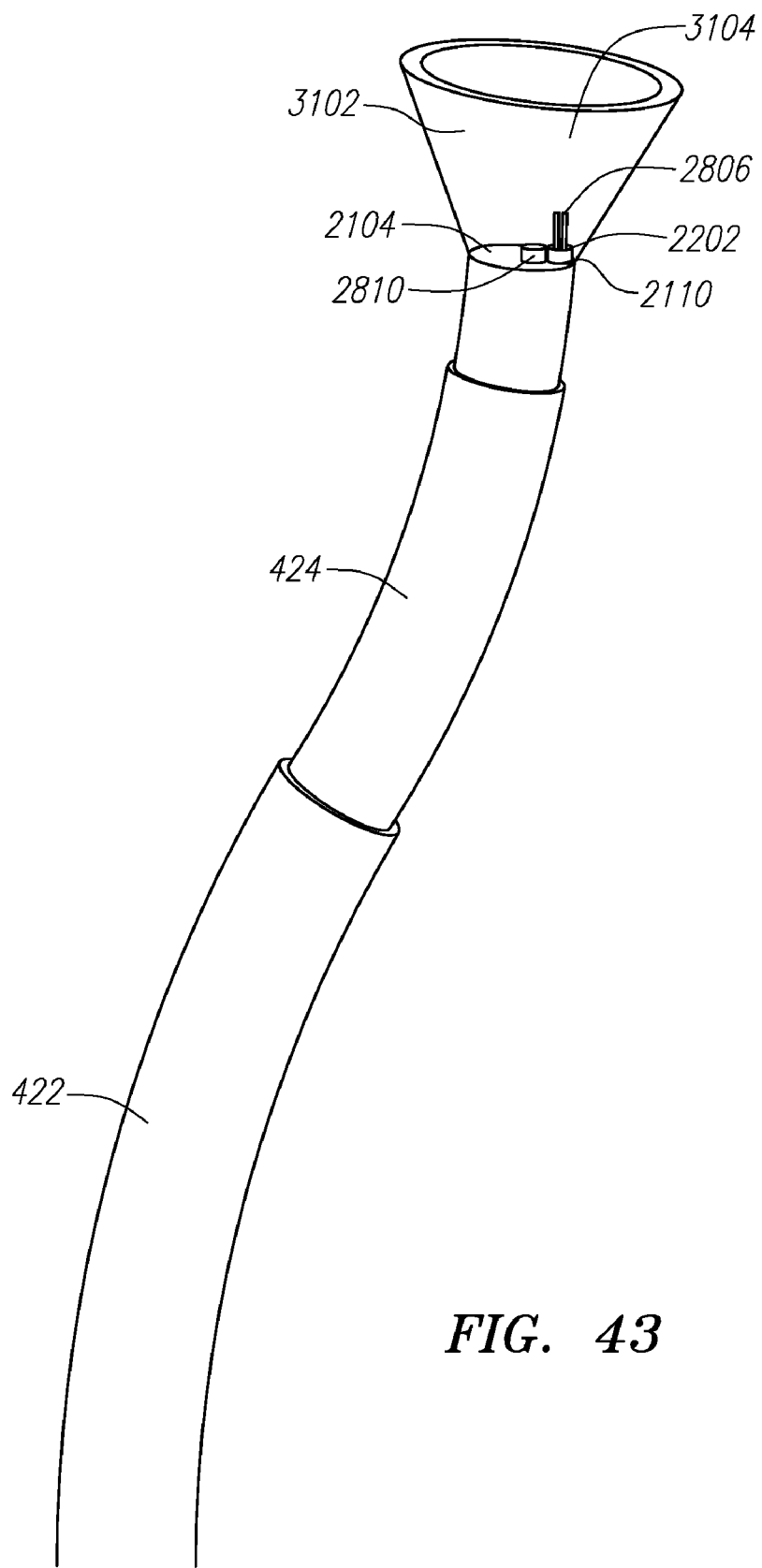
Figure 44:
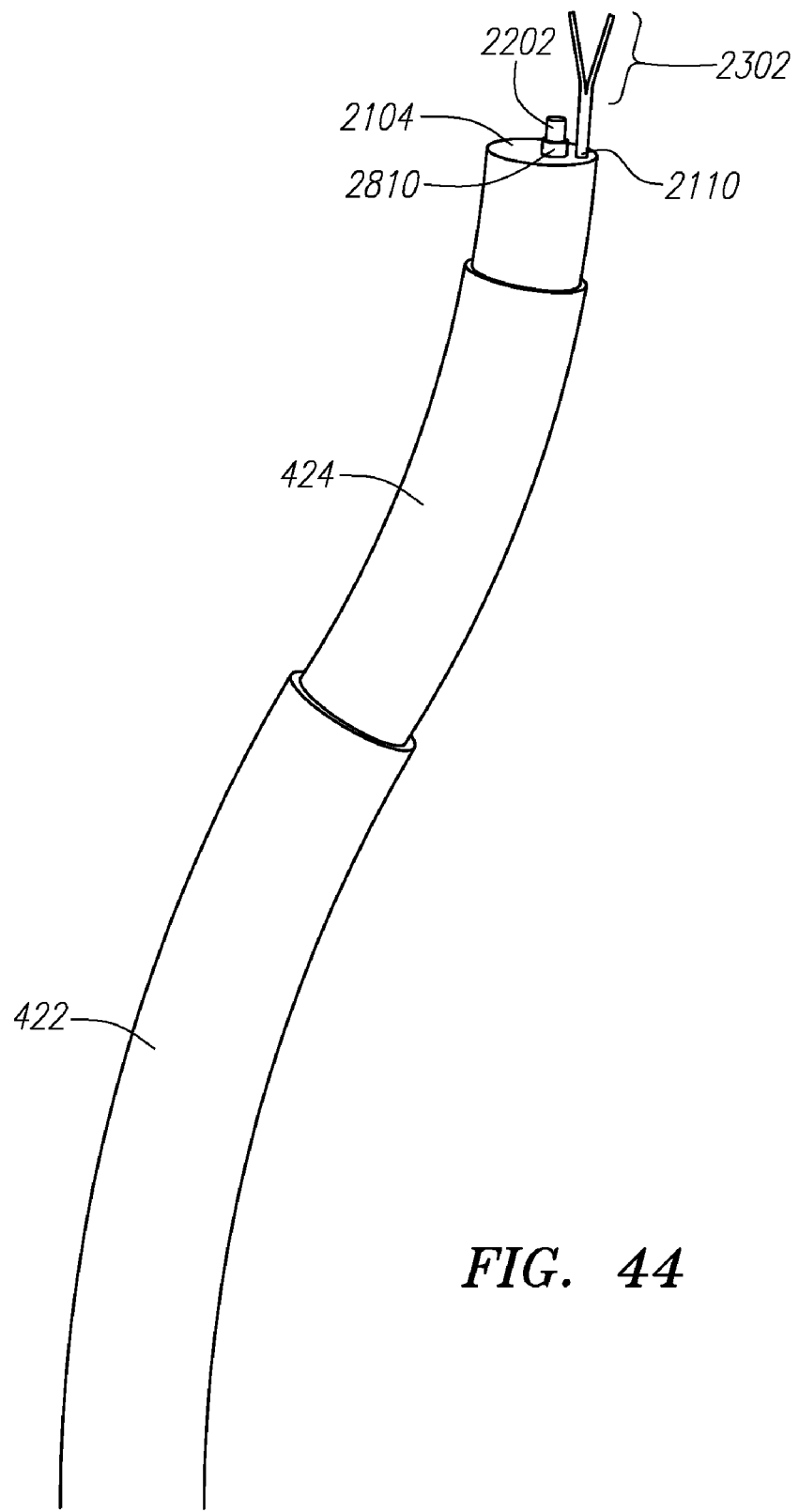
Figure 45:
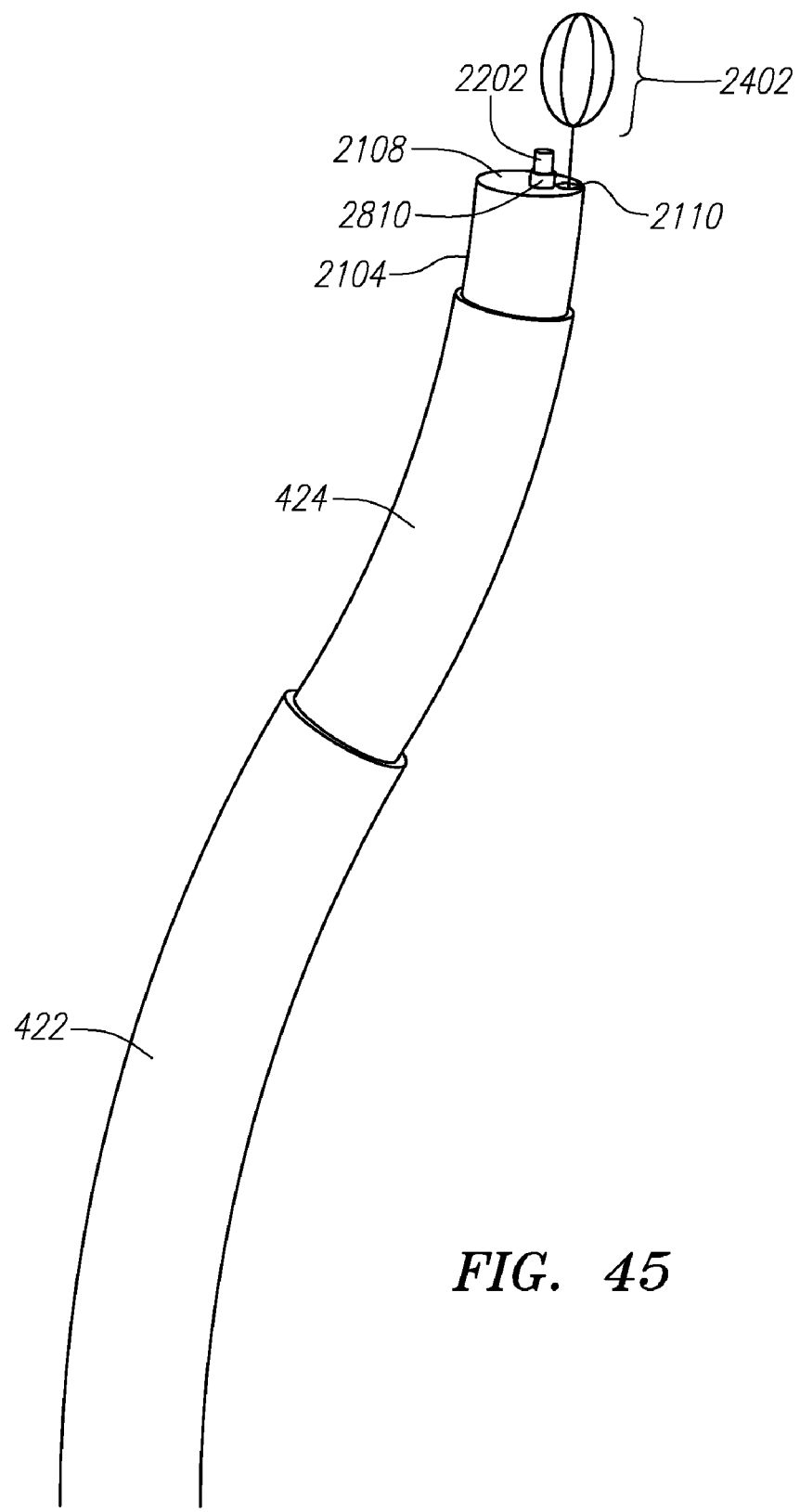

FIG. 37 through FIG. 41 depict an embodiment wherein an assembly of an image capture device (2104), which may optionally comprise a lens (2106), transmission fibers (2108) for imaging, and a working lumen (2110), through which various tools or combinations of tools may be positioned. The components of this embodiment are all packaged within one tubular structure as illustrated in the cross sectional view of FIG. 41, which may comprise a coextruded polymeric construct. FIG. 38 through FIG. 40 depict the interconnectivity of an image capture device (2104), such as a fiberscope comprising a proximal optics fitting (3802), an optics body member (3804), a proximal surface (3806) for interfacing with a camera device with the illumination fibers and working lumen, comprising a female luer fitting (3808) for accessing the working lumen (2110), a working lumen proximal member (3810), an illumination input tower (3812), an insertion portion (3814), a central body structure (3816). Variations of this embodiment are depicted in FIG. 42 through FIG. 45, with different distal configurations similar to those depicted in reference to the figures described above. FIG. 42 depicts a variation having a distally-disposed flexible cuff (3402) defining a working volume (3104) flushable with a saline port (2806) and imaged with an image capture device (2810) as described above. FIG. 43 depicts a similar variation having an inflatable cuff (3102). Tools such as graspers, energy sources, fibers, baskets, etc may be utilized through the working lumens (2110) of the embodiments depicted in FIG. 42, FIG. 43, FIG. 44, FIG. 45, etc. The embodiment of FIG. 44 comprises a grasping tool (2302) positioned through the working lumen of the assembly (2104—the assembly depicted in FIG. 37 through FIG. 41), which the embodiment of FIG. 45 comprises a basket tool (2402).

Each of the above discussed tools, configurations, and/or assemblies may be utilized for, among other things, endolumenal urinary intervention, such as the examination, removal, fragmentation, and/or destruction of stones such as kidney or bladder stones.

Figure 46A:
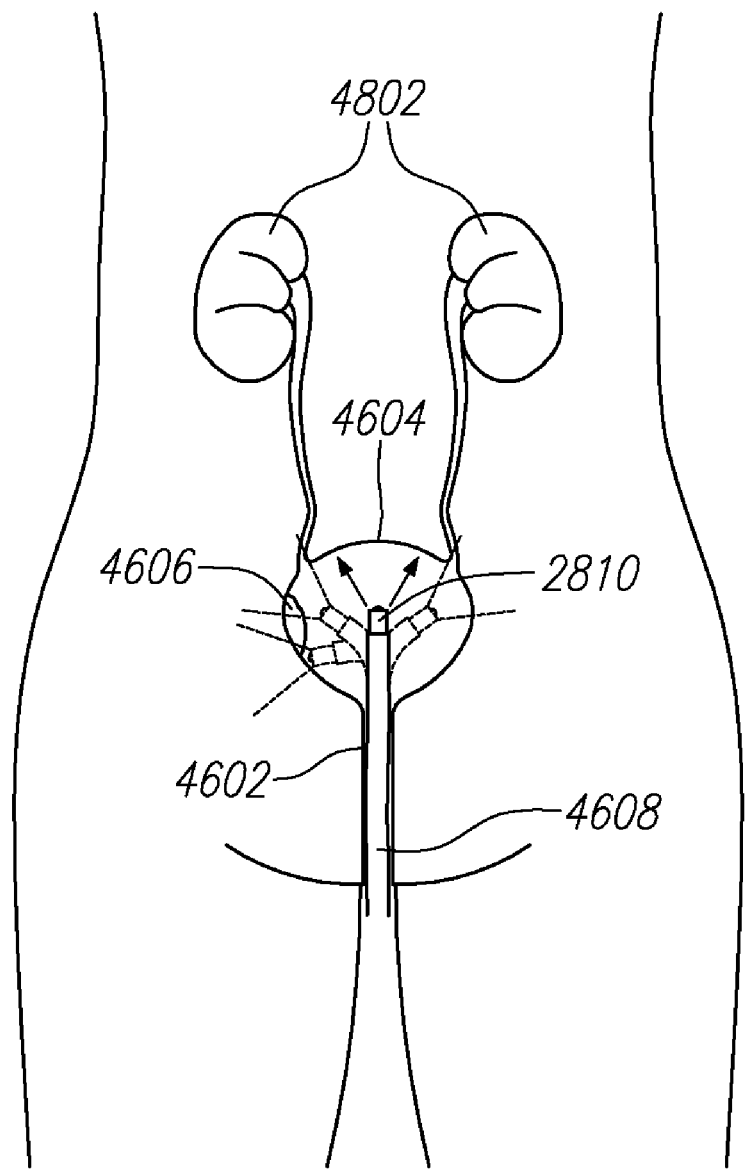
FIG. 46A illustrates a steerable instrument assembly being used in the bladder.
Figure 46B:
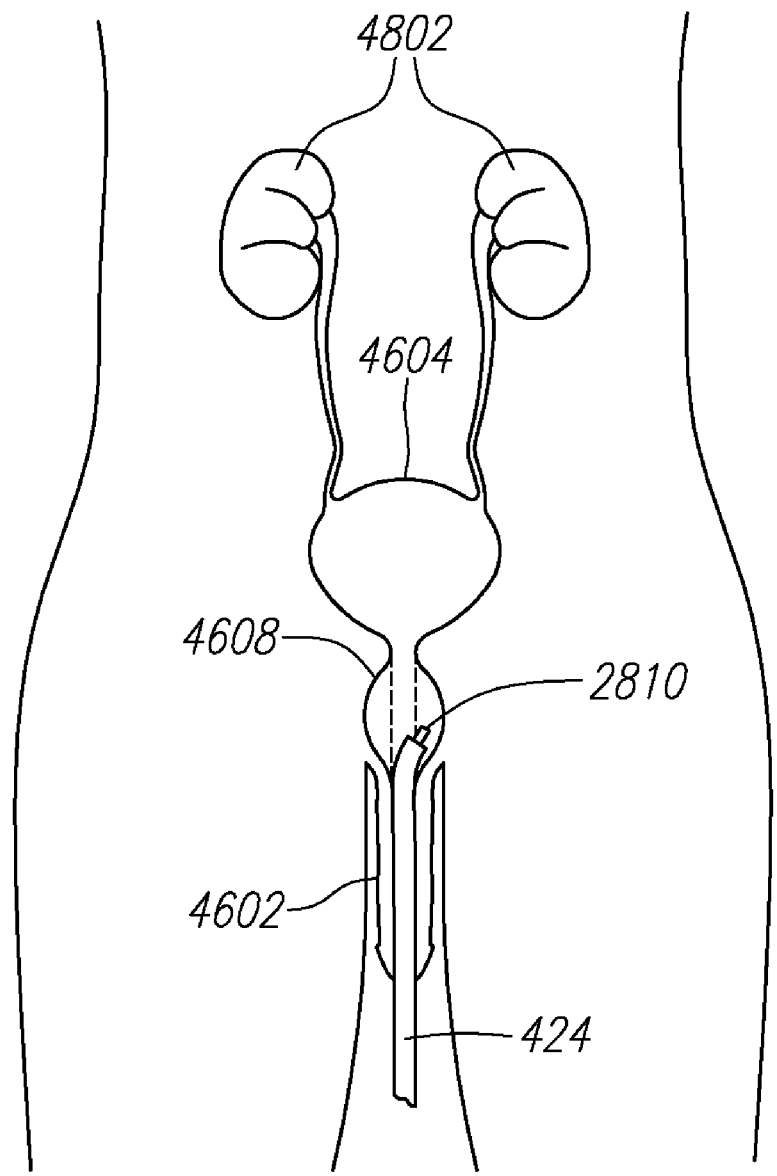
FIG. 46B illustrates a steerable instrument assembly being used in the prostate.

Referring to FIG. 46A, a steerable instrument assembly according to one embodiment may be steered through the urethra (4602) and into the bladder (4604), where an image capture device (2810) may be utilized, as facilitated by injected saline, to conduct a cystoscopy and potentially observe lesions (4606) of interest. The omni-directional steerability and precision of the robotic guide and/or sheath to which the image capture device is coupled facilitates collection of images of inside of the bladder (4606) which may be patched together to form a 3-dimensional image. The instrument assembly (108-422, 424, 2810) may also be utilized to advance toward and zoom the image capture device upon any defects, such as obvious bleeds or tissue irregularities. Indeed, aspects of the images captured utilizing the image capture device (2810) may be utilized in the controls analysis of the subject robotic catheter system to automate, or partially automate aspects of the system/tissue interaction. For example, as described above, more than one two-dimensional image may be oriented relative to each other in space to provide a three-dimensional mosaic type composite image of a subject tissue mass, instrument, or the like. Localization techniques may be utilized to assist with the "glueing together" of more than one image; for example, spatial coordinates and orientation may be associated with each image captured by the image capture device, to enable re-assembly of the images relative to each other in space. Such a three-dimensional composite image may be registered in three dimensions to the workspace or coordinate system of the subject elongate instrument or instrument assembly, to provide automated display, zooming, and reorientation of the images displayed relative to the distal portion of the elongate instruments as the instruments are moved around in the workspace. Further, the system may be configured to update the composite image with more recently-captured images as the instruments are navigated about in the workspace. Image recognition algorithms may be utilized to bolster the information gleaned from image capture; for example, a substantially round and dark shape in a particular location known to be at least relatively close to a lumen entry into or exit from a particular anatomic space may be analyzed and determined via application of the pertinent algorithms to be a given lumen entry or exit anatomical landmark, and the location of such landmark may be stored on a database along with the position and orientation variables of the elongate instruments utilized in the particular instance to arrive at such location—to enable easy return to such location using such variables. The system may thus be configured to allow for automated return of the instruments to a given landmark or other marker created manually or automatically upon the composite image and associated database. Further, given the composite image of the actual tissue in-situ, the system may be configured to not only to allow for the storage of and return to certain points, but also for the creation and execution of configurable "keepout zones", into which the instruments may be disallowed under navigation logic which may be configured to prevent touching of the instruments to certain tissue locations, navigation of the instruments into particular regions, etc. Similar procedures may be performed in the prostate (4608) as illustrated in FIG. 46B.

Figure 47:
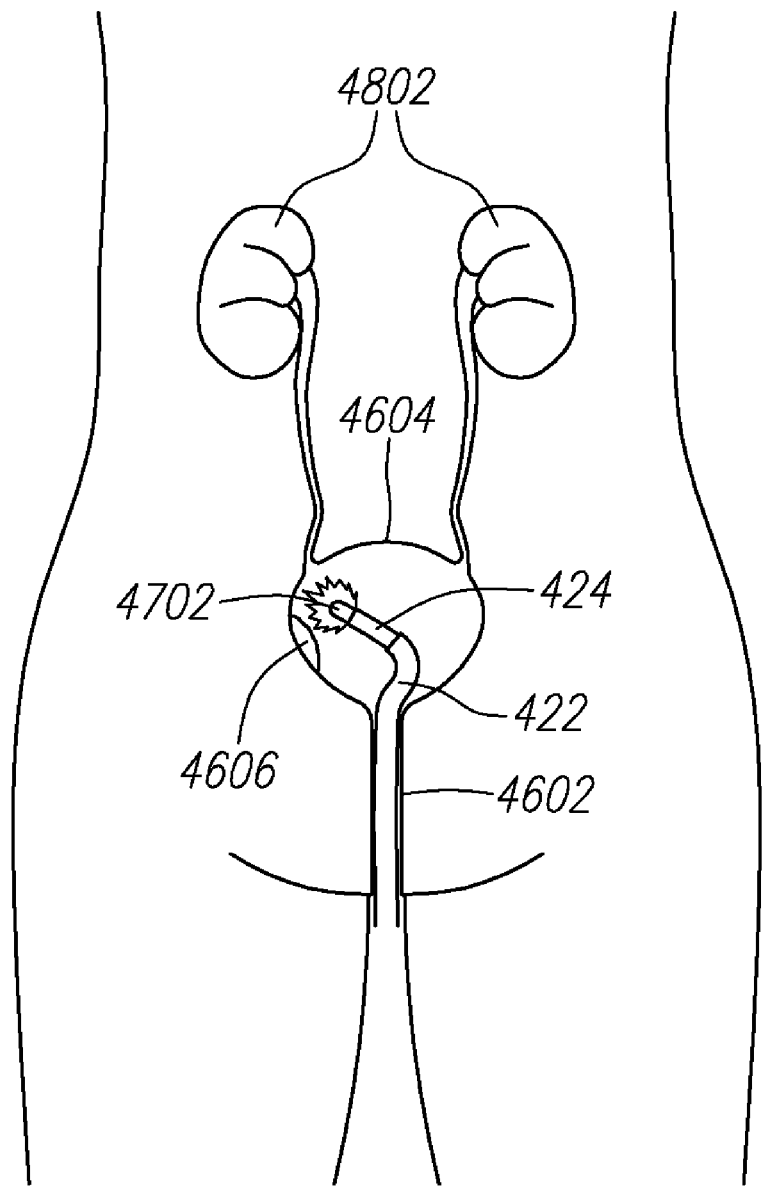
FIG. 47 illustrates another steerable instrument assembly.

Referring to FIG. 47, the instrument assembly (108-422, 424, 4702) may alternatively or additional comprise an interventional tool such as an ablation tool (4702) for ablating tumors or other lesions (4606) within the bladder (4604) or prostate (4608). Any of the above-discussed assemblies may be utilized for such a cystoscopy procedure.

Figure 48:
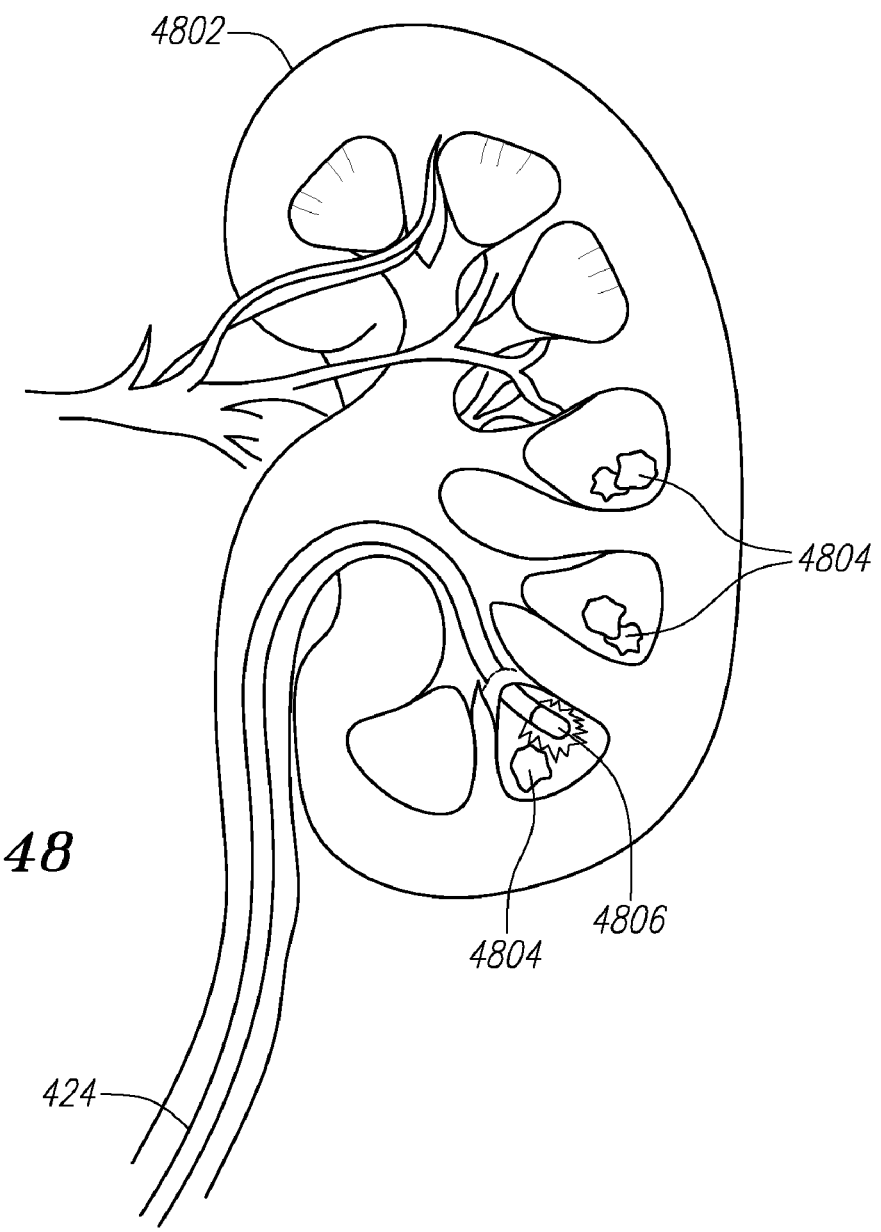
FIG. 48 and FIG. 49 respectively illustrates yet another steerable instrument assembly.
Figure 49:
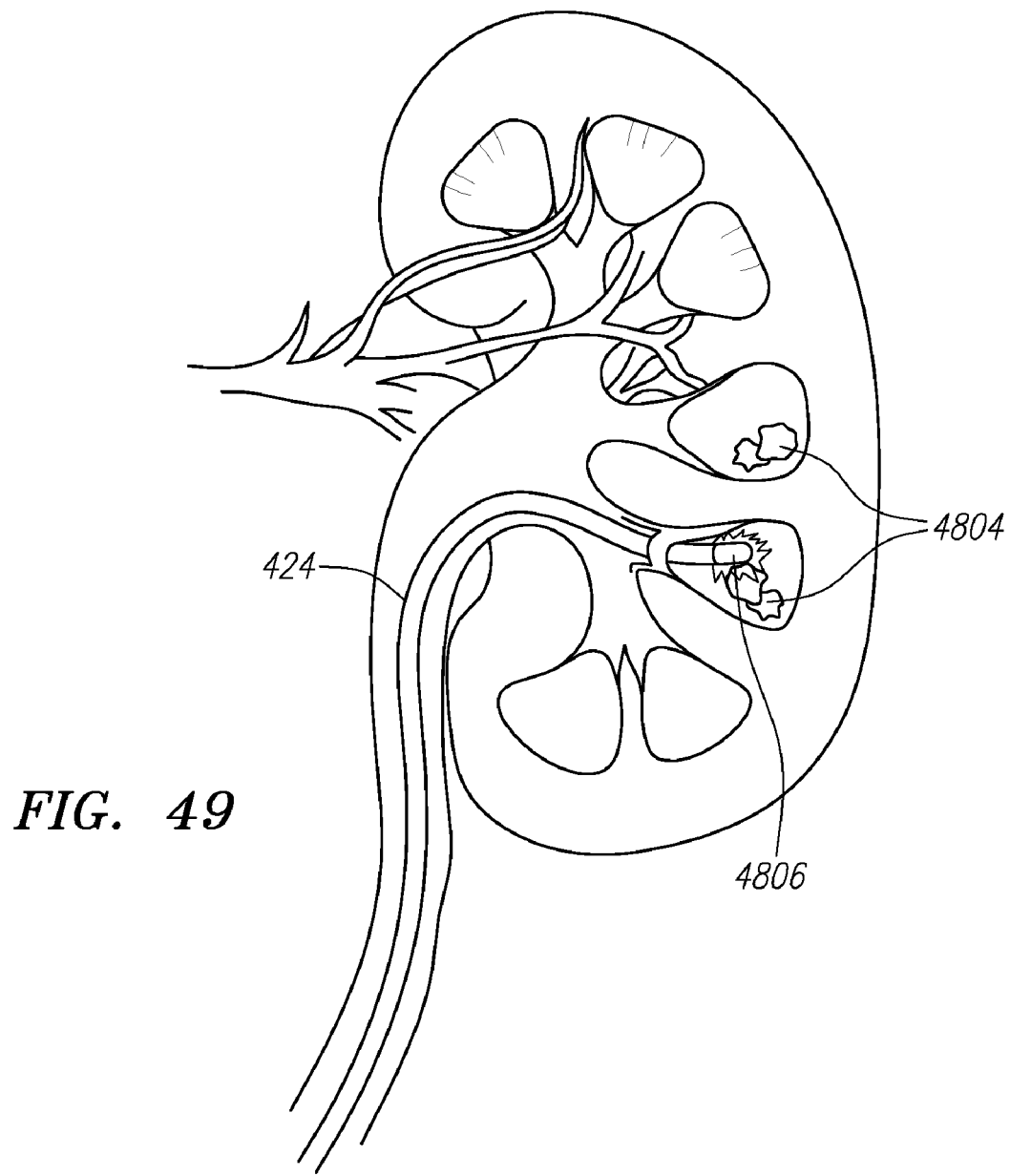

Each of the above-discussed constructs may also be utilized adjacent to or within the kidneys. Referring to FIG. 48 and FIG. 49, for illustrative purposes, a portion of a relatively simple instrument assembly embodiment (for example, a sheath distal tip may be positioned in the bladder at the entrance to the urethra while the more slender guide, 424, is driven toward and into the kidney, 4802) is depicted. Such assembly may be advanced toward and/or steerably driven into the kidney (4802), where stones (4804) may be captured with graspers or other tools, or where stones may be destroyed using chemistry, cryo, RF, laser lithotripsy, or laser ablation tools (4806), or other radiative techniques, such as ultrasound, as depicted in FIG. 48 and FIG. 49. Each of the tools, configurations, and/or assemblies discussed above in reference to FIG. 16 through FIG. 45 may be utilized for the examination, removal, fragmentation, and/or destruction of stones such as kidney or bladder stones. Preferably, an image capture device (2810) is positioned in or adjacent to the calices of the kidney to enable interactive viewing of objects such as stones, while various tool configurations may be utilized to examine, capture, grasp, crush, remove, destroy, etc, such stones, before withdrawing the instrument assembly.

Figure 50A:
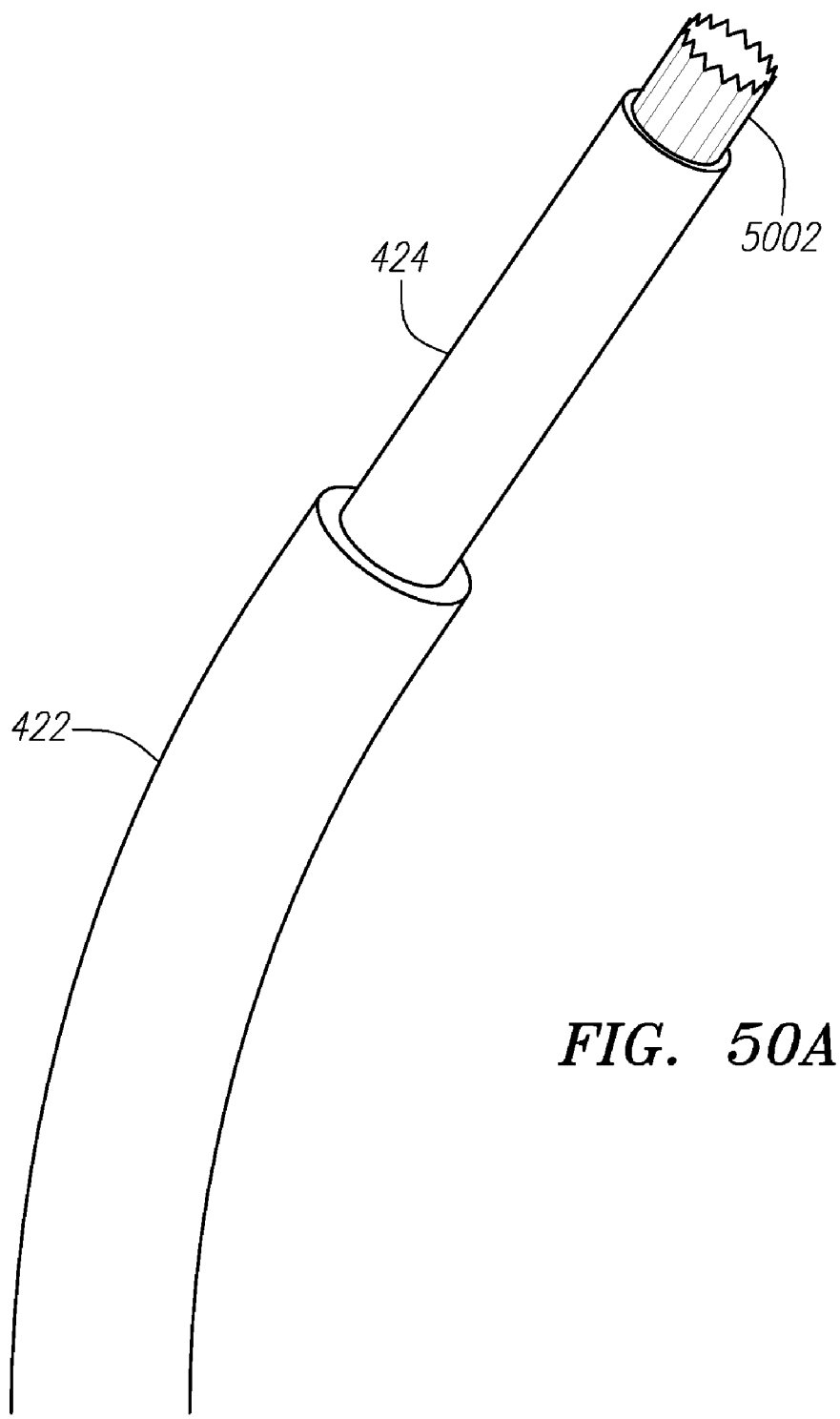
FIG. 50A illustrates one embodiment of a sheath and catheter assembly together with a retracted conical balloon apparatus.
Figure 50B:
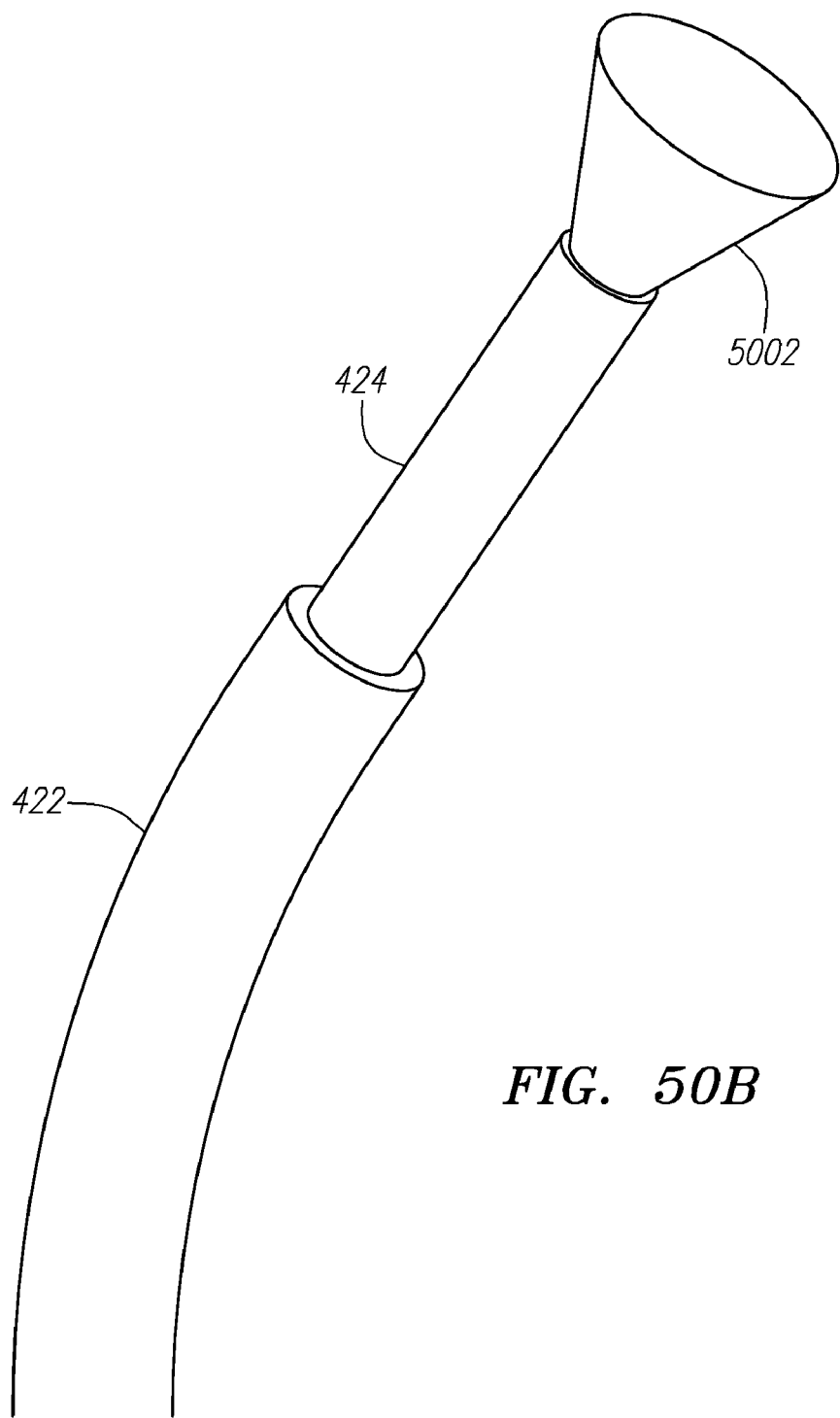
FIG. 50B illustrates the embodiment of FIG. 50A wherein the retracted conical balloon apparatus is deployed.

Additional instruments and tools may be operatively coupled to the instrument (108) to perform various minimally invasive surgical procedures. As may be appreciated, the instruments and tools may be operatively coupled to manually or robotically operated instruments (108). FIG. 50A illustrates one embodiment of a sheath (422) and guide (424) instrument (108) assembly that is operatively coupled to conical balloon instrument (5002), wherein the conical balloon is in a retracted configuration. In this embodiment, the balloon (5002) may be deployed by extruding the balloon structure (5002) from the distal tip of the guide catheter (424) and extricated by pulling the balloon structure (5002) back into the guide catheter (5002). FIG. 50B illustrates the embodiment shown in FIG. 50A wherein the retracted conical balloon (5002) is in a deployed configuration.

Figure 51:
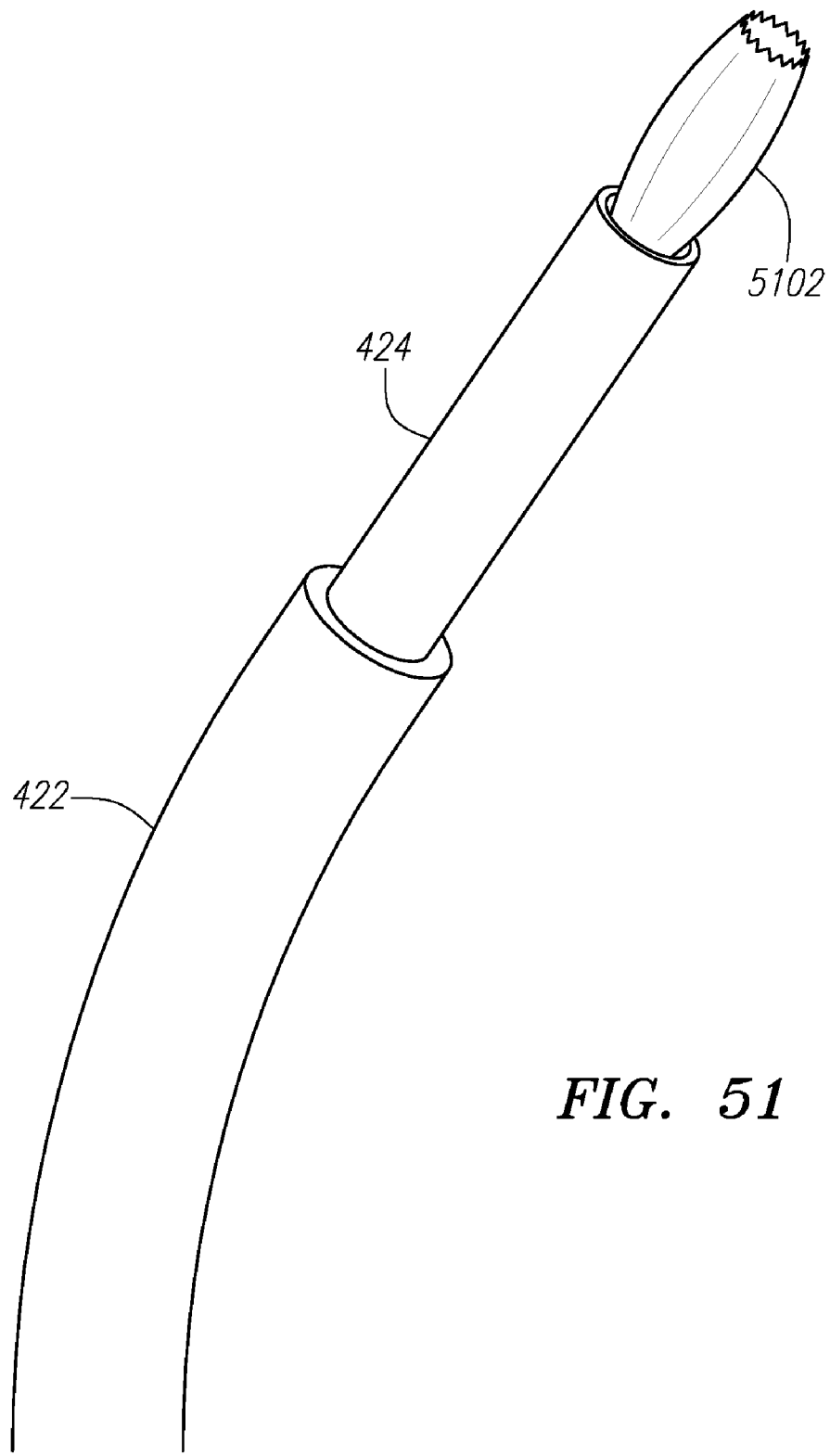
FIG. 51 illustrates one embodiment of a sheath and catheter assembly with a deflated balloon apparatus.
Figure 52:
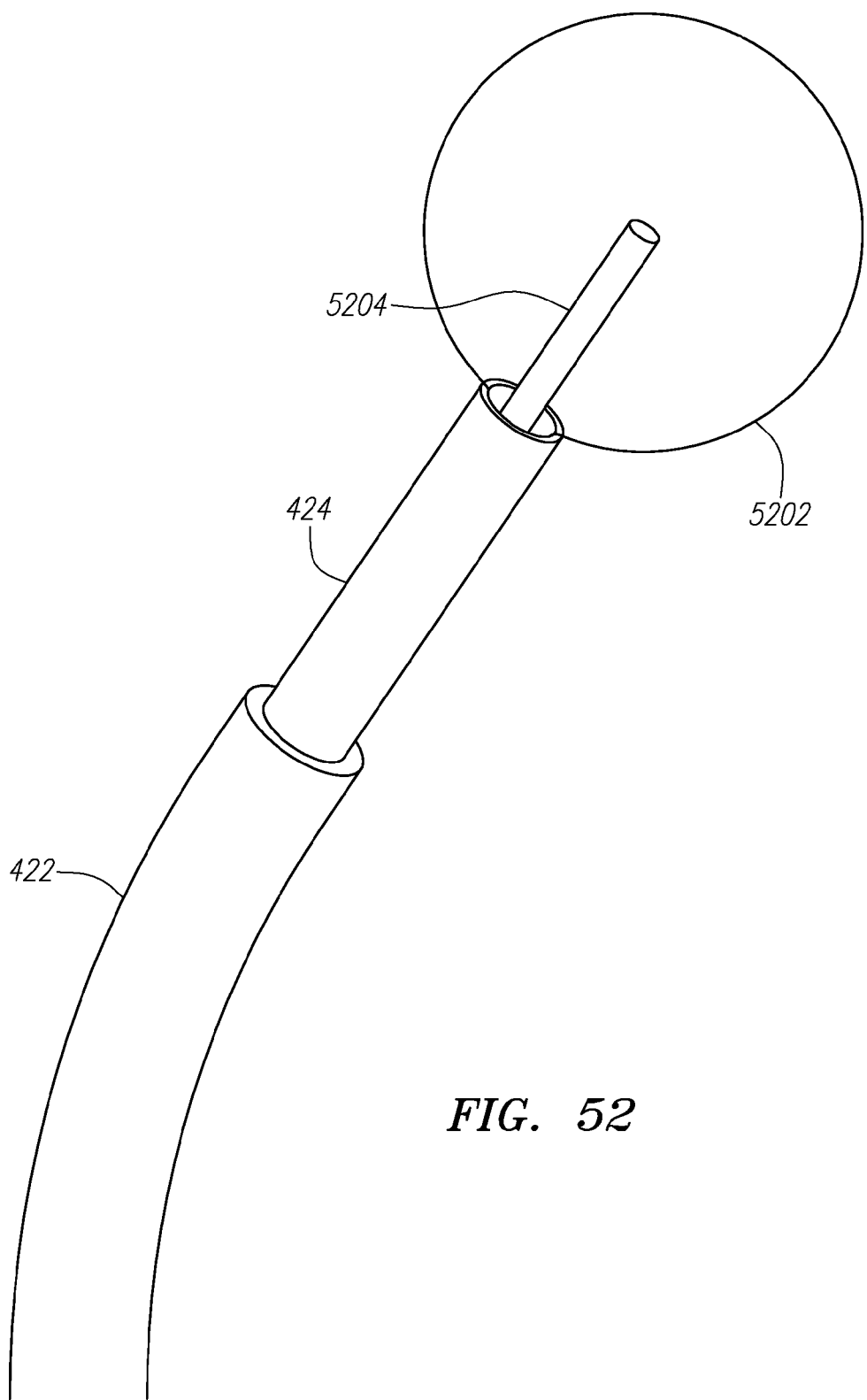
FIG. 52 illustrates a sheath and catheter assembly with one embodiment of an inflated balloon apparatus.
Figure 53:
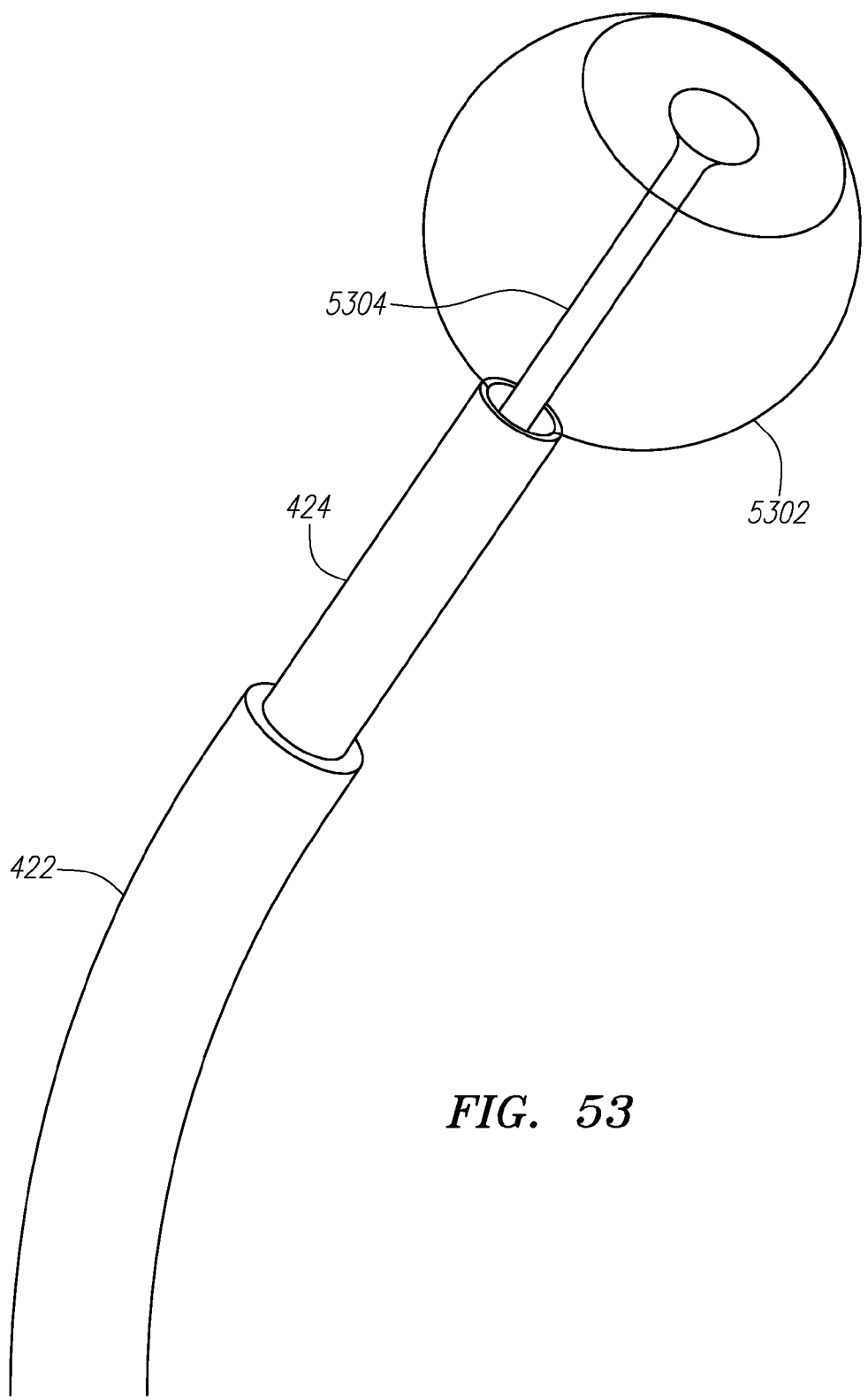
FIG. 53 illustrates a sheath and catheter assembly with one embodiment of a toroid shaped balloon.

FIG. 51 illustrates one embodiment of a sheath (422) and catheter (424) of the instrument assembly (108) with a deflated balloon (5102). In one embodiment, the balloon is deployed by inflating the balloon (5102) with a gas or liquid. For example, the balloon may be inflated by air, carbon dioxide, saline, contrast agent, etc., but is not limited as such. FIG. 52 illustrates a sheath (422) and catheter (424) with one embodiment of an inflated balloon (5202). In this example, an image capture device (5204) is located in the working lumen of the catheter (424). A user can manipulate the proximal end of the image capture device (5204). The device (5204) may be maneuvered about the interior of the balloon (5202) to view various areas. For one embodiment, the balloon (5202) is inflated with a gas or liquid that allows for visibility through it. In other words, the balloon (5202) is inflated with an appropriate material wherein the image capture device (5204) can operate properly and capture images with sufficient detail. For example, the balloon may be placed near or against tissues in the body of a patient to facilitate diagnostic or interventional operations. FIG. 53 illustrates a sheath (422) and catheter (424) with one embodiment of a toroid shaped balloon (5302). The balloon (5302) of this embodiment includes a lumen (5304) through its center and allows for the deployment of items such as tools, catheters, contrast agent, solutions, etc. from the proximal end of the catheter (424).

Figure 54:
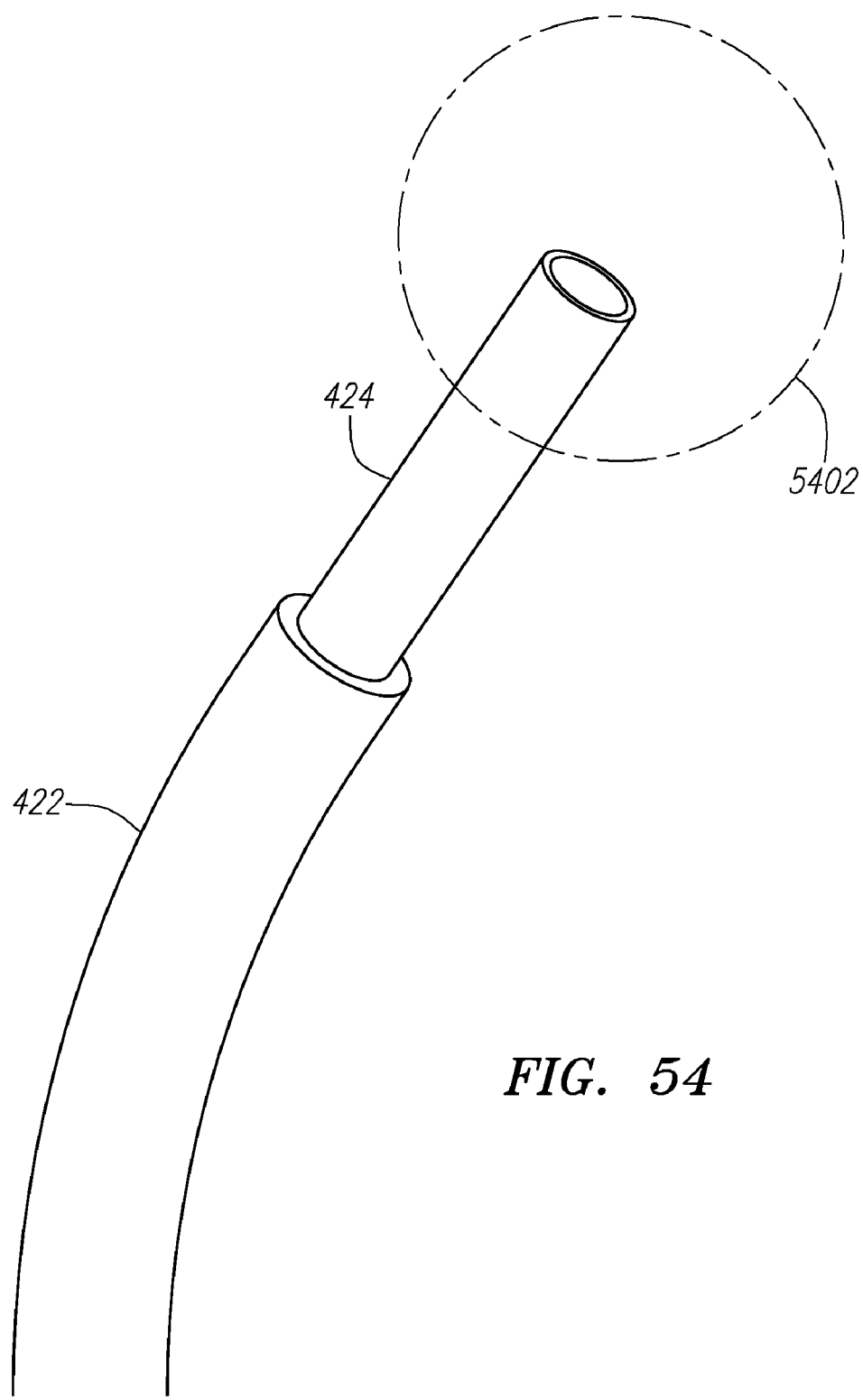
FIG. 54 illustrates a sheath and catheter assembly with distal tip portion of the catheter where a balloon apparatus may be deployed is highlighted.

FIG. 54 illustrates a sheath (422) and catheter (424) with distal tip portion (5402) of the catheter (424) where a balloon may be deployed is highlighted. The discussion that follows below for FIG. 55 through FIG. 87 is described in the context of the distal tip portion (5402) of the catheter (424). Although various types of material may be used to construct the balloon, it may be preferably in some embodiments to use a polyamide material that allows for the transmission of light through the material or a material that is optically transparent. For instance, it may be desirable to view tissues of an organ in a patient through the surface of an inflated balloon with an image capture device.

Figure 55:
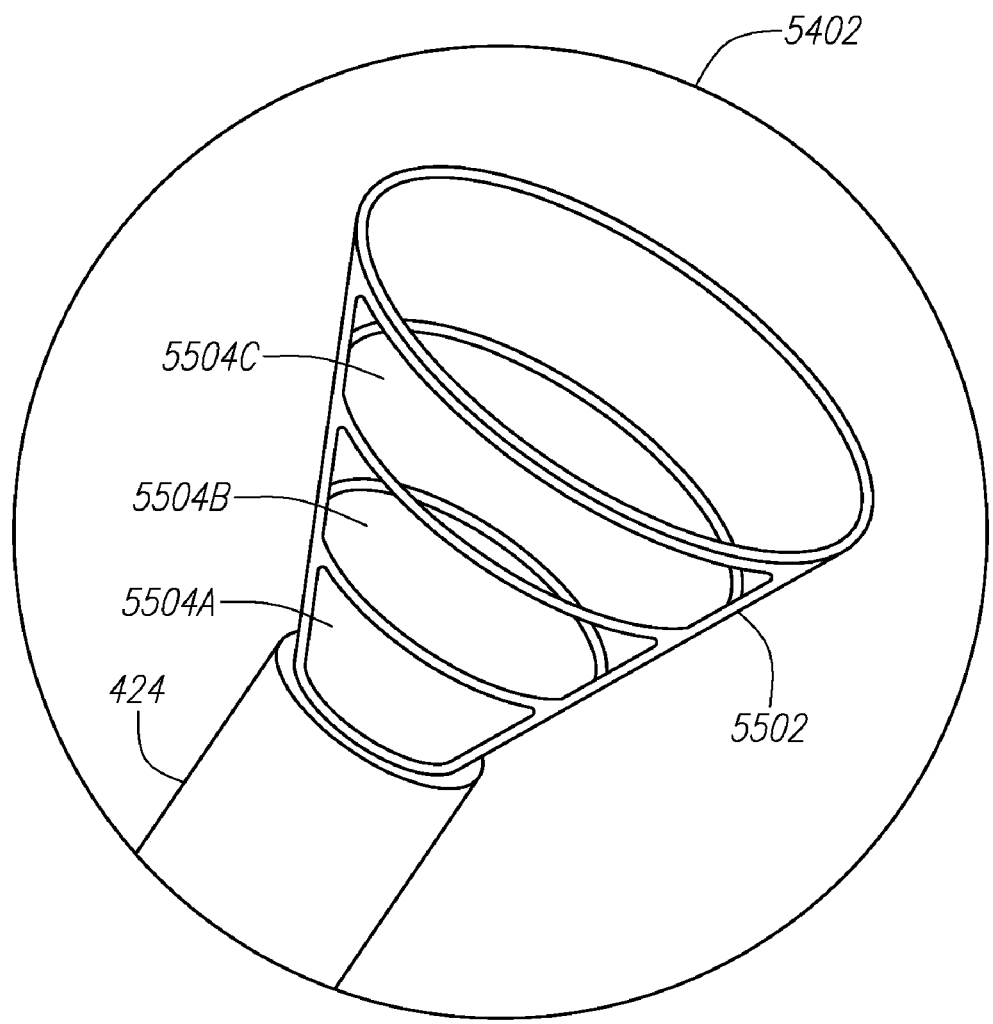
FIG. 55 illustrates one embodiment of a conical shaped balloon apparatus manufactured with a heat bonding process.

FIG. 55 illustrates one embodiment of an inflated conical shaped balloon (5502) manufactured by a heat bonding process. For example, the inflatable chambers are joined by a heat bonding by process. In this embodiment of a balloon (5502) implementation, the balloon (5502) is constructed with three inflatable chambers (5504A, 5504B, 5504C) through a heat bonding process. The chambers (5504A, 5504B, 5504C) are oriented around the axis of the catheter (424). In one embodiment, the pressure for each one of the three chambers may be independently controlled, thus allowing each chamber to be inflated to a different or the same pressure as the other chambers. In another embodiment, the three chambers may be all inflated to the same pressure. Depending on the balloon design, the chambers may function independent of the others wherein puncturing one of the chambers will not affect the other chambers.

Figure 56:
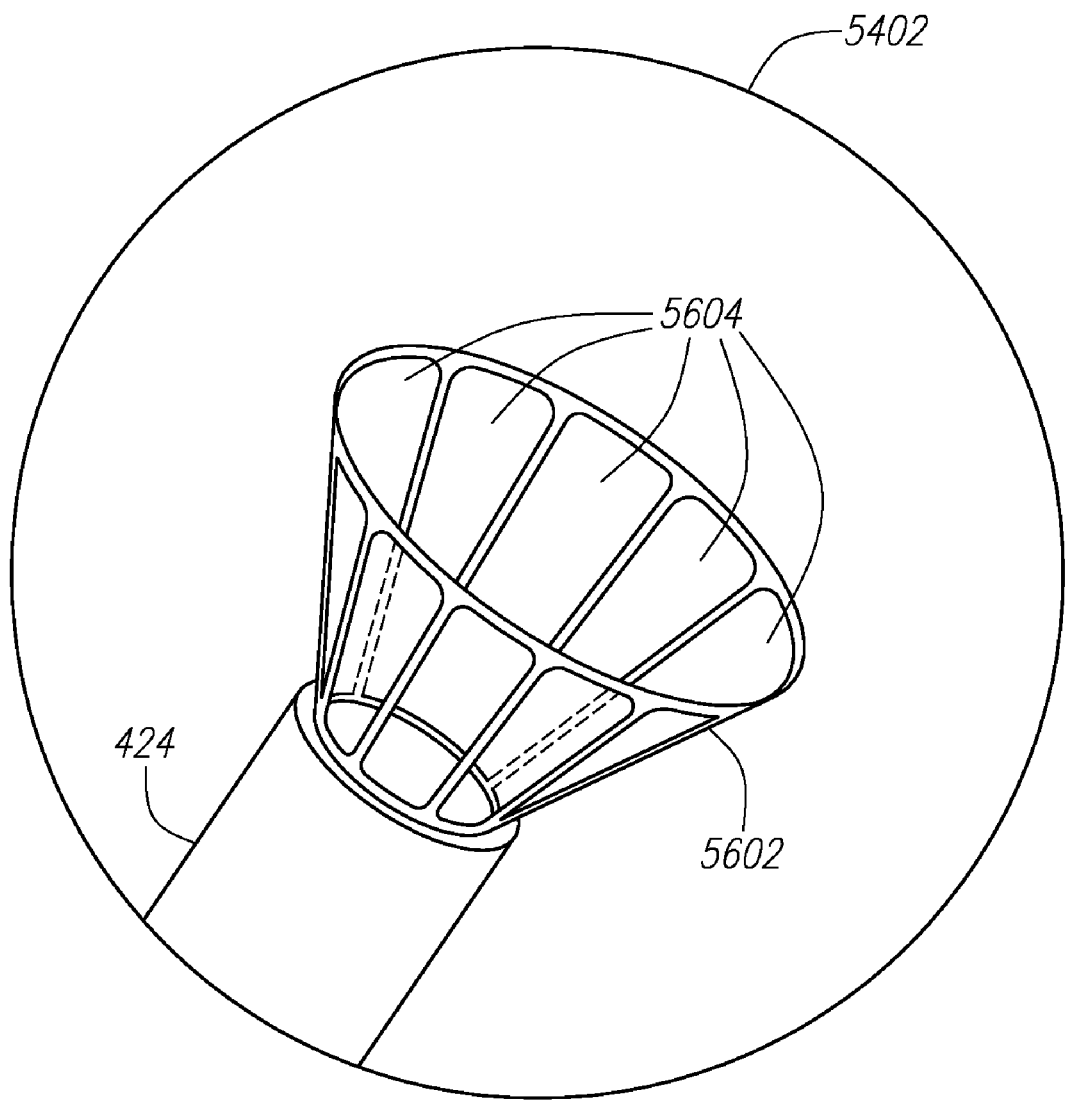
FIG. 56 illustrates another embodiment of a conical shaped balloon apparatus.
Figure 57:
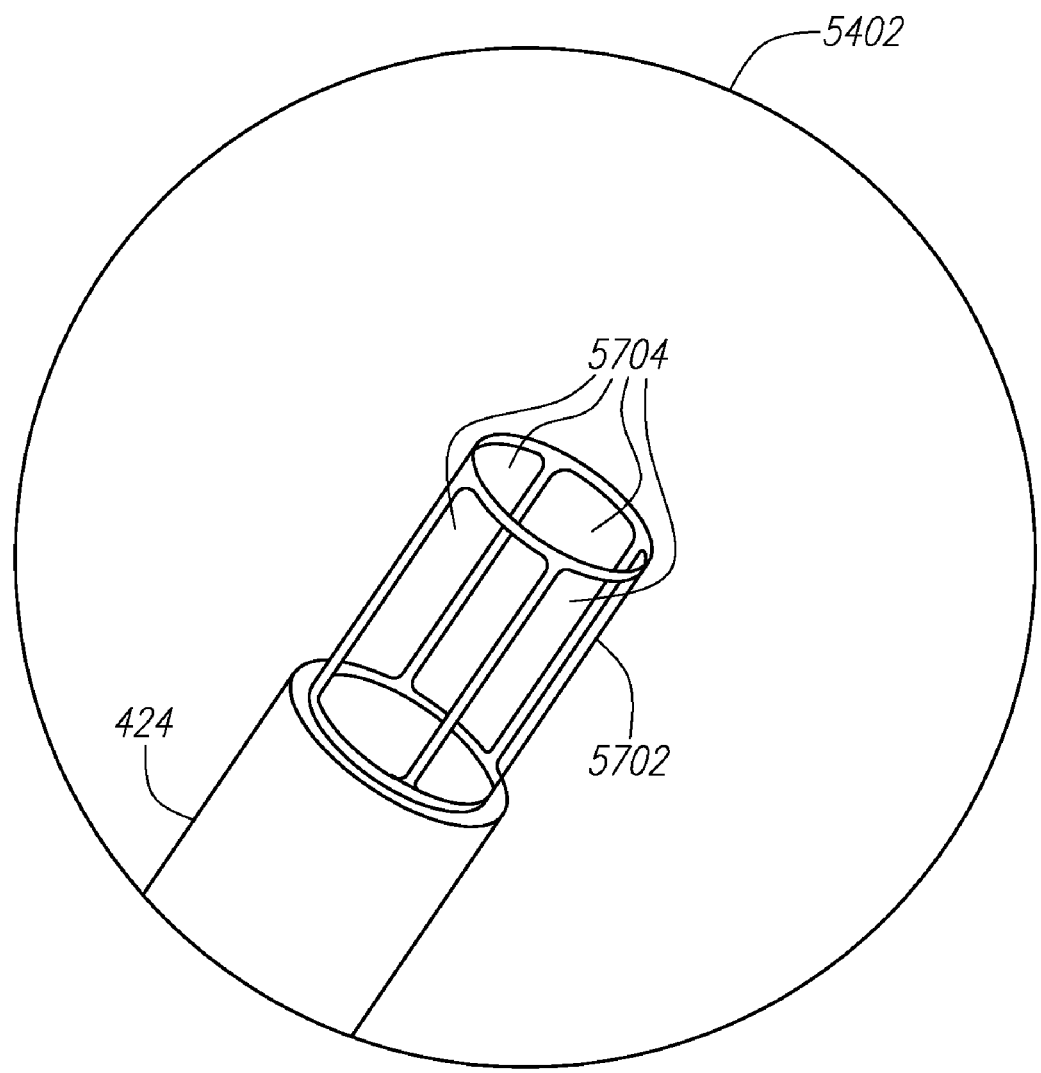
FIG. 57 illustrates one embodiment of a cylindrical shaped balloon apparatus manufactured with a heat bonding process.

FIG. 56 illustrates another embodiment of a conical shaped balloon (5602). Similar to the balloon (5502) illustrated in FIG. 55, this balloon (5602) is also constructed with a plurality of inflatable chambers (5604) by a heat bonding process. The chambers (5604) of this embodiment extend laterally along the axis of the catheter (424). FIG. 57 illustrates one embodiment of a cylindrical shaped balloon (5702) manufactured by a heat bonding process. The chambers (5704) of this embodiment also extend laterally along the axis of the catheter (424). Due to the cylindrical shape of the balloon (5702) of this embodiment, each of the chambers (5704) may be similar to the others in dimensions and capacity, whereas the chambers of the balloons illustrated in FIG. 55 and FIG. 56 may have different dimensions and capacities.

Figure 58:
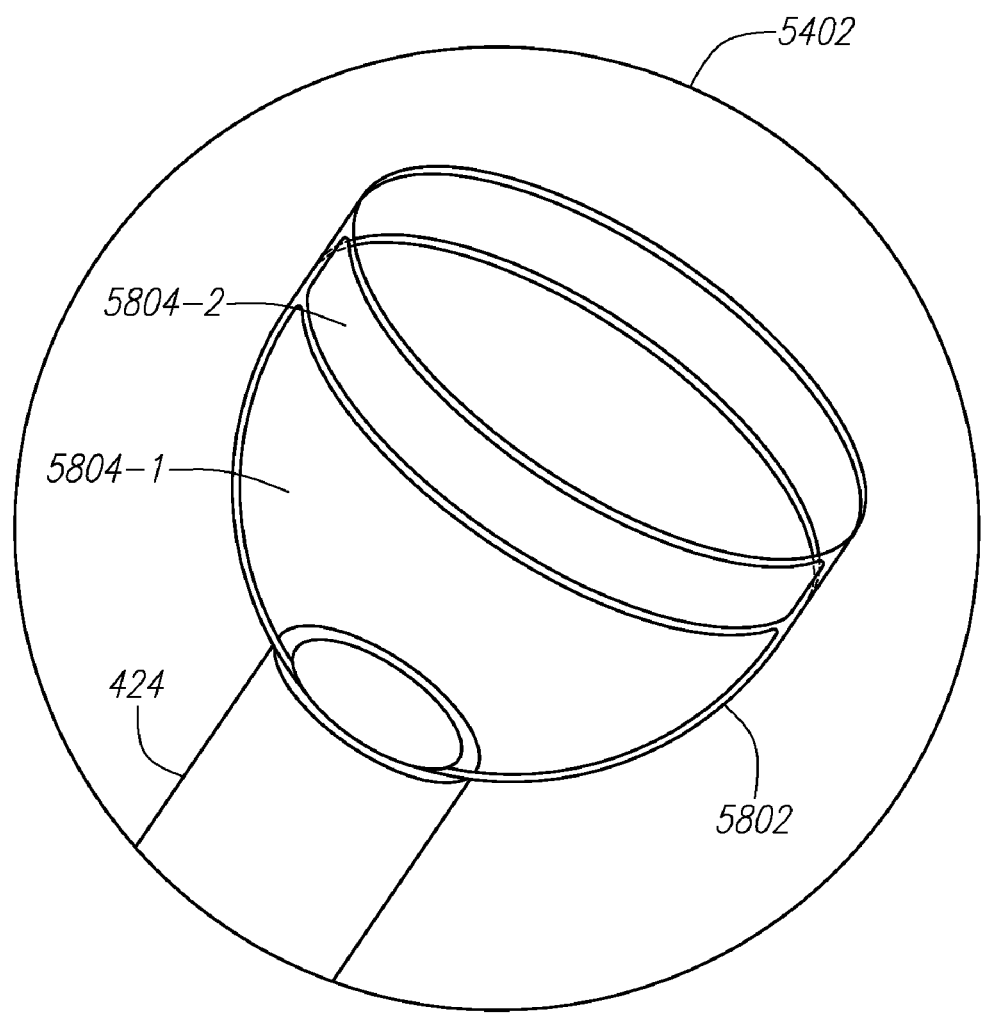
FIG. 58 illustrates one embodiment of a conical shaped balloon apparatus having two chambers that can be inflated to different pressures.
Figure 59:
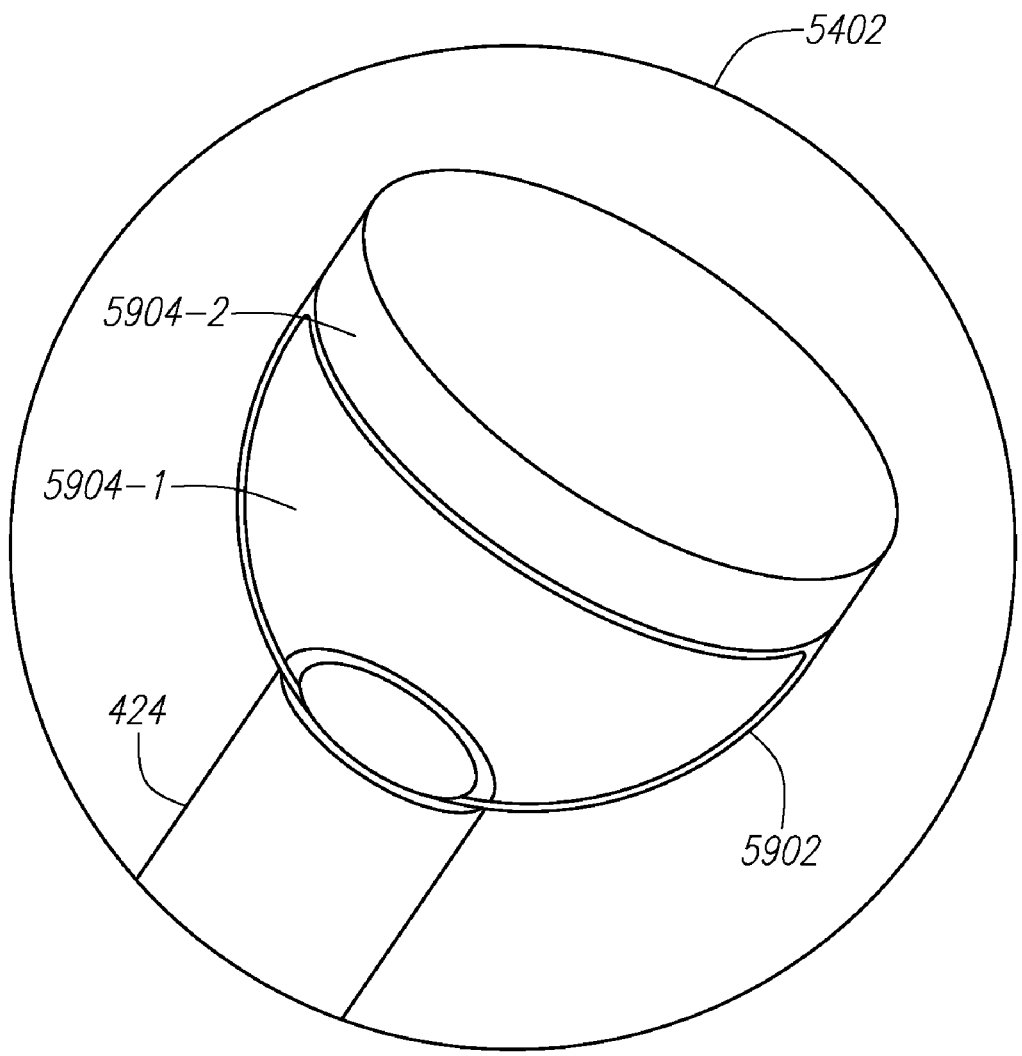
FIG. 59 illustrates one embodiment of a conical shaped balloon apparatus having one inflatable chamber and a soft distal tip.

FIG. 58 illustrates one embodiment of a conical shaped balloon (5802) having two or more chambers (**5804-1, 5804-2 ... 5804-*n*) that may be inflated to the same or different pressures. In one embodiment, the proximal chamber (5804-1) may be inflated to a higher pressure than the second chamber (5804-2). It may be desirable to inflate the second chamber (5804-2) to a lower pressure because the second chamber may come into contact with tissue and rest against the tissue, such that the lower pressure of the chamber (5804-2) could make a substantially softer contact with a tissue surface. As may be appreciated, it may be desirable in some applications or procedures to have a softer contact with the surface of tissues. FIG. 59 illustrates one embodiment of a conical shaped balloon (5902) having one inflatable chamber (5904-1) and a soft distal section (5904-2). The soft distal section (5904-2) may be slightly softer than the inflatable chamber (5904-1). In one embodiment, the soft distal section (5904-2**) may be a curtain or skirt constructed with a soft polyamide material or plastic having a relatively low Durometer hardness value.

Figure 60:
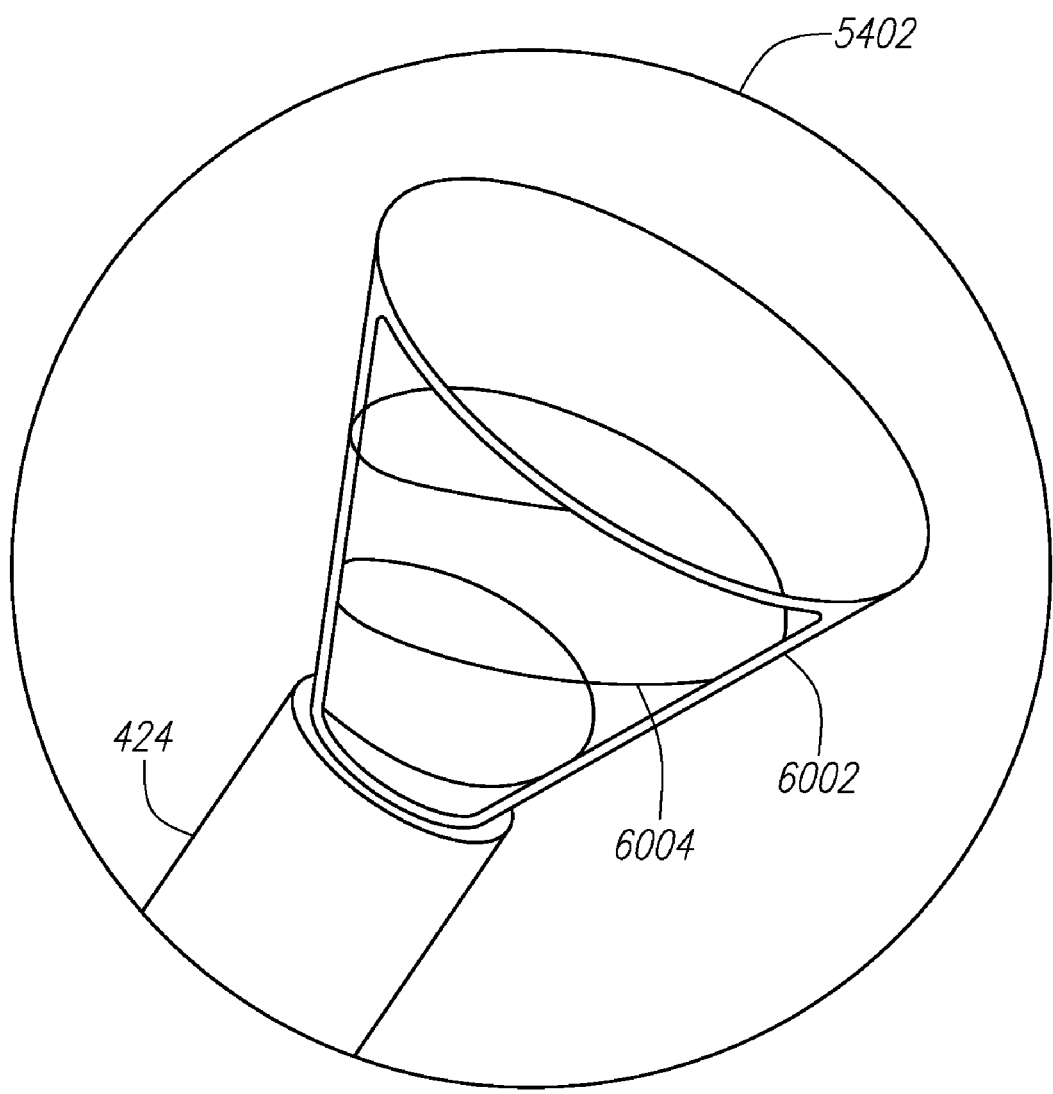
FIG. 60 illustrates one embodiment of a conical shaped balloon apparatus having structural reinforcement wires.
Figure 61:
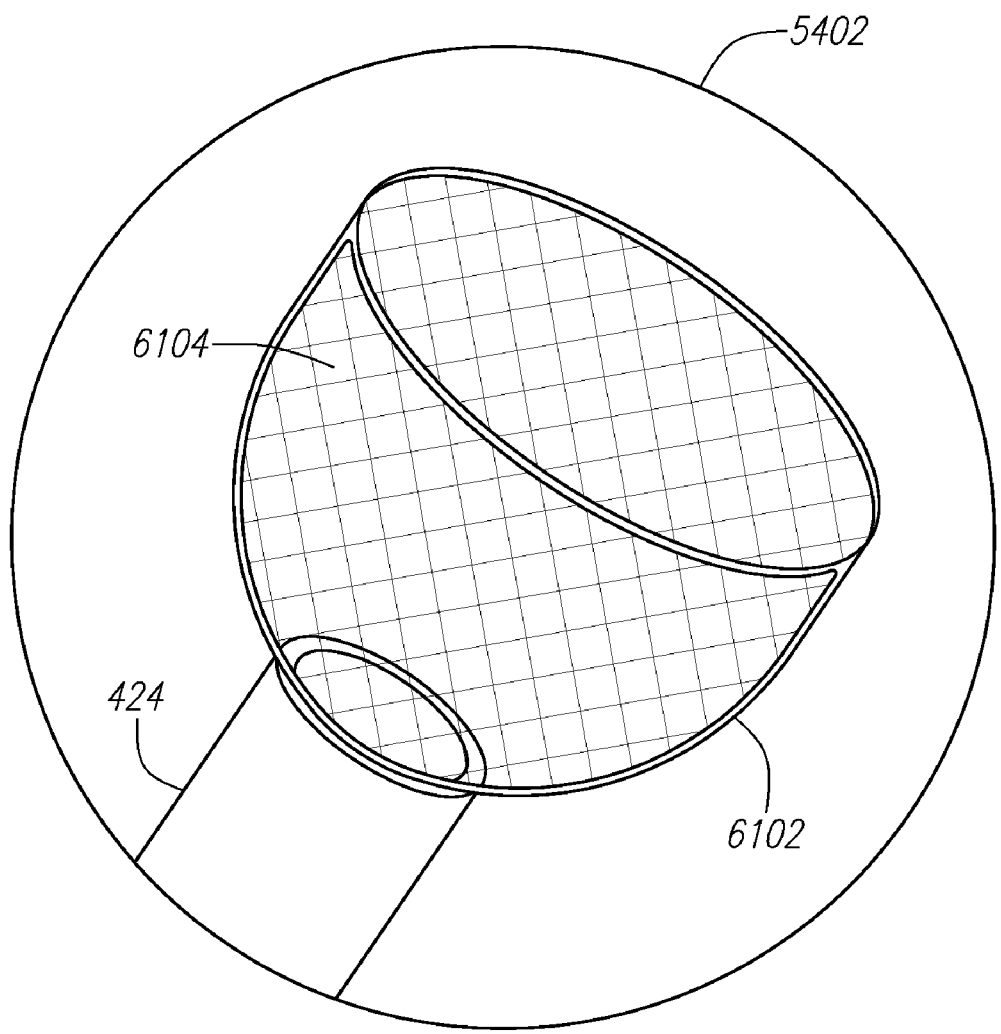
FIG. 61 illustrates one embodiment of a cup shaped balloon apparatus having a stent type or mesh type of reinforcement.
Figure 62:
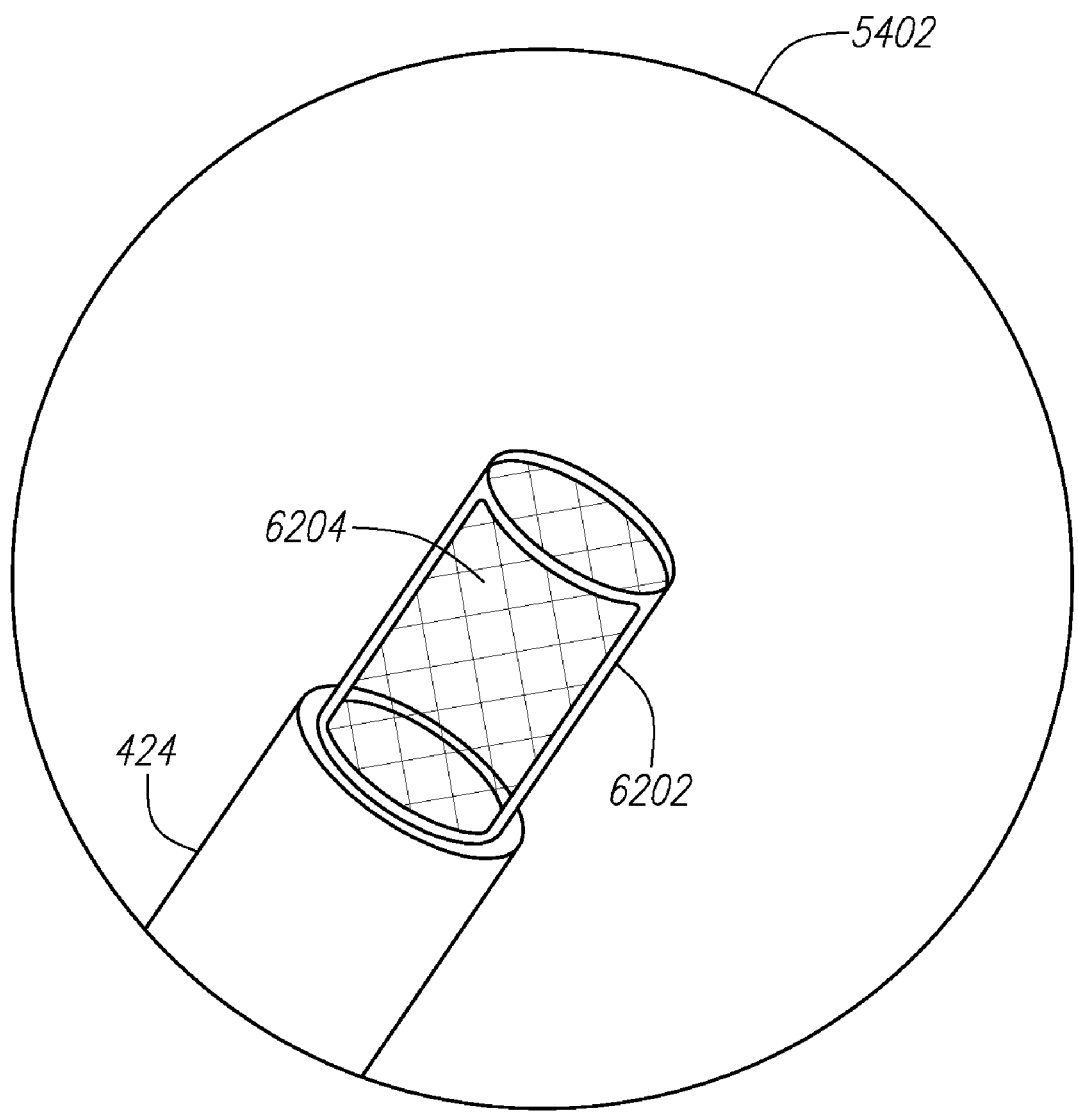
FIG. 62 illustrates one embodiment of a cylindrical shaped balloon apparatus having a stent type or mesh type of reinforcement.

Depending on the construction of a balloon, some reinforcement may be desirable in certain instances. For example, a user may not want a balloon to collapse during a procedure or a particular procedure may require the balloon to provide a minimal level of rigidity. FIG. 60 illustrates one embodiment of a conical shaped balloon (6002) having a structural reinforcement wire (6004) deployed within balloon (6002). In one instance, the wire (6004) is woven into the surface of the balloon (6002). In this example, the wire (6004) may be a coil that extends from the distal tip of the catheter (424) through the balloon (6002) to the distal edge of the balloon (6002). FIG. 61 illustrates one embodiment of a cup shaped balloon (6102) having a stent type of reinforcement (6104). In this embodiment, the stent structure is built into the balloon body and is collapsible. By pulling the balloon (6102) back into the distal tip of the catheter (424), the stent structure collapses. To deploy the balloon (6102), the balloon (6102) is pushed out from a working lumen or channel of the catheter (424) and the stent structure expands automatically. FIG. 62 illustrates one embodiment of a cylindrical shaped balloon (6202) having a stent type of reinforcement (6204).

Figure 63:
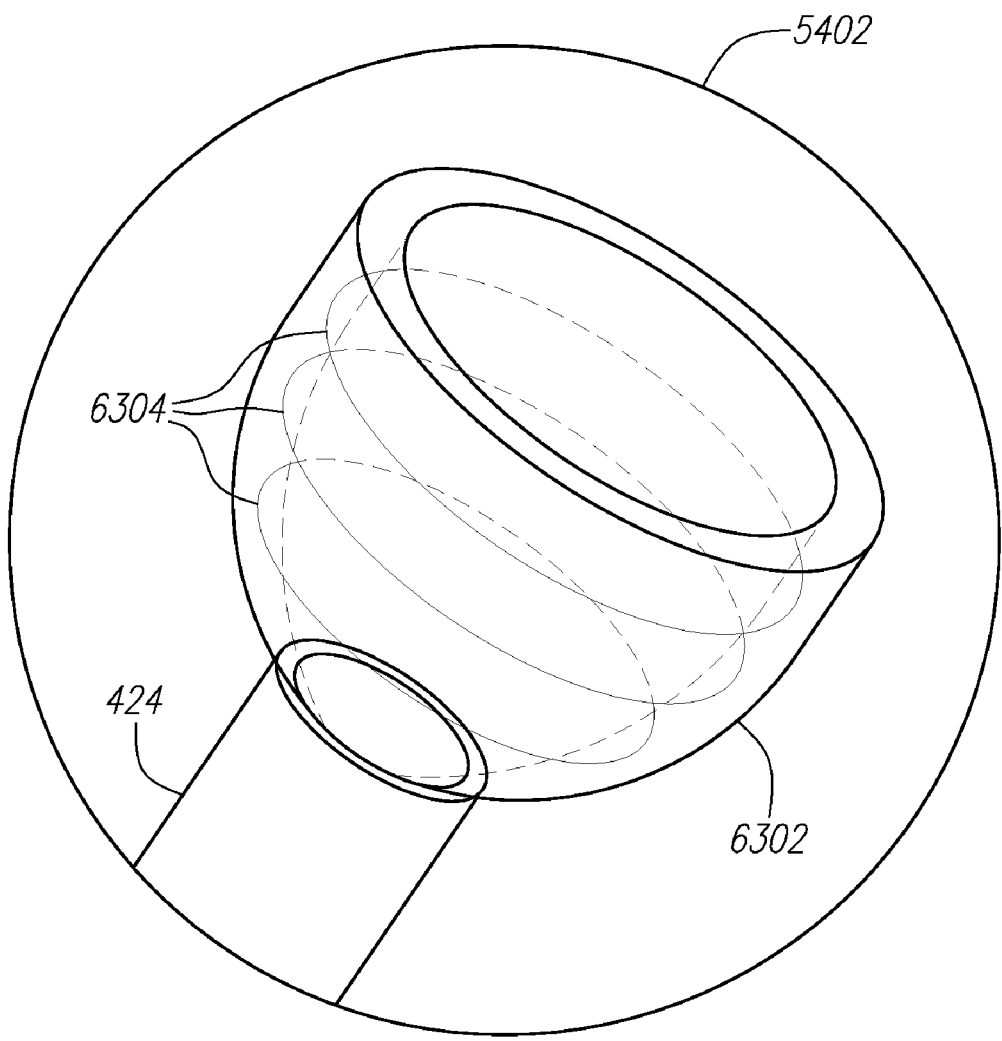
FIG. 63 illustrates one embodiment of a cup shaped balloon apparatus having lateral ring supports.
Figure 64:
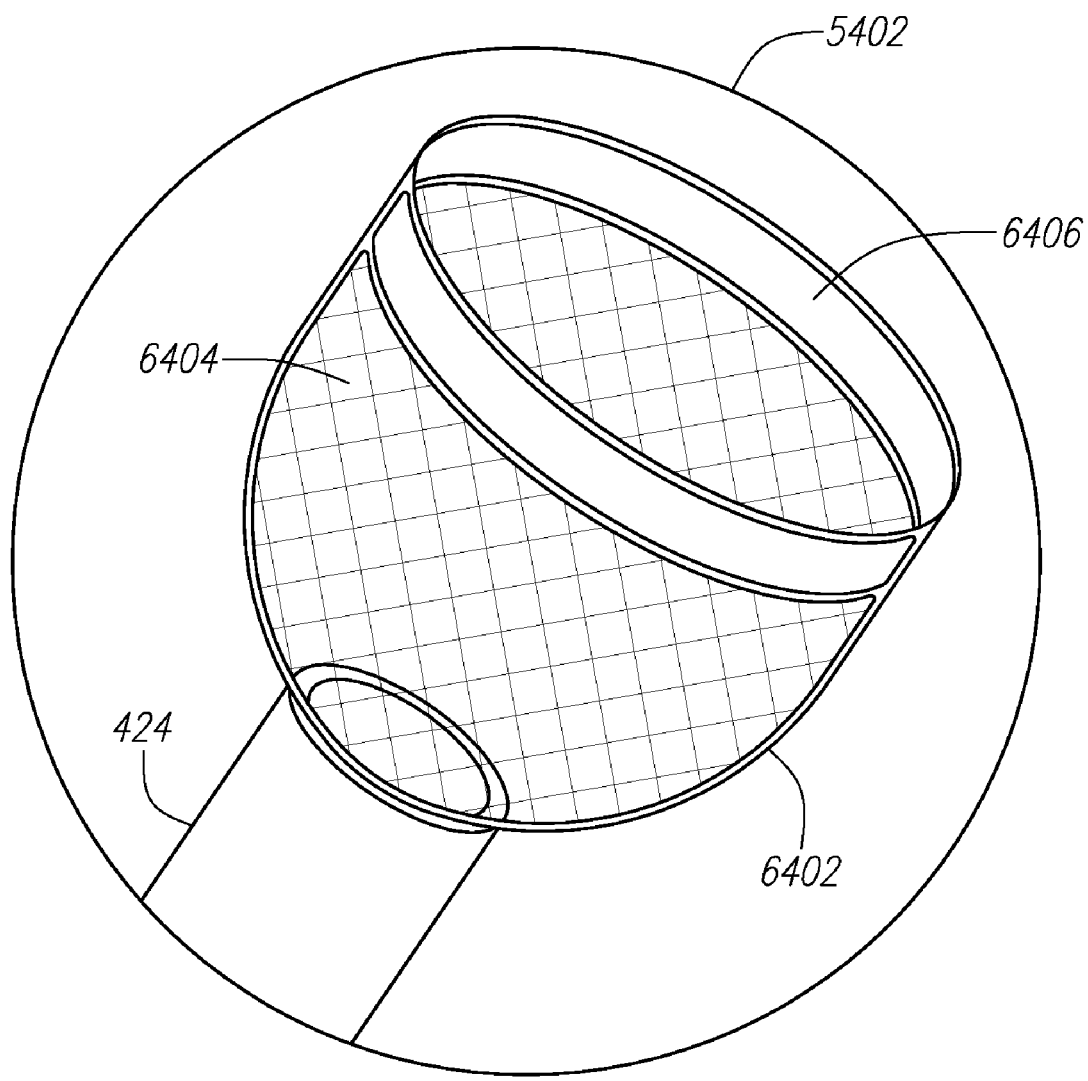
FIG. 64 illustrates one embodiment of a cup-shaped balloon apparatus having a first chamber with a stent or type of reinforcement structure and a distal second chamber without the stent or mesh type reinforcement.
Figure 65:
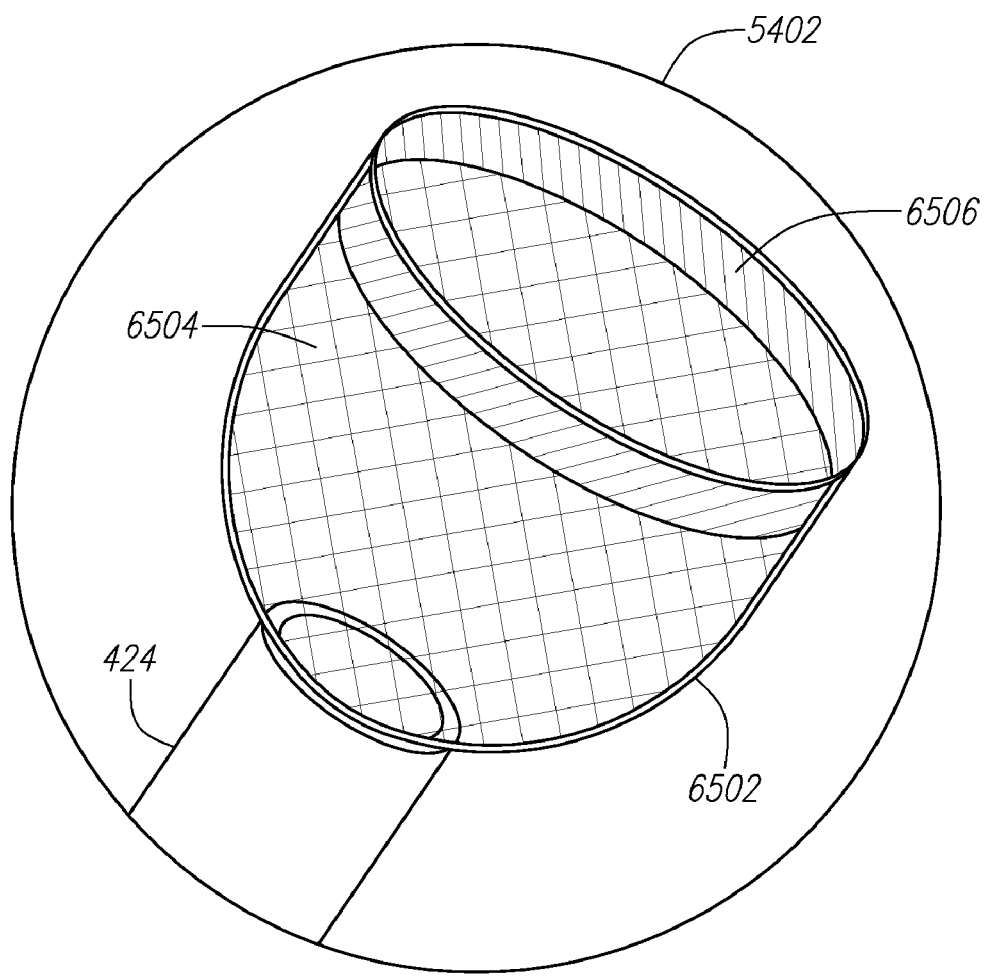
FIG. 65 illustrates one embodiment of a cup shaped balloon apparatus having a first chamber with a stent or mesh type of reinforcement structure and a distal edge portion constructed of a soft material.

FIG. 63 illustrates one embodiment of a cup shaped balloon (6302) having lateral support rings (6304). In this example, the ring supports are constructed of a polyamide material and located within the sidewalls of the balloon (6302). For one embodiment, the support rings (6304) are approximately the same size. In other embodiments, the support rings (6304) may vary in size depending on its designated location within the balloon (6302). FIG. 64 illustrates one embodiment of a cup shaped balloon (6402) having a first chamber (6404) with a stent type reinforcement structure and a distal second chamber (6406) without the stent type reinforcement. In this example, both chambers (6404, 6406) may be inflated to the same or different pressures. For one implementation, the distal second chamber (6406) is inflated to a pressure sufficiently low such that the surface of the second chamber (6406) may be pliable or relatively soft when in contact with tissue. FIG. 65 illustrates one embodiment of a cup shaped balloon (6502) having a first chamber (6504) with a stent type reinforcement structure and a distal edge (6506) constructed of a soft material. In this embodiment, the distal edge is constructed with a soft pliable polyamide material.

Figure 66:
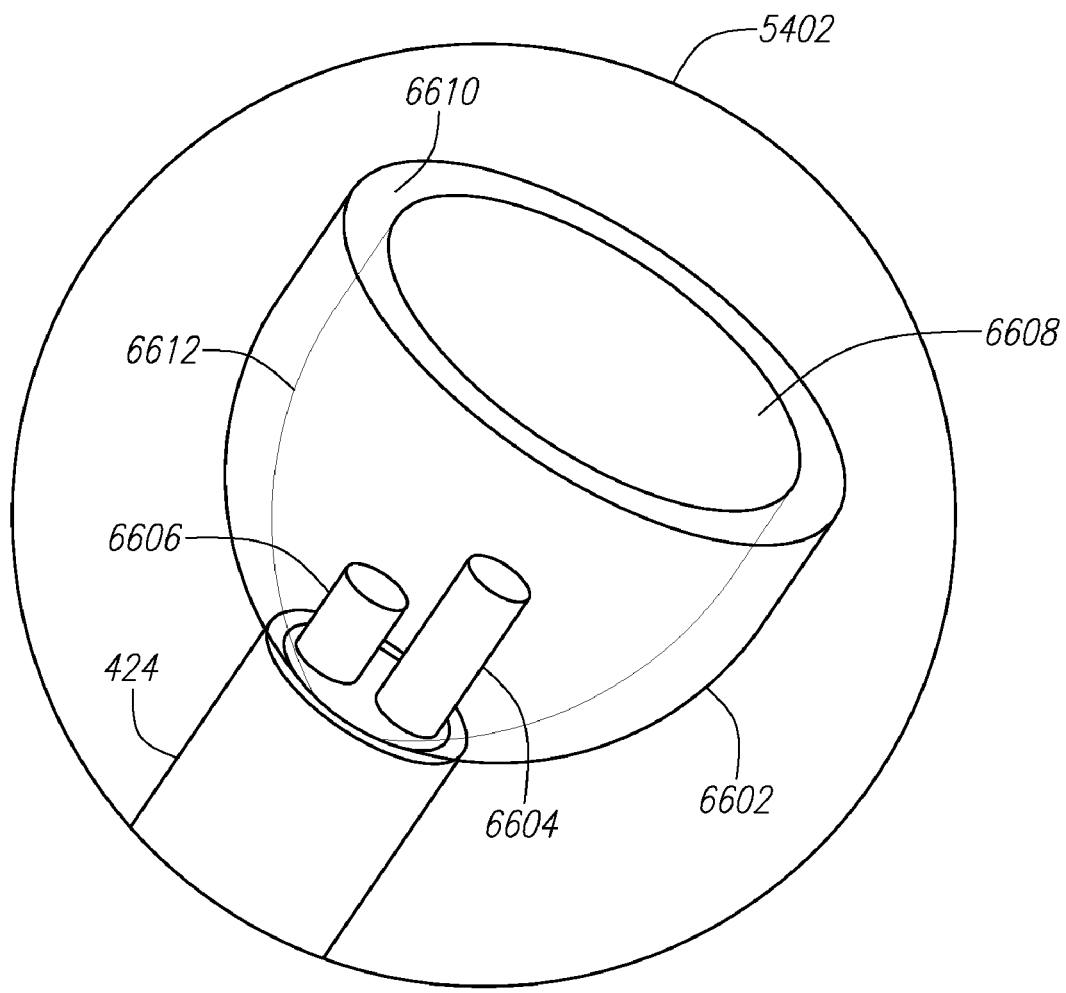
FIG. 66 illustrates one embodiment of a cup-shaped balloon apparatus with an image capture device and flush port at the distal portion of a catheter.
Figure 67:
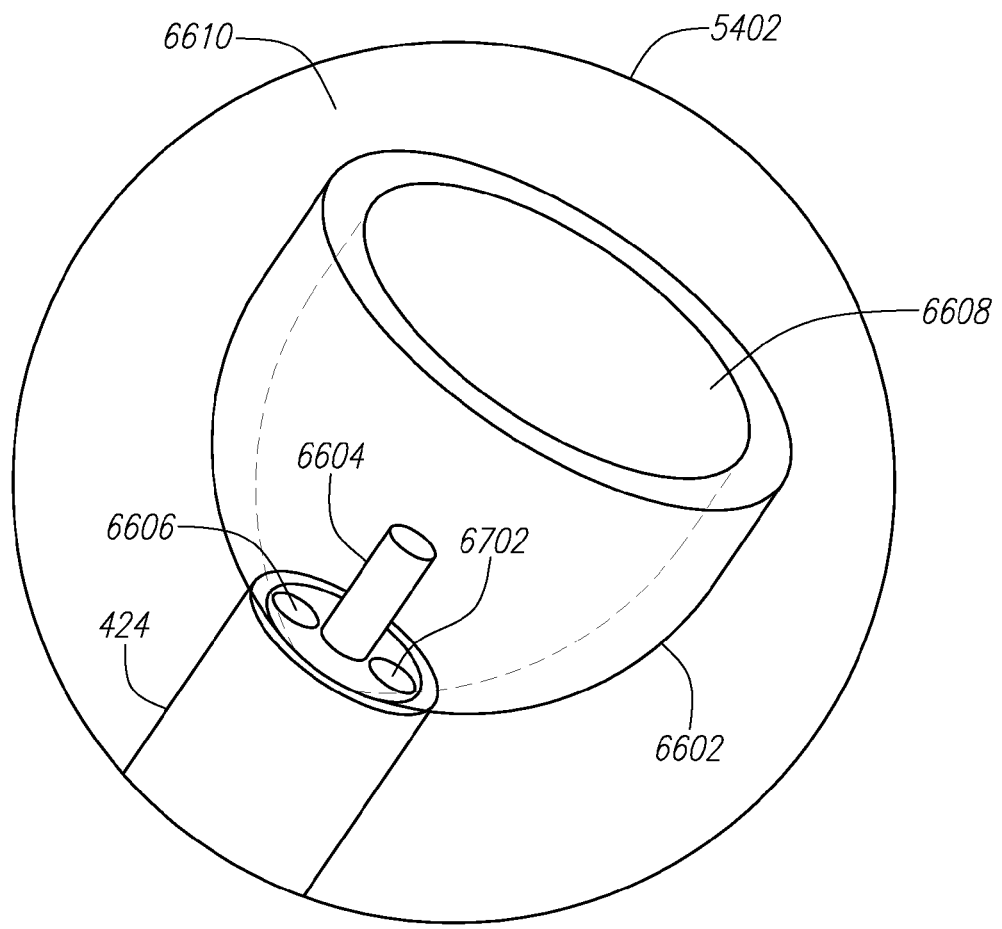
FIG. 67 illustrates one embodiment of a catheter having a cup-shaped balloon apparatus with an image capture device, a flush port, and a working lumen at the distal portion of a catheter.

FIG. 66 illustrates one embodiment of a cup shaped balloon (6602) together with an image capture device (6604) and flush port (6606) at the distal tip of a catheter (424). The cup shape of this embodiment allows for the creation of a working volume (6608). By placing the distal edge of the balloon (6610) up against tissue, a working volume (6608) is formed by the surface of the tissue and the inner surface of the balloon (6612). Although the working volume (6608) may contain blood during some procedures, the blood may be evacuated by flushing the working volume (6608) by injecting saline or carbon dioxide through the flush port (6606). With the working volume (6608) cleared, the image capture device (6604) may be used to examine the surrounding tissue. FIG. 67 illustrates one embodiment of a catheter (424) having a cup shaped balloon (6602) together with an image capture device (6604), a flush port (6606), and a working lumen (6702) at the distal tip of a catheter (424). The working lumen (6702) is a hollow channel in which tools or surgical instruments may be passed from the proximal end of the catheter (424) to the distal end of the catheter (424) to perform operations in the working volume (6608) of the balloon (6602).

Figure 68:
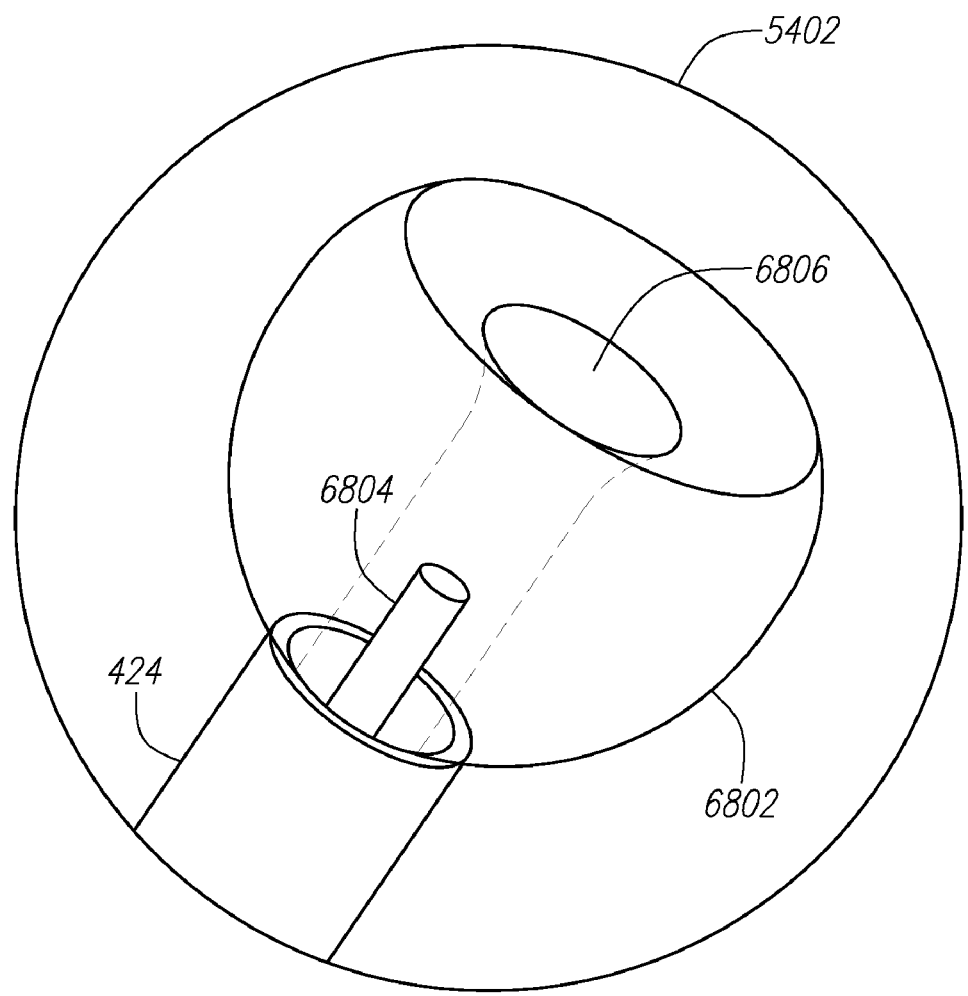
FIG. 68 illustrates one embodiment of a toroid-shaped balloon apparatus with a suction port at the distal portion of a catheter.

FIG. 68 illustrates one embodiment of a toroid shaped balloon (6802) with a suction port (6804) at the distal tip of a catheter (424). The balloon (6802) of this embodiment includes a working volume (6806) that can be evacuated by suctioning out the contents therein when the distal surface of the balloon (6802) is up against a surface. Furthermore, the suction provided by the suction port (6804) may allow the balloon to be anchored to a surface if a sufficient vacuum force is created in the working volume (6806).

Figure 69:
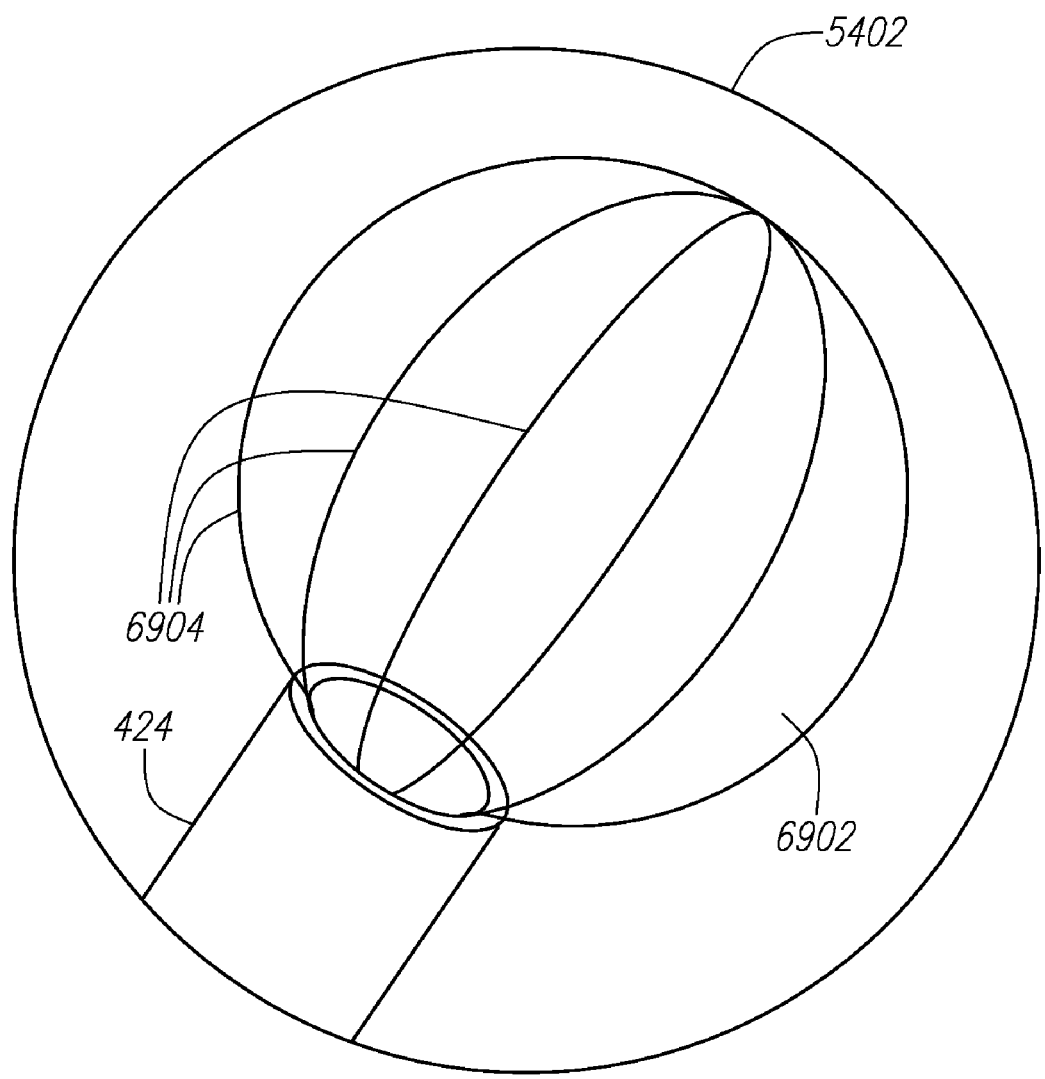
FIG. 69 illustrates one embodiment of a balloon apparatus with support ribs.

FIG. 69 illustrates one embodiment of a balloon (6902) that includes collapsible support ribs (6904).

Figure 70:
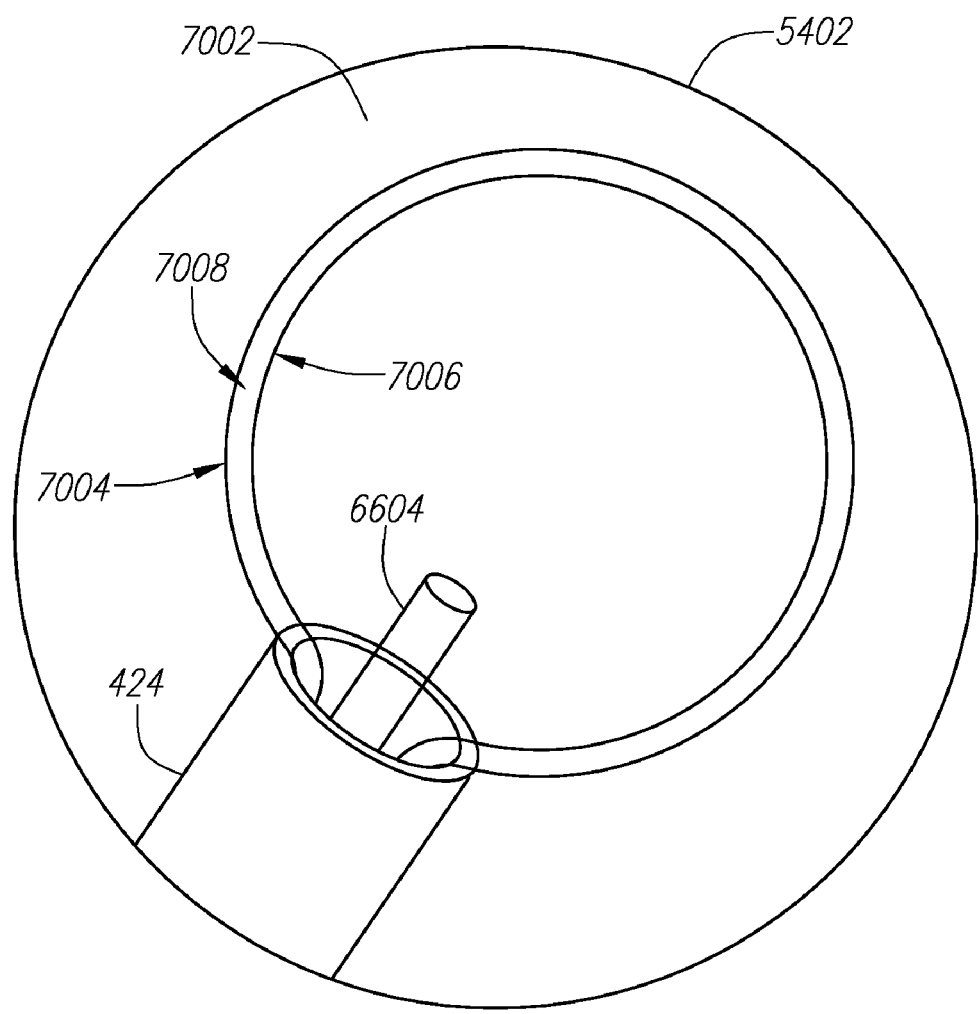
FIG. 70 illustrates one embodiment of two-layered balloon apparatus with an image capture device at the distal portion of a catheter.

FIG. 70 illustrates one embodiment of a two layered balloon (7002) together with an image capture device (6604) at the distal tip of a catheter (424). In this embodiment, the balloon (7002) has an outer layer (7004) and an inner layer (7006). Encapsulated between the two layers (7004, 7006) is a space (7008) which may be filled with a saline solution or a gas medium, e.g., carbon dioxide, etc. Preferably, the solution/gas medium encapsulated between the layers (7004, 7006) as well as the material of the balloon and the combination thereof, are transparent to the image capture device (6604), such that image capture device (734) would be able to "view" tissue outside of the balloon (7002). The image capture device (6604) may be any suitable image capturing device, e.g., optical, ultrasound, laser, CCD, etc.

Figure 71:
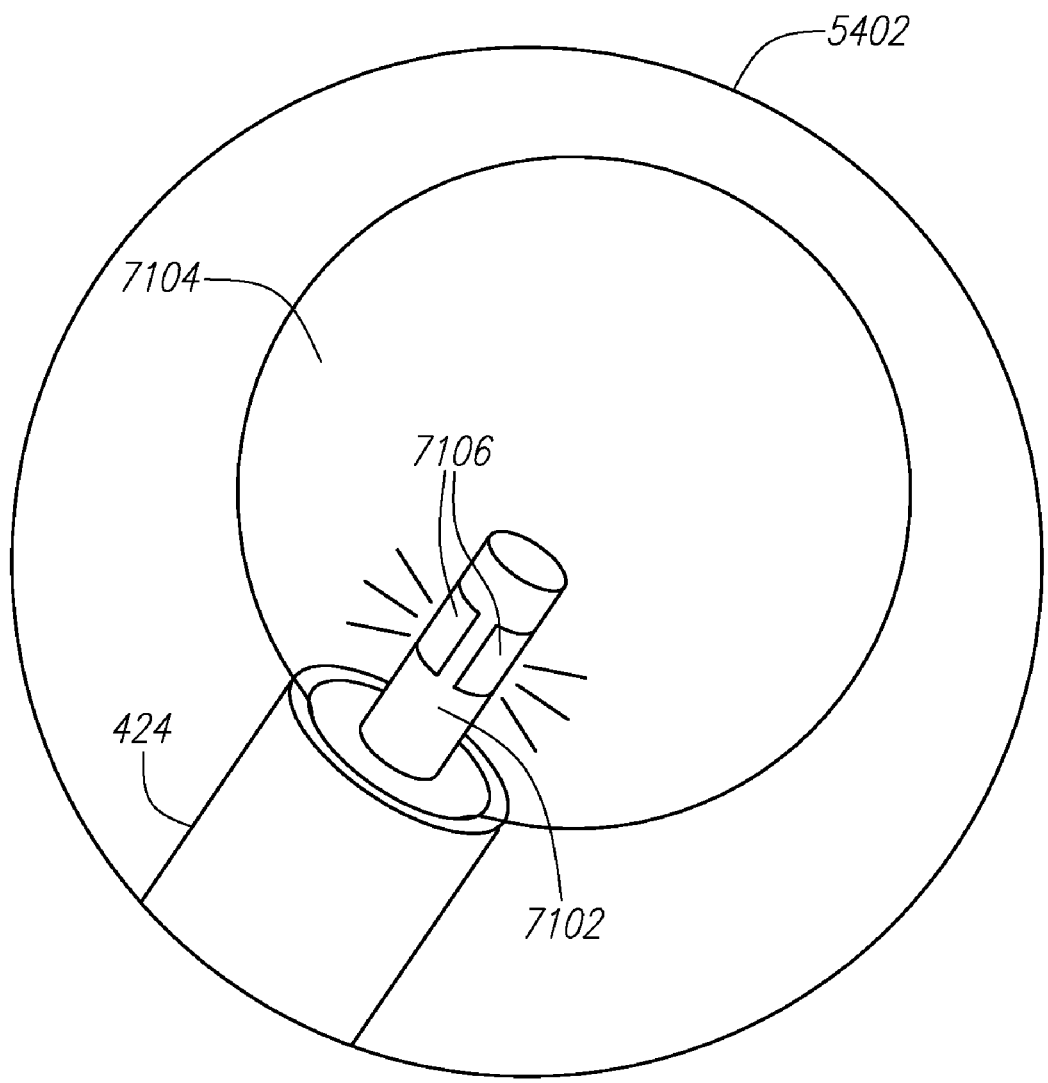
FIG. 71 illustrates one embodiment of a side-firing ultrasound transducer enclosed within an inflated balloon apparatus at the distal portion of a catheter.

FIG. 71 illustrates one embodiment of a side firing ultrasound transducer catheter (7102) enclosed within an inflated balloon (7104) at the distal tip of a catheter (424). In this embodiment, ultrasound transducer elements (7106) are mounted on the circumferential surface of the transducer catheter.

Figure 72:
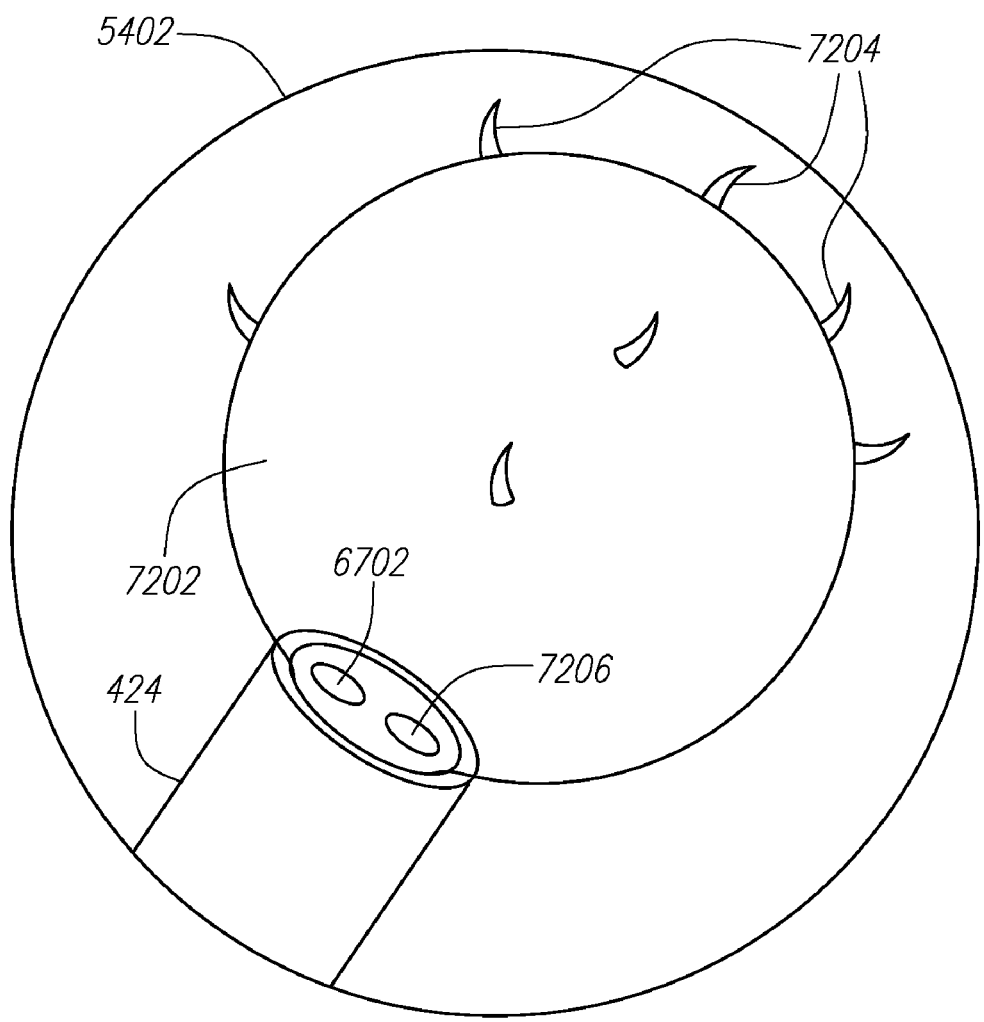
FIG. 72 illustrates one embodiment of a balloon apparatus with spikes at the distal portion of a catheter.
Figure 73:
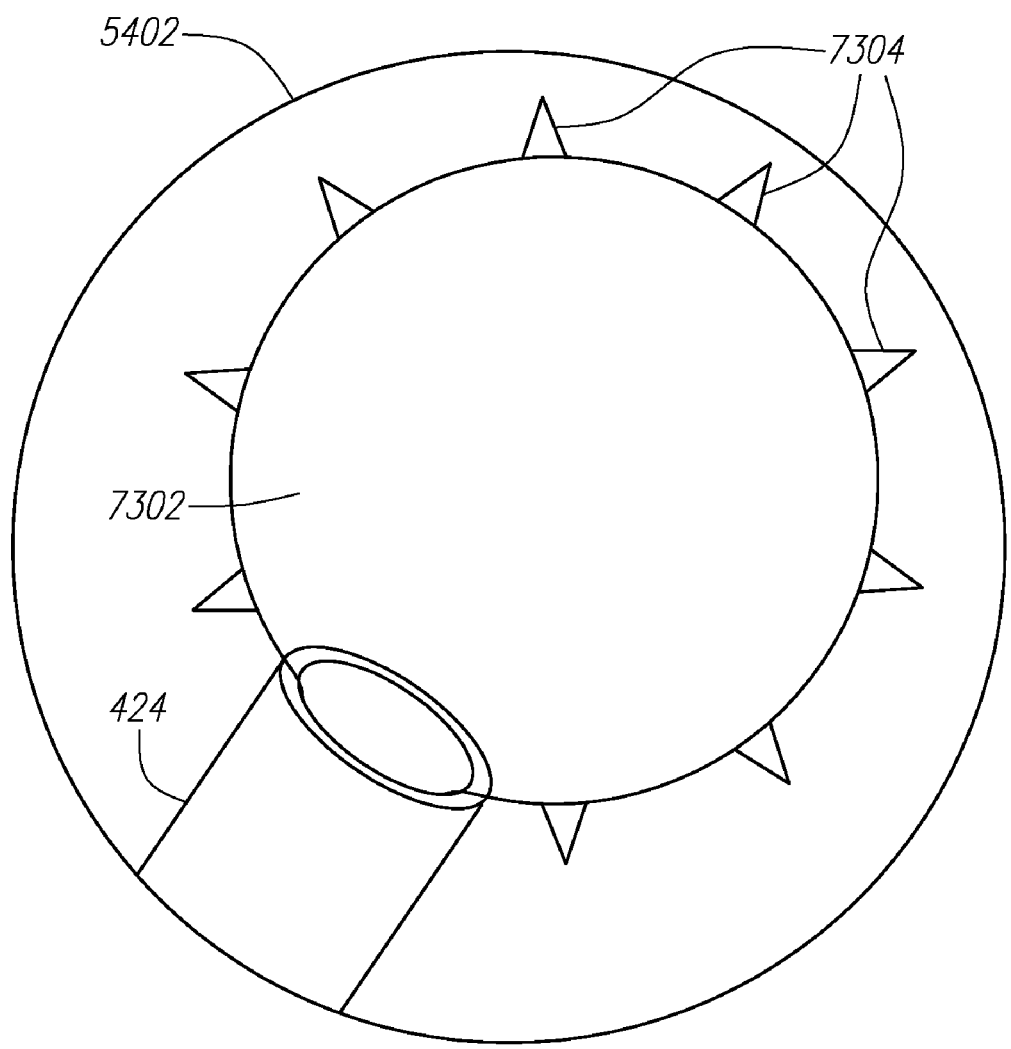
FIG. 73 illustrates one embodiment of a balloon apparatus with spines at the distal portion of a catheter.

FIG. 72 illustrates one embodiment of a balloon (7202) with a plurality of spikes (7204) at the distal tip of a catheter (424). In one embodiment, the spikes (7204) may be employed to temporarily anchor an inflated balloon (7202) to a tissue structure. The catheter (424) of this embodiment includes a first lumen (6702) and a second lumen (7206). As with other lumens, each can be used to transfer tools, imaging devices, catheters, illumination fibers, etc. from the proximal end of the catheter (424) to the distal tip. FIG. 73 illustrates one embodiment of a balloon (7302) with spines (7304) at the distal tip of a catheter (424). The spines (7304) may be employed for anchoring the balloon (7302) like the spikes (7204) discussed directly above.

Figure 74:
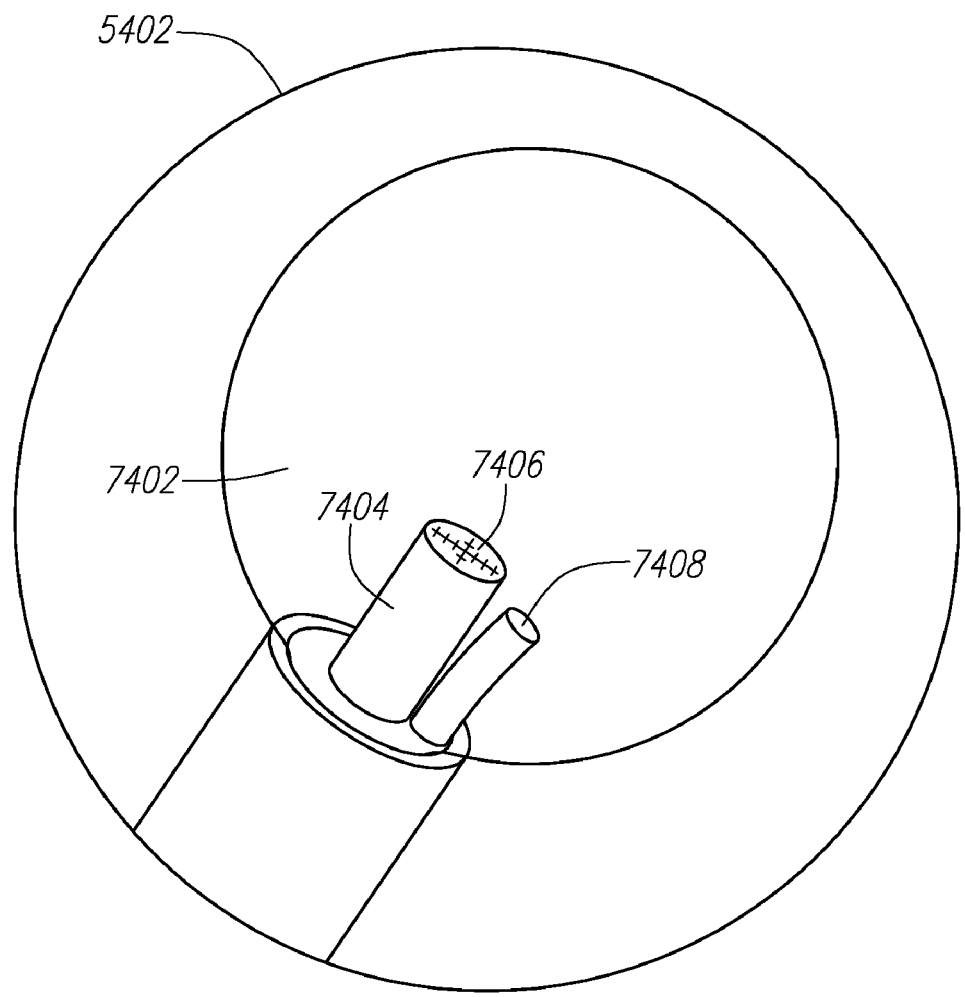
FIG. 74 illustrates one embodiment of an image capture device with a reticle and illumination fibers enclosed within a balloon apparatus at the distal portion of a catheter.
Figure 75:
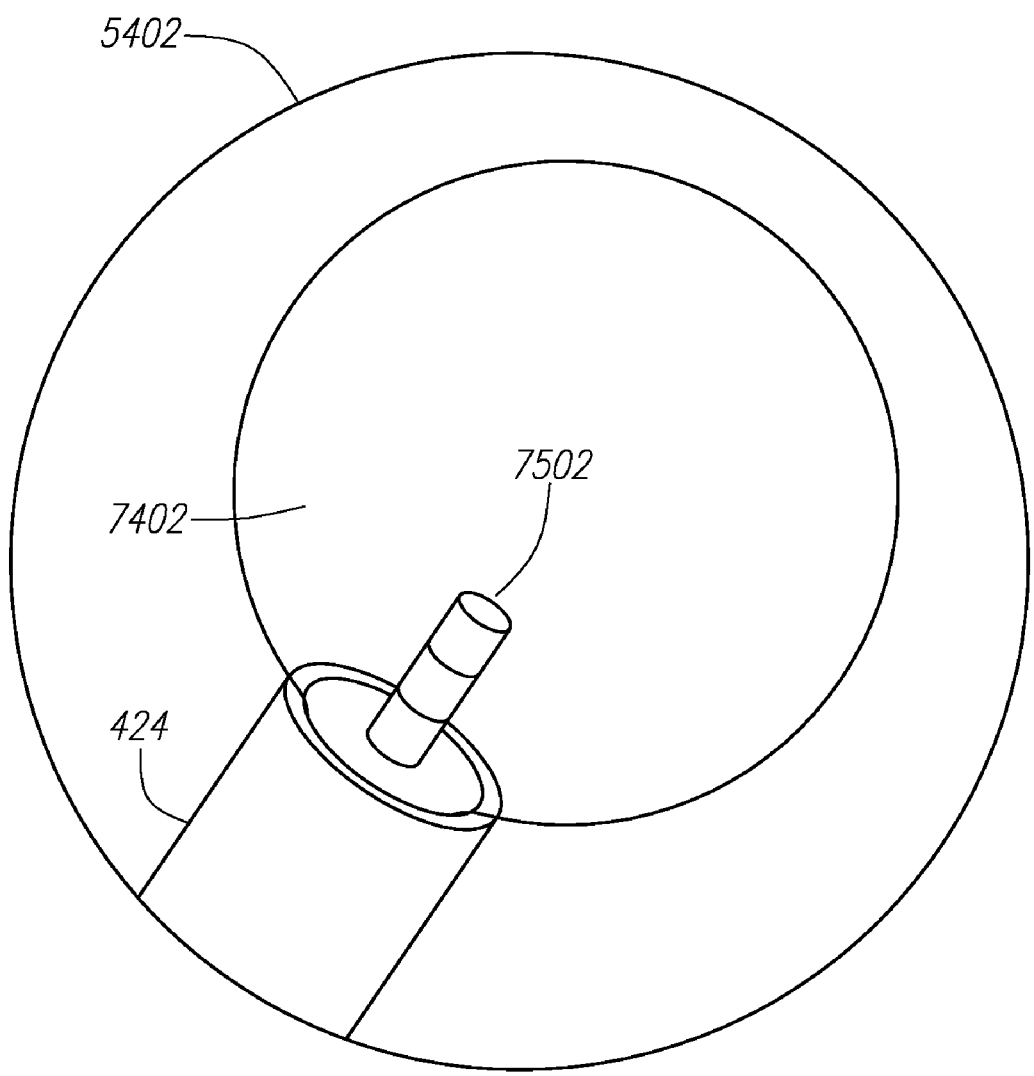
FIG. 75 illustrates one embodiment of an articulating endoscope enclosed within a balloon apparatus at the distal portion of a catheter.

FIG. 74 illustrates one embodiment of an image capture device (7404) with a reticle (7406) and illumination fibers (7408) enclosed within a balloon (7402) at the distal tip of a catheter (424). The depicted embodiment features an image capture device (7404) which may or may not have a lens. The illumination fibers (7408) may radiate light, infrared radiation, or other radiation to illuminate an area of interest. The image capture device (7404), which may comprise a fiberscope, CCD chip, infrared imaging device, such as those available from CardioOptics Incorporated, ultrasound device, or other image capture device, may be used, for example, to search for objects such as stones. In one embodiment, the reticle (7406) allows for the measurement of interesting tissue structures. FIG. 75 illustrates one embodiment of an articulating endoscope (7502) enclosed within a balloon (7402) at the distal tip of a catheter (424). The articulating endoscope (7502) of one embodiment may, in addition to moving in and out relative to the distal tip of the catheter (424); it is capable of additional manipulations, e.g., bend, roll, and pitch, within the volume defined by the balloon in order to access any desired position or area on the balloon surface.

Figure 76:
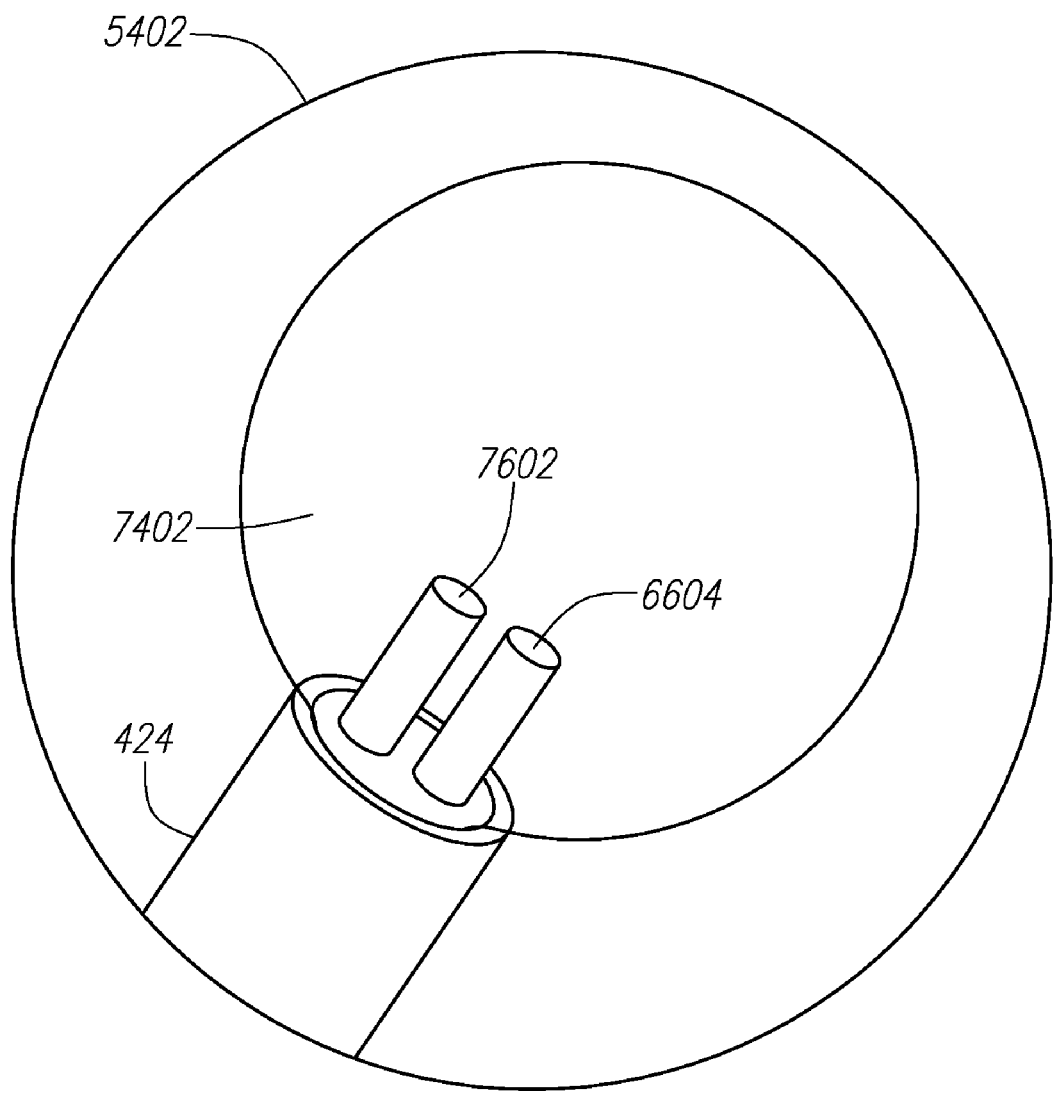
FIG. 76 illustrates one embodiment of a laser fiber and an image capture device enclosed within a balloon apparatus at the distal portion of a catheter.

FIG. 76 illustrates one embodiment of a laser fiber (7602) and an image capture device (6604) enclosed within a balloon (7402) at the distal tip of a catheter (424). In one embodiment, the laser fiber may be a lithotripsy laser fiber. Such a fiber may comprise a quartz fiber and be associated with a laser, such as a Holmium YAG laser, to apply energy to objects such as kidney stones. In one configuration, the laser source is positioned and interfaced with the fiber (16026) proximally, as in a typical lithotripsy configuration, with the exception that in the subject embodiment, the fiber is positioned down the working lumen of one or more robotic catheters. Since the distal tip of the lithotripsy fiber is configured to deliver energy to a target object, such as a kidney stone, the distal tip may be more generically described as an energy source. Indeed, in other embodiments, other energy sources, besides laser, may be utilized to effect tissue. For example, in other embodiments, the energy source may comprise an RF electrode, an ultrasound transducer, such as a high-frequency ultrasound transducer, or other radiative, conductive, ablative, or convective energy source.

Figure 77:
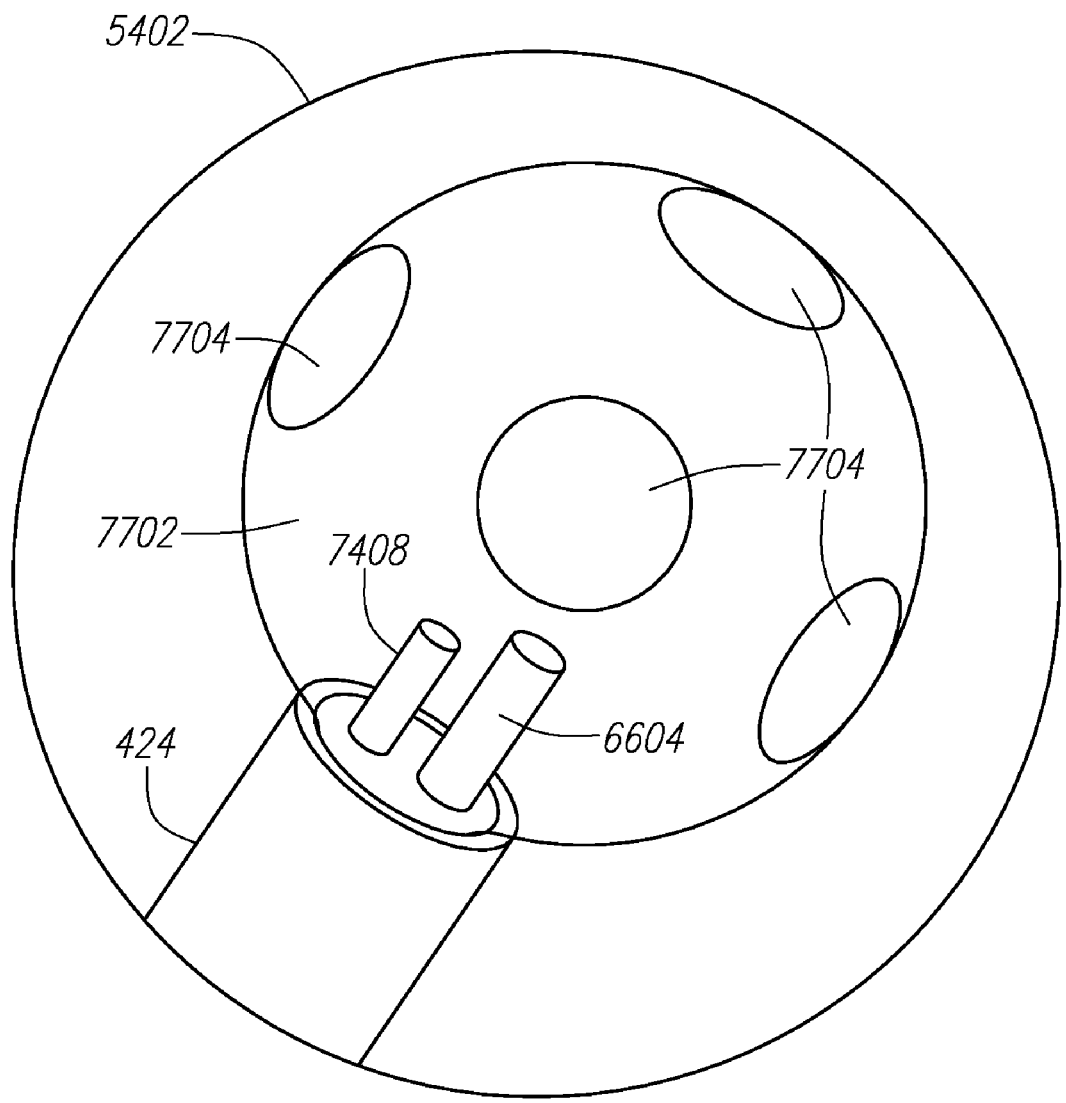
FIG. 77 illustrates one embodiment of an image capture device and illumination fibers enclosed within a balloon apparatus having magnifying lenses at the distal portion of a catheter.

FIG. 77 illustrates one embodiment of an image capture device (6604) and illumination fibers (7408) enclosed within a balloon (7702) having a plurality of magnifying lenses (7704) positioned at various locations on the balloon surface. When using the image capture device to view structures outside of the balloon during a procedure, one of the magnifying lenses may be maneuvered in the direction of the desired item. By positioning the image capture device to look at the item through the appropriate magnifying lens, the object may be magnified without the use of an additional magnifying apparatus on the catheter or system.

Figure 78:
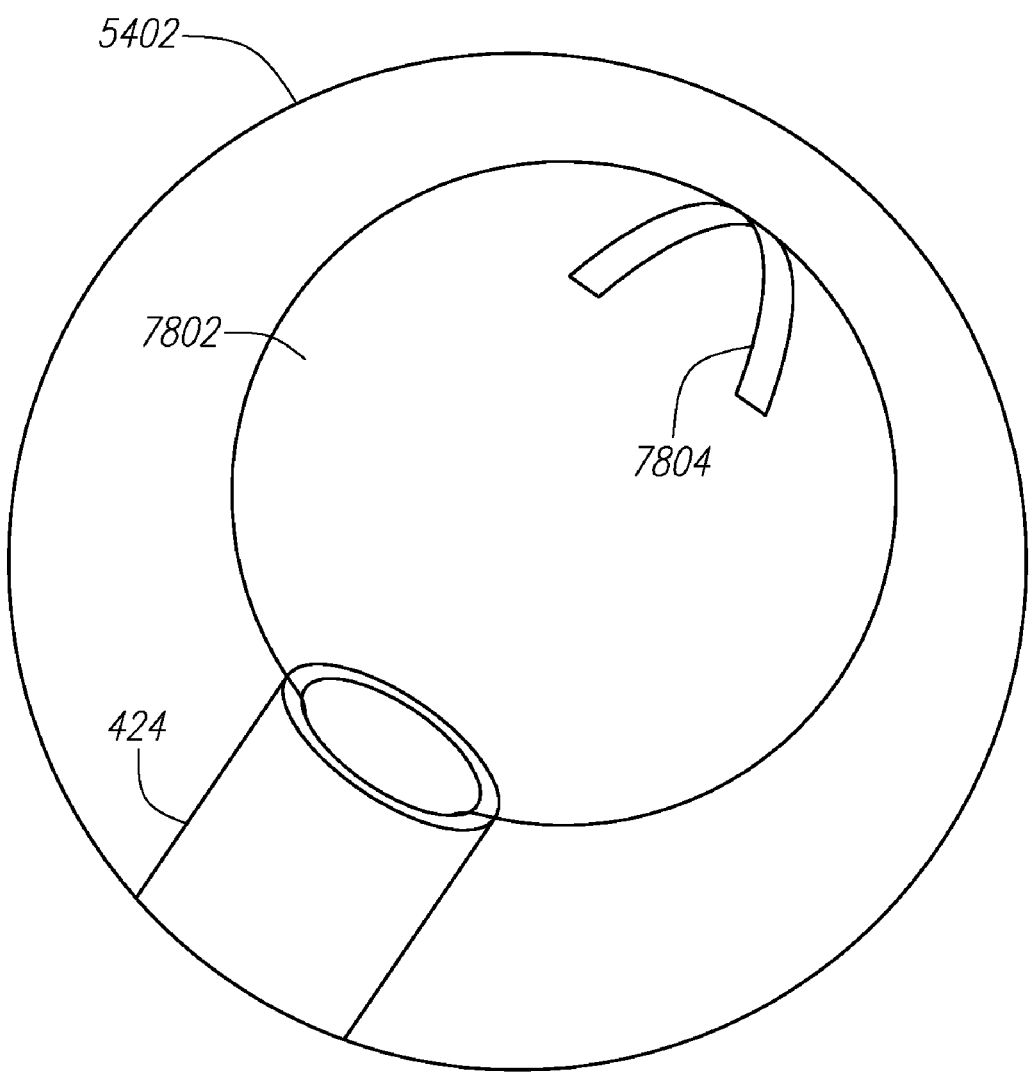
FIG. 78 illustrates one embodiment of a balloon apparatus having a radio frequency (RF) electrode deployed on its surface.

FIG. 78 illustrates one embodiment of a balloon (7802) having a radio frequency (RF) electrode (7804) deployed on its surface. In one procedure, the balloon may be positioned up against the target tissue. By maneuvering the electrode (7804) to the appropriate orientation and position, the target tissue may be ablated.

Figure 79:
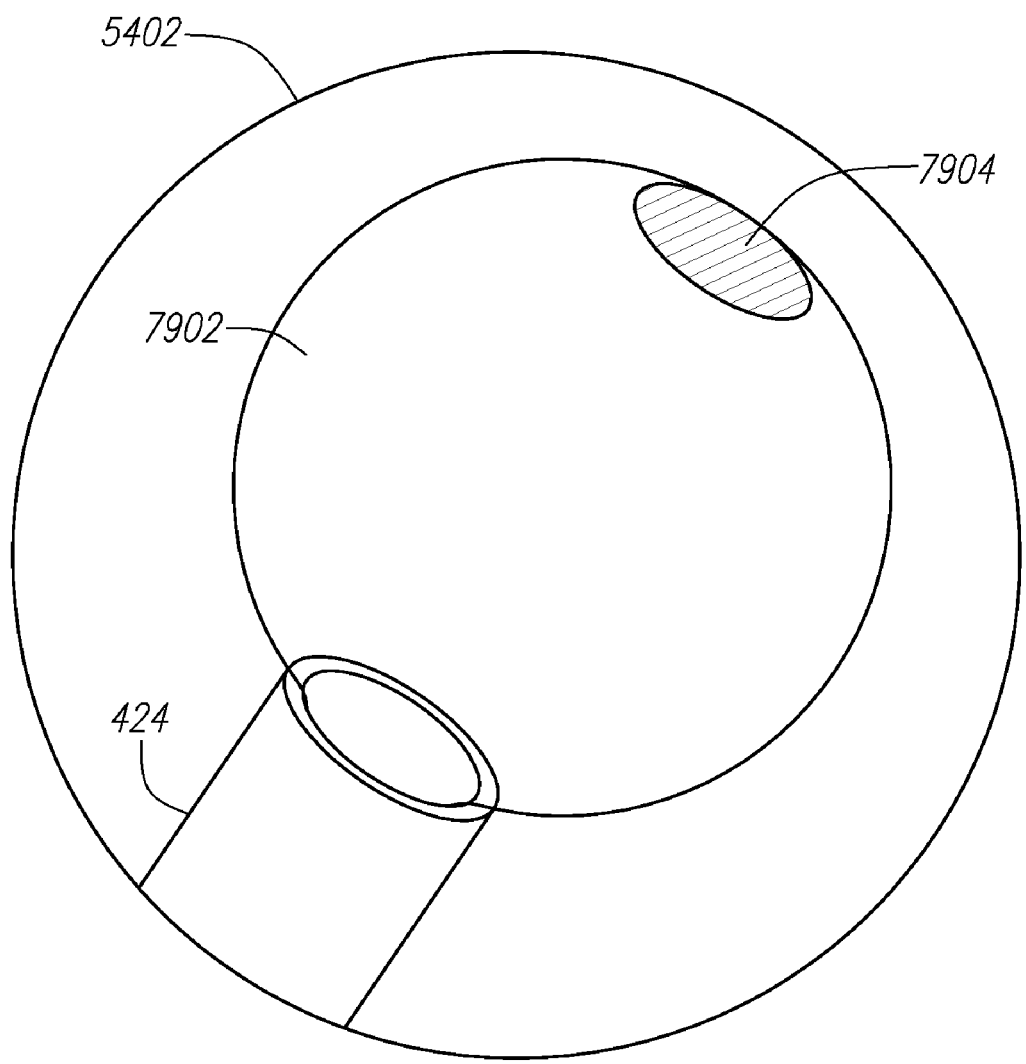
FIG. 79 illustrates one embodiment of a balloon apparatus having a magnet on its outer surface.

FIG. 79 illustrates one embodiment of a balloon (7902) having a magnet (7904) on its outer surface. Magnetic energy may be used to treat tissues in a patient.

Figure 80:
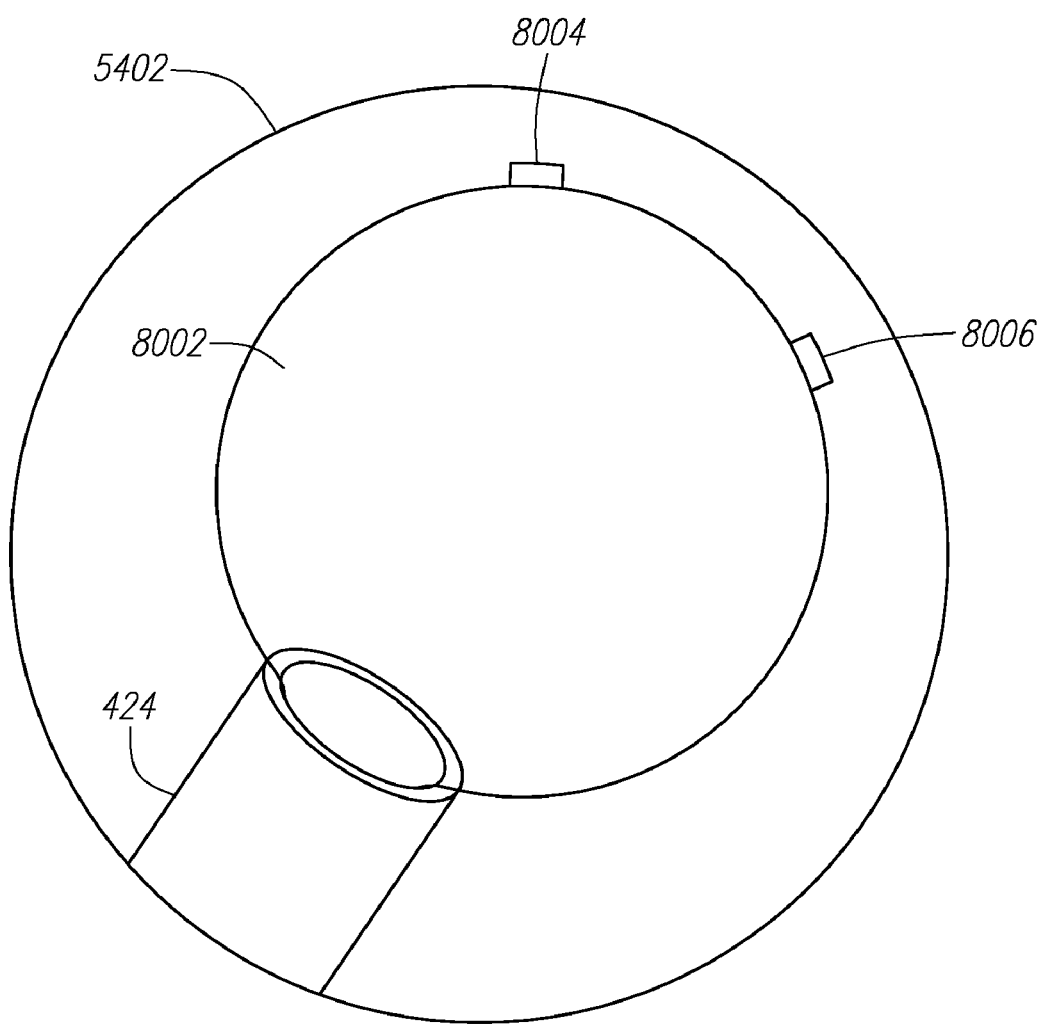
FIG. 80 illustrates one embodiment of balloon apparatus having a pair of mapping electrodes mounted on its outer surface.

FIG. 80 illustrates one embodiment of balloon (8002) having a pair of mapping electrodes (8004, 8006) mounted on the outer surface of the balloon. The mapping electrodes (8004, 8006) may be used to map the surface tissues or organs in a patient.

Figure 81:
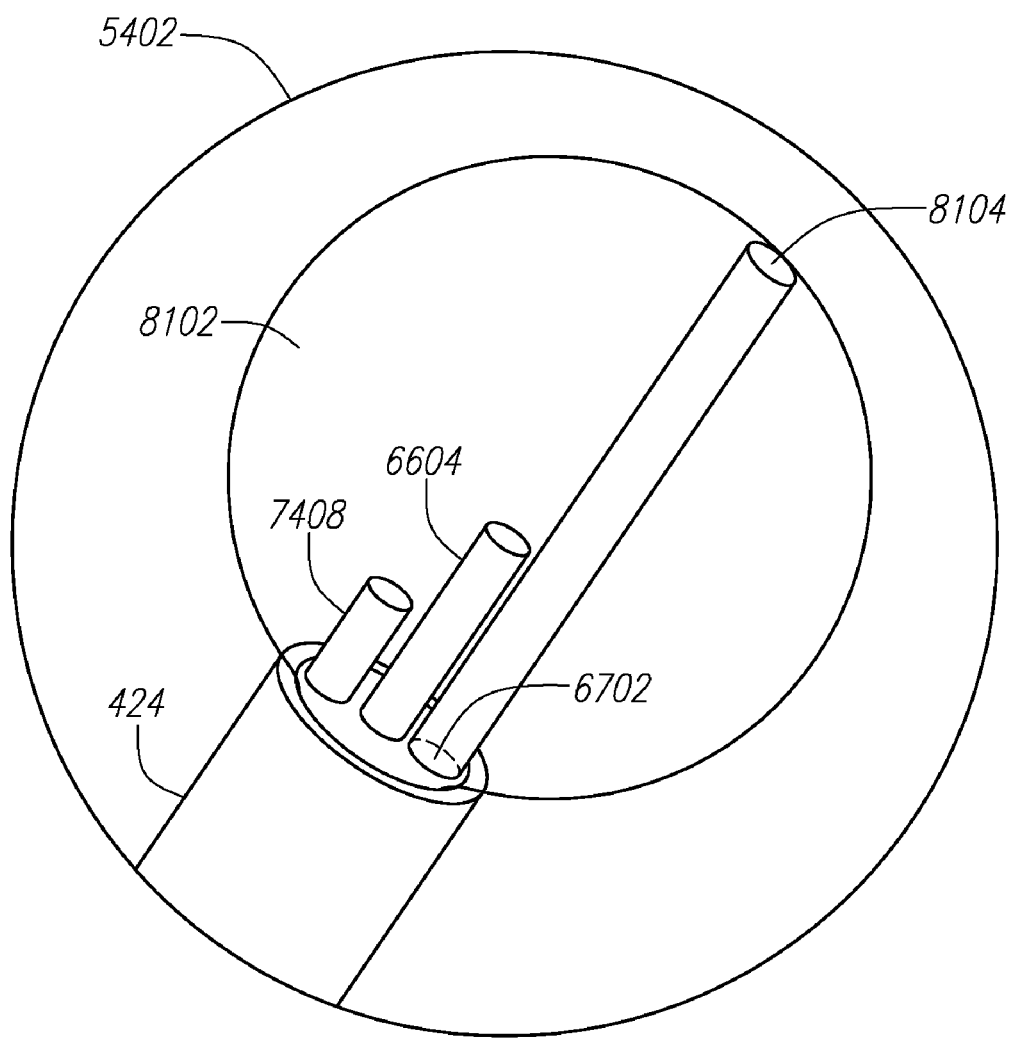
FIG. 81 illustrates one embodiment of a balloon apparatus having a through lumen.
Figure 82:
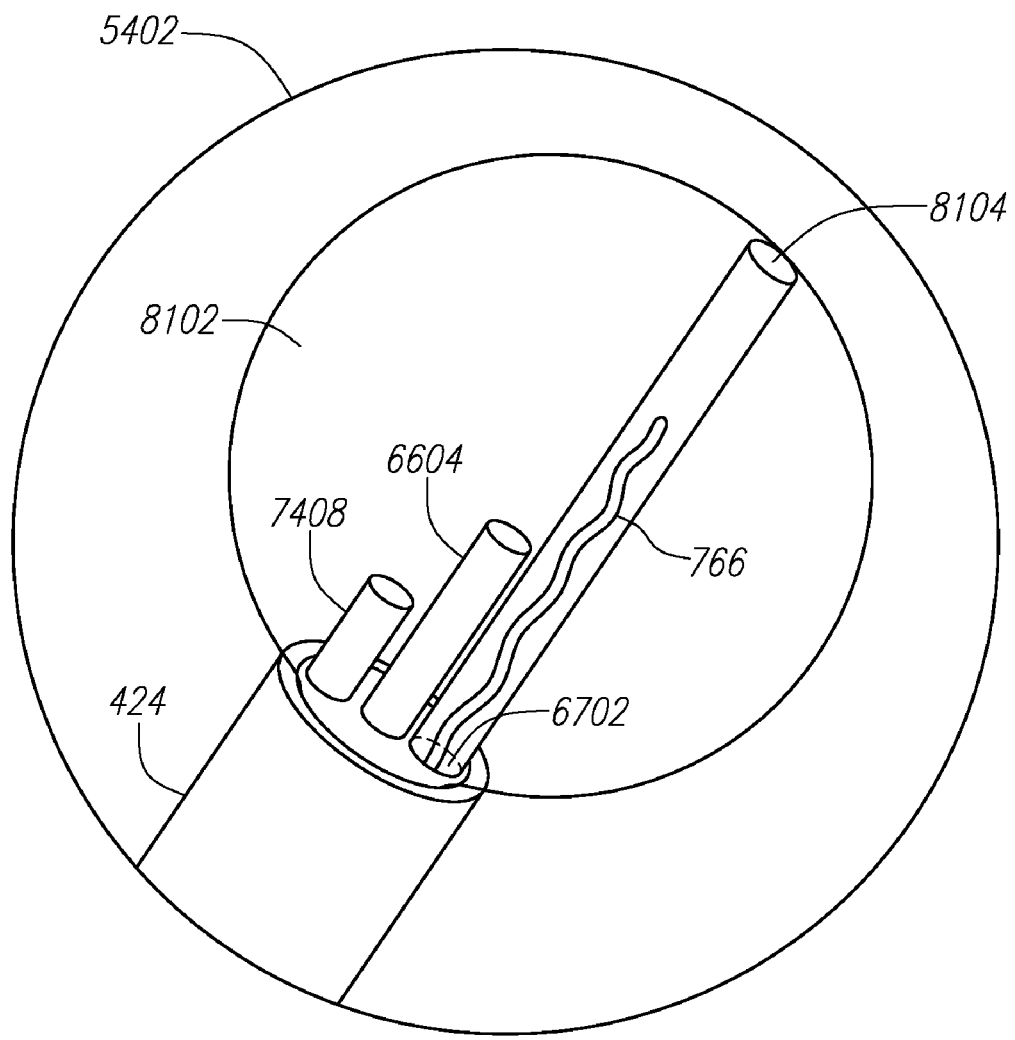
FIG. 82 illustrates one embodiment of a balloon apparatus having an ablation tool deployed in its through lumen.
Figure 83:
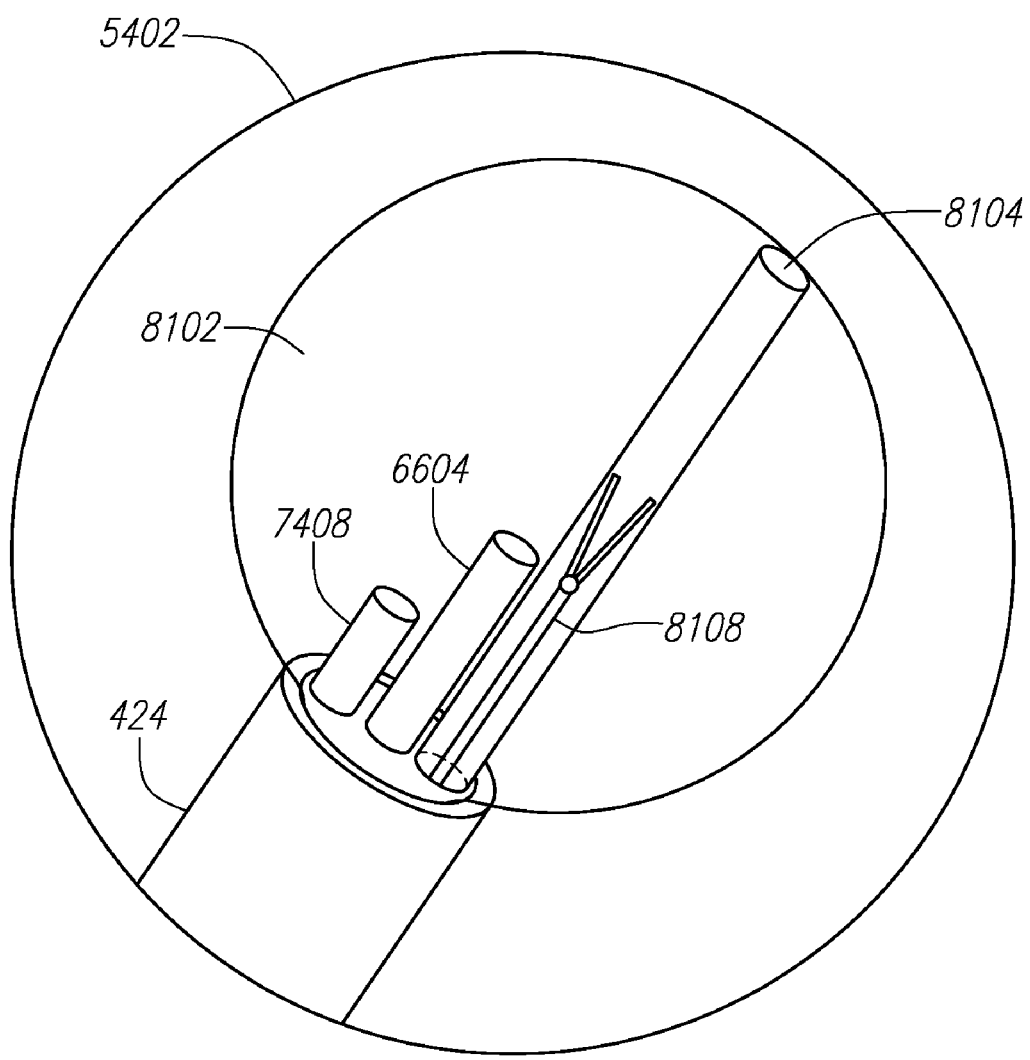
FIG. 83 illustrates one embodiment of a balloon apparatus having a grasper deployed in its through lumen.
Figure 84:
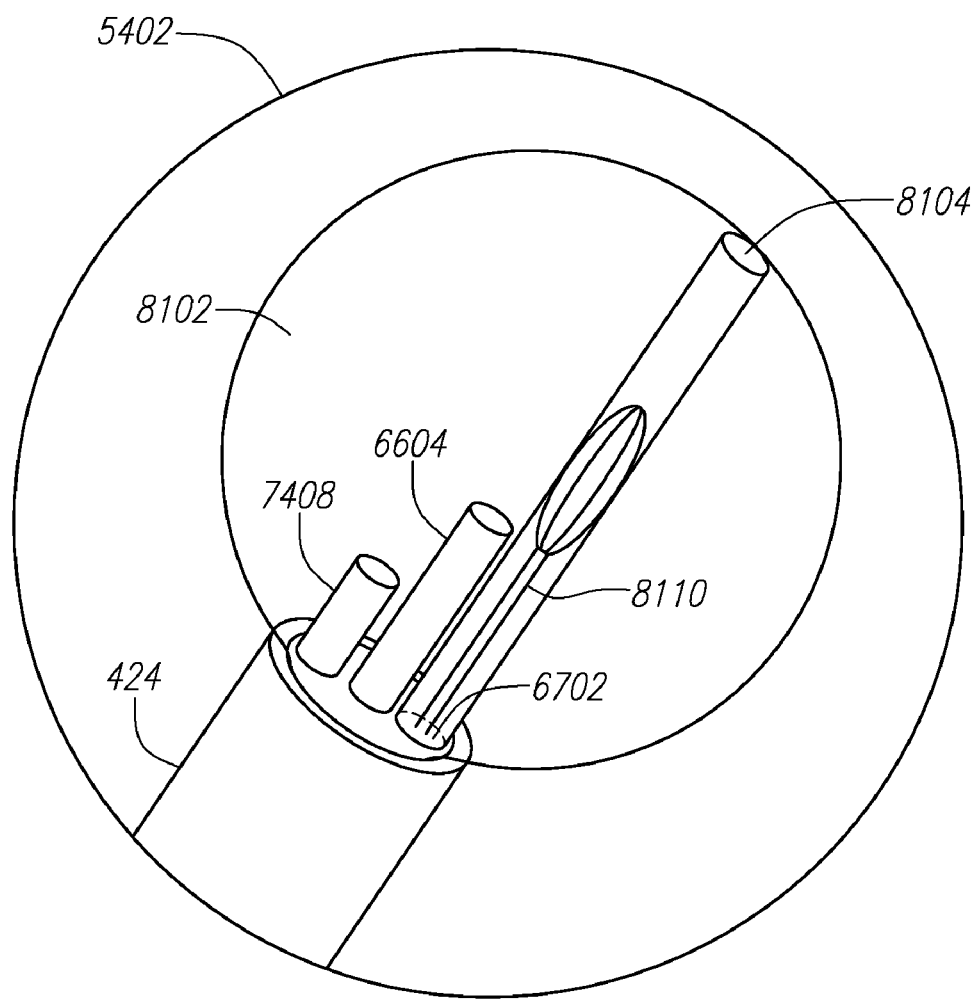
FIG. 84 illustrates one embodiment of a balloon apparatus having a basket tool deployed in its through lumen.

FIG. 81 illustrates one embodiment of a balloon (8102) having a through lumen (8104). Also located within the balloon (8102) are illumination fibers (7408) and an image capture device (6604). FIG. 82 illustrates one embodiment of a balloon (8102) having an ablation tool (8106) deployed in its through lumen (8104). FIG. 83 illustrates one embodiment of a balloon (8102) having a grasper (8108) deployed in its through lumen (8104). The grasper (8108) of one embodiment may be fitted with an energy source, such as a lithotripsy laser fiber in a configuration wherein an object, such as a kidney stone, grasped within the clutches of the grasper (8108) may be ablated, destroyed, fragmented, etc., by applied energy from the source, which is positioned to terminate approximately at the apex of the grasper (8108) which it is likely to be adjacent to captured objects. FIG. 84 illustrates one embodiment of a balloon (8102) having a basket tool (8110) deployed in its through lumen (8104). The energy source may be coupled to the pertinent capture device, or may be independently positioned through the working lumen of the guide instrument (424) to the desired location adjacent the capture device. Each of the tools described herein, such as graspers, baskets, and energy sources, may be controlled proximally as they exit the proximal end of the working lumen defined by the guide instrument (424), or they may be actuated automatically or electromechanically, for example through the use of electric motors and/or mechanical advantage devices.

Figure 85:
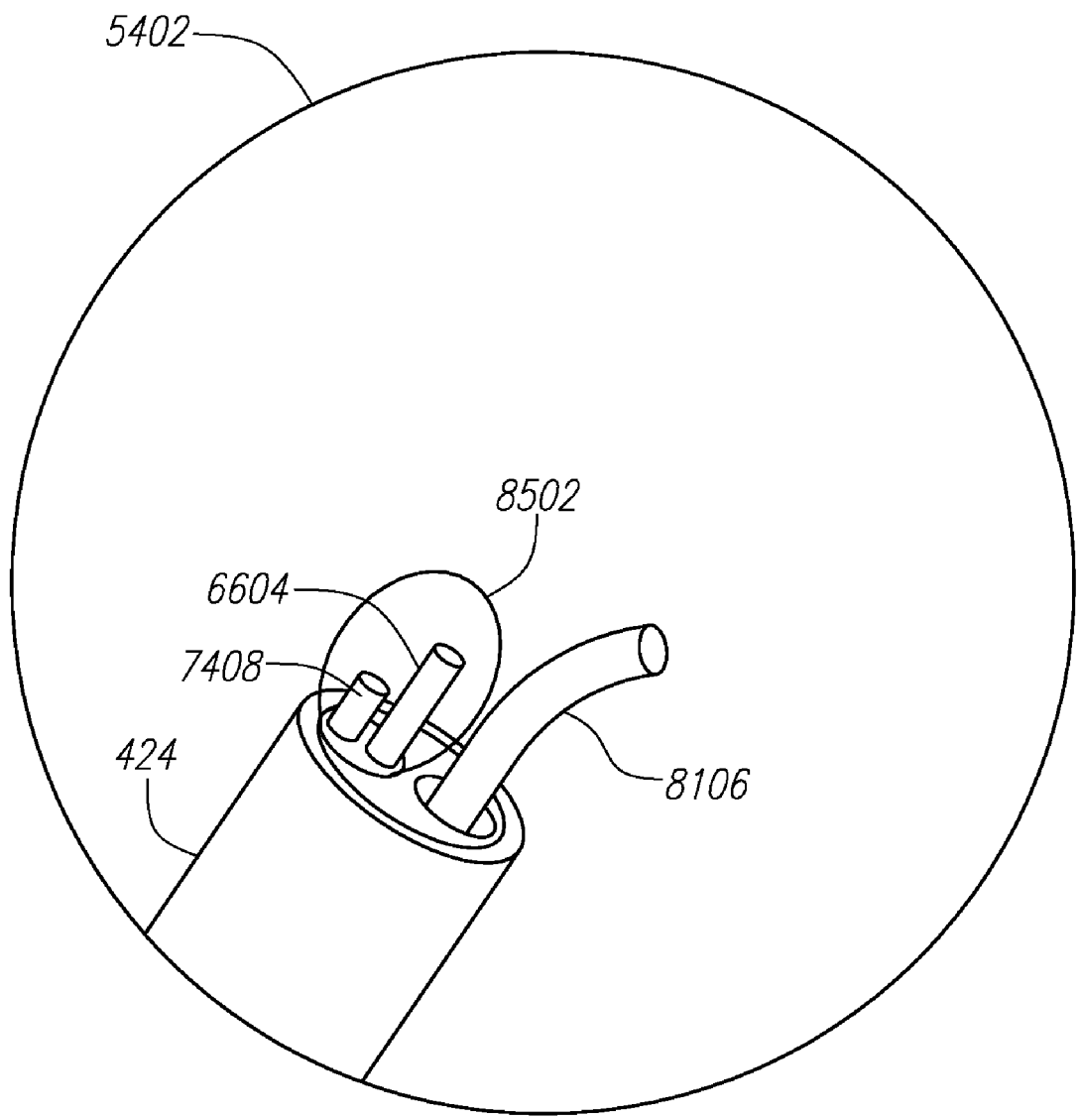
FIG. 85 illustrates a balloon apparatus and an ablation catheter deployed in a working lumen located outside of the balloon apparatus at a distal portion of a catheter.
Figure 86:
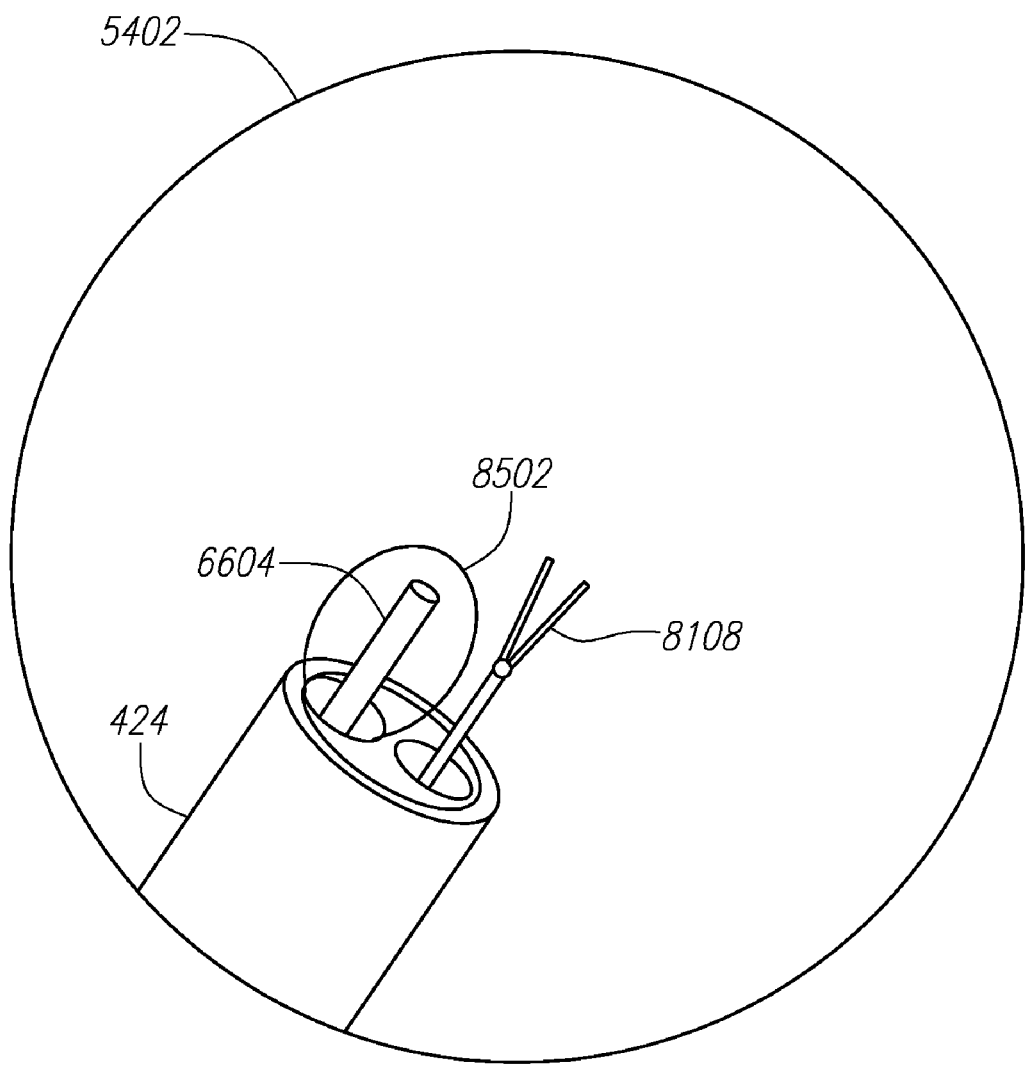
FIG. 86 illustrates a balloon apparatus and a grasper deployed in a working lumen located outside of the balloon apparatus at the distal portion of a catheter.
Figure 87:
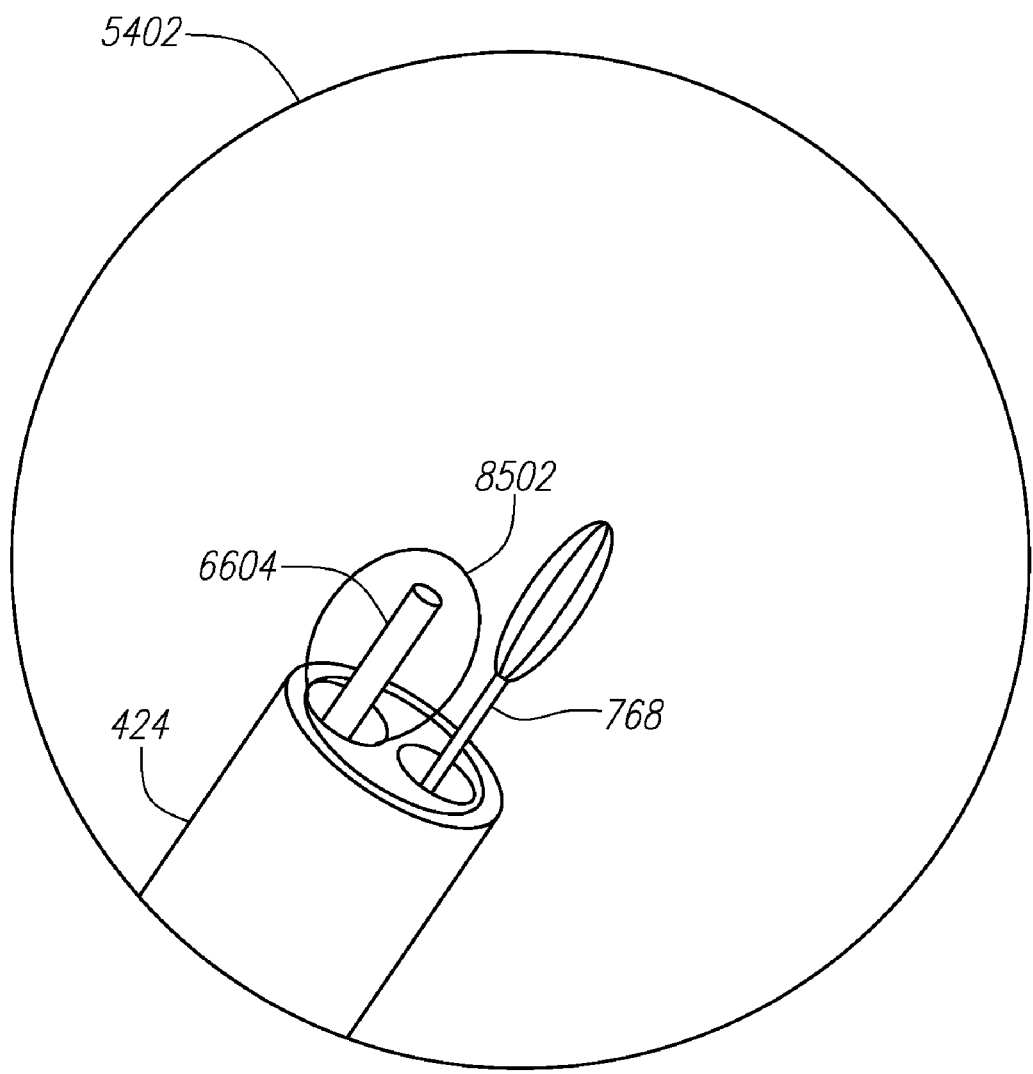
FIG. 87 illustrates a balloon apparatus and a basket tool apparatus deployed in a working lumen located outside of the balloon at the distal portion of a catheter.

FIG. 85 illustrates the distal tip of one embodiment of a catheter (424) having a balloon (8502) and an ablation catheter (8106) deployed in a working lumen located outside of the balloon (8502). In this embodiment, illumination fibers (7408) and an image capture device (6604) is located within the confines of the balloon (8502). FIG. 86 illustrates the distal tip of one embodiment of a catheter (424) having a balloon (8502) and a grasper (8108) deployed in a working lumen located outside of the balloon (8502). FIG. 87 illustrates the distal tip of one embodiment of a catheter having a balloon (8502) and a basket tool (8110) deployed in a working lumen located outside of the balloon (8502).

All of the aforementioned tools and instruments, e.g., balloons, ablation tools, baskets, graspers, scopes, etc. apparatuses are configured to be operatively coupled to the instrument assembly (108) in combination with the sheath catheter (422) and guide catheter (424). In some embodiments, the tools and instruments may be used with the guide catheter (424) without the sheath catheter (422). In other embodiments, additional catheters may be used with the tools and instruments. As apparent to one skilled in the art, the tools and instruments are configured to be either manually operated or robotically operated by the instrument driver (106) in connection with the instrument (108). Some of the circuitry, e.g., electrical, mechanical, hardware, software, firmware, etc. systems for controlling and operating all of the aforementioned tools and instruments may be configured at the instrument driver (106) and the system electronics rack (114).

Figure 90:
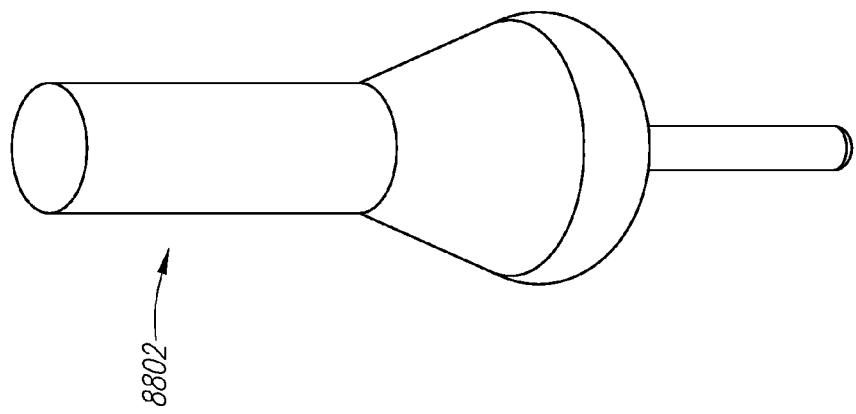
FIG. 88 through FIG. 90 respectively illustrates various views of one embodiment of a mold for manufacturing a balloon apparatus.
Figure 89:
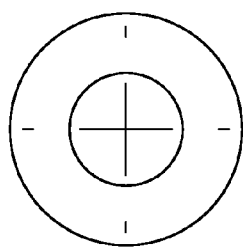
Figure 88:
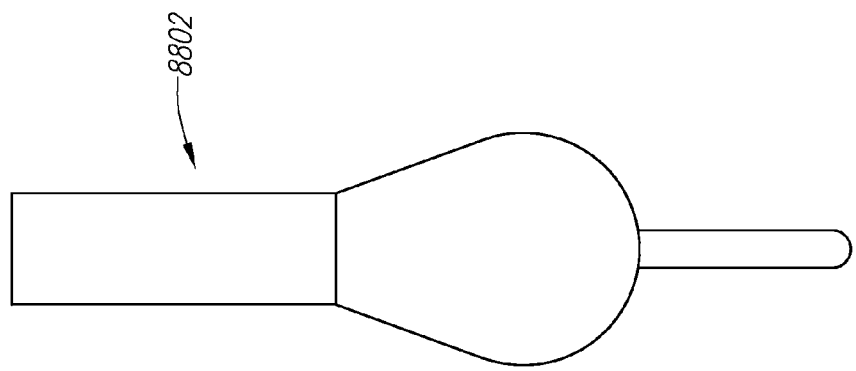
Figure 95:
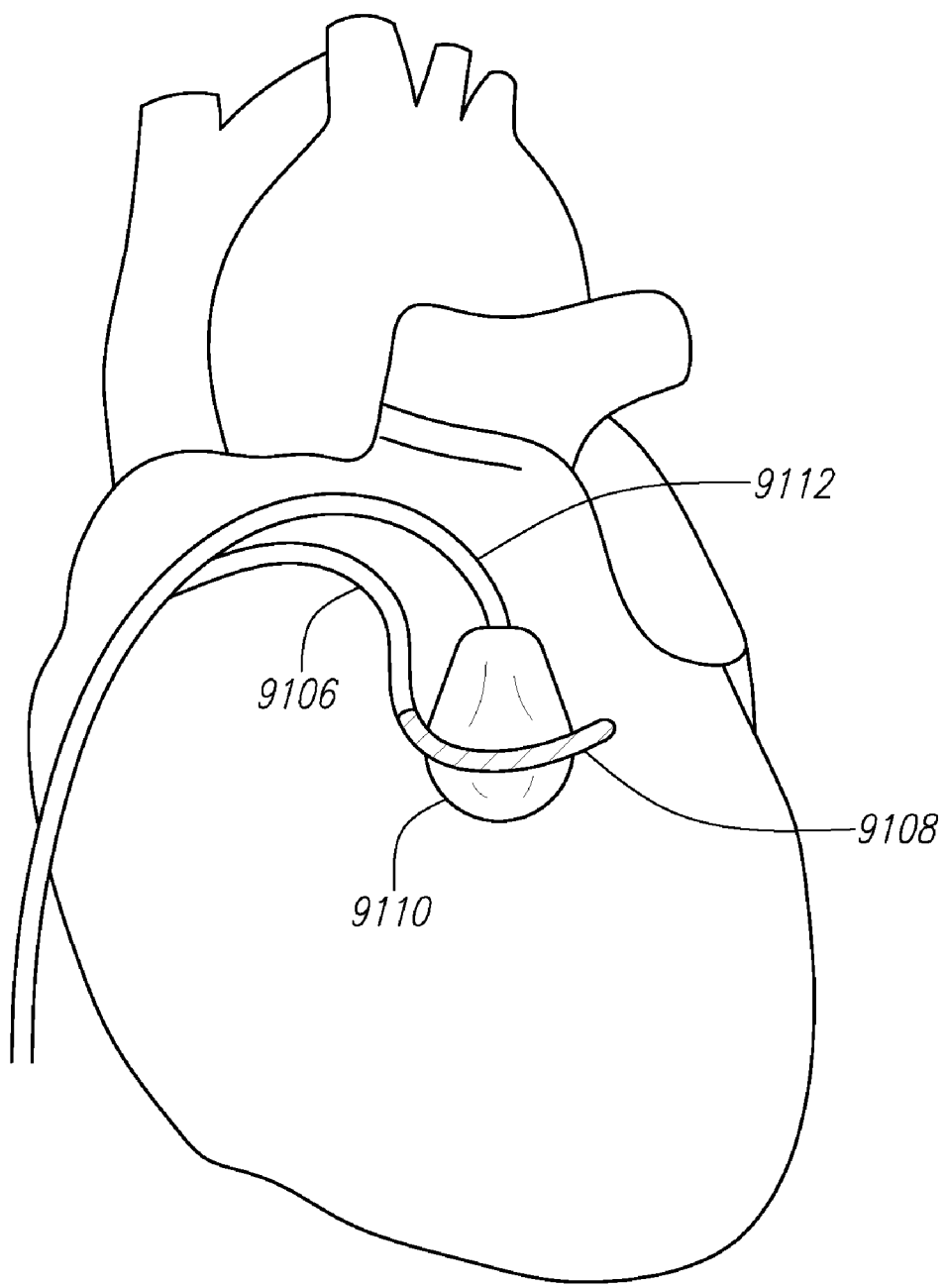

FIGS. 88 through 90 illustrate various views of one embodiment of a mold (8802) for manufacturing a balloon. FIG. 88 illustrates a side view of the mold (8802) for manufacturing the balloon. In one embodiment, the balloon is formed over the ball structure towards the bottom of the mold. FIG. 89 illustrates a top view of the mold (8802). FIG. 90 illustrates an isometric view of the mold (8802).

FIG. 91 through FIG. 95 illustrate one embodiment of a method for deploying an angioplasty ring (9116) using a balloon apparatus (9110, 9112), within the balloon apparatus may be similar to the embodiment described in FIG. 74. That is, the balloon apparatus includes an image capture device 7404 to enable visual access through the balloon. In this embodiment, the balloon portion (9110) of the balloon apparatus (9110, 9112) is used to hold the ring (9116) in place while the ring is being deployed by a second catheter (9106). For example, an angioplasty ring (9116) may be applied to the mitral annulus (9104) near the mitral valve of the heart (9102). As illustrated in FIG. 91, a catheter (9106) may be maneuvered toward the mitral valve by the guide catheter (424). A ring applicator (9108) at the distal portion of the catheter (9106) is position near the mitral annulus (9104) by the mitral valve. The balloon apparatus (9110) deployed by the catheter (9112) moves the ring applicator (9108) into position over the mitral annulus (9104). Once the ring applicator (9108) is in position, the ring (9116) is secured in place by one or more clips (9114). The ring (9116) or the clip (9114) may be adjusted, e.g., by tension wires (not shown), to clinch the ring more tightly on the mitral annulus (9104) around the mitral valve.

Figure 96:
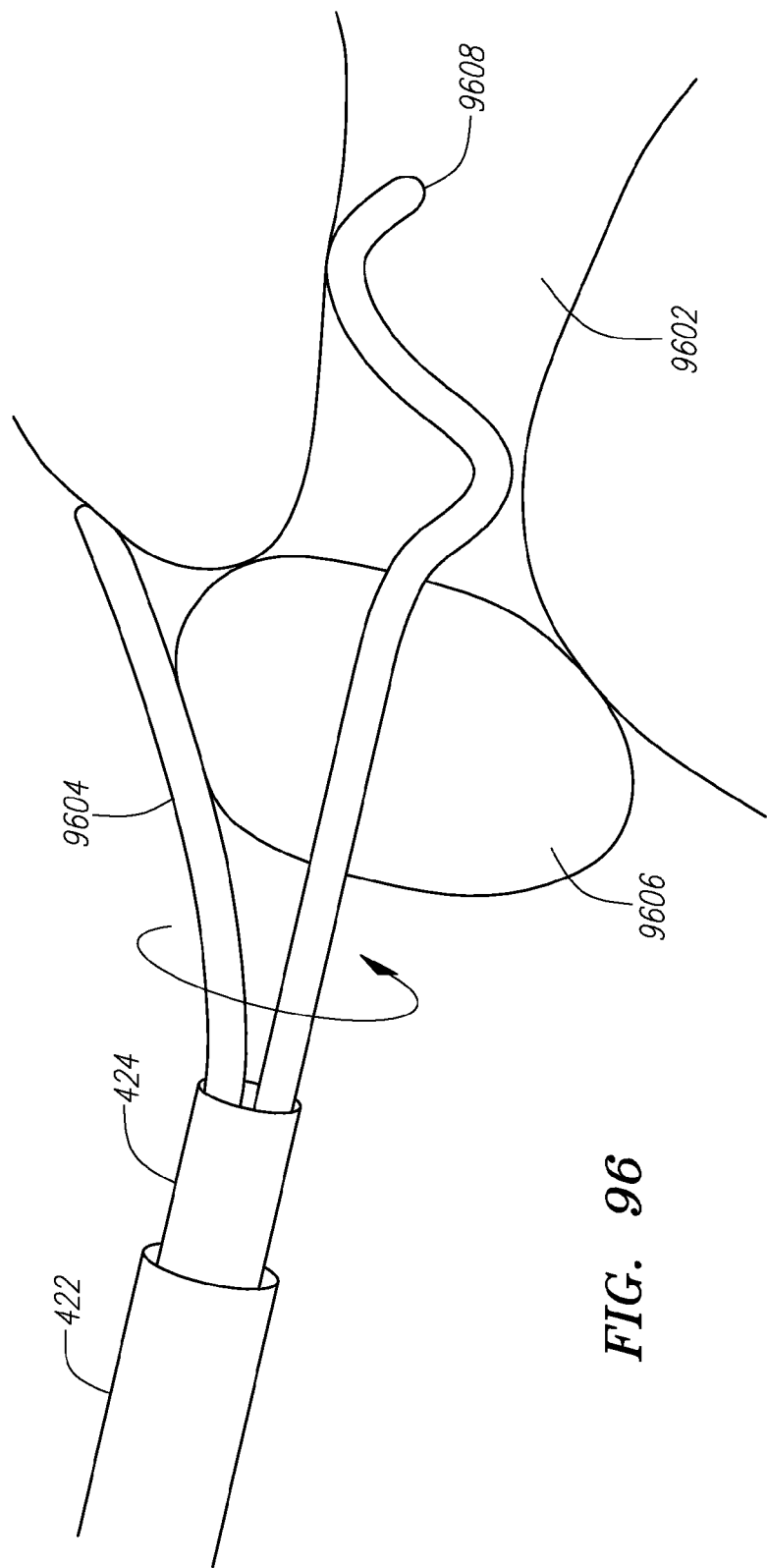
FIG. 96 illustrates one method for performing ablation using a balloon apparatus.

FIG. 96 illustrates one embodiment of a method for ablation using a balloon apparatus. In this embodiment, the ablation catheter (9604) travels around the outer edge of the first balloon (9606) to ablate the desired tissue at an operation site (9602).e.g., pulmonary vein. A second catheter or balloon (9608) may be used to anchor the first balloon (9606)) to the pulmonary vein. In this example, the first balloon (9606) serves as a guide for the ablation catheter (9604).

Figure 97:
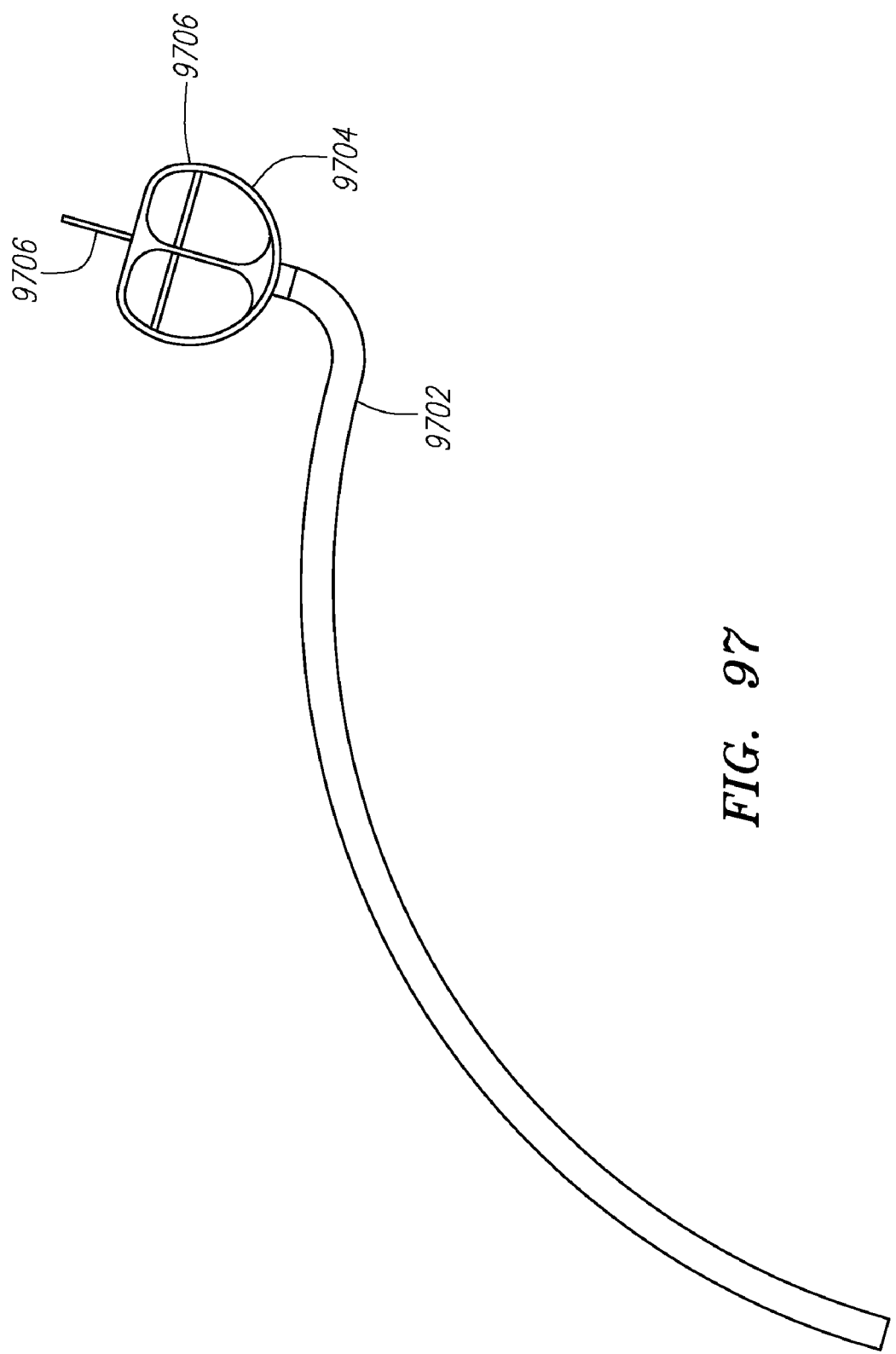
FIG. 97 illustrates one embodiment of a toroid-shaped balloon apparatus that is deployed and an ablation tool.

FIG. 97 illustrates one embodiment of a catheter (9702) with a toroid shaped balloon (9704) deployed at its distal tip and an ablation catheter (9706) for performing various ablation procedures. The catheter (9702) may be advanced to the operation site with the balloon (9704) initially in a deflated or undeployed configuration. Once the catheter (9702) is advanced to the operation site, the balloon (9704) may be inflated or deployed using a suitable medium, e.g., saline solution, air, etc., to position or secure the catheter (9792). An ablation operation may be performed using the ablation catheter (9706).

Figure 98:
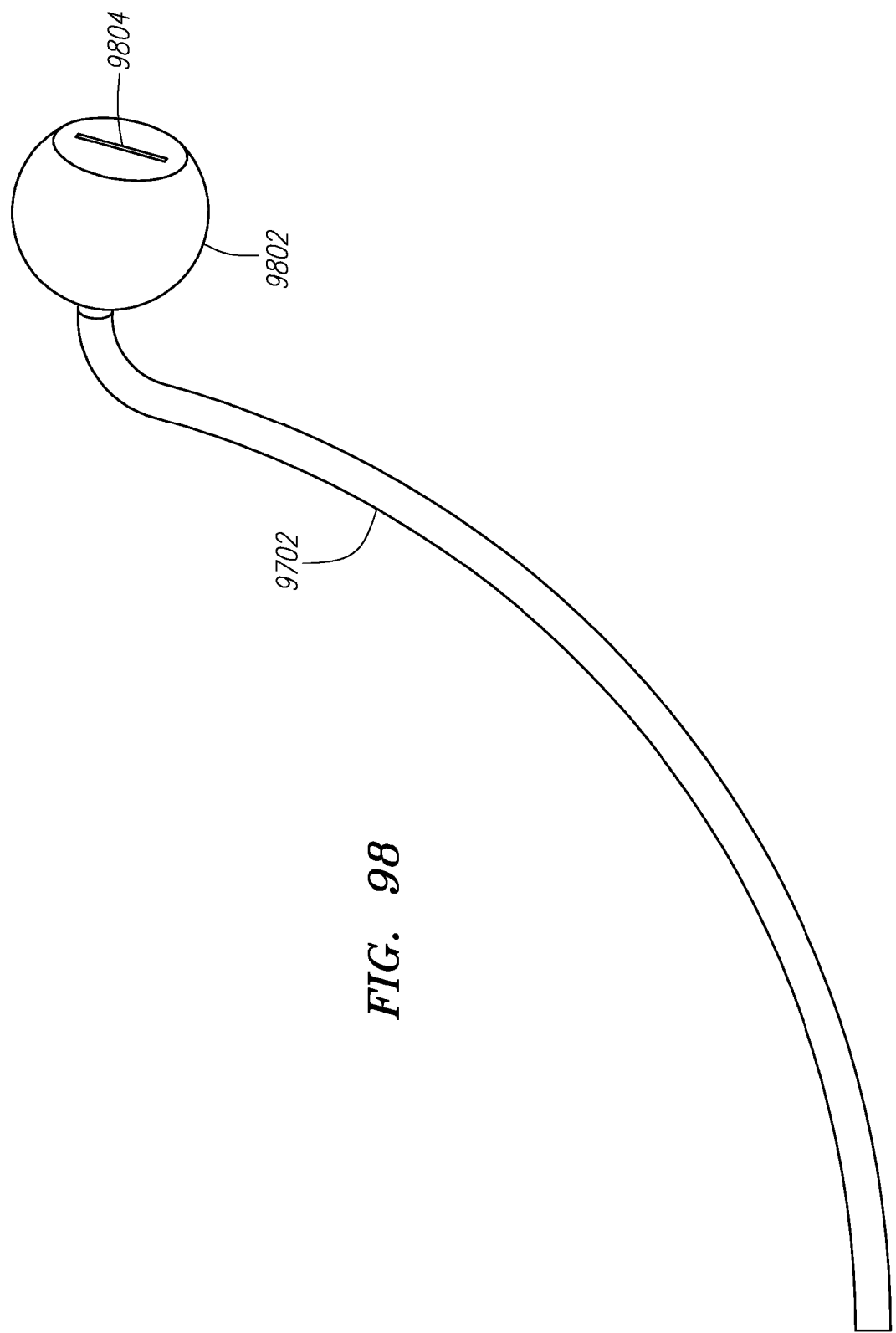
FIG. 98 illustrates one embodiment of a circular-shaped balloon apparatus with an electrode strip mounted on its outer surface.

FIG. 98 illustrates one embodiment of a catheter (9702) with a circular shaped balloon (9802) with an electrode strip (9804) mounted on its outer surface. In one embodiment, the electrode strip is employed for performing ablation procedures.

Figure 99:
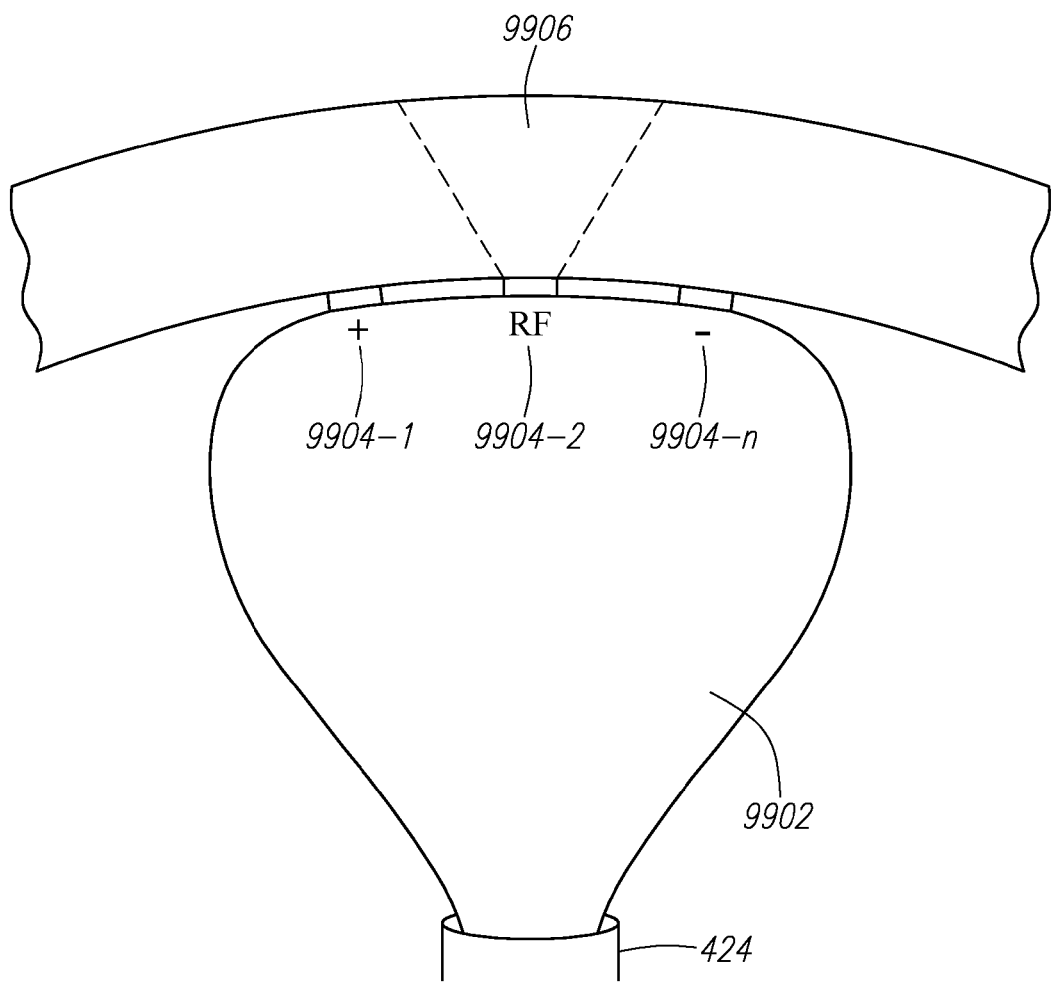
FIG. 99 illustrates one a method of performing electro-anatomic mapping and RF ablation with a balloon apparatus using electrodes.
Figure 100:
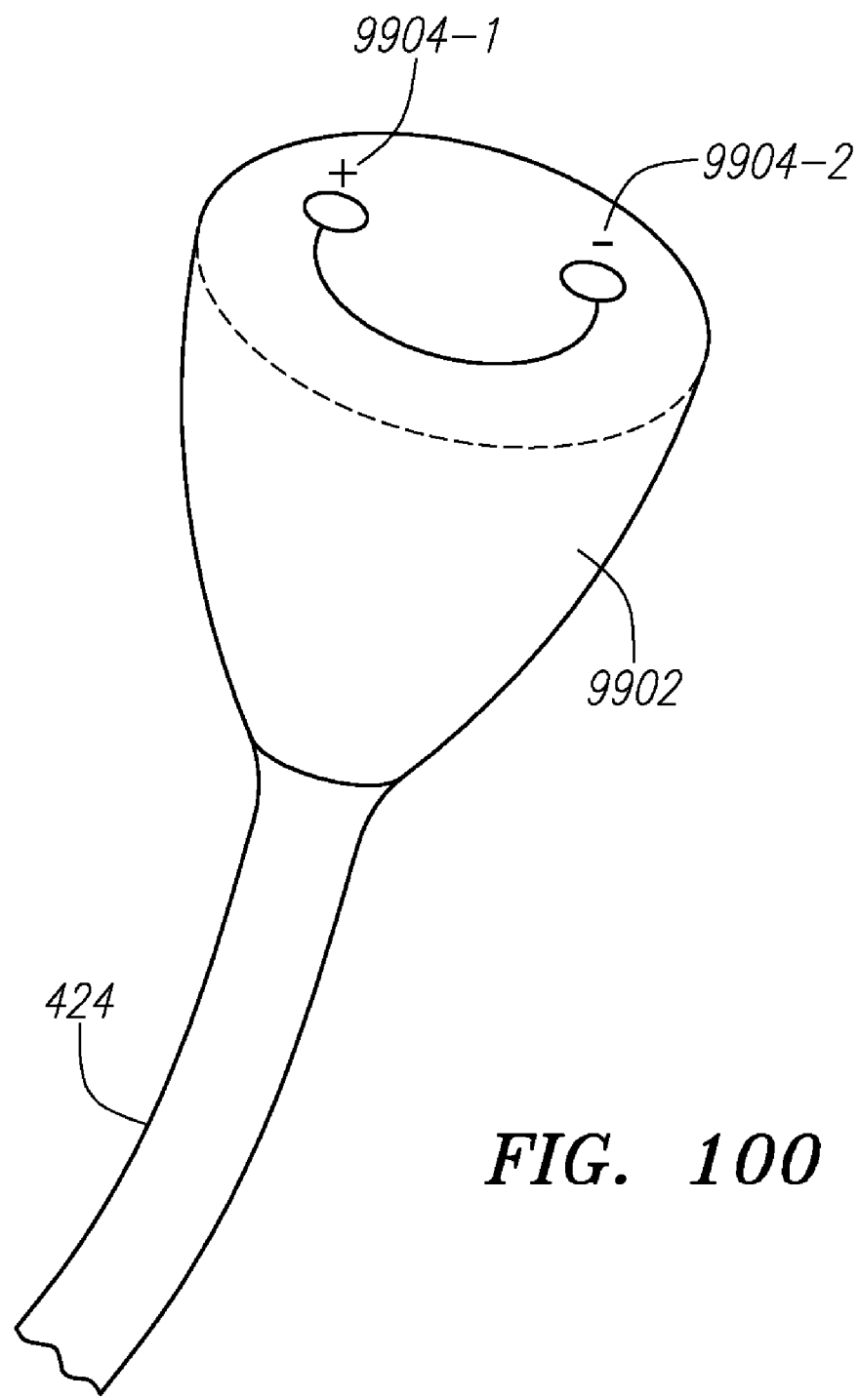
FIG. 100 illustrates the top surface of a balloon apparatus of FIG. 99.

FIG. 99 illustrates one embodiment of a method for RF mapping with a balloon (9902) mounted with electrodes (9904-1, 9904-2 . . . , 9904-*n*). Depending on the specific circuitry coupled to each of the electrodes and the signal commands to operate the electrodes, different procedures may be accomplished using the electrodes (9904-1, 9904-2 . . . 9904-*n*). In one embodiment, the electrodes (9904-1, 9904-2 . . . , 9904-*n*) may be used for mapping a cavity or the interior volume of an organ of a patient to generate a three-dimensional map of the cavity or interior volume. In a second embodiment, the electrodes may be used for performing ablation procedures on tissues of an organ in a patient. FIG. 100 illustrates a portion of the top surface of the balloon (9902) that was illustrated in FIG. 99**

Figure 101:
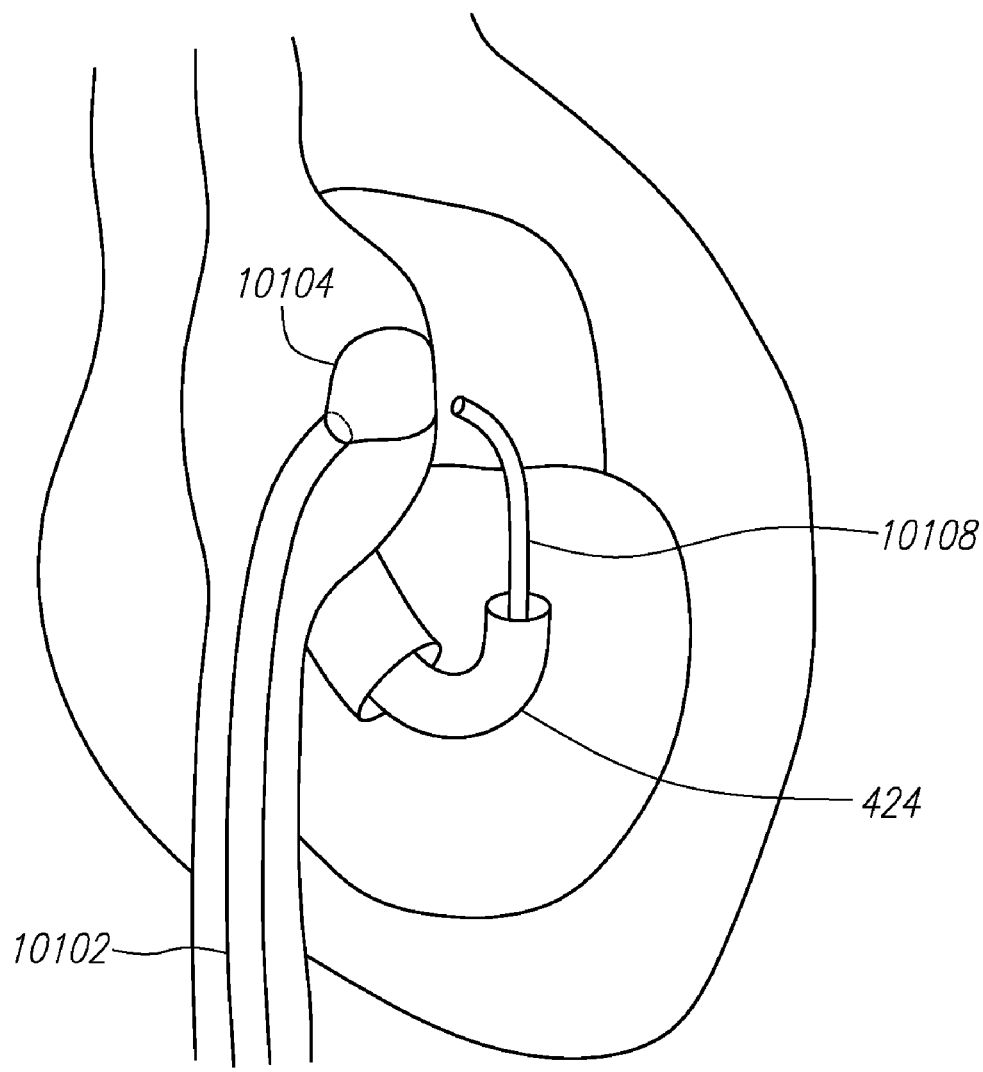
FIG. 101 through 104 respectively illustrates one method for performing patent foramen ovale procedure using a balloon apparatus.
Figure 102:
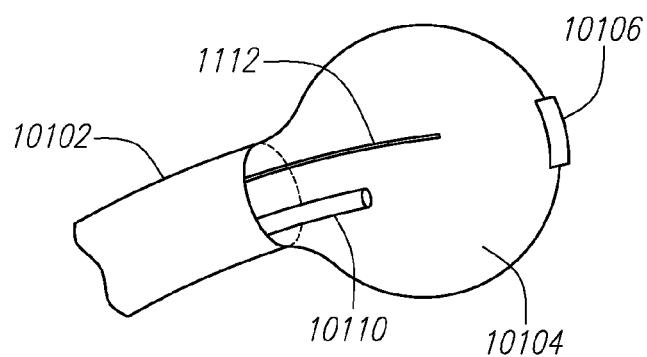
Figure 103:
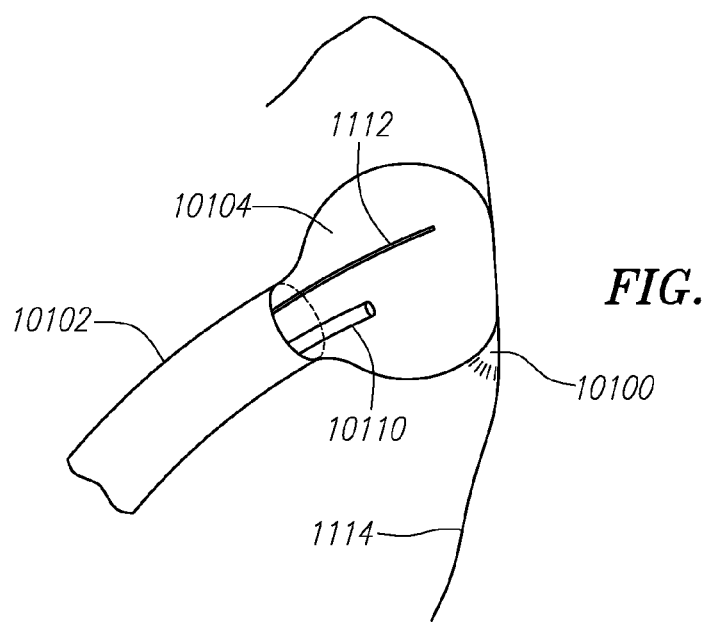
Figure 104:
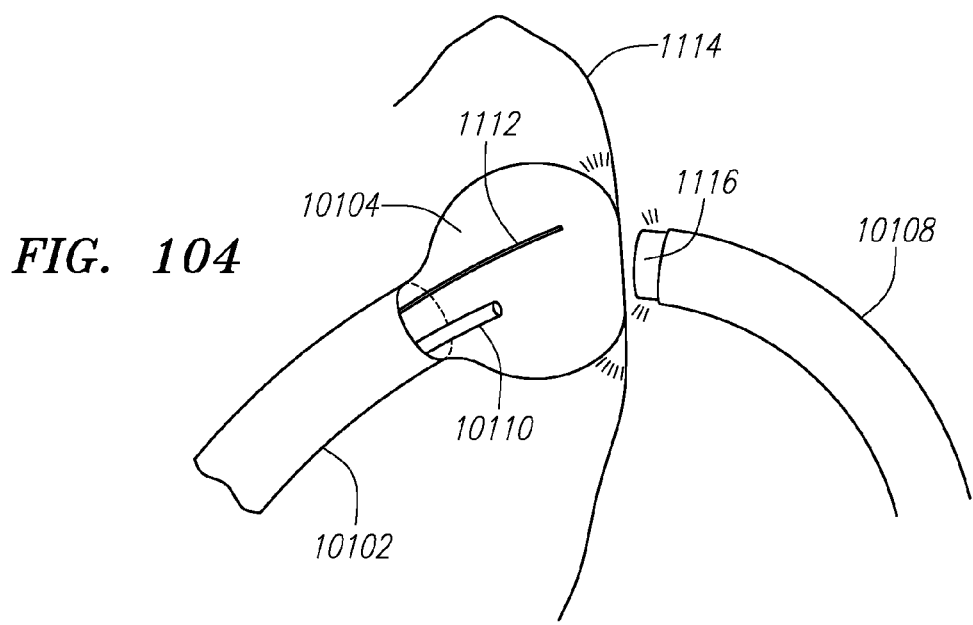

FIG. 101 through FIG. 104 illustrate one embodiment of a method for performing a patent foramen ovale (PFO) procedure using a balloon apparatus. As illustrated in FIG. 101, a first catheter with (10102) the balloon structure (10104) travels up the inferior vena cava to the right atrium. This balloon (10102) includes a magnet (10106) mounted on its surface. A second catheter (10108) travels to the left atrium of the heart through a retro grade path. The two catheters meet at the wall separating the atriums as illustrated in FIG. 101 and FIG. 104. The second catheter (10108) may include a metallic material at its distal portion, such that the magnet (10106) on the balloon (10102) may be attracted to the distal portion of the catheter (10108) against the tissue (1114) and substantially holding and positioning the balloon (10102) at a desired location against the tissue (1114). FIG. 102 and FIG. 103 illustrate the balloon apparatus (10102) includes a scope (10110) and a needle or an ablation instrument (1112). As the balloon (10102) is held at a substantially desired location, the needle or ablation instrument (1112) may be used to perform the procedure for closing the PFO as the scope (10110) is used to view or monitor the procedure.

Figure 105:
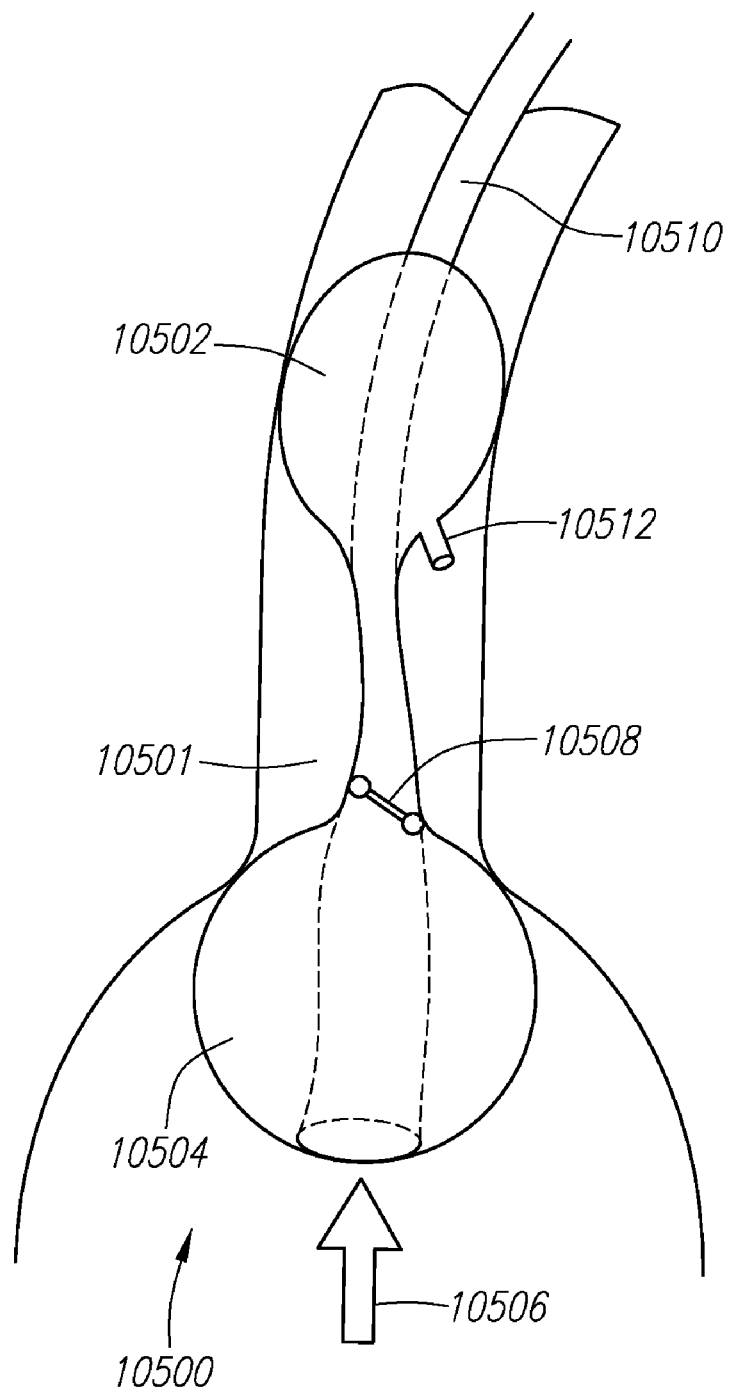
FIG. 105 illustrates one embodiment of a method for aortic valve destenosis/decalcification using a balloon apparatus.

FIG. 105 illustrates one embodiment of a method for performing aortic valve destenosis and/or decalcification using one or more balloons. In one embodiment, two balloon structures may be deployed. A first balloon (10502) anchors the catheter structure (10510) in the aorta to the heart (10500). A lumen through the balloons is configured to allow for the passage and flow of blood (10506). However, the flow is controlled by a valve (10508) within the second balloon structure (10504). When the structures are anchored, blood flow (10506) through the first balloon is restricted and controlled by the valve (10508) in the second balloon structure (10504). A second catheter (not shown) may be advanced and navigated to the first balloon (10502) and through an opening or port (10512) at the first balloon (10502) to dispense a biodecalcifying solution or a mechanical instrument, e.g., scraper and vacuum tube, etc., for perform destenosis and/or decalcification procedures.

In addition to the operations and procedures as discussed, each of the above discussed tools, systems, and/or assemblies may be utilized for, among other things, endolumenal urinary intervention, such as the examination, removal, fragmentation, and/or destruction of stones such as kidney or bladder stones The prostate has a tendency to grow in aging males. In some cases, the prostate may grow to a sufficient size that would put pressure on the urethra and cause problems with urination, such as incomplete emptying of the bladder or dribbling of urine. This condition is known as benign prostatic hyperplasia (BPH). There are a number of treatments for BPH. A transurethral resection of the prostate (TURP) is one treatment that is usually performed to address BPH. TURP is a urological operation to remove some or all of an enlarged prostate gland so that urine can flow more freely. This procedure is performed by observing the prostate through the urethra and removing tissue by electrocautery or sharp dissection. While the patient is under anesthesia, the surgeon inserts a resectoscope into the penis through the urethra. Some resectoscopes may include a camera, light, valves for controlling irrigating fluid, and/or specially adapted surgical instruments. These instruments allow the surgeon to see the prostate clearly. A wire loop attachment that carries an electric current is typically used to "chip away" at the prostate by removing obstructing tissue and to seal blood vessels. During the operation, the bladder is flushed with sterile solution to remove the chippings of prostate tissue. The debris is removed by irrigation and any remaining debris is eliminated in the urine over time. A catheter with a large lumen may be inserted through the urethra to irrigate and drain the bladder after the surgical procedure is completed.

Another procedure to treat the prostate may involve the use of a laser. Laser surgery uses a high-energy laser to destroy overgrown prostate tissue. The laser does not penetrate tissue deeply, so surrounding tissue is not harmed. There are a various types of laser surgery available. Transurethral evaporation of the prostate (TUEP) is one type. This procedure is similar to TUVP. The difference is that prostate tissue is destroyed with laser energy instead of electrical current. The procedure is generally safe and causes limited bleeding. It is often effective, with noticeable improvement in urine flow soon after the procedure. Due to the evolution of laser technology, this procedure has largely been replaced by new laser treatments such as PVP and HoLEP. Visual laser ablation of the prostate (VLAP) is another type of laser surgery. This treatment involves applying sufficient laser energy to dry up and destroy excess prostate cells. Another type of surgery is photosensitive vaporization of the prostate (PVP). PVP is newer form of laser treatment for prostate gland enlargement. This procedure and its results are similar to transurethral resection of the prostate (TURP), which is the most common surgical treatment for enlarged prostate. However, PVP uses laser energy instead of the electrical current used by TURP to destroy prostate tissue. Holmium laser enucleation of the prostate (HoLEP) is yet another type of surgery. This is a newer laser procedure used for men with urinary retention due to enlarged prostate and is similar to PVP.

Figure 106:
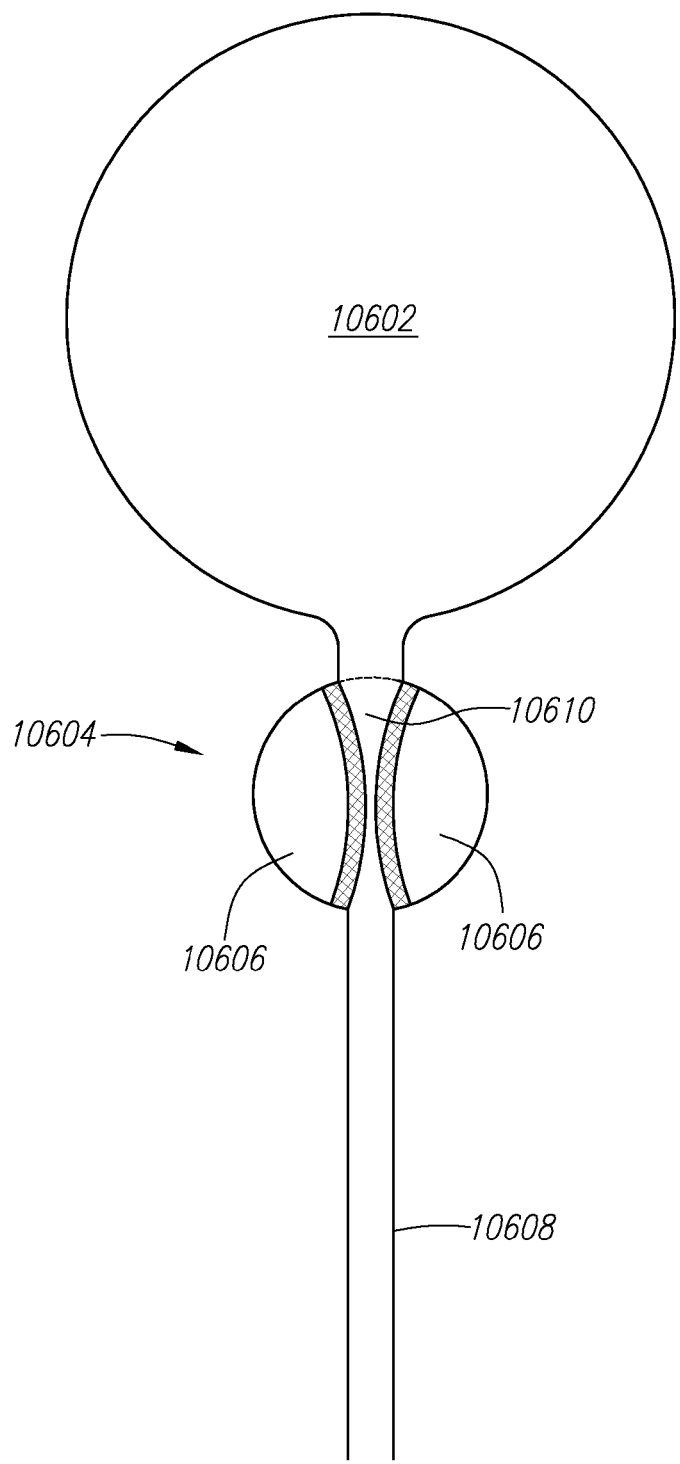
FIG. 106 illustrates a prostate with benign prostatic hyperplasia.
Figure 107:
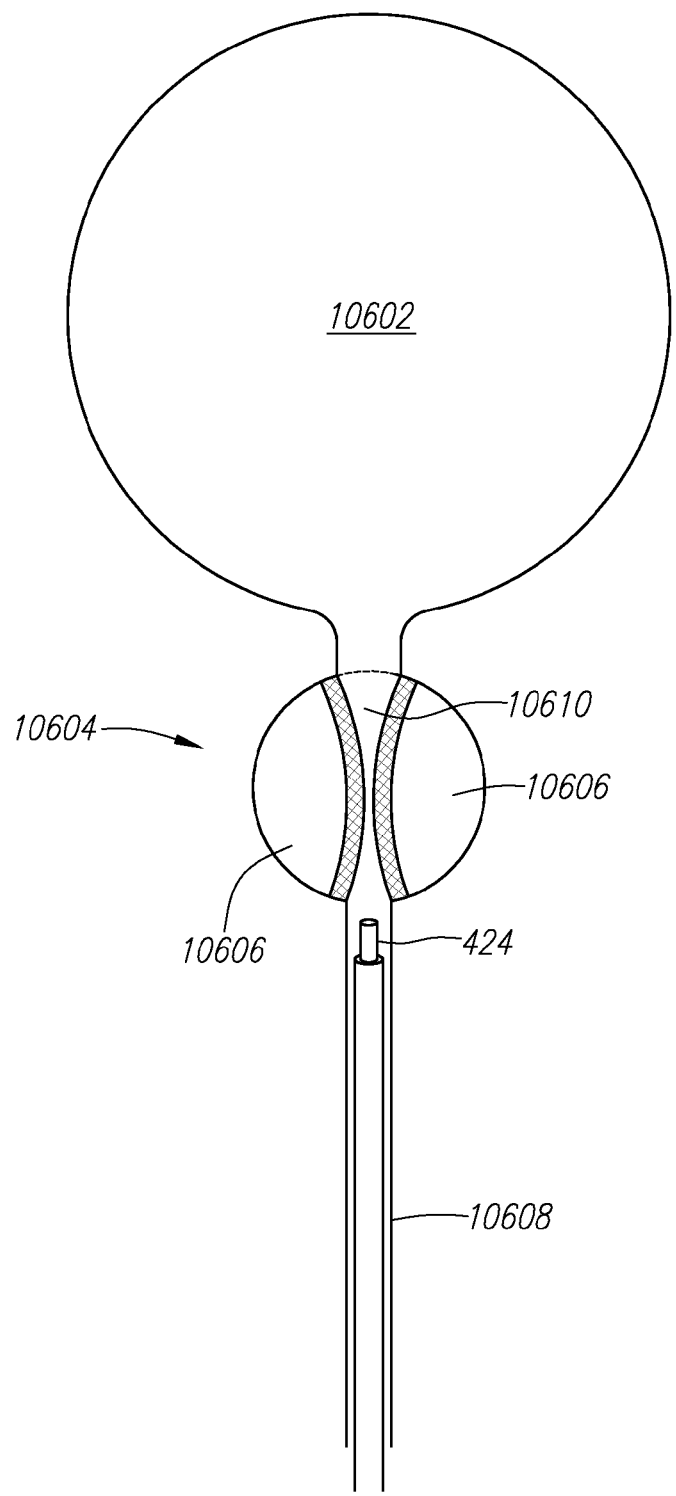
FIG. 107 illustrates a steerable sheath and guide catheter traveling up a urethra.
Figure 108:
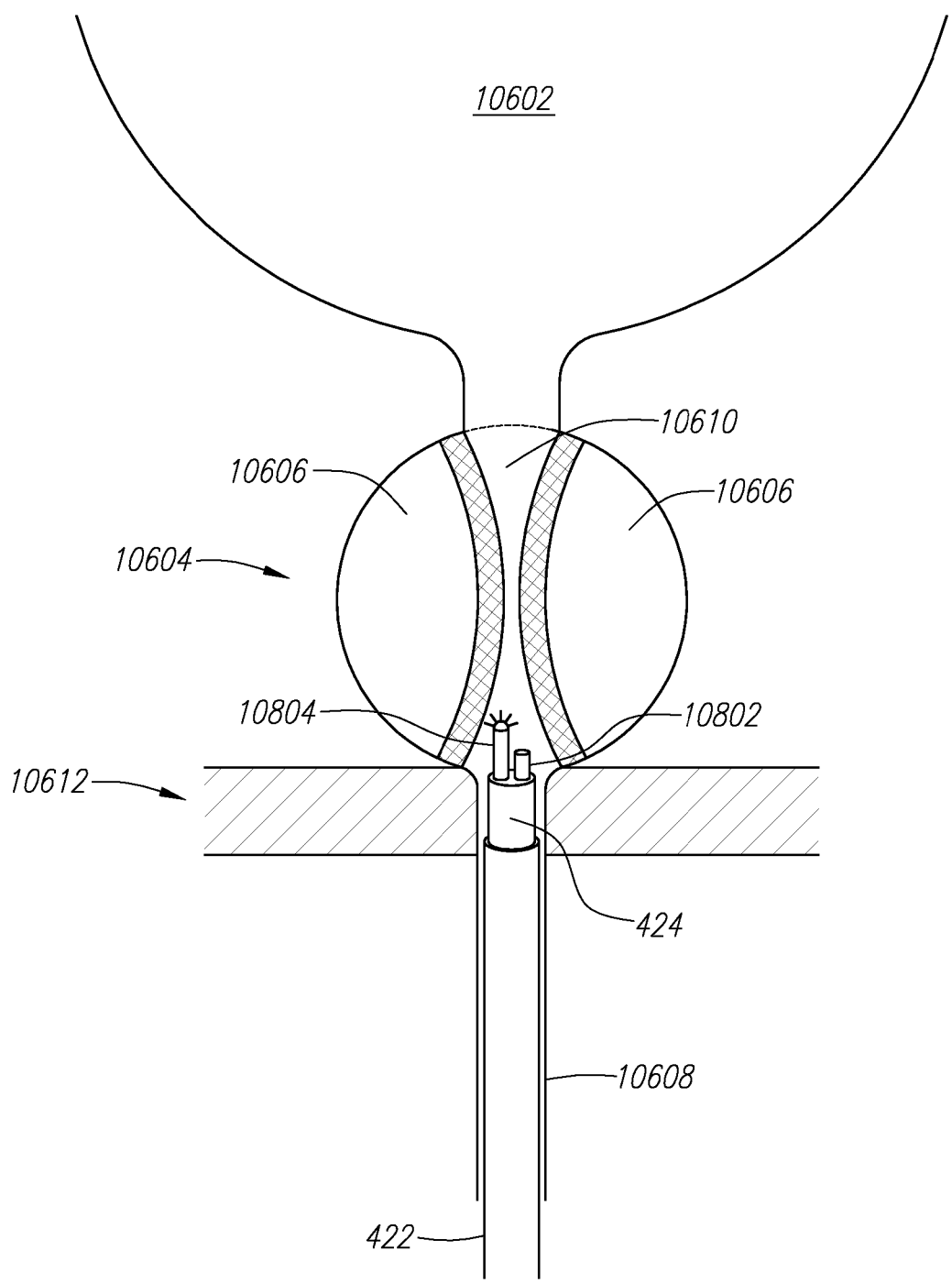
FIG. 108 illustrates a close-up view of the prostate with one embodiment of a catheter that includes a laser and imaging fiber.

FIG. 106 through FIG. 115 illustrate various apparatuses and methods for performing prostate surgery. FIG. 106 illustrates a prostate (10604) with benign prostatic hyperplasia. As illustrated, the channel about the lateral lobe (10606) in the prostate gland (10604) through which the bladder (10602) empties out to the urethra (10608) is narrowed in the region of the median lobe (10610). FIG. 107 illustrates a steerable sheath (422) and guide catheter (424) traveling up the urethra (10608). FIG. 108 illustrates a close-up view of the prostate gland (1604) and the external urethral sphincter tissue (10612) near the prostate gland. In one embodiment, the steerable guide catheter (424) includes an imaging fiber (10802) and laser (10804). As discussed above, the laser (10804) may be used to perform the various types of laser surgery for addressing BPH. The imaging fiber (10802) may be a fiberscope, CCD chip, infrared imaging device, such as those available from CardioOptics Incorporated, ultrasound device, or any other image capture device, for example, to search for objects or to view tissue.

Figure 109:
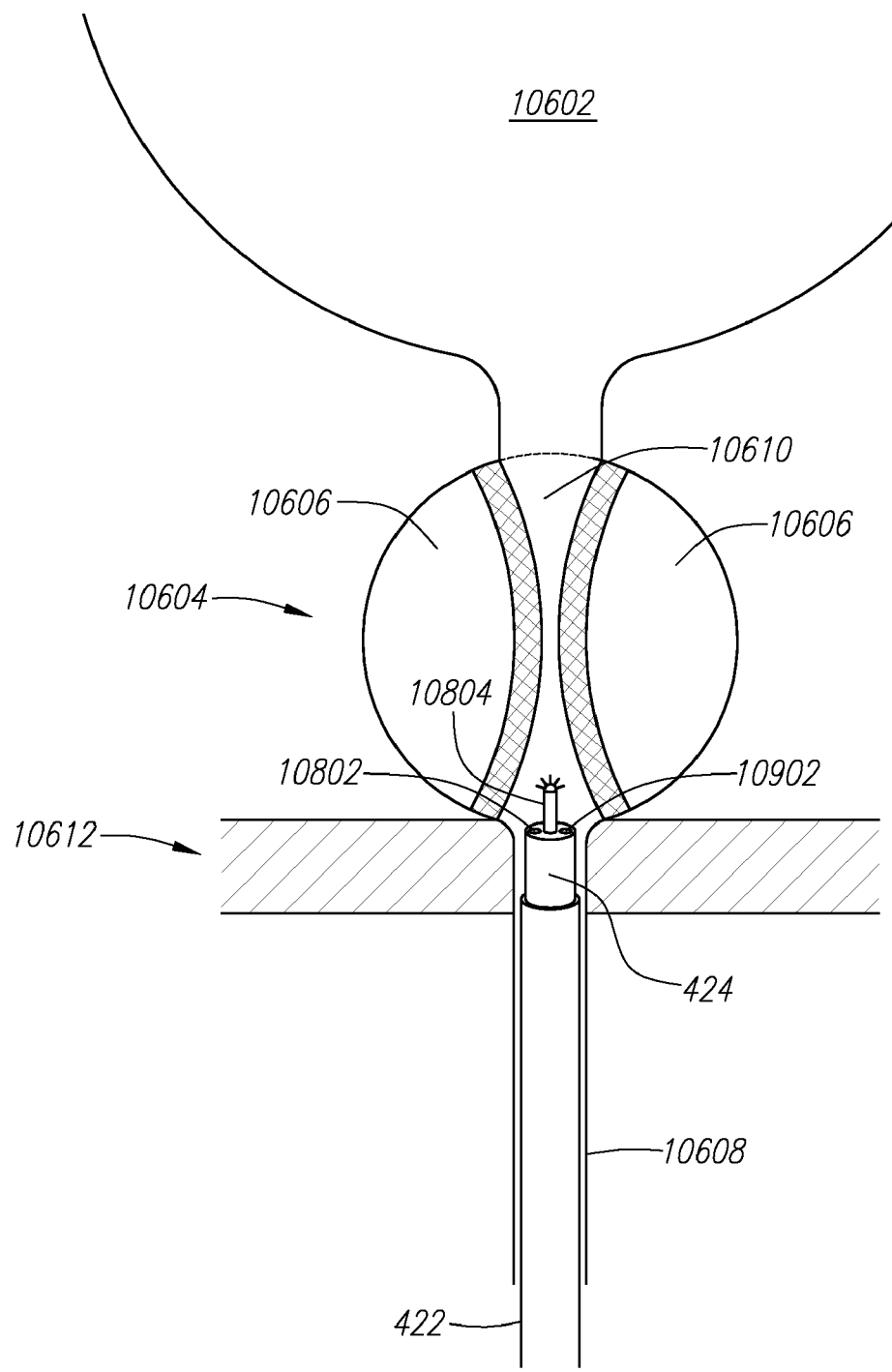
FIG. 109 illustrates another close-up view of the prostate with one embodiment of a catheter that includes a laser, imaging fiber, and flush port.
Figure 110:
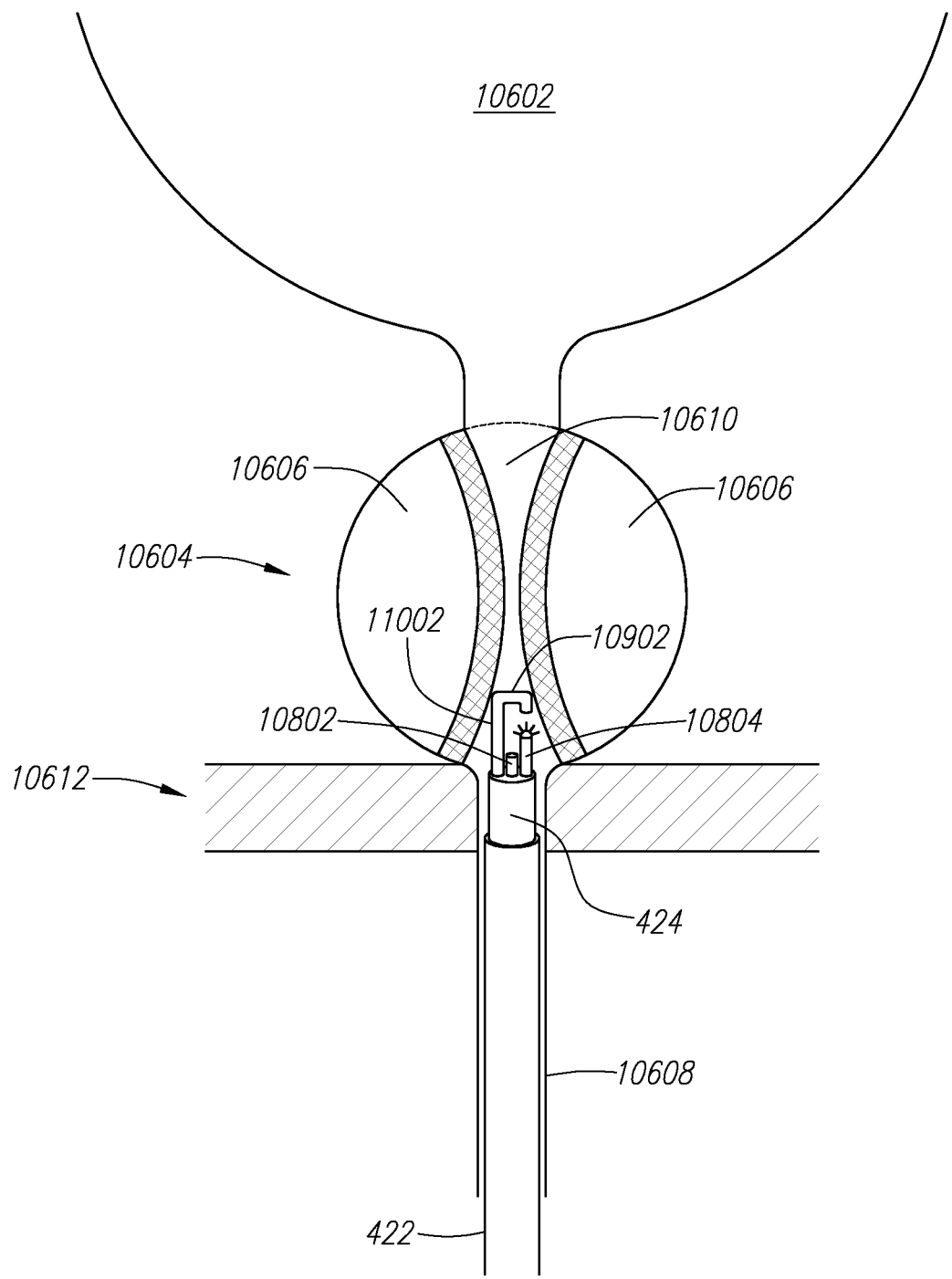
FIG. 110 illustrates yet another close-up view of the prostate with another embodiment of a catheter that includes a laser, imaging fiber, and flush port.
Figure 111:
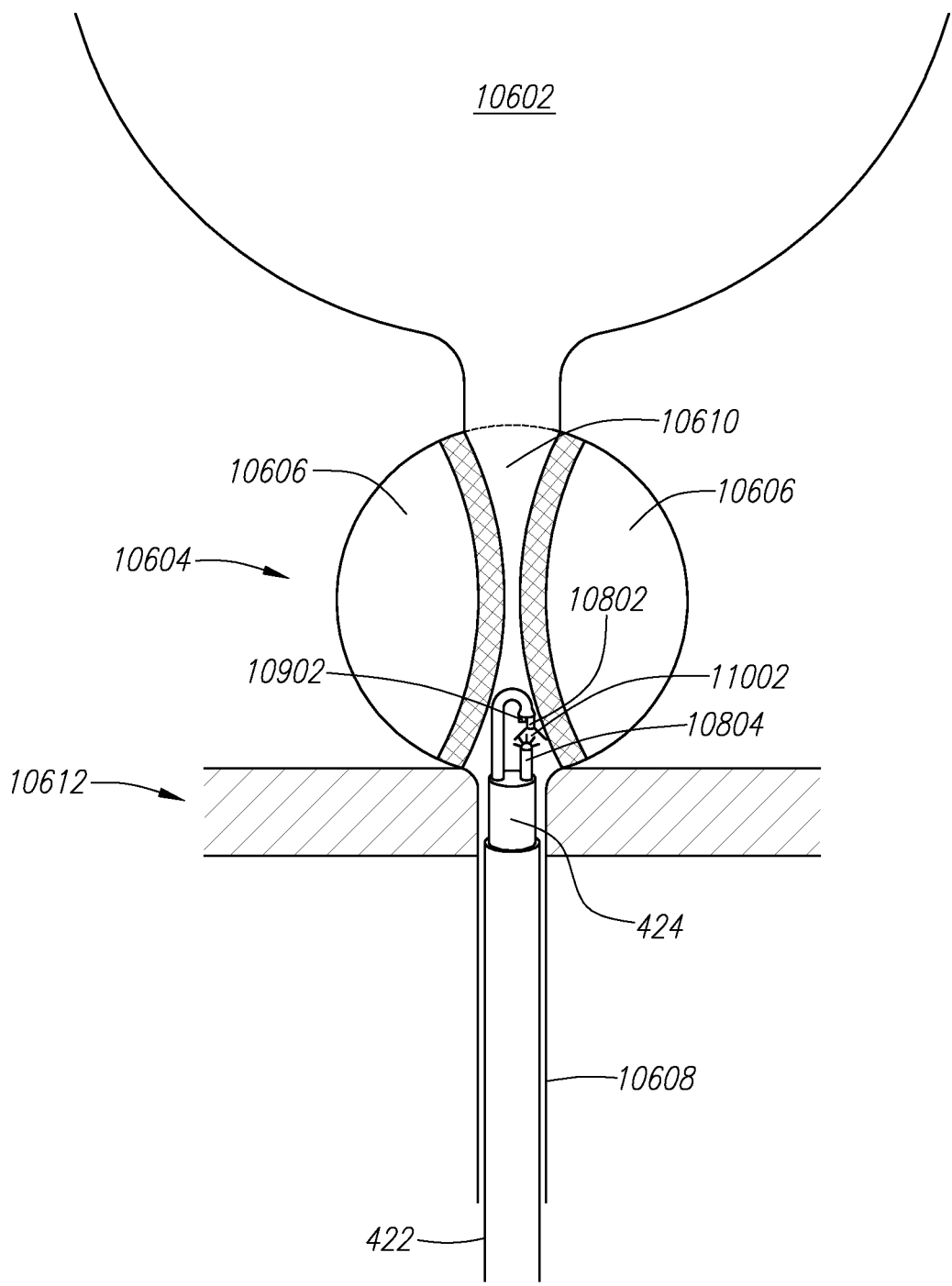
FIG. 111 illustrates additional close-up view of the prostate with yet another embodiment of a catheter that includes a laser, imaging fiber, and flush port.
Figure 112:
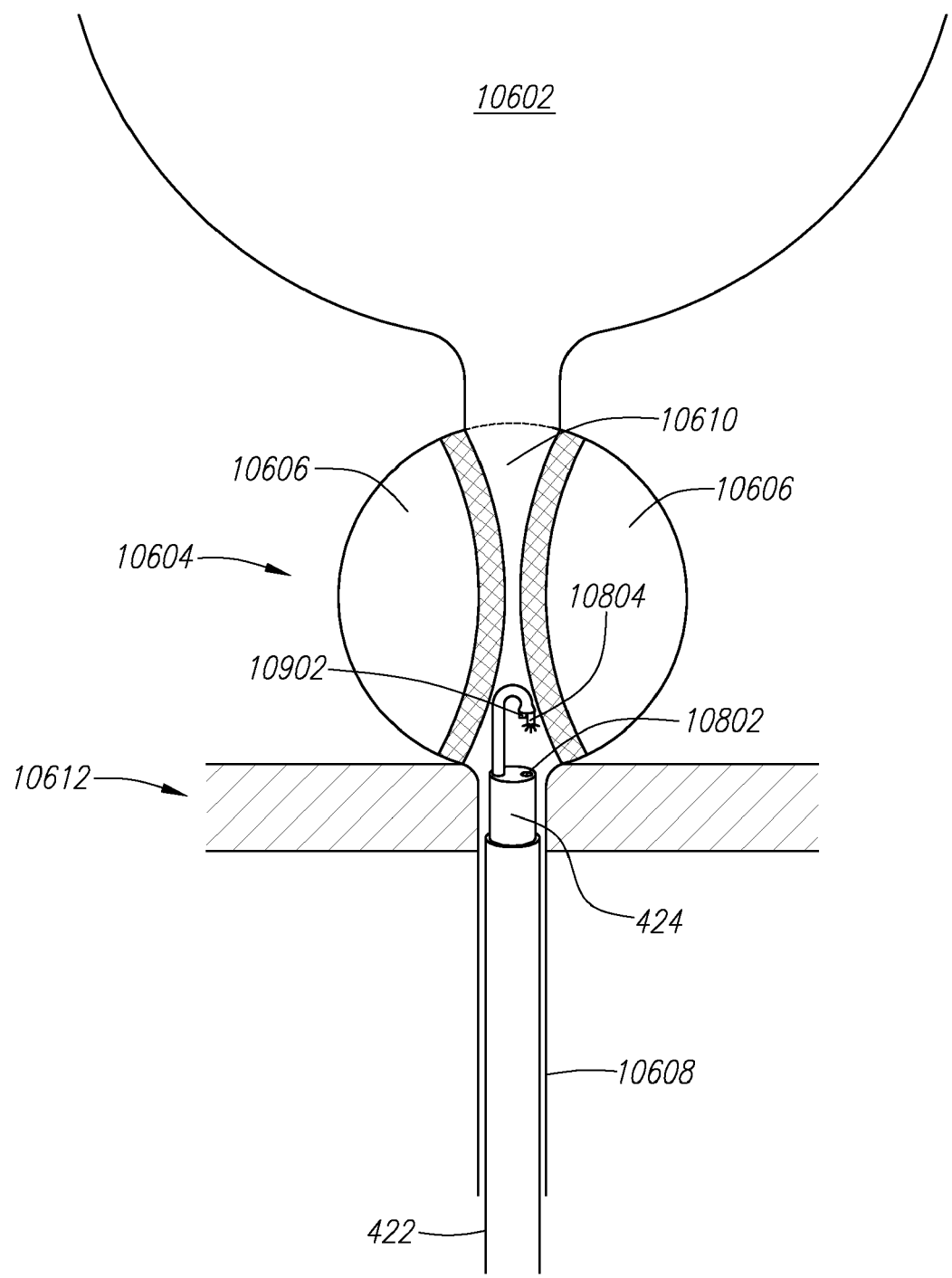
FIG. 112 illustrates a further close-up view of the prostate with still another embodiment of a catheter that includes a laser, imaging fiber, and flush port.

FIG. 109 illustrates another close-up view of the prostate gland (10604) with one embodiment of a catheter (424) that includes an imaging fiber (10802), laser (10804), and flush port (10902). In this embodiment, a flush port (10902) is also available in the catheter (424) for supplying irrigating fluid and to flush the prostate (10604) during a laser surgery procedure. FIG. 110 illustrates yet another close-up view of the prostate (10604) with another embodiment of a catheter (424) that includes an imaging fiber (10802), laser (10804), and flush port (11002). In this embodiment, the flush port (11002) points in an opposite from the imaging fiber (10802) and laser (10804). During a procedure, the solution from the flush port can travel down the urethra (10608) to carry away prostate tissue chipped away by the laser (10804) while the imaging fiber (10802) provides a user, operator, or surgeon a view of the procedure from a viewpoint near the laser. FIG. 111 illustrates an additional close-up view of the prostate (10604) with yet another embodiment of a catheter (424) that includes an imaging fiber (10802), laser (10804), and flush port (10902). In this embodiment, the imaging fiber (10802) and flush port (10902) point downward towards the urethra (10608) and opposite to the laser (10804). The imaging fiber (10802) provides a user a better view of the laser (10804) in operation as the solution from the flush port flushes debris away from the imaging fiber (10802). FIG. 112 illustrates a further close-up view of the prostate (10604) with still another embodiment of a catheter (424) that includes an imaging fiber (10802), laser (10804), and flush port (10902). In this embodiment, the laser (10804) and flush port (10902) are directed downward toward the urethra, whereas the imaging fiber (10802) is directed upward towards the bladder (10602).

Figure 113:
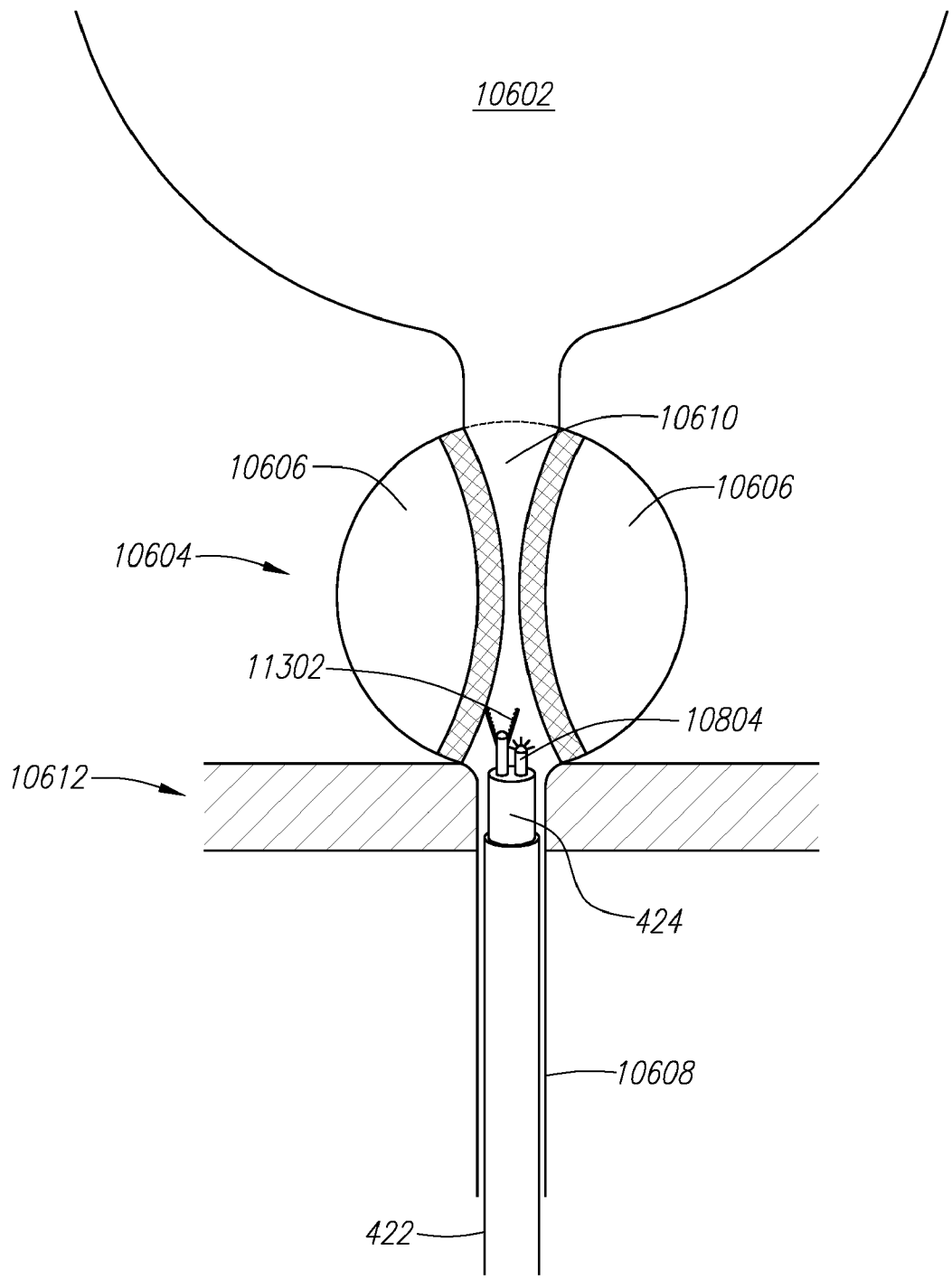
FIG. 113 illustrates a yet further close-up view of the prostate with one embodiment of a catheter that includes a laser and grasper.
Figure 114:
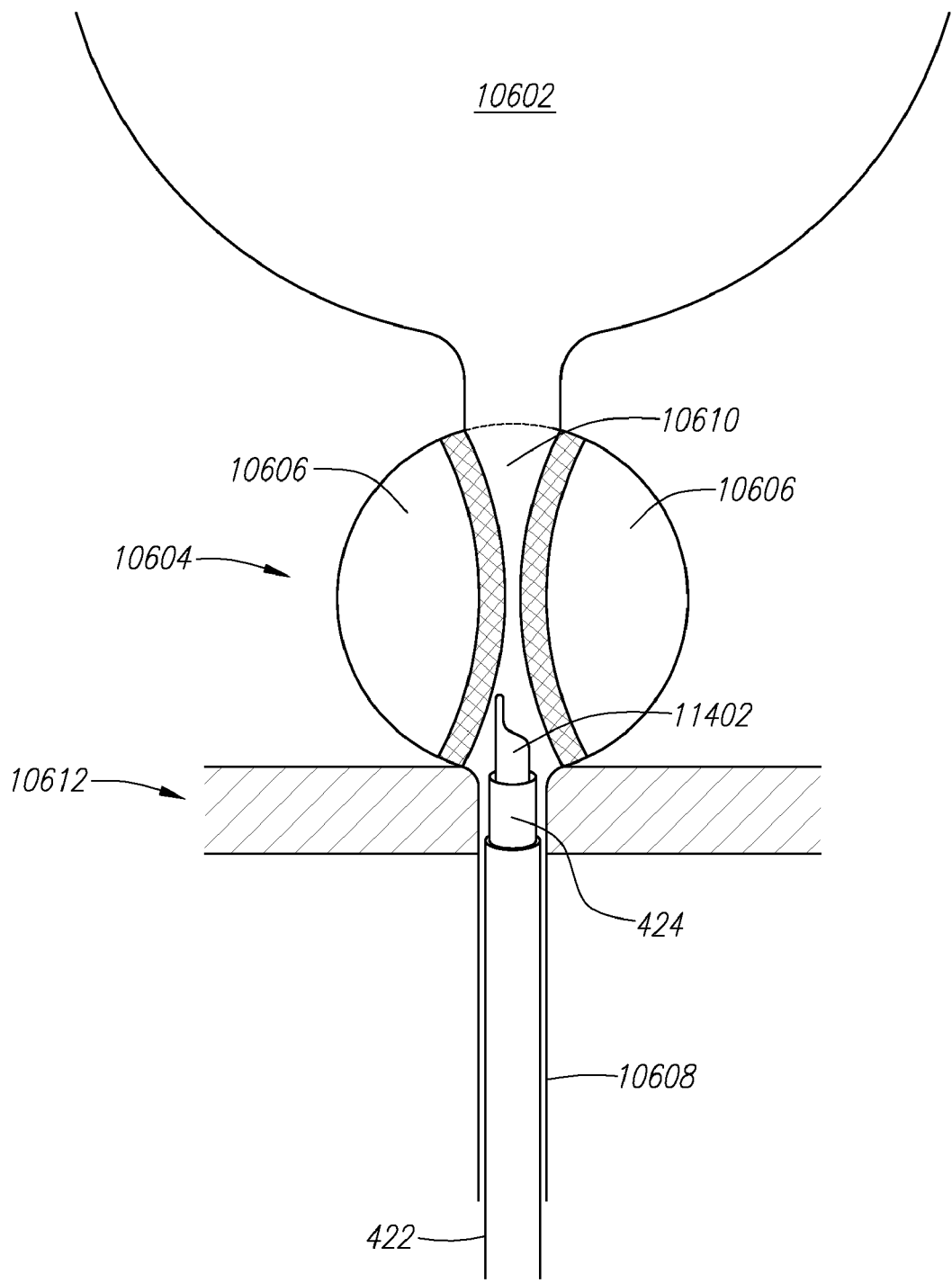
FIG. 114 illustrates another close-up view of the prostate with one embodiment of a resectoscope deployed within the working lumen of a steerable guide catheter.
Figure 115:
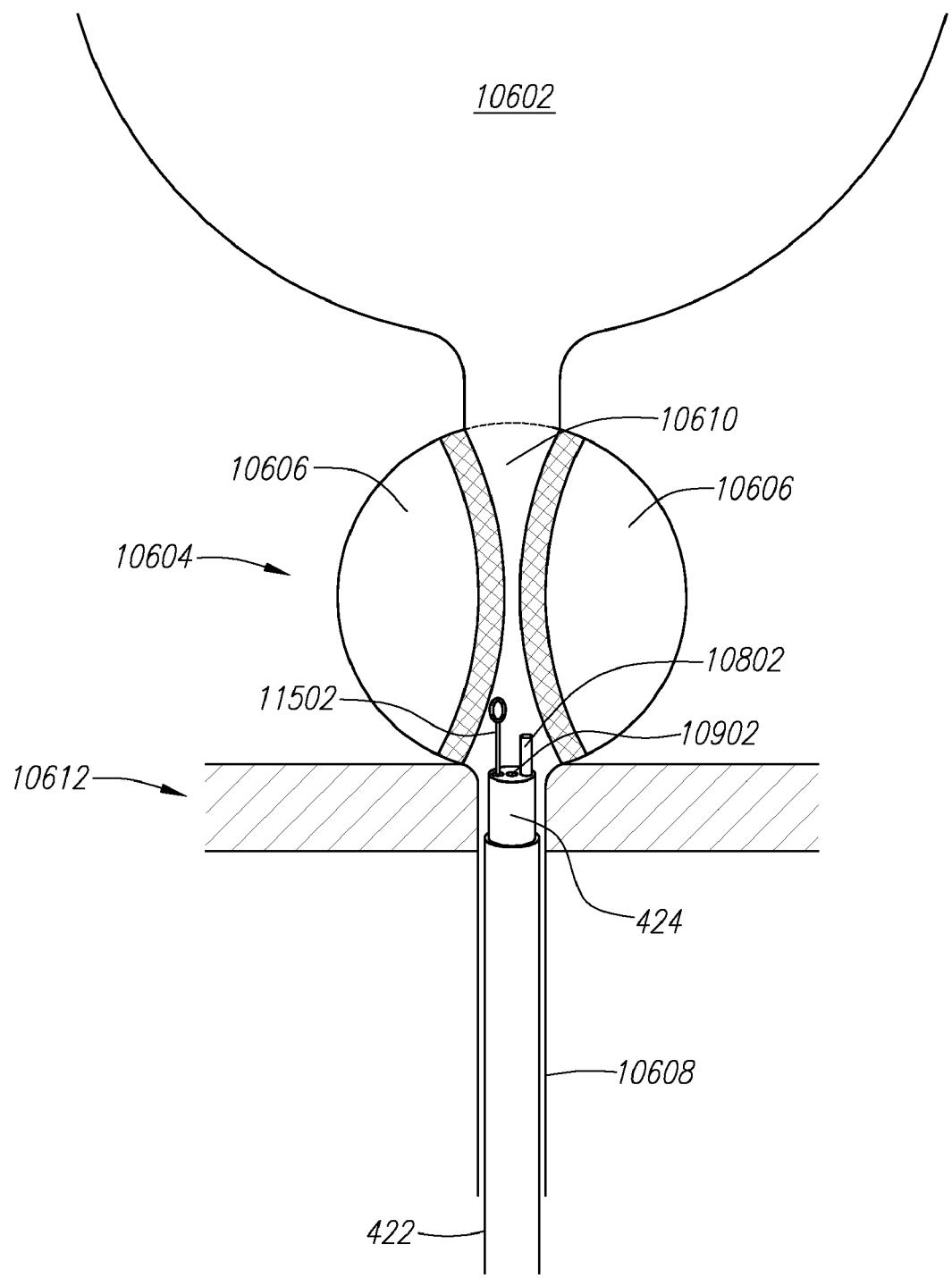
FIG. 115 illustrates yet another close-up view of the prostate with one embodiment of a catheter that includes a wire loop, imaging fiber, and flush port.

FIG. 113 illustrates a yet further close-up view of the prostate (10604) with one embodiment of a catheter (424) that includes a laser (10804) and grasper (11302). This embodiment includes a grasper (11302) to grasp and remove any tissue samples as desired. FIG. 114 illustrates another close-up view of the prostate (10604) with one embodiment of a resectoscope (11402) deployed within the working lumen of a steerable guide catheter (424). As discussed above, some embodiments of a resectoscope can also include an image capture device, flush ports, or other tools. Thus with an implementation as shown in FIG. 114, a TURP procedure can be conducted. Tiny cutting blades deployed by the resectoscope (11402) can scrape away excess prostate tissue. FIG. 115 illustrates yet another close-up view of the prostate (10804) with one embodiment of a catheter (424) that includes a wire loop tool (11502), imaging fiber (10802), and flush port (10902). This wire loop tool (11502) may be configured such that it may be electrified to chip away or remove and cauterize the excess tissue for treating BPH.

All of the aforementioned balloons, ablation tools, electrodes, etc. apparatuses are configured to be operatively coupled to the instrument assembly (108) in combination with the sheath catheter (422) and guide catheter (424). In some embodiments, the tools or instruments, e.g., balloons, ablation tools, electrodes, etc., may be used with the guide catheter (424) without the sheath catheter (422). In other embodiments, additional catheters may be used with the tools or instruments. As apparent to one skilled in the art, the tools and instruments are configured to be either manually operated or robotically operated by the instrument driver (106) in connection with the instrument (108). Some of the circuitry, electrical, and mechanical systems for controlling and operating all of the aforementioned tools and instruments may be configured at the instrument driver (106) and the system electronics rack (114).

Figure 116:
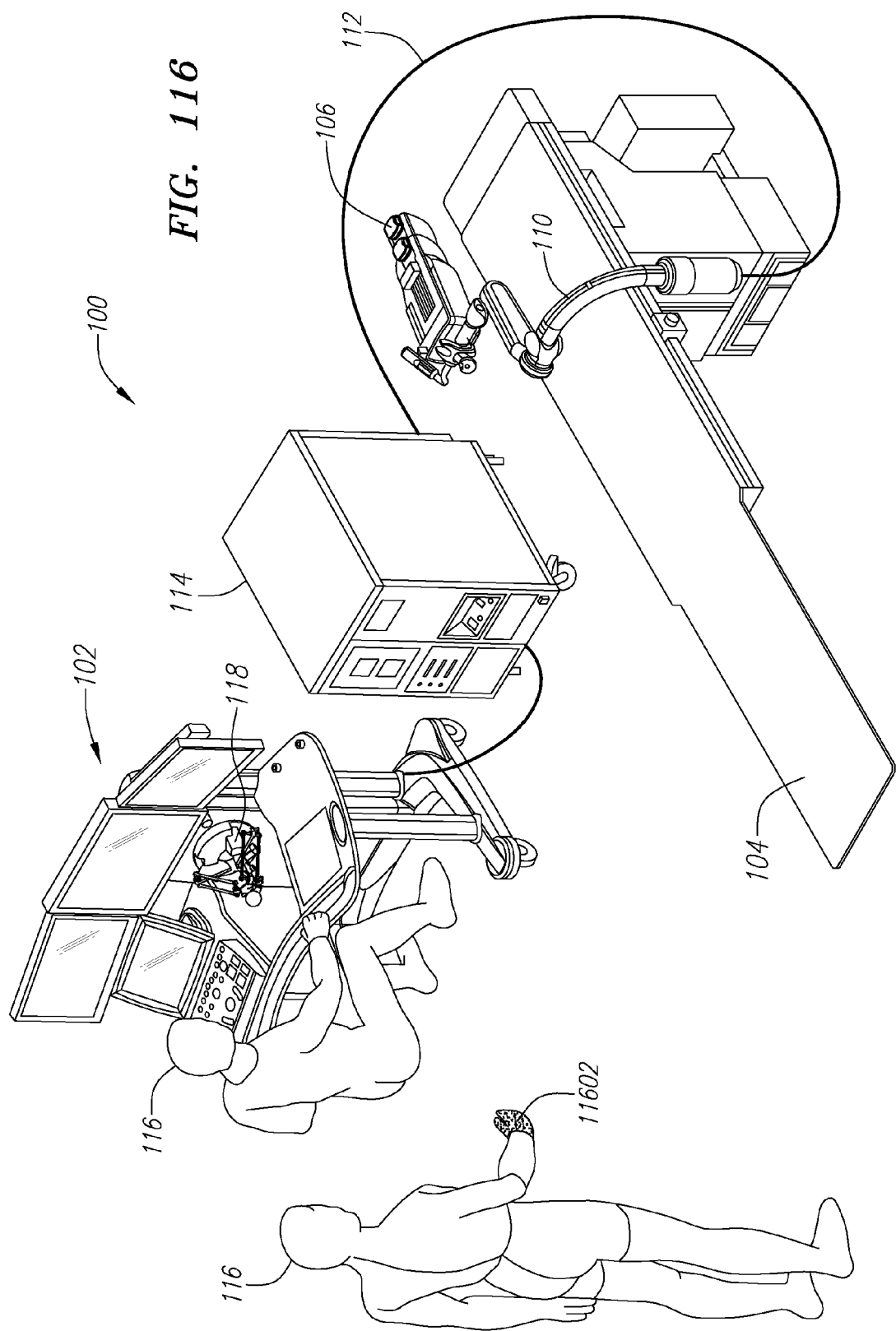
FIG. 116 illustrates one embodiment of a robotic catheter system that includes both a master input device and a pair of data gloves.

FIG. 116 illustrates another embodiment of a robotic surgical system (100). As illustrated in FIG. 116, this embodiment of the robotic surgical system (100) includes both a master input device (118) and a pair of data gloves (11602) for providing input to the system (100). The data gloves (11602) may be connected to the operator control station (102) or the electronics rack (114) by a wire or wireless connection. This embodiment essentially provides two input system for one or more operators (116) to provide input to the system (100). For example, a first operator or surgeon (116) may provide input to system (100) by manipulating the master input device (118) and a second operator or surgeon (116) may provide input to system (100) by the wireless data glove (99) either near control station (102) or a some distance away from both the operator control station (102) and the operation table (104).

Accordingly, the instrument driver (106) and instrument (108) may be controlled by one or more operators via the manipulation of the master input device (118) or pair of data gloves (11602), or a combination of both the master input device (118) and the data gloves (11602). For example, the insertion and removal of an instrument (108) mounted on the instrument driver (106) may be controlled via the data gloves (11602) and/or the master input device (118). Instrument (108) may include steerable catheters (422, 424). In addition, tools or other types of end-effectors may be mounted or inserted through the working lumens at the end of the instrument assembly (108), such as the sheath (422) and guide (424). In some embodiments, the data gloves are configured to also control and manipulate these tools and end-effectors. In other embodiments, the data gloves simply control the steering (pitch, yaw, rotation, etc) for the instrument assembly, e.g., sheath (422) and/or guide (424). In yet another embodiment, the data gloves (11602) may maneuver an imaging fiber located at the tip of instrument (108) such that the field of view can be changed based on movements of a data glove A data glove (11602) is generally defined as a glove equipped with sensors that sense the movements of the hand and interfaces those movements with a computer in the electronics rack (114). Data gloves may interactive devices that resemble gloves worn on the hands, which may facilitate tactile sensing and fine-motion control in robotics and virtual reality. Data gloves are commonly used in virtual reality environments where the user sees an image of the data glove and can manipulate the movements of the virtual environment using the glove. Data gloves are one of several types of electromechanical devices used in haptics applications. Tactile sensing involves simulation of the sense of human touch and includes the ability to perceive pressure, linear force, torque, temperature, and surface texture. Fine-motion control involves the use of sensors to detect the movements of the user's hand and fingers, and the translation of these motions into signals that can be used by a virtual hand (for example, in gaming) or a robotic hand (for example, in remote-control surgery). Sophisticated data gloves also measure movement of the wrist and elbow. A data glove may also contain control buttons or act as an output device, e.g. vibrating under control of the computer. The user usually sees a virtual image of the data glove and can point or grip and push objects.

Figure 117:
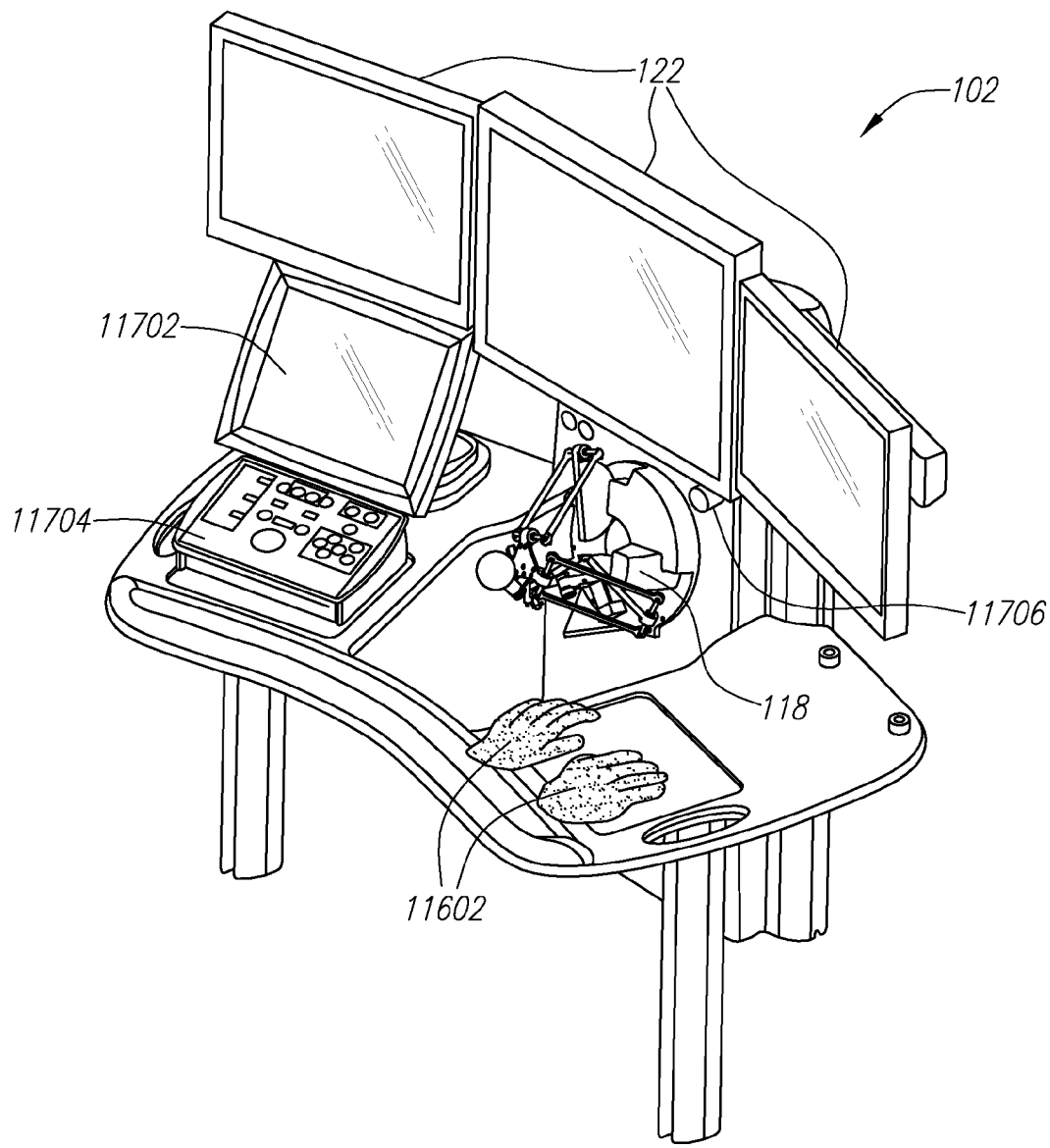
FIG. 117 illustrates the operator control station of FIG. 116.
Figure 118:
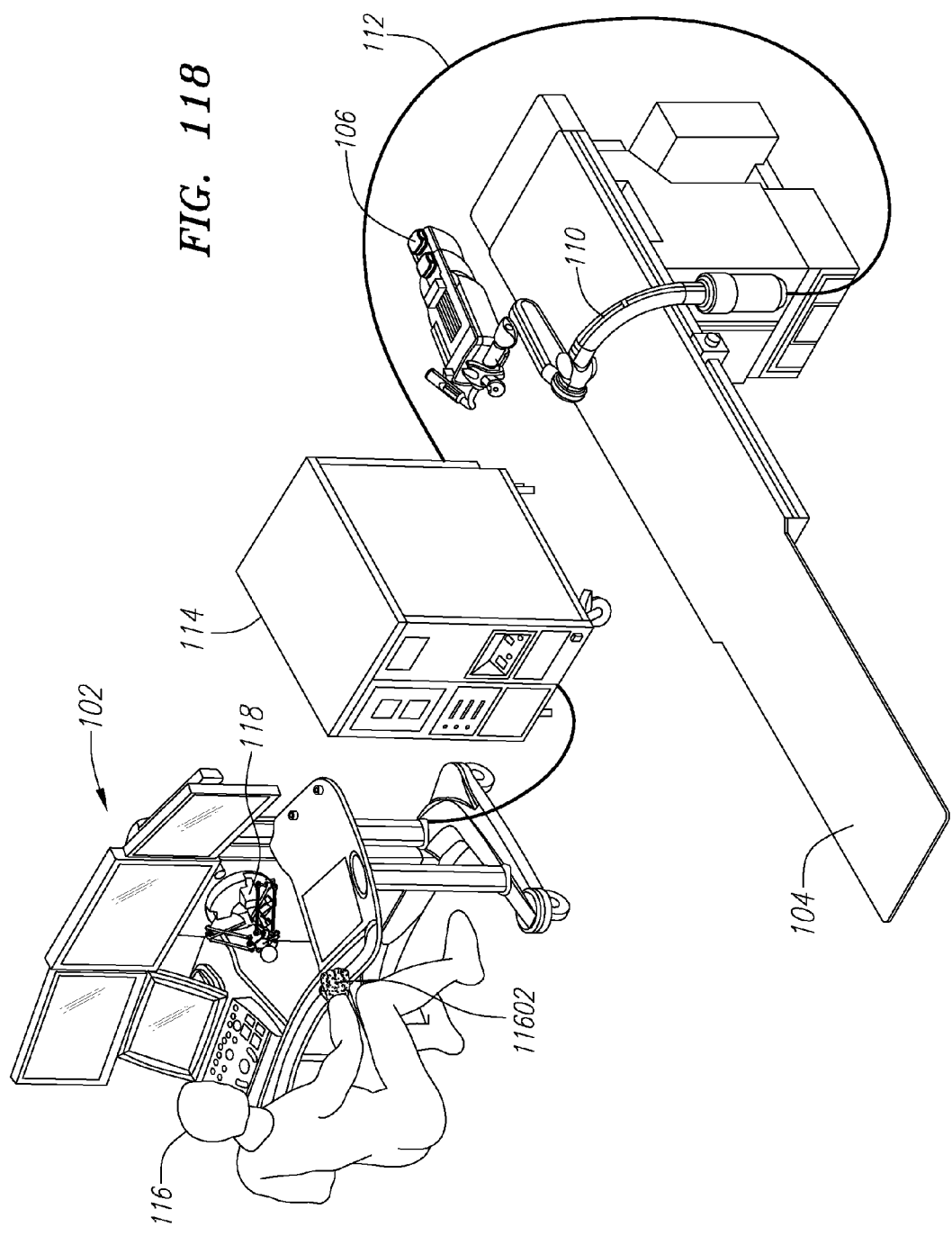
FIG. 118 illustrates another embodiment of an operator control station that includes a master input device and a pair of data gloves.

FIG. 117 illustrates one embodiment of the operator control station of the system (100). The operator control station (102) of this embodiment includes three display monitors (122), a touch-screen user interface (11702), a control button console (11704), a master input device (118), and a pair of data gloves (11602). Master input device (118) and wireless data gloves (11602) serve as user interfaces through which the user can control the operation of the instrument driver (106), the instrument (108), and any additional attachments, tools, instruments, etc. As shown in FIG. 117, the master input device (118) is located about the center of the operator control station (102) just under the center screen. The data gloves (11602) are coupled to the control station (102) via a cable or wireless connection. Wireless data gloves enables a user or surgeon to provide command or operate the system (100) substantially untethered remotely from the operator station (102). Also depicted is a device disabling switch (11706) configured to disable activity of the instrument temporarily. As illustrated in FIG. 118, the electronics rack (114) may be support by a cart or configured with wheels for easy movability within the operating room or catheter lab, one advantage of which is location of the operator control station (102) which may be moved away from the operation table (104) and radiation sources, thereby substantially decrease or eliminate the potential for exposure to radiation or reduce the radiation dosage to the operator.

Figure 119:
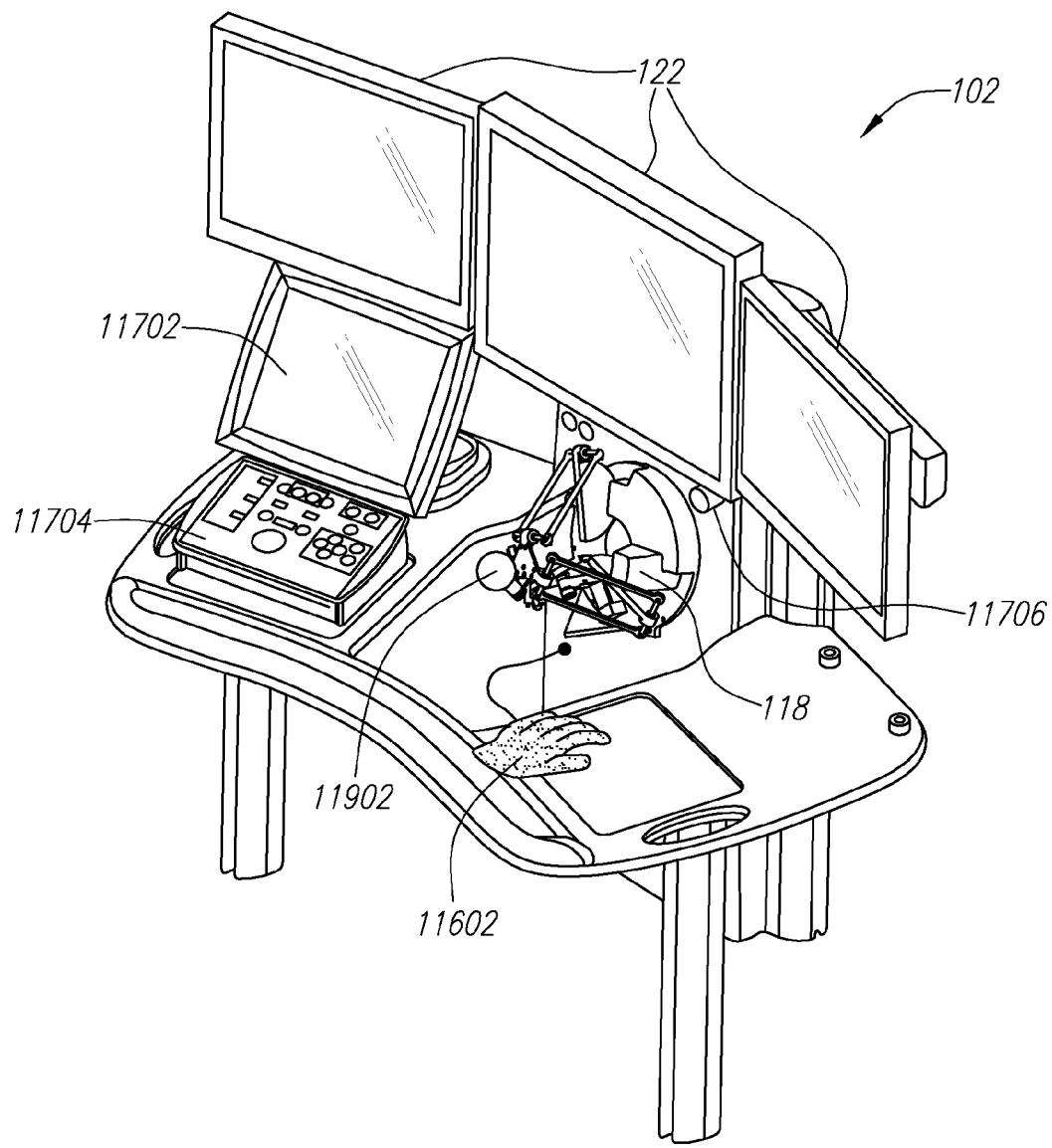
FIG. 119 illustrate the input devices of the control station in FIG. 118.

Referring to FIG. 119, one embodiment of an operator control station (102) is depicted showing a control button console (11704), which may include a computer, a computer control interface device, such as a mouse, a visual display system (122), a master input device (118), and a pair of data gloves (11602). In addition to buttons on the button console (11704), footswitches and other known types of user control interfaces may be utilized to provide an operator interface with the system controls.

Still referring to FIG. 119, the master input device (118) of this embodiment may be a multi-degree-of-freedom device having multiple joints and associated encoders. An operator interface (11902) may be configured for comfortable interface with the hand or fingers or the operator 116. The depicted embodiment of the operator interface (11902) is substantially spherical. Further, the master input device may have integrated haptics capability for providing tactile feedback to the user. Also illustrated in FIG. 119 is a pair of data gloves (11602) coupled to the operator control station. In this embodiment, a single user can utilize the master input device (11902) or the pair of data gloves (11602), or even a combination of both, to control the instrument driver (106) and one or more instruments (108). However, it is also possible for two users to take turns controlling the instrument driver (106) and associated instruments (108). For instance, one person may be seated at the control station in position to manipulate the master input device (118) while a second person may be wearing the data gloves. By gating or multiplexing which master device is active at a given time, the two people can switch off running or operating the system (100). One scenario where this may be useful is where a resident is working at the control station and a chief surgeon wearing the data gloves is ready to step in as needed. Even though the examples illustrated with these figures show data gloves in close proximity to the control station, the operating distance of the gloves may vary depending on the implementation. For example, the gloves can be configured to operate away from the control station or a remote location, such as a different room from which the current procedure is happening. Thus, the operating range may be limited by the physical length of a cable connection, if any, or by the wireless connectivity.

Figure 120:
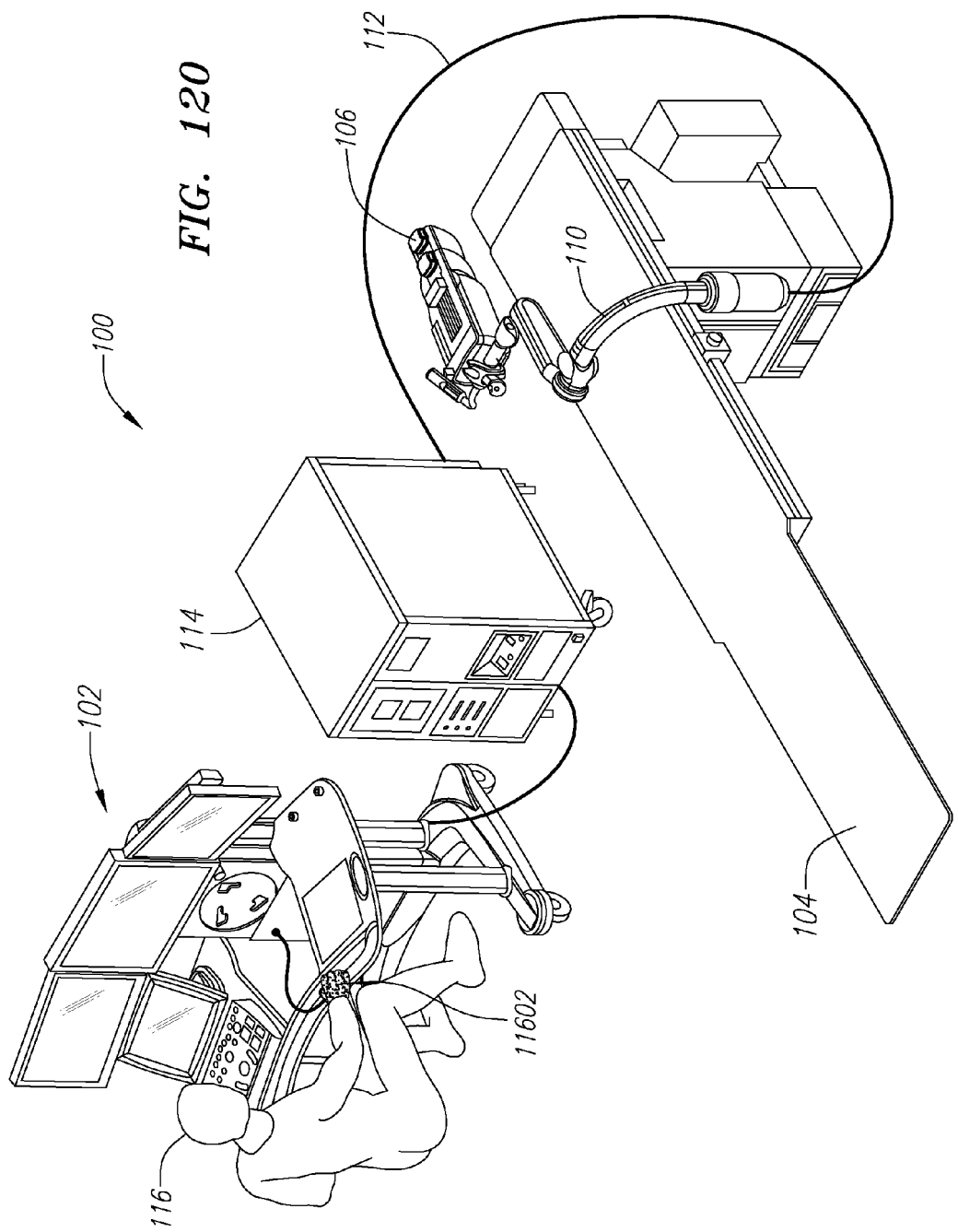
Figure 121:
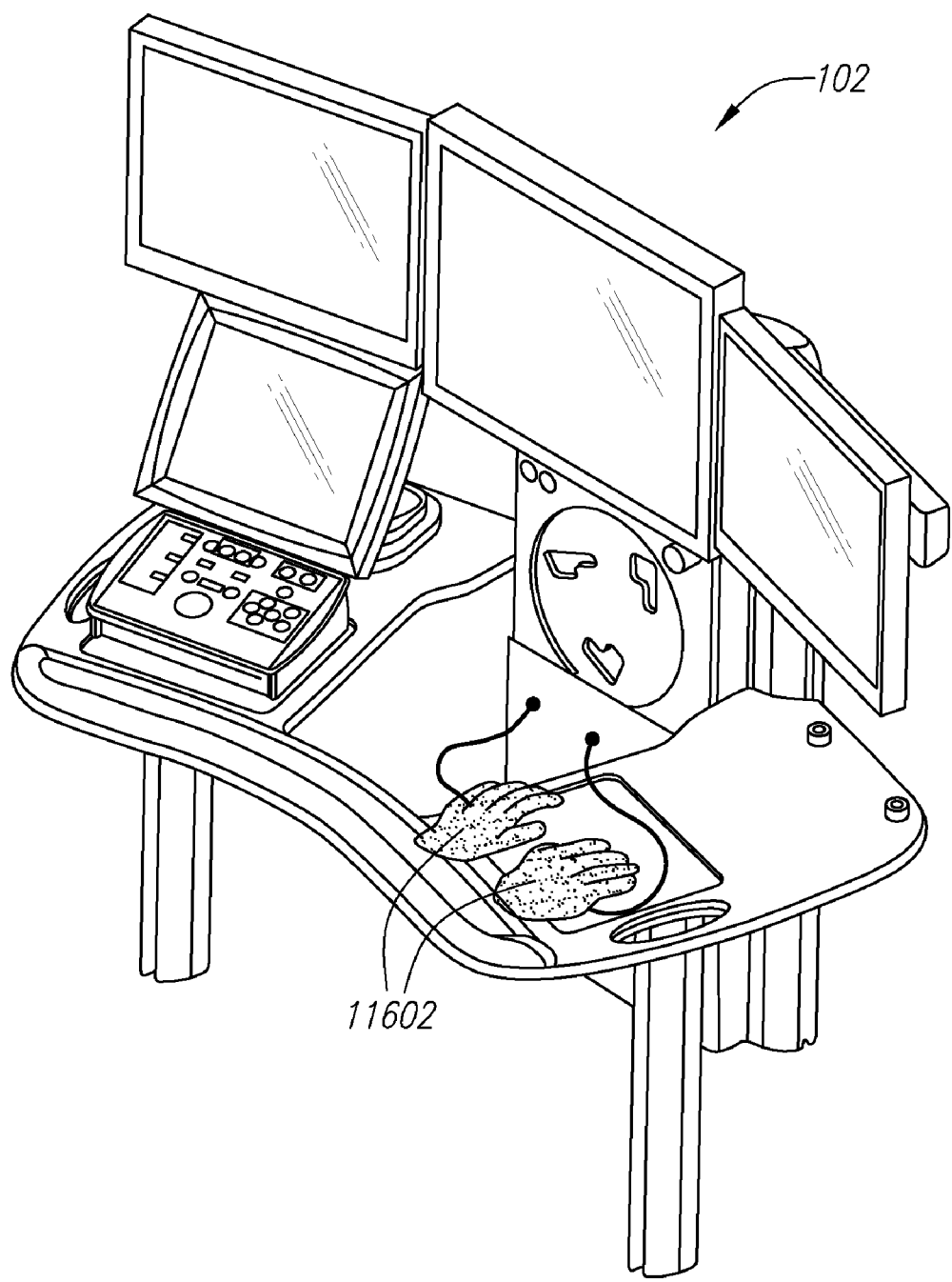
Figure 122:
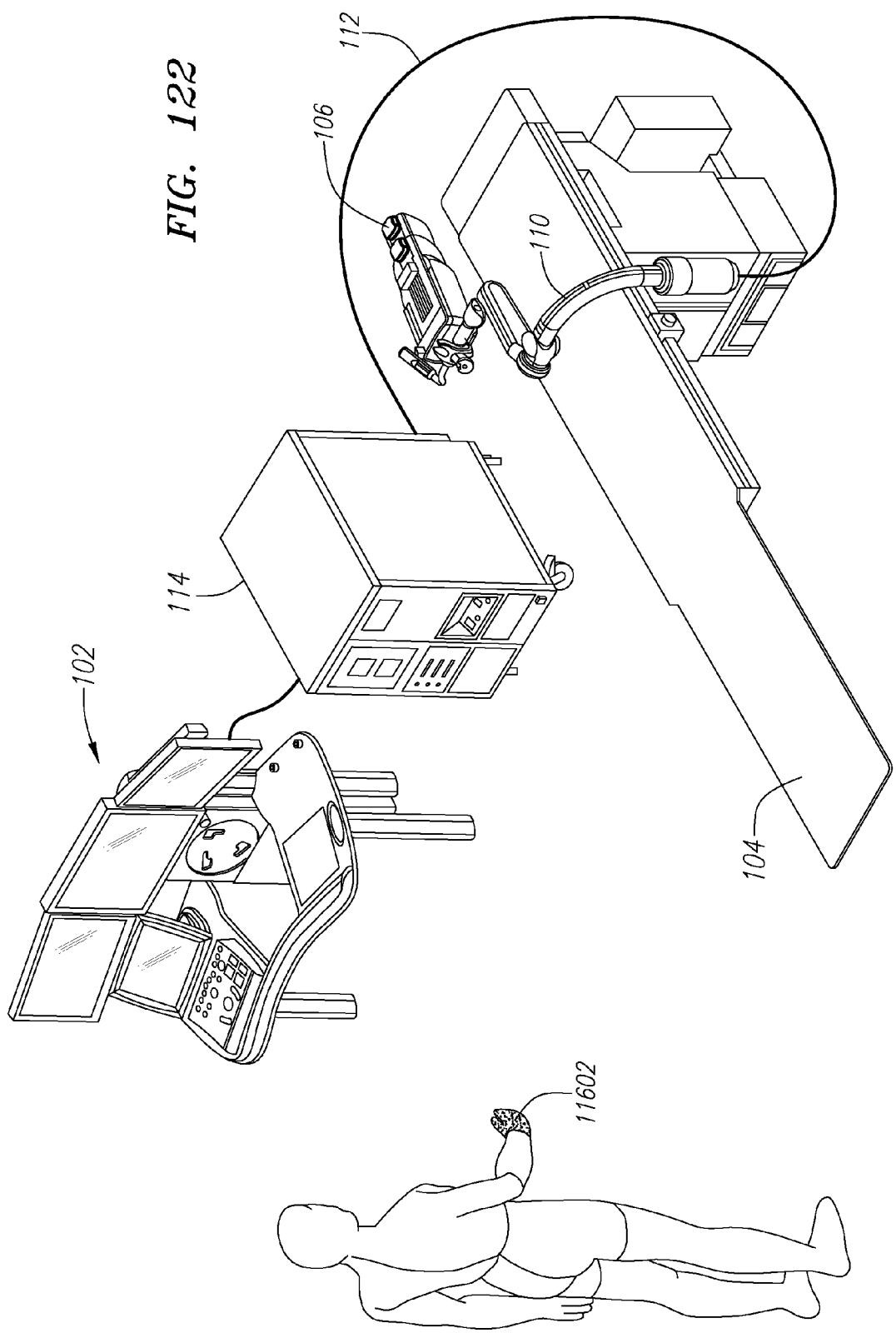
Figure 123:
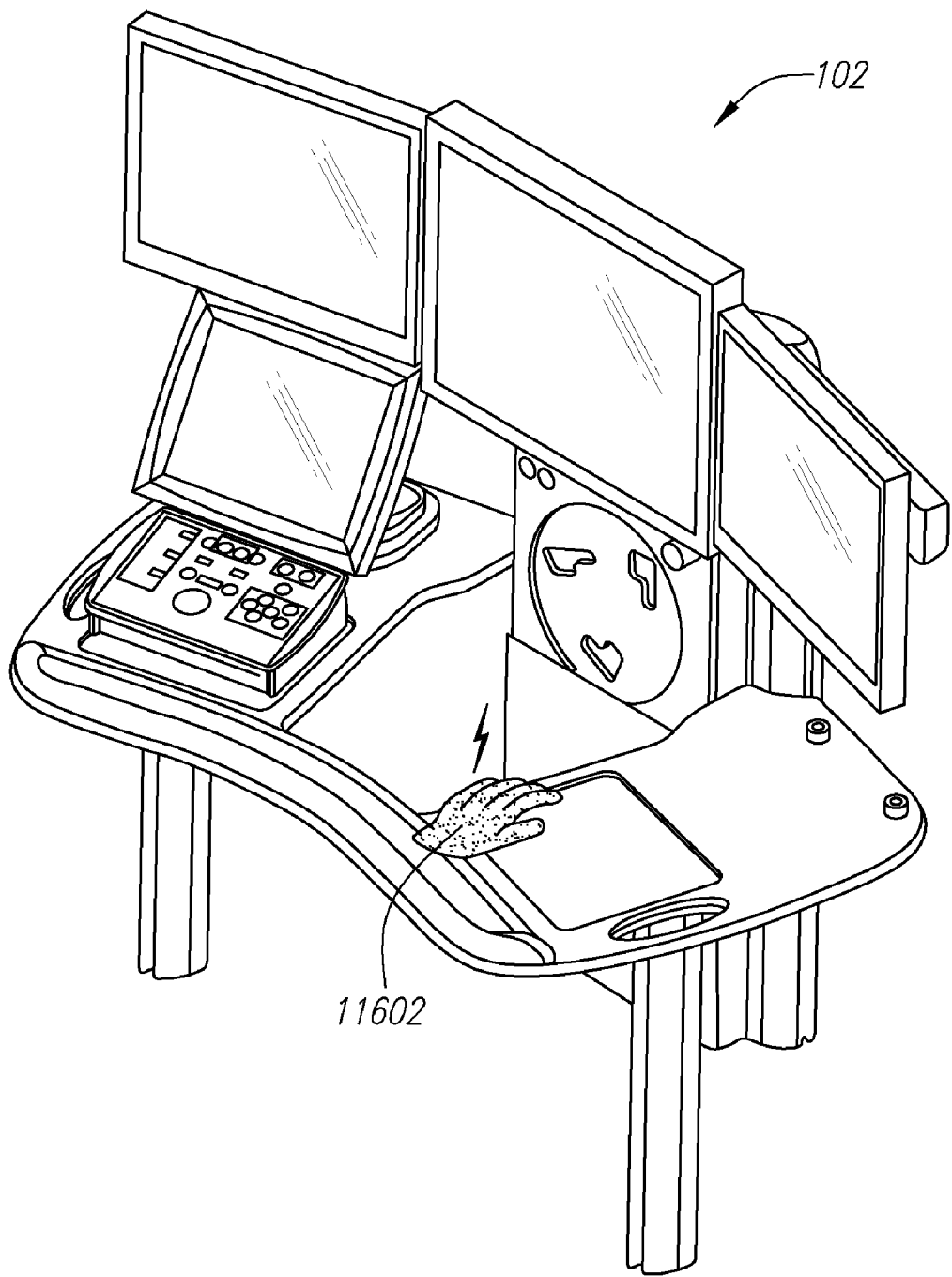

FIG. 120 illustrates one embodiment of a robotic catheter system (100) that includes data gloves (11602). In this embodiment, the user (116) is seated at a station without a master input device and input is provided through the data gloves (11602). FIG. 121 illustrates the operator control station (102) of FIG. 120. As shown in this example, the data gloves (11602) are connected to the console with cables. Note that this system (100) also has the data gloves (11602) in lieu of a master input device (118). FIG. 122 illustrates another embodiment of an operator control station (102) including a pair of wireless data gloves (11602) wherein the user (116) can remotely operate the station (102) and instrument driver (106) away from the station (102). FIG. 123 illustrate the input devices of the control station (102) of FIG. 122 with a wireless data glove (11602) resting on the table top.

The data gloves (11602) of implementation for part of a hand data motion capturing solution for the receiving user input. In one embodiment, the data gloves (11602) can measure finger flexure as well as the abduction between the fingers. Finger flexure is measured at two places on the finger: at the first finger joint (knuckle) and at the second finger joint. Abduction sensors can be located between fingers. In another embodiment, the data gloves (11602) measure finger flexure, but not abduction. In this instance, each sensor measures finger flexure as an average of knuckle and the first joint. A plurality of sensitive data sensors is mounted on the gloves to accurately sense/detect user movements and communicate data signals to system software and hardware. Although one embodiment employs data gloves having five or fourteen data sensors, different numbers of data sensors can be used depending on the resolution desired. One embodiment of the data gloves (11602) features an auto calibration function, 8-bit flexure and abduction resolution, and low drift. Greater resolution can be achieved in sensed movements by increasing the number of data bits in the sensor resolution and increasing the sampling rate. In one embodiment, the glove data can also be captured and recorded at the system for later evaluation. In another embodiment, multiple gloves can be supported simultaneously. Similarly, a single data glove can be employed with other embodiments.

The data gloves (11602) may be a preferable user input device in some instances because this solution can offer comfort, ease of use, and a small form factor, especially when compared to other types of input devices. In one implementation, the data gloves (11602) are constructed with stretch Lycra® fiber (as marketed by INVISTA of Wichita, Kans.), but other types of material such as cotton and nylon are also suitable. Although different sizes of data gloves can be manufactured and utilized, one implementation makes use of a one size fits all design wherein the glove can stretch to fit different users without comprising the integrity or sensitivity of the data gloves. Furthermore, various physical aspects of the data glove can differ based upon the design. For instance, some gloves may be manufactured without finger tips. Other gloves may extend beyond a user's wrist. Another glove may include control buttons or switches.

For the embodiments described in these examples, the pair of data gloves (11602) includes a left hand glove and a right hand glove. In some embodiments, a single data glove may be used, instead of two gloves. Depending on the system architecture and the user software, the data gloves (11602) can be used for a variety of functions. Note that the data gloves are not limited to controlling the instrument driver (106) and associated instruments (108). For example, one embodiment of system may employ the data gloves in combination with a head mounted display. In essence, the user may be given the experience of working within a virtual environment. Thus a user wearing the combination of the head mounted display can visualize operating conditions and scenery at distal end of an catheter and to manipulate a tool or tissue at the distal end of the catheter with the data gloves. In one implementation, the data gloves are capable of providing tactile feedback to the user in response to contact at the distal tip of the catheter. In yet another embodiment, the display from the screens (122) and a set of virtual controls may be projected into the head mounted display. By using the data gloves (11602), a user may be able to operate various virtual system controls within the virtual environment in addition to controlling the instrument driver and catheters. In some aspects, the data gloves may serve as a more instinctive or intuitive type of control as a user may be more comfortable with the concept of virtually grasping or manipulating objects by simple hand motions and having an item being virtually controlled respond as if the user was physically touching the item.

The data gloves (11602) can employ a high speed connectivity interface to communicate with the control system. In one embodiment, the signals are transmitted from the data gloves (11602) to the system via a physical cable such as an RS-232 cable, USB cable, or serial data cable, but are not limited to these examples. For one embodiment, the data gloves are designed without any magnetic parts so that the data gloves can be safely used in a magnetic resonance imaging (MRI) environment. In this case, the sensed data is communicated to the system by way of an optical fiber. In another embodiment, the data signals are transmitted from the data gloves (11602) to the system wireless via radio waves or infrared transmissions through protocols such as, but not limited to, Bluetooth, WiFi, ZigBee, IEEE 802.11, IrDa, 3G, and RFID. Depending on the particular implementation, the sensors may be powered by the system via the cable connection. In a wireless embodiment, the sensors may be powered by a rechargeable or disposable battery pack coupled to the gloves. Data gloves, such as the data gloves in the 5DT Data Glove Ultra series or the 5DT Data Glove MRI series, are available from manufacturers such as 5DT (Fifth Dimension Technologies), Inc. of Irvine, Calif. Additional data gloves include the ShapeHand™ available from Measurand Inc. of Fredericton, NB, Canada and the CyberGlove® II Wireless Data Glove available from Immersion Corporation of San Jose, Calif.

Similarly, master input devices are available from manufacturers such as SensAble Technologies, Inc. of Woburn, Mass. under the trade name Phantom® Haptic Devices or from Force Dimension of Lausanne, Switzerland under the trade name Omega Haptic Device. In one embodiment featuring an Omega-type master input device, the motors of the master input device are utilized for gravity compensation. In other words, when the operator releases the master input device from his hands, the master input device is configured to stay in position, or hover around the point at which is was left, or another predetermined point, without gravity taking the handle of the master input device to the portion of the master input device's range of motion closest to the center of the earth. In another embodiment, haptic feedback is utilized to provide feedback to the operator that he has reached the limits of the pertinent instrument workspace. In another embodiment, haptic feedback is utilized to provide feedback to the operator that he has reached the limits of the subject tissue workspace when such workspace has been registered to the workspace of the instrument (i.e., should the operator be navigating a tool such as an ablation tip with a guide instrument through a 3-D model of a heart imported, for example, from CT data of an actual heart, the master input device is configured to provide haptic feedback to the operator that he has reached a wall or other structure of the heart as per the data of the 3-D model, and therefore help prevent the operator from driving the tool through such wall or structure without at least feeling the wall or structure through the master input device). In another embodiment, contact sensing technologies configured to detect contact between an instrument and tissue may be utilized in conjunction with the haptic capability of the master input device to signal the operator that the instrument is indeed in contact with tissue.

Figure 124:
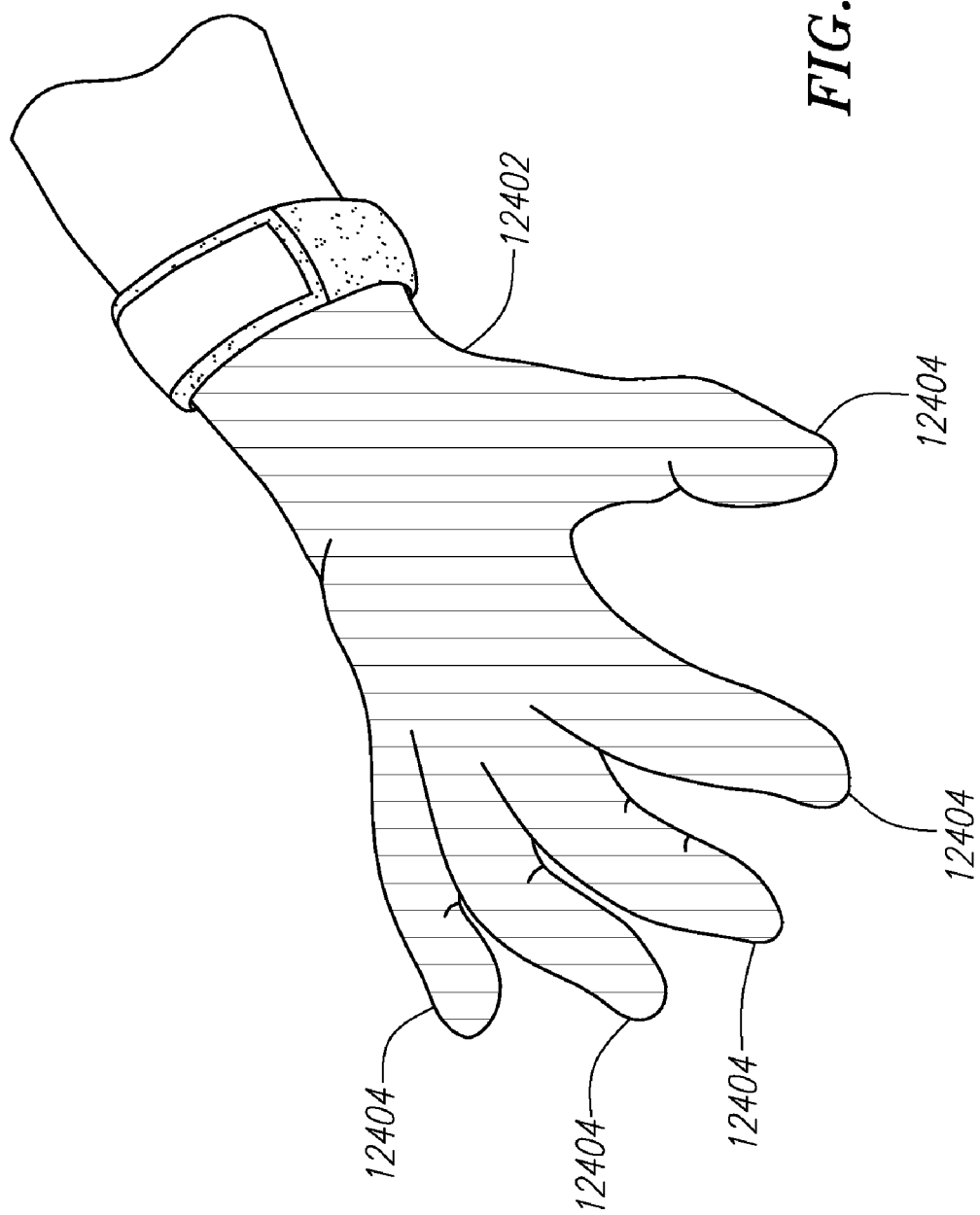
Figure 125:
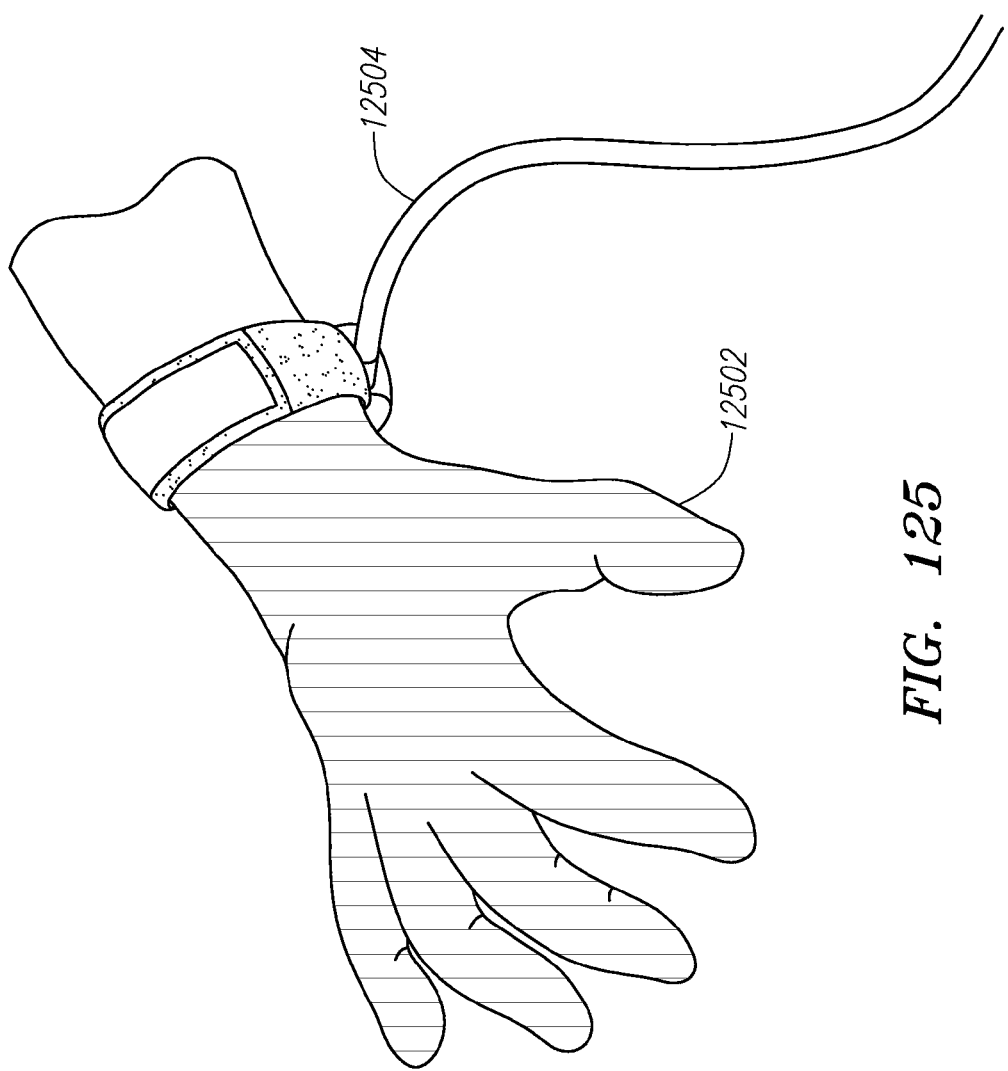
Figure 126:
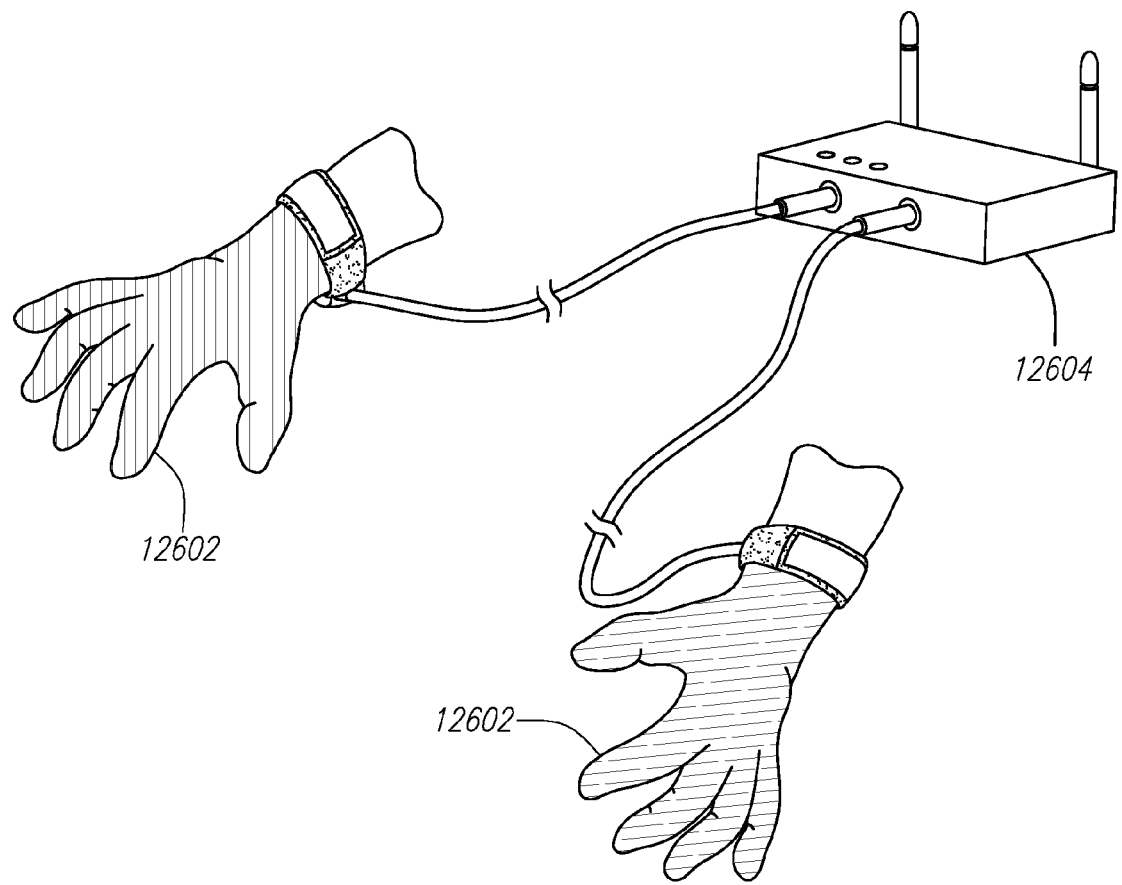
Figure 127:
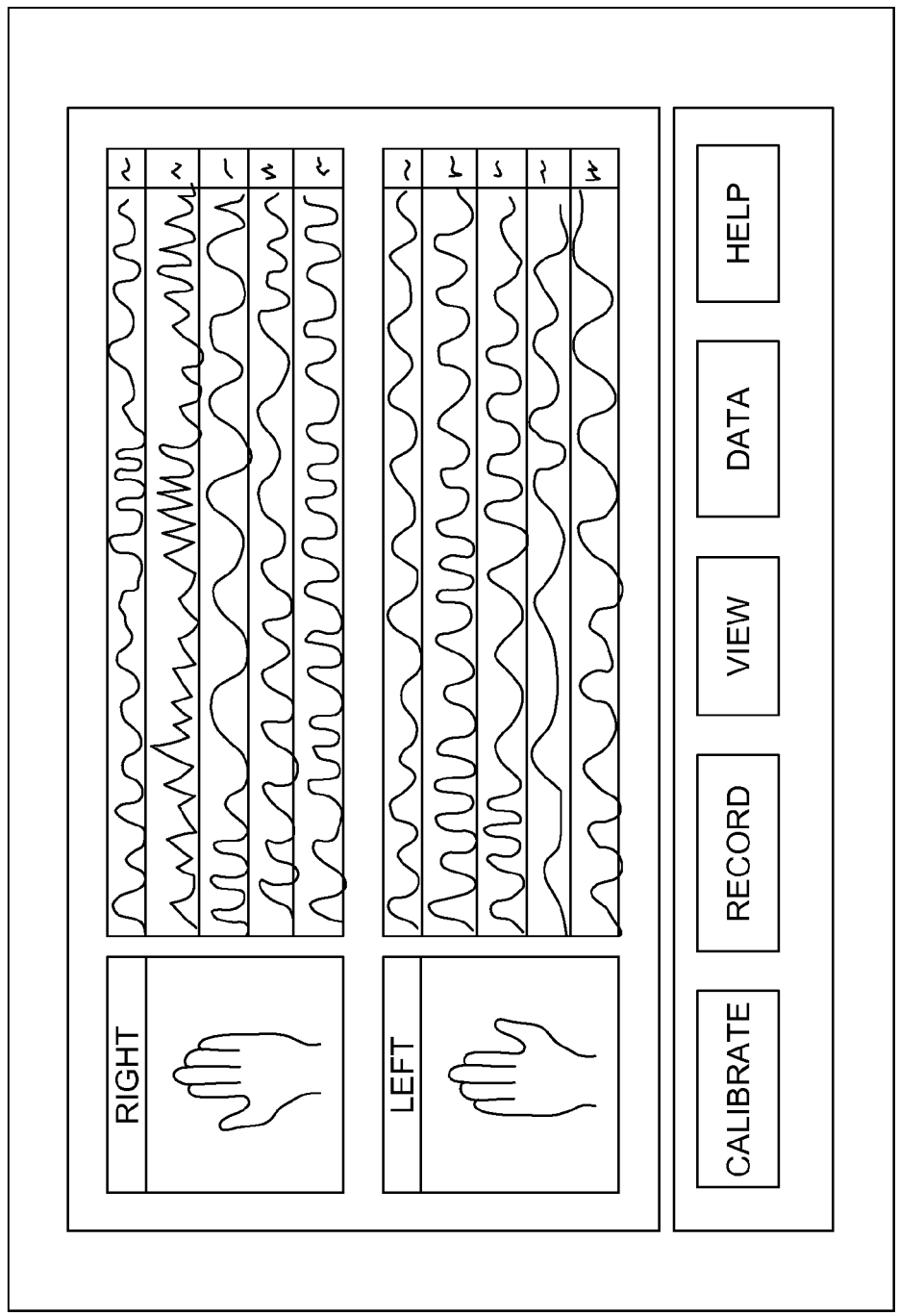

FIG. 124 illustrates one embodiment of the data glove (12402). In this implementation, one sensor (12404) is located on each finger. In an alternative embodiment, two sensors are located on each finger, in addition to a sensor at the abduction between each finger. FIG. 125 illustrates one embodiment of a wired data glove (12502). In this example, the data glove (12502) is physically connected to the system (100) and communicates via the cable (12504). FIG. 126 illustrates one embodiment of a wireless data glove arrangement. In this embodiment, the data gloves (12602) are coupled to a wireless transmitting unit (12604). Wireless transmitting unit (12604) transmits data wirelessly from the gloves (12602) via radio or infrared transmissions or other suitable form of wireless transmission to the system (100). FIG. 127 illustrates a display screen showing the sensor data signals received by the system (100) from the data gloves in accordance to one embodiment.

Figure 128:
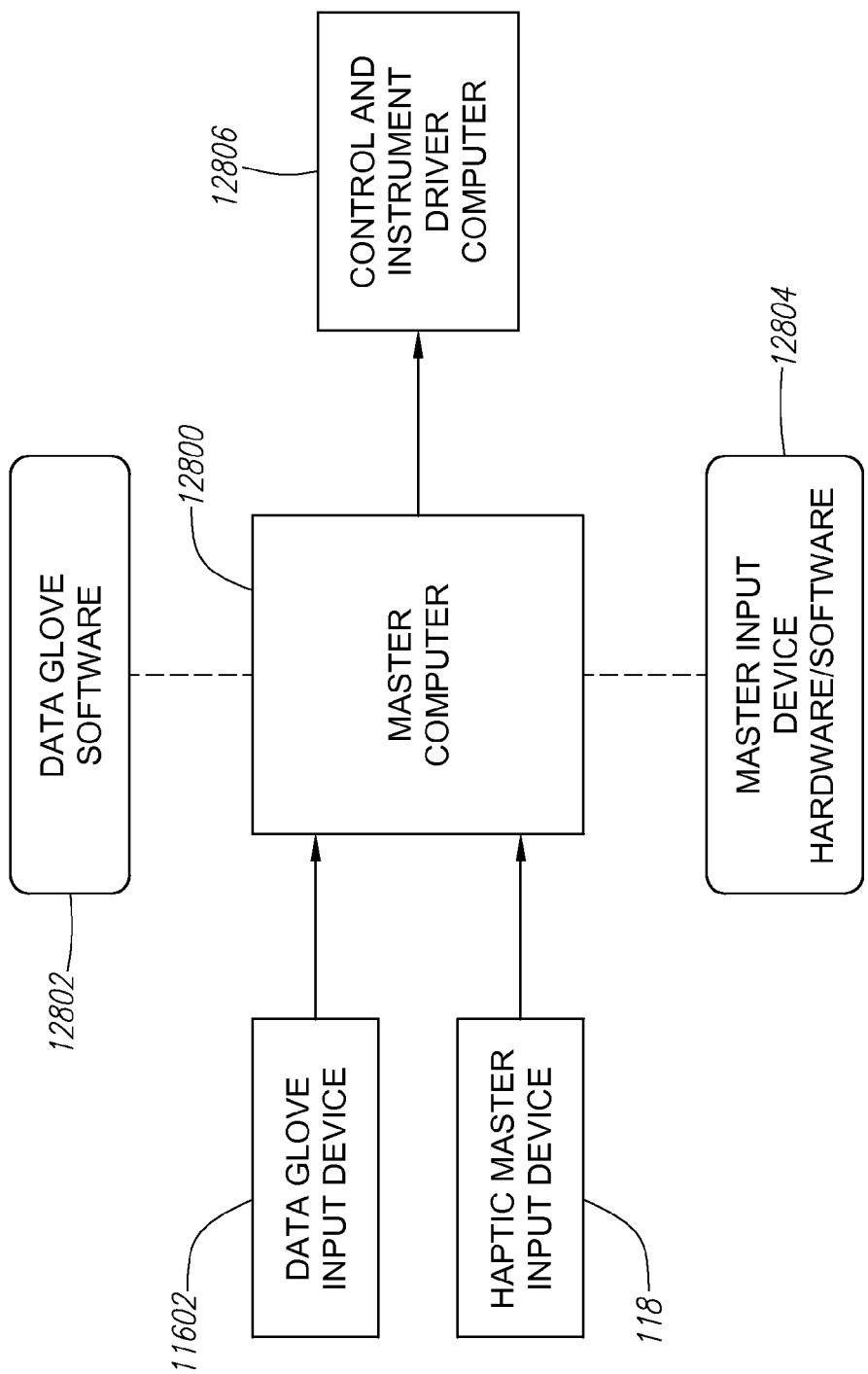

Referring to FIG. 128, an overview of an embodiment of a controls system flow diagram is depicted. As illustrated, a master computer (12800) runs master input device software (12804), data glove software (12802), visualization software, instrument localization software, and software to interface with operator control station buttons and/or switches. In this embodiment, a data glove input device (11602) and a master input device (118) are coupled to the master computer (12800). The master computer (12800) processes the commands and forwards instructions to the control and instrument driver computer, which maneuvers the instrument driver and mounted instruments in response.

In one embodiment, the master input device software is a proprietary module packaged with an off-the-shelf master input device system, such as the Phantom® from SensAble Technologies, Inc., which is configured to communicate with the Phantom® Haptic Device hardware at a relatively high frequency as prescribed by the manufacturer. Other suitable master input devices are available from suppliers such as Force Dimension of Lausanne, Switzerland. The master input device (118) may also have haptics capability to facilitate feedback to the operator, and the software modules pertinent to such functionality may also be operated on the master computer (12800). In one embodiment, the data glove software is a device driver or software model, such as a driver for the 5DT Data Glove. In other embodiments, software support for the data glove master input device is provided through application drivers such as Kaydara MOCAP, Discreet 3D Studio Max, Alias Maya, and SoftImage|XSI.

While multiple embodiments and variations of the many aspects of the invention have been disclosed and described herein, such disclosure is provided for purposes of illustration only. Many combinations and permutations of the disclosed system, apparatus, and methods are useful in minimally invasive medical diagnosis and intervention, and the invention is configured to be flexible and adaptable. The foregoing illustrated and described embodiments of the invention are suitable for various modifications and alternative forms, and it should be understood that the invention generally, as well as the specific embodiments described herein, are not limited to the particular forms or methods disclosed, but also cover all modifications, alternatives, and equivalents as defined by the scope of the appended claims. Further, the various features and aspects of the illustrated embodiments may be incorporated into other embodiments, even if not so described herein, as will be apparent to those skilled in the art. In addition, although the description describes data being mapped to a three dimensional model, data may be mapped to any mapping or coordinate system, including two dimensional, static or dynamic time-varying map, coordinate system, model, image, etc. All directional references (e.g., upper, lower, upward, downward, left, right, leftward, rightward, top, bottom, above, below, vertical, horizontal, clockwise, counterclockwise, etc.) are only used for identification purposes to aid the reader's understanding of the invention without introducing limitations as to the position, orientation, or applications of the invention. Joining references (e.g., attached, coupled, connected, and the like) are to be construed broadly and may include intermediate members between a connection of elements (e.g., physically, electrically, optically as by an optically fiber, and/or wirelessly connected) and relative physical movements, electrical signals, optical signals, and/or wireless signals transmitted between elements. Accordingly, joining references do not necessarily infer that two elements are directly connected in fixed relation to each other. It is intended that all matters contained in the description or shown in the accompanying drawings shall be interpreted as illustrative only and not limiting. Modifications, alternatives, and equivalents in the details, structures, or methodologies may be made without departing from the spirit and scope of the invention as defined by the appended claims.

What we claim is:

1. A method for performing a medical procedure on an abnormality of a prostate of a patient using a robotically steerable catheter having a distal catheter portion and a surgical tool carried by the distal catheter portion, comprising:
   inserting a steerable sheath into the urethra using a robotically controlled system, wherein the distal catheter portion is advanced within the steerable sheath along the urethra until the surgical tool is adjacent the prostate;
   manipulating the catheter using the robotically controlled system;
   imaging an area of the prostate using an imaging device to obtain an image of the area of the prostate;

locating an anatomical landmark using the image of the area of the prostate, and storing a position and orientation of the robotically steerable catheter to arrive at the anatomical landmark;

creating a restricted zone, based on the image of the area of the prostate, into which the surgical tool is restricted from entering by a navigation logic of the robotically controlled system;

operating the surgical tool using the robotically controlled system to treat abnormality of the prostate; and wherein the operation of the surgical tool is at least partially automatically controlled based on the image obtained by the imaging device.

2. The method of claim 1, wherein advancing the steerable sheath and distal catheter portion along the urethra and operating the surgical tool comprises inputting user commands into an operator control station and transmitting corresponding signals to at least one drive unit coupled to the steerable sheath and catheter.

3. The method of claim 2, wherein the corresponding signals are remotely transmitted from the operator control station to the at least one drive unit.

4. The method of claim 1, wherein the abnormality is benign prostatic hyperplasia that narrows the urethra.

5. The method of claim 1, wherein the abnormality is treated by destroying tissue of the prostate.

6. The method of claim 1, wherein the tool is a laser, and the abnormality is treated by conveying laser energy from the laser to destroy tissue of the prostate.

7. The method of claim 1, wherein the tool is a resectoscope, and the abnormality is treated by scraping tissue away from the prostate with the resectoscope.

8. The method of claim 7, wherein the instrument is a tissue grasper that is operated to remove tissue samples from the prostate.

9. The method of claim 1, wherein the tool is a wire loop tool, and the abnormality is treated by conveying electrical energy from the wire loop tool.

10. The method of claim 1, wherein the catheter has an instrument carried by the distal catheter end, the method further comprising operating the instrument using the robotically controlled system.

11. The method of claim 10, wherein the instrument is an imaging device that is operated to image the prostate.

12. The method of claim 11, wherein the imaging device is an optical imaging fiber.

13. The method of claim 10, wherein the instrument is a flush port that is operated to irrigate and flush the prostate.

14. The method of claim 13, wherein treatment of the prostate comprises removing tissue from the prostate, and the flushing of the prostate carries the removed tissue away from the prostate down the urethra.

* * * * *